(12) United States Patent
Hays et al.

(10) Patent No.: US 7,816,320 B2
(45) Date of Patent: Oct. 19, 2010

(54) FORMULATIONS OF HUMAN GROWTH HORMONE COMPRISING A NON-NATURALLY ENCODED AMINO ACID AT POSITION 35

(75) Inventors: Anna-Maria Hays, La Jolla, CA (US); Ying Buechler, Carlsbad, CA (US); David C. Litzinger, Poway, CA (US)

(73) Assignee: AMBRX, Inc., La Jolla, CA (US)

( * ) Notice: Subject to any disclaimer, the term of this patent is extended or adjusted under 35 U.S.C. 154(b) by 272 days.

(21) Appl. No.: 11/316,483

(22) Filed: Dec. 21, 2005

(65) Prior Publication Data

US 2006/0135427 A1 Jun. 22, 2006

Related U.S. Application Data

(60) Provisional application No. 60/638,616, filed on Dec. 22, 2004, provisional application No. 60/680,617, filed on May 13, 2005, provisional application No. 60/728,035, filed on Oct. 17, 2005.

(51) Int. Cl.
*A61K 38/27* (2006.01)
*A61K 39/00* (2006.01)
*C07K 14/00* (2006.01)

(52) U.S. Cl. ............... 514/12; 424/198.1; 530/350; 530/399

(58) Field of Classification Search .............. None
See application file for complete search history.

(56) References Cited

U.S. PATENT DOCUMENTS

| | | | |
|---|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,446,235 A | 5/1984 | Seeburg |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,601,980 A | 7/1986 | Goeddel et al. |
| 4,604,359 A | 8/1986 | Goeddel et al. |
| 4,619,794 A | 10/1986 | Hauser |
| 4,634,677 A | 1/1987 | Goeddel et al. |
| 4,658,021 A | 4/1987 | Goeddel et al. |
| 4,659,839 A | 4/1987 | Nicolotti et al. |
| 4,665,180 A | 5/1987 | Alink |
| 4,670,393 A | 6/1987 | Seeburg |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,898,830 A | 2/1990 | Goeddel et al. |
| 4,902,502 A | 2/1990 | Nitecki et al. |
| 4,904,584 A | 2/1990 | Shaw |
| 4,929,555 A | 5/1990 | Cregg et al. |
| 4,963,495 A | 10/1990 | Chang et al. |
| 5,021,234 A | 6/1991 | Ehrenfeld |
| 5,057,417 A | 10/1991 | Hammonds et al. |
| 5,063,158 A | 11/1991 | Schoner et al. |
| 5,089,398 A | 2/1992 | Rosenberg et al. |
| 5,122,614 A | 6/1992 | Zalipsky |
| 5,162,601 A | 11/1992 | Slightom |
| 5,183,660 A | 2/1993 | Ikeda et al. |
| 5,192,669 A | 3/1993 | Schoner et al. |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |
| 5,290,686 A | 3/1994 | Kendal et al. |
| 5,324,639 A | 6/1994 | Brierley et al. |
| 5,324,844 A | 6/1994 | Zalipsky |
| 5,350,836 A | 9/1994 | Kopchick et al. |

(Continued)

FOREIGN PATENT DOCUMENTS

DE 3218121 A1 11/1983

(Continued)

OTHER PUBLICATIONS

Alam, KS et al. "Expression and purification of a mutant human growth hormone that is resistant to proteolytic cleavage by thrombin, plasmin and human plasma in vitro," J Biotechnol. Oct. 27, 1998;65(2-3):183-90.

(Continued)

*Primary Examiner*—Lorraine Spector
*Assistant Examiner*—Elly-Gerald Stoica
(74) *Attorney, Agent, or Firm*—John W. Wallen, III; Kristin S. Eaton

(57) ABSTRACT

Formulations of modified human growth hormone polypeptides are provided.

18 Claims, 88 Drawing Sheets

U.S. PATENT DOCUMENTS

| | | | |
|---|---|---|---|
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,534,617 A | 7/1996 | Cunningham et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| 5,681,809 A | 10/1997 | Kopchick et al. |
| 5,688,666 A | 11/1997 | Bass et al. |
| 5,688,763 A | 11/1997 | Hammonds, Jr. et al. |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,795,745 A | 8/1998 | Goeddel et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,834,598 A | 11/1998 | Lowman et al. |
| 5,843,733 A | 12/1998 | Estes |
| 5,849,535 A | 12/1998 | Cunningham et al. |
| 5,849,860 A | 12/1998 | Hakimi et al. |
| 5,854,026 A | 12/1998 | Cunningham et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,898,030 A * | 4/1999 | Samaritani ................. 514/12 |
| 5,900,461 A | 5/1999 | Harris |
| 5,932,462 A | 8/1999 | Harris et al. |
| 5,939,285 A | 8/1999 | Devauchelle et al. |
| 5,955,346 A | 9/1999 | Wells et al. |
| 5,962,411 A | 10/1999 | Rosen et al. |
| 5,965,393 A | 10/1999 | Hasnain et al. |
| 5,980,948 A | 11/1999 | Goedemoed et al. |
| 5,981,485 A * | 11/1999 | O'Connor et al. ............ 514/12 |
| 5,989,868 A | 11/1999 | Harrison et al. |
| 5,990,237 A | 11/1999 | Bentley et al. |
| 6,004,573 A | 12/1999 | Rathi et al. |
| 6,004,931 A | 12/1999 | Cunningham et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,022,711 A | 2/2000 | Cunningham et al. |
| 6,057,292 A | 5/2000 | Cunningham et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,136,563 A | 10/2000 | Cunningham et al. |
| 6,143,523 A | 11/2000 | Cunningham et al. |
| 6,168,932 B1 | 1/2001 | Uckun et al. |
| 6,183,985 B1 | 2/2001 | Shuster |
| 6,183,987 B1 | 2/2001 | Van De Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,436,674 B1 | 8/2002 | Honjo et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,566,328 B1 | 5/2003 | Rosen et al. |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 * | 5/2003 | Schultz et al. ................. 435/6 |
| 2003/0105224 A1 | 6/2003 | Roberts et al. |
| 2003/0105275 A1 | 6/2003 | Bentley et al. |
| 2003/0108609 A1 * | 6/2003 | Berry et al. ................. 424/486 |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0153003 A1 | 8/2003 | Wells et al. |
| 2003/0158333 A1 | 8/2003 | Roberts et al. |
| 2003/0162949 A1 | 8/2003 | Cox |
| 2003/0171285 A1 | 9/2003 | Finn et al. |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley et al. |
| 2004/0138106 A1 | 7/2004 | Schultz et al. |
| 2004/0198637 A1 | 10/2004 | Schultz et al. |
| 2005/0009049 A1 | 1/2005 | Chin et al. |

| | | | |
|---|---|---|---|
| 2005/0085619 A1 | 4/2005 | Wilson et al. | |
| 2005/0170404 A1 | 8/2005 | Cho et al. | |
| 2005/0220762 A1 | 10/2005 | Cho et al. | |

FOREIGN PATENT DOCUMENTS

| | | |
|---|---|---|
| EP | 036 676 A1 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| JP | 83-118008 A | 1/1985 |
| WO | 036 776 A2 | 9/1981 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | WO 91/05853 | 5/1991 |
| WO | 92/01801 A1 | 2/1992 |
| WO | 92/02628 A1 | 2/1992 |
| WO | 92/16555 A1 | 10/1992 |
| WO | 92/16619 A1 | 10/1992 |
| WO | WO 92/19736 | 11/1992 |
| WO | 93/03173 A1 | 2/1993 |
| WO | 93/15189 A1 | 8/1993 |
| WO | WO/93/12812 * | 8/1993 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | WO 95/20398 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 9/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/67291 A2 | 12/1999 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | 01/05956 A2 | 1/2001 |
| WO | 01/27301 A2 | 4/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | WO 03/062276 | 7/2003 |
| WO | WO 03/089582 | 10/2003 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | 2005/007624 A2 | 1/2005 |
| WO | 2005/007870 A2 | 1/2005 |
| WO | 2005/019415 A2 | 3/2005 |
| WO | 2005/035727 A2 | 4/2005 |
| WO | 2005/074524 A2 | 8/2005 |
| WO | 2005/074546 A2 | 8/2005 |
| WO | 2005/074650 A2 | 8/2005 |

OTHER PUBLICATIONS

Alves Dos Santos, CM et al. "The signal transduction of the growth hormone receptor is regulated by the ubiquitin/proteasome system and continues after endocytosis," J Biol Chem. Apr. 6, 2001;276(14):10839-46. Epub Jan. 10, 2001.

Amit, T et al. "A membrane-fixed, truncated isoform of the human growth hormone receptor," J Clin Endocrinol Metab. Nov. 1997;82(11):3813-7.

Appa Rao, KBC et al. "High-level expression of ovine growth hormone in *Escherichia coli*: single-step purification and characterization," Protein Expr Purif. Nov. 1997;11(2):201-8.

Atwell, S et al. "Structural plasticity in a remodeled protein-protein interface," Science. Nov. 7, 1997;278(5340):1125-8.

Barazzone, P et al. "Binding, internalization, and lysosomal association of 125I-human growth hormone in cultured human lymphocytes: a quantitative morphological and biochemical study," J Cell Biol. Nov. 1980;87(2 Pt 1):360-9.

Bass, SH et al. "A systematic mutational analysis of hormone-binding determinants in the human growth hormone receptor," Proc Natl Acad Sci U S A. May 15, 1991;88(10):4498-502.

Baumann, G. "Growth hormone heterogeneity: genes, isohormones, variants, and binding proteins," Endocr Rev. Nov. 1991;12(4):424-49.

Bazan, JF. "Haemopoietic receptors and helical cytokines," Immunology Today (1990); 11: 350-354.

Bazan, JF. "Structural design and molecular evolution of a cytokine receptor superfamily," Proc Natl Acad Sci U S A. Sep. 1990;87(18):6934-8.

Bazan, JF et DB McKay. "Unraveling the structure of IL-2," Science. Jul. 17, 1992;257(5068):410-3.

Becker, GW et al. "Isolation and characterization of a sulfoxide and a desamido derivative of biosynthetic human growth hormone," Biotechnol Appl Biochem. Aug. 1988;10(4):326-37.

Behncken, SN et al. "Growth hormone (GH)-independent dimerization of GH receptor by a leucine zipper results in constitutive activation," J Biol Chem. Jun. 2, 2000;275(22):17000-7.

Bell, JA et al. "Crystallization and preliminary x-ray characterization of bovine growth hormone. Purification of bovine prolactin and growth hormone," J Biol Chem. Jul. 15, 1985;260(14):8520-5.

Bernat, B et al. "Determination of the energetics governing the regulatory step in growth hormone-induced receptor homodimerization," Proc Natl Acad Sci U S A. Feb. 4, 2003;100(3):952-7. Epub Jan. 27, 2003.

Bewley, TA et al. "Human pituitary growth hormone. Physicochemical investigations of the native and reduced-alkylated protein," Biochemistry Dec. 1969;8(12):4701-8.

Bieth, E et al. "Human growth hormone receptor: cloning and expression of the full-length complementary DNA after site-directed inactivation of a cryptic bacterial promoter," Gene Jul. 18, 1997;194(1):97-105.

Bignon, C et al. "Preparation of the extracellular domain of the rabbit prolactin receptor expressed in Escherichia coli and its interaction with lactogenic hormones," J Biol Chem. Feb. 4, 1994;269(5):3318-24.

Boutin, JM, et al. "Cloning and expression of the rat prolactin receptor, a member of the growth hormone/prolactin receptor gene family," Cell Apr. 8, 1988;53(1):69-77.

Brostedt, P and P Roos. "Isolation of dimeric forms of human pituitary growth hormone," Prep Biochem. 1989;19(3):217-29.

Chang, CN et al. "High-level secretion of human growth hormone by Escherichia coli" Gene 1987;55(2-3):189-96.

Chawla, RK et al. "Structural variants of human growth hormone: biochemical, genetic, and clinical aspects," Annu Rev Med. 1983;34:519-47.

Chen, C et al. "The role of receptor dimerization domain residues in growth hormone signaling," J Biol Chem. Feb. 21, 1997;272(8):5133-40.

Chiba, T et al. "Tryptophan residue of Trp-Ser-X-Trp-Ser motif in extracellular domains of erythropoietin receptor is essential for signal transduction," Biochim. Biophys. Res. Comm. (1992);184: 485-490.

Chihara, K et al. "Short stature caused by a natural growth hormone antagonist," Horm Res. 1998;49 Suppl 1:41-5.

Conte, F et al. "Identification of a region critical for proteolysis of the human growth hormone receptor," Biochem Biophys Res Commun. Jan. 18, 2002;290(2):851-7.

Cunningham, BC and JA Wells. "High-resolution epitope mapping of hGH-receptor interactions by alanine-scanning mutagenesis," Science Jun. 2, 1989;244(4908):1081-5.

Cunningham, BC et al. "Receptor and antibody epitopes in human growth hormone identified by homolog-scanning mutagenesis," Science Mar. 10, 1989;243(4896):1330-6.

Cunningham, BC and JA Wells. "Rational design of receptor-specific variants of human growth hormone," Proc Natl Acad Sci U S A. Apr. 15, 1991;88(8):3407-11.

Cunningham, BC et al. "Dimerization of the extracellular domain of the human growth hormone receptor by a single hormone molecule," Science Nov. 8, 1991;254(5033):821-5.

Cunningham, BC et JA Wells. "Comparison of a structural and a functional epitope," J. Mol Biol. Dec. 5, 1993;234(3):554-63.

Dastot, F et al. "Alternatively spliced forms in the cytoplasmic domain of the human growth hormone (GH) receptor regulate its ability to generate a soluble GH-binding protein," Proc Natl Acad Sci U S A. Oct. 1, 1996;93(20):10723-8.

Dattani, MT et al. "G120R, a human growth hormone antagonist, shows zinc-dependent agonist and antagonist activity on Nb2 cells," J Biol Chem. Apr. 21, 1995;270(16):9222-6.

Davis, S et al. "LIFRβ and gp130 as heterodimerizing signal transducers of the tripartite CNTF receptor," Science 1993; 260: 1805-1808.

De Vos, AM et al. "Human growth hormone and extracellular domain of its receptor: crystal structure of the complex" Science Jan. 17, 1992;255(5042):306-12.

Diederichs, K et al. "Novel fold and putative receptor binding site of granulocyte-macrophage colony-stimulating factor," Science 1991; 154: 1779-1782.

Dienys, G et al. "Dimerization of human growth hormone in the presence of metal ions," Bioconjug Chem. Sep.-Oct. 2000;11(5):646-51.

Elkins, PA et al. "Ternary complex between placental lactogen and the extracellular domain of the prolactin receptor," Nat Struct Biol. Sep. 2000;7(9):808-15.

Frank, SJ. "Receptor dimerization in GH and erythropoietin action—it takes two to tango, but how?" Endocrinology. Jan. 2002;143(1):2-10.

Fuh, G et al. "The human growth hormone receptor. Secretion from Escherichia coli and disulfide bonding pattern of the extracellular binding domain," J Biol Chem. Feb. 25, 1990;265(6):3111-5.

Fuh, G et al. "Rational design of potent antagonists to the human growth hormone receptor," Science Jun. 19, 1992;256(5064):1677-80.

Gent, J et al. "Ligand-independent growth hormone receptor dimerization occurs in the endoplasmic reticulum and is required for ubiquitin system-dependent endocytosis," Proc Natl Acad Sci U S A. Jul. 23, 2002;99(15):9858-63. Epub Jul. 8, 2002.

Gertler, A et al. "Real-time kinetic measurements of the interactions between lactogenic hormones and prolactin-receptor extracellular domains from several species support the model of hormone-induced transient receptor dimerization," J Biol Chem. Oct. 4, 1996;271(40):24482-91.

Godowski, PJ et al. "Characterization of the human growth hormone receptor gene and demonstration of a partial gene deletion in two patients with Laron-type dwarfism," Proc Natl Acad Sci U S A. Oct. 1989;86(20):8083-7.

Goeddel, DV et al. "Direct expression in Escherichia coli of a DNA sequence coding for human growth hormone" Nature Oct. 18, 1979;281(5732):544-8.

Gomez-Orellana, I et al. "Thermodynamic characterization of an intermediate state of human growth hormone," Protein Sci. Jun. 1998;7(6):1352-8.

Gout, PW et al. "Prolactin-stimulated growth of cell cultures established from malignant Nb rat lymphomas," Cancer Res. Jul. 1980;40(7):2433-6.

Hill, CP et al. "The Structure of Granulocyte-Colony-Stimulating Factor and its Relationship to Other Growth Factors," Proc. Natl. Acad. Sci. USA (1993); 90:5167-71.

Hughes, JP and HG Friesen. "The nature and regulation of the receptors for pituitary growth hormone," Annu Rev Physiol. 1985;47:469-82.

Igout, A, et al. "Expression and secretion of the human placental growth hormone in Escherichia coli," Nucleic Acids Res. May 25, 1989;17(10):3998.

Isaksson, OG, et al. "Mode of action of pituitary growth hormone on target cells," Annu Rev Physiol. 1985;47:483-99.

Johnston, LB et al. "Analysis of the intracellular signalling domain of the human growth hormone receptor in children with idiopathic short stature," Clin Endocrinol (Oxf). Apr. 2000;52(4):463-9.

Kasukawa, Y et al. "Evidence that sensitivity to growth hormone (GH) is growth period and tissue type dependent: studies in GH-deficient lit/lit mice," Endocrinology. Sep. 2003;144(9):3950-7.

Khan, RH et al. "Solubilization of recombinant ovine growth hormone with retention of native-like secondary structure and its refolding from the inclusion bodies of *Escherichia coli*," Biotechnol Prog. Sep.-Oct. 1998;14(5):722-8.

Klaus, W et al. "The three-dimensional high resolution structure of human interferon alpha-2a determined by heteronuclear NMR spectroscopy in solution," J Mol Biol. Dec. 12, 1997;274(4):661-75.

Kopchick, JJ et al. "Growth hormone receptor antagonists: discovery, development, and use in patients with acromegaly," Endocr Rev. Oct. 2002;23(5):623-46.

Kostyo, JL et al. "Biological characterization of purified native 20-kDa human growth hormone," Biochim Biophys Acta. Sep. 11, 1987;925(3):314-24.

Krawczak, M et al. "Evolution of the proximal promoter region of the mammalian growth hormone gene," Gene Sep. 3, 1999;237(1):143-51.

Lee, N et al. "Interferon-alpha 2 variants in the human genome," J Interferon Cytokine Res. Apr. 1995;15(4):341-9.

Leung, DW et al. "Growth hormone receptor and serum binding protein: purification, cloning and expression," Nature Dec. 10-16, 1987;330(6148):537-43.

Lewis, UJ et al. "A naturally occurring structural variant of human growth hormone," J Biol Chem. Apr. 25, 1978;253(8):2679-87.

Lewis, UJ et al. "An interchain disulfide dimer of human growth hormone," J Biol Chem. Jun. 10, 1977;252(11):3697-702.

Lewis, UJ et al. "Altered proteolytic cleavage of human growth hormone as a result of deamidation," J Biol Chem. Nov. 25, 1981;256(22):11645-50.

Li, CH, "Human growth hormone: 1974-1981," Mol Cell Biochem. Jul. 7, 1982;46(1):31-41.

Linzer, Dih et F. Talamantes. "Nucleotide sequence of mouse prolactin and growth hormone mRNAs and expression of these mRNAs during pregnancy," J Biol Chem. Aug. 15, 1985;260(17):9574-9.

Liu, JC et al. "Episodic evolution of growth hormone in primates and emergence of the species specificity of human growth hormone receptor," Mol Biol Evol. Jun. 2001;18(6):945-53.

MacGillivray, MH et al. "Outcome of a four-year randomized study of daily versus three times weekly somatropin treatment in prepubertal naive growth hormone-deficient children. Genentech Study Group." J Clin Endocrinol Metab. May 1996;81(5):1806-9.

Mathews, LS et al. "Regulation of rat growth hormone receptor gene expression," J Biol Chem. Jun. 15, 1989;264(17):9905-10.

Matthews, DJ et al. "A sequential dimerization mechanism for erythropoietin receptor activation," Proc Natl Acad Sci U S A. Sep. 3, 1996;93(18):9471-6.

Mcfarland, KC et al. "Lutropin-choriogonadotropin receptor: an unusual member of the G protein-coupled receptor family," Science Aug. 4, 1989;245(4917):494-9.

Milburn, MV et al. "A novel dimer configuration revealed by the crystal structure at 2.4 A resolution of human interleukin-5" Nature 1993; 363:172-176.

Mills, JB, et al. "Fragments of human growth hormone produced by digestion with thrombin: chemistry and biological properties," Endocrinology Aug. 1980;107(2):391-9.

Mordenti, J et al. "Interspecies scaling of clearance and volume of distribution data for five therapeutic proteins," Pharm Res. Nov. 1991;8(11):1351-9.

Mott, HR and ID Campbell. "Four-helix bundle growth factors and their receptors: protein-protein interactions," Curr Opin Struct Biol. Feb. 1995;5(1):114-21.

Murgolo, NJ et al. "A homology model of human interferon alpha-2," Proteins Sep. 1993;17(1):62-74.

Oliva, A et al. "Comparative study of protein molecular weights by size-exclusion chromatography and laser-light scattering," J Pharm Biomed Anal. Jul. 2001;25(5-6):833-41.

Pal, G et al. "The functional binding epitope of a high affinity variant of human growth hormone mapped by shotgun alanine-scanning mutagenesis: insights into the mechanisms responsible for improved affinity," J Mol Biol. Sep. 5, 2003;332(1):195-204.

Pantel, J et al. "Species-specific alternative splice mimicry at the growth hormone receptor locus revealed by the lineage of retroelements during primate evolution," J Biol Chem. Jun. 23, 2000;275(25):18664-9.

Paonessa, G et al. "Two distinct and independent sites on IL-6 trigger gp 130 dimer formation and signaling," EMBO J. May 1, 1995;14(9):1942-51.

Pearce, KH et al. "Growth hormone binding affinity for its receptor surpasses the requirements for cellular activity," Biochemistry. Jan. 5, 1999;38(1):81-9.

Pearce, KH et al. "Structural and mutational analysis of affinity-inert contact residues at the growth hormone-receptor interface," Biochemistry. Aug. 13, 1996;35(32):10300-7.

Powers, R et al. "Three-dimensional solution structure of human interleukin-4 by multidimensional heteronuclear magnetic resonance spectroscopy," Science Jun. 19, 1992;256(5064):1673-7.

Radhakrishnan, R et al. "Zinc mediated dimer of human interferon-alpha 2b revealed by X-ray crystallography," Structure Dec. 15, 1996;4(12):1453-63.

Redfield, C et al. "Secondary structure and topology of human interleukin 4 in solution," Biochemistry Nov. 19, 1991;30(46):11029-35.

Ross, RJM et al. "Binding and functional studies with the growth hormone receptor antagonist, B2036-PEG (pegvisomant), reveal effects of pegylation and evidence that it binds to a receptor dimer," J Clin Endocrinol Metab. Apr. 2001;86(4):1716-23.

Rottman, JN et JI Gordon. "Comparison of the patterns of expression of rat intestinal fatty acid binding protein/human growth hormone fusion genes in cultured intestinal epithelial cell lines and in the gut epithelium of transgenic mice," J Biol Chem. Jun. 5, 1993;268(16):11994-2002.

Rowland, JE et al. "A novel bioassay for human somatogenic activity in serum samples supports the clinical reliability of immunoassays," Clin Endocrinol (Oxf). Apr. 2002;56(4):475-85.

Schiffer, C et al. "Structure of a phage display-derived variant of human growth hormone complexed to two copies of the extracellular domain of its receptor: evidence for strong structural coupling between receptor binding sites," J Mol Biol. Feb. 15, 2002;316(2):277-89.

Schoner, BE et al. "Role of mRNA translational efficiency in bovine growth hormone expression in *Escherichia coli*," Proc Natl Acad Sci U S A. Sep. 1984;81(17):5403-7.

Seeburg, PH. "The human growth hormone gene family: nucleotide sequences show recent divergence and predict a new polypeptide hormone," DNA 1982;1(3):239-49.

Silva, CM et al. "Characterization and cloning of STAT5 from IM-9 cells and its activation by growth hormone," Mol Endocrinol. May 1996;10(5):508-18.

Sobrier, ML et al. "Expression and binding properties of two isoforms of the human growth hormone receptor," FEBS Lett. Mar. 15, 1993;319(1-2):16-20.

Sobrier, ML et al. "Nine novel growth hormone receptor gene mutations in patients with Laron syndrome," J Clin Endocrinol Metab. Feb. 1997;82(2):435-7.

Souza, SC et al. "A single arginine residue determines species specificity of the human growth hormone receptor," Proc Natl Acad Sci U S A. Feb. 14, 1995;92(4):959-63.

Spencer, SA et al. "Rabbit liver growth hormone receptor and serum binding protein. Purification, characterization, and sequence," J Biol Chem. Jun. 5, 1988;263(16):7862-7.

Stallings-Mann, ML et al. "Alternative splicing of exon 3 of the human growth hormone receptor is the result of an unusual genetic polymorphism," Proc Natl Acad Sci U S A. Oct. 29, 1996;93(22):12394-9.

Sundstrom, M et al. "Crystal structure of an antagonist mutant of human growth hormone, G120R, in complex with its receptor at 2.9 A resolution," J Biol Chem. Dec. 13, 1996;271(50):32197-203.

Syed, RS et al. "Efficiency of signalling through cytokine receptors depends critically on receptor orientation," Nature. Oct. 1, 1998;395(6701):511-6.

Talamantes, F et R Ortiz. "Structure and regulation of expression of the mouse GH receptor," J Endocrinol. Oct. 2002;175(1):55-9.

Teh, LC et al. "Methionine oxidation in human growth hormone and human chorionic somatomammotropin. Effects on receptor binding and biological activities," J Biol Chem. May 15, 1987;262(14):6472-7.

Trahair, JF et al. "Use of transgenic mice to study the routing of secretory proteins in intestinal epithelial cells: analysis of human growth hormone compartmentalization as a function of cell type and differentiation," J Cell Biol. Dec. 1989;109(6 Pt 2):3231-42.

Tsunekawa, B et al. "The binding between the stem regions of human growth hormone (GH) receptor compensates for the weaker site 1 binding of 20-kDa human GH (hGH) than that of 22-kDa hGH," J Biol Chem. May 26, 2000;275(21):15652-6.

Ultsch, MH et al. "The crystal structure of affinity-matured human growth hormone at 2 A resolution," J Mol Biol. Feb. 11, 1994;236(1):286-99.

Urbanek, M et al. "Functional characterization of the alternatively spliced, placental human growth hormone receptor," J Biol Chem. Sep. 5, 1993;268(25):19025-32.

Van Der Lely, AJ et al. "Long-term treatment of acromegaly with pegvisomant, a growth hormone receptor antagonist," Lancet Nov. 24, 2001;358(9295):1754-9.

Wada, M. et al. "The 20-kilodalton (kDa) human growth hormone (hGH) differs from the 22-kDa hGH in the complex formation with cell surface hGH receptor and hGH-binding protein circulating in human plasma," Mol Endocrinol. Jan. 1998;12(1):146-56.

Walsh, STR et al. "Site2 binding energetics of the regulatory step of growth hormone-induced receptor homodimerization," Protein Sci. Sep. 2003;12(9):1960-70.

Walter, MR et al. "Three-dimensional structure of recombinant human granulocyte-macrophage colony-stimulating factor," J Mol Biol. Apr. 20, 1992;224(4):1075-85.

Wang, X et al. "A 40-amino acid segment of the growth hormone receptor cytoplasmic domain is essential for GH-induced tyrosine-phosphorylated cytosolic proteins," J Biol Chem. Mar. 17, 1995;270(11):6261-6.

Weiss, GA et al. "Rapid mapping of protein functional epitopes by combinatorial alanine scanning," Proc Natl Acad Sci U S A. Aug. 1, 2000;97(16):8950-4.

Wells, JA. "Binding in the growth hormone receptor complex," Proc Natl Acad Sci U S A. Jan. 9, 1996;93(1):1-6.

Wen, D et al. "Erythropoietin structure-function relationships. Identification of functionally important domains," J. Biol. Chem. 1994; 269(36):22839-22846.

Zink, T et al. "Secondary structure of human granulocyte colony-stimulating factor derived from NMR spectroscopy," FEBS Lett. Dec. 21, 1992;314(3):435-9.

Zink, T et al. "Structure and dynamics of the human granulocyte colony-stimulating factor determined by NMR spectroscopy. Loop mobility in a four-helix-bundle protein," Biochemistry Jul. 19, 1994;33(28):8453-63.

Bam, NB et al. "Tween protects recombinant human growth hormone against agitation-induced damage via hydrophobic interactions," J Pharm Sci. Dec. 1998;87(12):1554-9.

Bam, NB et al. "Molten globule intermediate of recombinant human growth hormone: stabilization with surfactants," Biotechnol Prog. Nov.-Dec. 1996;12(6):801-9.

Bam, NB et al. "Stability of protein formulations: investigation of surfactant effects by a novel EPR spectroscopic technique," Pharm Res. Jan. 1995;12(1):2-11.

Battersby, JE et al. "Affinity purification and microcharacterization of recombinant DNA-derived human growth hormone isolated from an in vivo model," Anal Chem. Jan. 15, 1995;67(2):447-55.

Battersby, JE et al. "Diketopiperazine formation and N-terminal degradation in recombinant human growth hormone," Int J Pept Protein Res. Sep. 1994;44(3):215-22.

Becker, GW et JM Hsiung. "Expression, secretion and folding of human growth hormone in Escherichia coli. Purification and characterization," FEBS Lett. Aug. 11, 1986;204(1):145-50.

Bedu-Addo, F et al. "Preformulation development of recombinant pegylated staphylokinase SY161 using statistical design," AAPS PharmSci. 2002;4(4):E19.

Bondos, SE et A Bicknell. "Detection and prevention of protein aggregation before, during, and after purification," Anal Biochem. May 15, 2003;316(2):223-31.

Brems, DN et al. "Equilibrium denaturation of human growth hormone and its cysteine-modified forms," J Biol Chem. Apr. 5, 1990;265(10):5504-11.

Callahan, WJ et al. "Sodium chloride enhances the storage and conformational stability of BDNF and PEG-BDNF," Pharm Res. Mar. 2001;18(3):261-6.

Capan, Y et al. "Preparation and characterization of poly(D,L-lactide-co-glycolide) microspheres for controlled release of human growth hormone," AAPS PharmSciTech. 2003;4(2):E28.

Carpenter, JF et al. "Application of infrared spectroscopy to development of stable lyophilized protein formulations," Eur J Pharm Biopharm. May 1998;45(3):231-8.

Chang, JYH et al. "Periplasmic secretion of human growth hormone by Escherichia coli," Biochem Soc Trans. Apr. 1989;17(2):335-7.

Chapman, GE et al. "The 20,000 molecular weight variant of human growth hormone. Preparation and some physical and chemical properties," J Biol Chem. Mar. 10, 1981;256(5):2395-401.

Charman, SA et al. "Techniques for assessing the effects of pharmaceutical excipients on the aggregation of porcine growth hormone," Pharm Res. Jul. 1993;10(7):954-62.

Cheah, K-C et al. "Secretion of eukaryotic growth hormones in Escherichia coli is influenced by the sequence of the mature proteins," Gene. Jan. 28, 1994;138(1-2):9-15.

Chi, EY et al. "Physical stability of proteins in aqueous solution: mechanism and driving forces in nonnative protein aggregation," Pharm Res. Sep. 2003;20(9):1325-36.

Chi, EY et al. "Roles of conformational stability and colloidal stability in the aggregation of recombinant human granulocyte colony-stimulating factor," Protein Sci. May 2003;12(5):903-13.

Cholewinski, M et al. "Degradation pathways, analytical characterization and formulation strategies of a peptide and a protein. Calcitonine and human growth hormone in comparison," Pharm Acta Helv. Dec. 1996;71(6):405-19.

Clackson, T et JA Wells. "A hot spot of binding energy in a hormone-receptor interface," Science. Jan. 20, 1995;267(5196):383-6.

Cleland, JL et al. "The development of stable protein formulations: a close look at protein aggregation, deamidation, and oxidation," Crit Rev Ther Drug Carrier Syst. 1993;10(4):307-77.

Costantino, HR et al. "Effect of excipients on the stability and structure of lyophilized recombinant human growth hormone," J Pharm Sci. Nov. 1998;87(11):1412-20.

Costantino, HR et al. "Protein spray freeze drying. 2. Effect of formulation variables on particle size and stability," J Pharm Sci. Feb. 2002;91(2):388-95.

Cueto, M et al. "New approach to stability assessment of protein solution formulations by differential scanning calorimetry," Int J Pharm. Feb. 18, 2003;252(1-2):159-66.

Cunico, RL et al. "Characterization of polyethylene glycol modified proteins using charge-reversed capillary electrophoresis," J Chromatogr 1991; 559:467-477.

Dalboge, H et al. "A novel enzymatic method for production of authentic hGH from an Eschericia coli produced hGH-precursor," Bio/Technology 1987; 5:161-164.

De Oliveira, JE et al. "High-yield purification of biosynthetic human growth hormone secreted in Escherichia coli periplasmic space," J Chromatogr A. Aug. 13, 1999;852(2):441-50.

Defelippis, MR et al. "Evidence for a self-associating equilibrium intermediate during folding of human growth hormone," Biochemistry. Feb. 16, 1993;32(6):1555-62.

Dong, A et al. "Infrared spectroscopic studies of lyophilization-and temperature-induced protein aggregation," J Pharm Sci. Apr. 1995;84(4):415-24.

Eckhardt, BM et al. "Effect of freezing on aggregation of human growth hormone," Pharm Res. Nov. 1991;8(11):1360-4.

Fee, CJ. "Size-exclusion reaction chromatography (SERC): a new technique for protein PEGylation," Biotechnol Bioeng. Apr. 20, 2003;82(2):200-6.

Filikov, AV et al. "Computational stabilization of human growth hormone," Protein Sci. Jun. 2002;11(6):1452-61.

Flodh, H. "Human growth hormone produced with recombinant DNA technology: development and production," Acta Paediatr Scand Suppl. 1986;325:1-9.

Gellerfors, P et al. "Separation and identification of growth hormone variants with high performance liquid chromatography techniques," Acta Paediatr Scand Suppl. 1990;370:93-100.

Haro, LS et al. "Divalent metal cation chelators enhance chromatographic separation of structurally similar macromolecules: separation of human growth hormone isoforms," J Chromatogr B Biomed Sci Appl. Dec. 11, 1998;720(1-2):39-47.

Ikeda, M et al. "A novel bioassay based on human growth hormone (hGH) receptor mediated cell proliferation: measurement of 20K-hGH and its modified forms," Growth Horm IGF Res. Oct. 2000;10(5):248-55.

Jespersen, AM et al. "Characterisation of a trisulphide derivative of biosynthetic human growth hormone produced in *Escherichia coli*," Eur J Biochem. Jan. 15, 1994;219(1-2):365-73.

Johnson, BA et al. "Formation of isoaspartate at two distinct sites during in vitro aging of human growth hormone," J Biol Chem. Aug. 25, 1989;264(24):14262-71.

Jones, RL et al. "Large-scale preparation of highly purified pyrogen-free human growth hormone for clinical use," J Endocrinol. Jul. 1979;82(1):77-86.

Jorgensen, TK et al. "Quantifying biosynthetic human growth hormone in *Escherichia coli* with capillary electrophoresis under hydrophobic conditions," J Chromatogr A. Aug. 21, 1998;817(1-2):205-14.

Kappelgaard, A-M et al. "Liquid growth hormone: preservatives and buffers," Horm Res. 2004;62 Suppl 3:98-103.

Karlsson, G et al. "Separation of oxidized and deamidated human growth hormone variants by isocratic reversed-phase high-performance liquid chromatography," J Chromatogr A. Sep. 3, 1999;855(1):147-55.

Karlsson, G et al. "Usage of nonporous polymeric particles for reversed-phase high-performance liquid chromatography of oxidized and deamidated forms of recombinant human growth hormone," J Chromatogr Sci. Jul. 2004;42(6):285-7.

Kasimova, MR et al. "NMR studies of the backbone flexibility and structure of human growth hormone: a comparison of high and low pH conformations," J Mol Biol. May 3, 2002;318(3):679-95.

Kasimova, MR et al. "The conformational equilibrium of human growth hormone," J Mol Biol. Mar. 27, 1998;277(2):409-18.

Kasraian, K et al. "Sustained in vivo activity of recombinant bovine granulocyte colony stimulating factor (rbG-CSF) using Hepes buffer," Pharm Dev Technol. Aug. 2001;6(3):441-7.

Katakam, M et al. "Effect of surfactants on the physical stability of recombinant human growth hormone," J Pharm Sci. Jun. 1995;84(6):713-6.

Kim, HE et al. "Microencapsulation of dissociable human growth hormone aggregates within poly(D,L-lactic-co-glycolic acid) microparticles for sustained release," Intl J of Pharm 2001; 229:107-16.

Kunitani, M et al. "On-line characterization of polyethylene-glycol modified proteins," J Chromatogr. 1991; 588:125-137.

Lai, MC et al. "Chemical stability of peptides in polymers. 2. Discriminating between solvent and plasticizing effects of water on peptide deamidation in poly(vinylpyrrolidone)," J Pharm Sci. Oct. 1999;88(10):1081-9.

Liu, JL et al. "In vitro methionine oxidation of recombinant human leptin," Pharm Res. Apr. 1998;15(4):632-40.

Maa, Y-F et al. "Spray-drying of air-liquid interface sensitive recombinant human growth hormone," J Pharm Sci. Feb. 1998;87(2):152-9.

Maisano, F et al. "Immobilized metal-ion affinity chromatography of human growth hormone," J Chromatogr. Jun. 23, 1989;472(2):422-7.

Manning, MC et al. "Stability of protein pharmaceuticals," Pharm Res. Nov. 1989;6(11):903-18.

Mukhija, R et al. "High-level production and one-step purification of biologically active human growth hormone in *Escherichia coli*," Gene. Nov. 20, 1995;165(2):303-6.

Naglak, TJ et Hy Wang. "Recovery of a foreign protein from the periplasm of *Escherichia coli* by chemical permeabilization," Enzyme Microb Technol. Aug. 1990;12(8):603-11.

Olson, KC et al. "Purified human growth hormone from *E. coli* is biologically active," Nature. Oct. 1, 1981;293(5831):408-11.

Pan, F-M et W-C Chang. "Purification of growth hormones by reversed-phase high-performance liquid chromatography," J Chromatogr. Apr. 2, 1993;613(2):326-9.

Panda, AK. "Bioprocessing of therapeutic proteins from the inclusion bodies of *Escherichia coli*," Adv Biochem Eng Biotechnol. 2003;85:43-93.

Patience, RL and LH Rees. "Comparison of reversed-phase and anion-exchange high-performance liquid chromatography. For the analysis of human growth hormones," J Chromatogr. Feb. 21, 1986;352:241-53.

Pearlman, R et T Nguyen. "Pharmaceutics of protein drugs," J Pharm Pharmacol. Feb. 1992;44 Suppl 1:178-85.

Pikal, MJ et al. "The effects of formulation variables on the stability of freeze-dried human growth hormone," Pharm Res. Apr. 1991;8(4):427-36.

Rathore, AS et al. "Optimization of an osmotic shock procedure for isolation of a protein product expressed in *E. coli*," Biotechnol Prog. Sep.-Oct. 2003;19(5):1541-6.

Reddy, KR. "Controlled-release, pegylation, liposomal formulations: new mechanisms in the delivery of injectable drugs," Ann Pharmacother. Jul.-Aug. 2000;34(7-8):915-23.

Remmele, RL et al. "Interleukin-1 receptor (IL-1R) liquid formulation development using differential scanning calorimetry," Pharm Res. Feb. 1998;15(2):200-8.

Riggin, RM et al. "High-performance size-exclusion chromatographic determination of the potency of biosynthetic human growth hormone products," J Chromatogr. Jan. 8, 1988;435(2):307-18.

Riggin, RM et al. "A reversed-phase high-performance liquid chromatographic method for characterization of biosynthetic human growth hormone," Anal Biochem. Nov. 15, 1987;167(1):199-209.

Sharma, VK et DS Kalonia. "Polyethylene glycol-induced precipitation of interferon alpha-2a followed by vacuum drying: development of a novel process for obtaining a dry, stable powder," AAPS PharmSci. Jan. 26, 2004;6(1):E4.

Takahashi, Y et al. "Brief report: short stature caused by a mutant growth hormone," N. Engl J Med. Feb. 15, 1996;334(7):432-6.

Tang, X et MJ Pikal. "Design of freeze-drying processes for pharmaceuticals: practical advice," Pharm Res. Feb. 2004;21(2):191- 200.

Tatford, OC et al. "Analytical techniques for the evaluation of liquid protein therapeutics," Biotechnol Appl Biochem. Aug. 2004;40(Pt 1):67-81.

Tkac, J et al. "Evaluation of disruption methods for the release of intracellular recombinant protein from *Escherichia coli* for analytical purposes," Biotechnol Appl Biochem. Aug. 2004;40(Pt 1):83-8.

Treuheit, MJ et al. "Inverse relationship of protein concentration and aggregation," Pharm Res. Apr. 2002;19(4):511-6.

Tsubery, H et al. "Prolonging the action of protein and peptide drugs by a novel approach of reversible polyethylene glycol modification," J Biol Chem. Sep. 10, 2004;279(37):38118-24. Epub Jun. 8, 2004.

Wang, W. "Instability, stabilization, and formulation of liquid protein pharmaceuticals," Int J Pharm. Aug. 20, 1999;185(2):129-88.

Welinder, BS et al. "Reversed-phase high-performance liquid chromatography of human growth hormone," J Chromatogr. Jul. 10, 1987;398:309-16.

Wu, SL et al. "Application of high-performance hydrophobic-interaction chromatography to the characterization of recombinant DNA-derived human growth hormone," J Chromatogr. Feb. 2, 1999;500:595-606.

Yan, Y-B et al. "Protein thermal aggregation involves distinct regions: sequential events in the heat-induced unfolding and aggregation of hemoglobin," Biophys J. Mar. 2004;86(3):1682-90.

Yang, T-H et al. "Use of Infrared Spectroscopy to Assess Secondary Structure of Human Growth Hormone within Biodegradable Microspheres," J Pharm Sci Feb. 1999; 88(2):161-165.

Duncan, R. "The dawning era of polymer therapeutics," Nat Rev Drug Discov May 2003;2(5):347-60.

Gaertner, HF et RE Offord. "Site-specific attachment of functionalized poly(ethylene glycol) to the amino terminus of proteins," Bioconjug Chem Jan.-Feb. 1996;7(1):38-44.

Gu, Z et al. "Chromatographic methods for the isolation of, and refolding of proteins from, *Escherichia coli* inclusion bodies," Protein Expr Purif. Jun. 2002;25(1):174-9.

Hohsaka, T et M Sisido. "Incorporation of non-natural amino acids into proteins," Curr Opin Chem Biol. Dec. 2002;6 (6):809-15.

Lilie, H et al. "Advances in refolding of proteins produced in *E. coli*," Curr Opin Biotechnol. Oct. 1998;9(5):497-501.

Tsumoto, K et al. "Practical considerations in refolding proteins from inclusion bodies," Protein Expr Purif. Mar. 2003;28(1):1-8.

Wang, W. "Instability, stabilization, and formulation of liquid protein pharmaceuticals," Int J Pharm. Aug. 20, 1999;185 (2):129-88.

Abuchowski, A. et al. "Cancer therapy with chemically modified enzymes. I. Antitumor properties of polyethylene glycol-asparaginase conjugates," Cancer Biochem Biophys. Jun. 1984;7(2):175-86.

Altschul, SF et al. "Gapped BLAST and PSI-BLAST: a new generation of protein database search programs," Nucleic Acids Res. Sep. 1, 1997;25(17):3389-402.

Altschul, SF et al. "Basic local alignment search tool," J Mol Biol. Oct. 5, 1990;215(3):403-10.

Amann, E et al., "Vectors bearing a hybrid trp-lac promoter useful for regulated expression of cloned genes in *Escherichia coli*," Gene. Nov. 1983;25(2-3):167-78.

Anderson, JC et al., "Exploring the limits of codon and anticodon size," Chem Biol. Feb. 2002;9(2):237-44.

Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.

Arnold, FH. "Protein engineering for unusual environments," Curr Opin Biotechnol. Aug. 1993;4(4):450-5.

Azoulay, M., et al. "Glutamine analogues as Potential Antimalarials," Eur. J. Med. Chem. (1991); 26(2):201-5.

Bain, JD, et al. "Biosynthetic site-specific incorporation of a non-natural amino acid into a polypeptide," J. Am Chem Soc 1989;111(20):8013-8014.

Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.

Barany, F. et al., "Genetic disease detection and DNA amplification using cloned thermostable ligase," Proc Natl Acad Sci U S A. Jan. 1, 1991;88(1):189-93.

Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.

Bass, S et al., "Mutant Trp repressors with new DNA-binding specificities," Science (1988) 242:240-245.

Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977; 112:535-542.

Boissel, JP et al., "Erythropoietin structure-function relationships. Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortie, "Strategies and applications of in vitro mutagenesis," Science. Sep. 20, 1985;229 (4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. "Functionalization of Poly(ethylene glycol) and Monomethoxy-Poly(ethylene glycol), "Makromol. Chem. 1981;182:1379-84.

Budisa, N. et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins: a promising new approach for X-ray structure analysis of proteins," J Mol Biol. Jul. 25, 1997;270(4):616-23.

Budisa, N. et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al. "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124 (31):9026-7.

Chin, JW et al., "Addition of a photocrosslinking amino acid to the genetic code of *Escherichia coli*," Proc Nati Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11): 1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987; 238(4832):1401-1403.

Cornish, VW, et al., "Site-Specific Protein Modification Using a Ketone Handle," J. Am. Chem. Soc. 1996; 118 (34):8150-8151.

Cornish, VW et al., "Probing Protein Structure and Function with an Expanded Genetic Code,"Angew Chem Int Ed Engl,1995;34(6):621-33.

Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.

Cregg, JM et al., "Pichia pastoris as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of Kluyveromyces fragilis," J Bacteriol. Jun. 1984;158(3):1165-7.

Dawson, P. E. and S. B. H. Kent, "Synthesis of native proteins by chemical ligation," Annu. Rev. Biochem. 2000; 69:923-60.

De Boer, Ha et al., "The tac promoter: a functional hybrid derived from the trp and lac promoters," Proc Natl Acad Sci U S A. Jan. 1983;80(1):21-5.

De Louvencourt, L et al., "Transformation of *Kluyveromyces lactis* by killer plasmid DNA," J Bacteriol. May 1983;154(2):737-42.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "Kluyveromyces as a host for heterologous gene expression: expression and secretion of prochymosin," Biotechnology (N Y). Feb. 1990;8(2):135-9.

Van Hest, JC and DA Tirrell, "Efficient introduction of alkene functionality into proteins in vivo," FEBS Lett. May 22, 1998;428(1-2):68-70.

Debinski, W et al. "A wide range of human cancers express interleukin 4 (IL4) receptors that can be targeted with chimeric toxin composed of IL4 and *Pseudomonas* exotoxin," J Biol Chem. Jul. 5, 1993;268(19):14065-70.

Deiters, A., et al., "Adding Amino Acids with Novel Reactivity to the Genetic Code of *Saccharomyces cerevisiae*," J. Am. Chem. Soc. 2003; 125(39):11782-11783.

Delgado, C et al., "The uses and properties of PEG-linked proteins," Crit Rev Ther Drug Carrier Syst. 1992;9 (3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.

Ellman, JA, et al. "Site-specific incorporation of novel backbone structures into proteins," Science. Jan. 10, 1992;255 (5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A.(1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., " Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10 (11):1043-50.

Fraser, MJ et al., "Expression of eucaryotic genes in insect cell cultures," In Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824.

Furter, R. "Expansion of the genetic code: site-directed p-fluorophenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992; 3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast *Hansenula polymorphica*," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8 (18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34 (9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25 (3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Natl Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.

Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic Code," J. Am. Chem. Soc. 1999; 121(51):12194-12195.

Van Hest, J. C. et al., "Efficient Incorporation of Unsaturated Methionine Analogues into Proteins in Vivo," J. Am. Chem. Soc. 2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985; 11(2):141-52.

Vlak, JM et al., "Functional studies on the p10 gene of *Autographa californica* nuclear polyhedrosis virus using a recombinant expressing a p10-beta-galactosidase fusion gene," J Gen Virol. Apr. 1988;69 ( Pt 4):765-76.

Wang, Q., et al., "Bioconjugation by Copper(I)-Catalyzed Azide-Alkyne [3+2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Wang, L & PG Schultz, "Expanding the genetic code," Chem Commun (Camb). Jan. 7, 2002;1:1-11.

Weissmann, C. "The cloning of interferon and other mistakes." in Interferon 3 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," NATURE (1986) 321(6072):718.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17 (23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyltRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81 (2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha- amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. and D. A. Tirrell, "Protein Engineering by in Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of gamma-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327 (6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with *Pseudomonas* exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts *Candida maltosa* and *Pichia guilliermondii*," J. Basic Microbiol. 1985; 25:141-4.

Kurtz et al., "Integrative transformation of *Candida albicans*, using a cloned *Candida* ADE2 gene," Mol Cell Biol. Jan. 1986;6(1):142-9.

Kurtzhals, P. et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules, " Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254 (2):157-78.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with *Autographa californica* nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307 (3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. "Oligonucleotide-directed double-strand break repair in plasmids of *Escherichia coli*: a method for site-specific mutagenesis," Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide-1,4-Galactosyltransferase from Rat Brain," J. Biol. Chem. 1998; 273(22):13570-7.

Noren, CJ et al. "A general method for site-specific incorporation of unnatural amino acids into proteins," Science. 1989 Apr 14;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res.Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferonbeta-la with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. 1988 Nov 18;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Yelton, MM et al., "Transformation of *Aspergillus nidulans* by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9 (3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42 (22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.

Zoller, MJ & M. Smith, "Oligonucleotide-directed mutagenesis of DNA fragments cloned into M13 vectors" Methods Enzymol. 1983;100:468-500.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. BIOL. CHEM. 1996; 271 (39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast *Hansenula polymorpha* by autonomous replication and integration vectors," Mol. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase a Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MaIK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N. et al., "Efficient introduction of aryl bromide functionality into proteins in vivo," FEBS Lett. Feb. 4, 2000;467 (1):37-40.

Shimatake, H et M Rosenberg, "Purified gamma regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254 (5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in *Saccharomyces cerevisiae*," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich *Entamoeba histolytica* protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111 (21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in *Aspergillus nidulans*," Gene. Dec. 1983;26(2-3):205-21.

Zoller, MJ & Smith M, "Oligonucleotide-directed mutagenesis: a simple method using two oligonucleotide primers and a single-stranded DNA template," Methods Enzymol. 1987;154:329-50.

Mehl, RA et al. "Generation of a bacterium with a 21 amino acid genetic code," J Am Chem Soc. Jan. 29, 2003;125 (4):935-9.

Santoro, SW et al. "An efficient system for the evolution of aminoacyl-tRNA synthetase specificity," Nat Biotechnol. Oct. 2002;20(10):1044-8. Epub Sep. 16, 2002.

Caliceti, P. et FM Veronese. "Pharmacokinetic and biodistribution properties of poly(ethylene glycol)-protein conjugates," Adv Drug Deliv Rev. Sep. 26, 2003;55(10):1261-77.

Clark, EDB, "Refolding of recombinant proteins," Curr Opin Biotechnol Apr. 1, 1998;9(2):157-63.

Clark, EDB, "Protein refolding for industrial processes," Curr Opin Biotechnol Apr. 2001;12(2):202-7.

Davis, GD et al., "New fusion protein systems designed to give soluble expression in *Escherichia coli*," Biotechnol Bioeng Nov. 20, 1999;65(4):382-8.

* cited by examiner

Title: Formulations of Human Growth Hormone Comprising a Non-Naturally Encoded Amino Acid
Inventors: Anna-Maria Hays et al.    Appl. No.: Not Assigned
Docket Number: AMBX-0077.00US    Atty: John W. Wallen, III    Telephone: (858) 875-2403

|   |   | A<br>20mM Sodium Acetate pH 4.5 | B<br>20mM Sodium Citrate pH 6.0 | C<br>50mM Histidine pH 6.5 | D<br>50mM Sodium Phosphate pH 7.0 | E<br>50mM Sodium Bicarbonate pH 7.3 | F<br>50mM HEPES pH 7.5 |
|---|---|---|---|---|---|---|---|
| 1 | No additions | 4.56 | 5.92 | 6.59 | 7.01 | 9.02 | 7.49 |
| 2 | 15mM Trehalose | 4.51 | 5.88 | 6.54 | 7.00 | 9.02 | 7.47 |
| 3 | 15mM Sucrose | 4.47 | 5.87 | 6.58 | 6.97 | 8.92 | 7.49 |
| 4 | 15mM Mannitol | 4.46 | 5.86 | 6.64 | 6.99 | 8.52 | 7.49 |
| 5 | 75mM $(NH_4)_2SO_4$ | 4.54 | 5.86 | 6.50 | 7.05 | 8.14 | 7.54 |
| 6 | 250mM Glycine | 4.47 | 5.83 | 6.70 | 7.02 | 7.88 | 7.51 |
| 7 | 250mM Arginine | 4.50 | 5.79 | 6.51 | 6.96 | 7.65 | 7.47 |
| 8 | 100mM Glutamate | 4.54 | 5.76 | 6.45 | 7.03 | 8.64 | 7.56 |

Figure 1

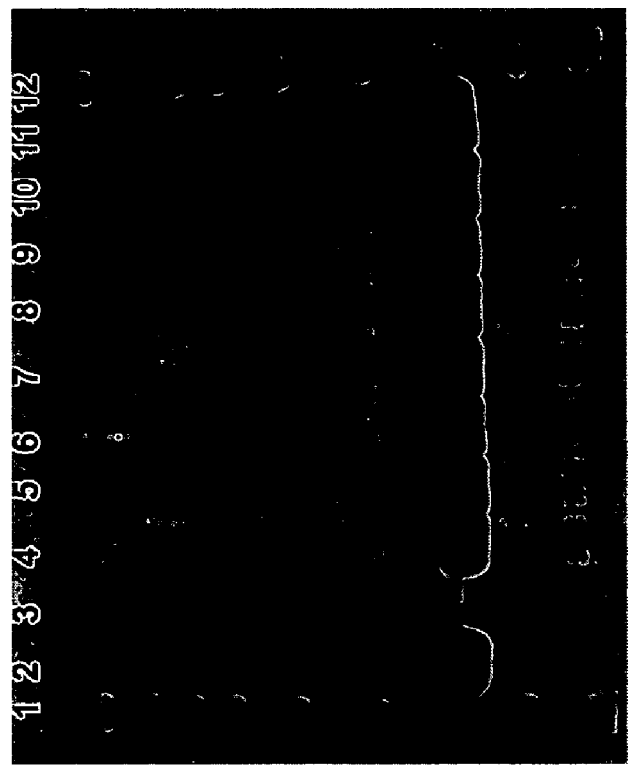
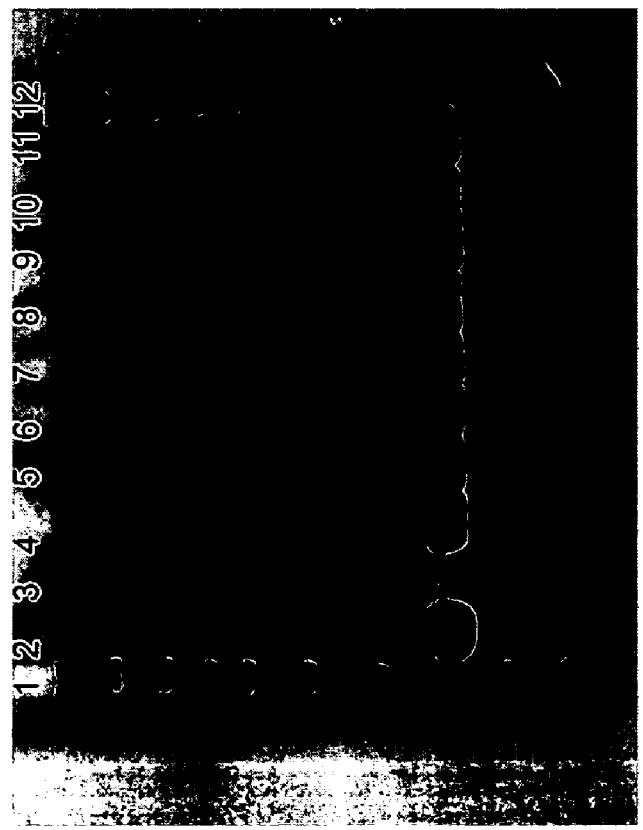
Figure 2 cont.

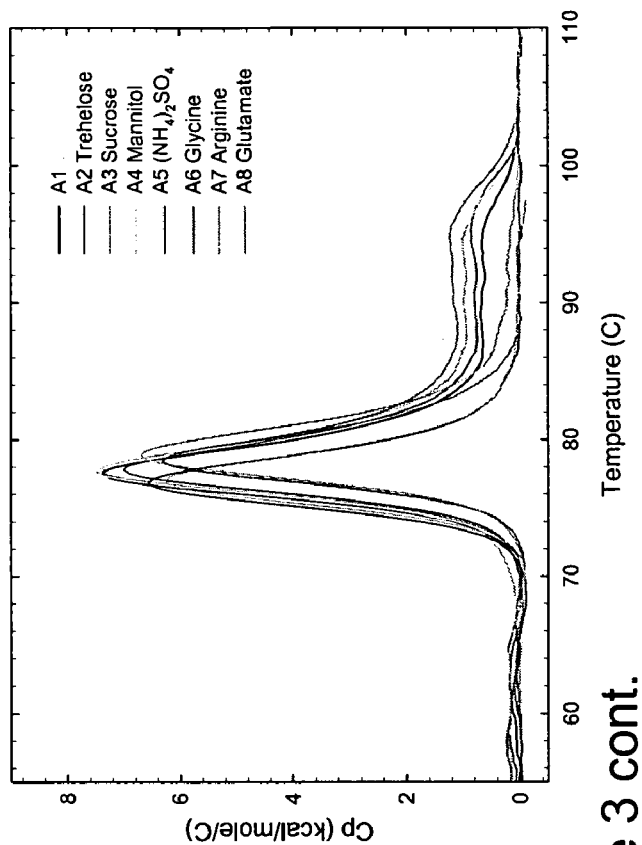
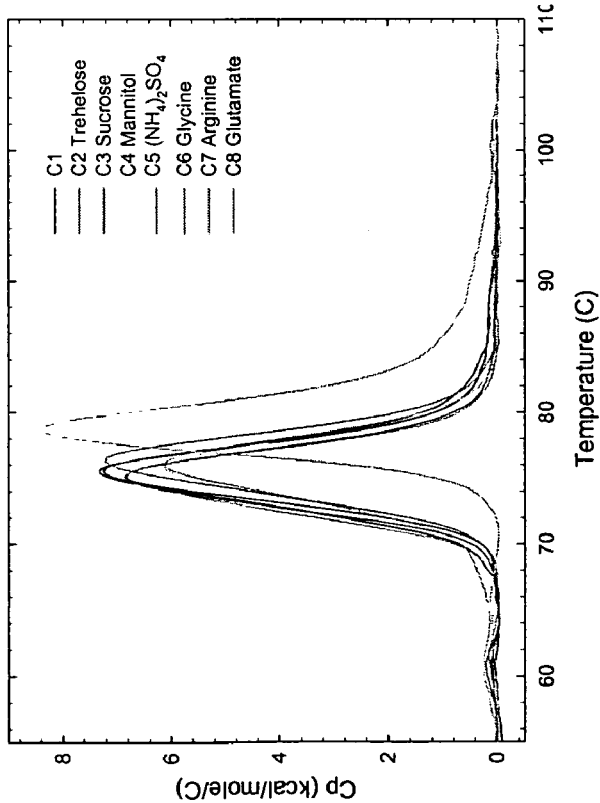
Figure 3 cont.

| | | A 20 mM Sodium Acetate pH 4.5 | | B 20 mM Sodium Citrate pH 6.0 | | C 50 mM Histidine pH 6.5 | | D 50 mM Sodium Phosphate pH 7.0 | | E 50 mM Sodium Bicarbonate pH 7.3 | | F 50 mM HEPES pH 7.5 | |
|---|---|---|---|---|---|---|---|---|---|---|---|---|---|
| | | $T_m$ | $\Delta T_m$ | $T_m$ | $\Delta T_m$ | $T_m$ | $\Delta T_m$ | $T_m$ | $\Delta T_m$ | $T_m$ | $\Delta T_m$ | $T_m$ | $\Delta T_m$ |
| 1 | No additions | 72.06 | 0 | 77.47 | 0 | 75.45 | 0 | 77.45 | 0 | 80.78 | 0 | 79.29 | 0 |
| 2 | 15 mM Trehalose | 71.67 | -0.39 | 77.48 | +0.01 | 75.2 | -0.25 | 77.77 | +0.32 | 81.21 | +0.43 | 80.02 | +0.73 |
| 3 | 15 mM Sucrose | 71.79 | -0.27 | 77.31 | -0.16 | 75.25 | -0.2 | 77.67 | +0.22 | 81.59 | +0.81 | 80.32 | +1.03 |
| 4 | 15 mM Mannitol | 72.08 | +0.02 | 77.25 | -0.22 | 75.8 | +0.35 | 77.69 | +0.24 | 81.46 | +0.68 | 80.05 | +0.76 |
| 5 | 150 mM $(NH_4)SO_4$* | 67.61 | -4.45 | 76.6 | -0.87 | 75.62 | +0.17 | 76.9 | -0.55 | 77.09 | -3.69 | 77.53 | -1.76 |
| 6 | 250 mM Glycine | 73.18 | +1.12 | 78.09 | +0.62 | 76.34 | +0.89 | 78.62 | +1.17 | 80.71 | -0.07 | 80.9 | +1.61 |
| 7 | 250 mM Arginine | 71.47 | -0.59 | 79.32 | +1.85 | 78.73 | +3.28 | 79.04 | +1.59 | 79.15 | -1.63 | 79.22 | -0.07 |
| 8 | 250 mM Glutamate | 71.36 | -0.7 | 76.95 | -0.52 | 76.07 | +0.62 | 76.97 | -0.48 | 77.14 | -3.64 | 77.71 | -1.58 |

Figure 5

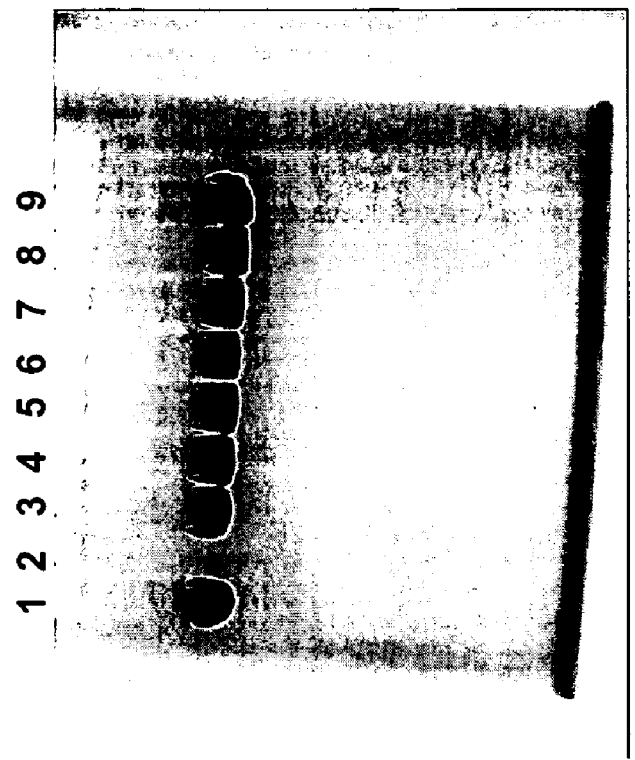
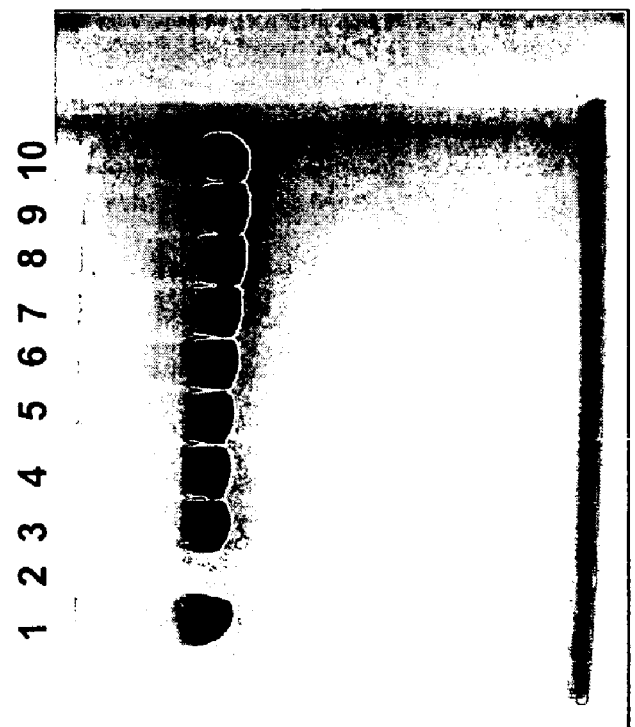
Figure 29

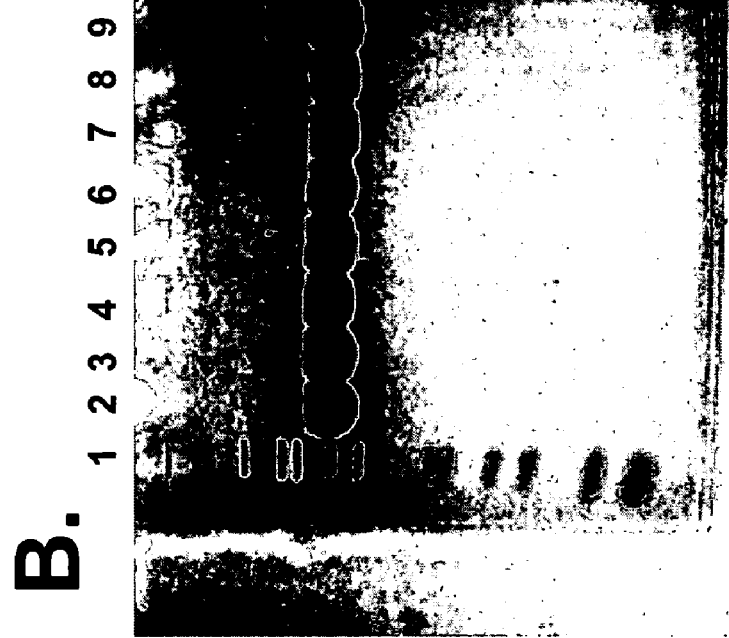
Figure 37

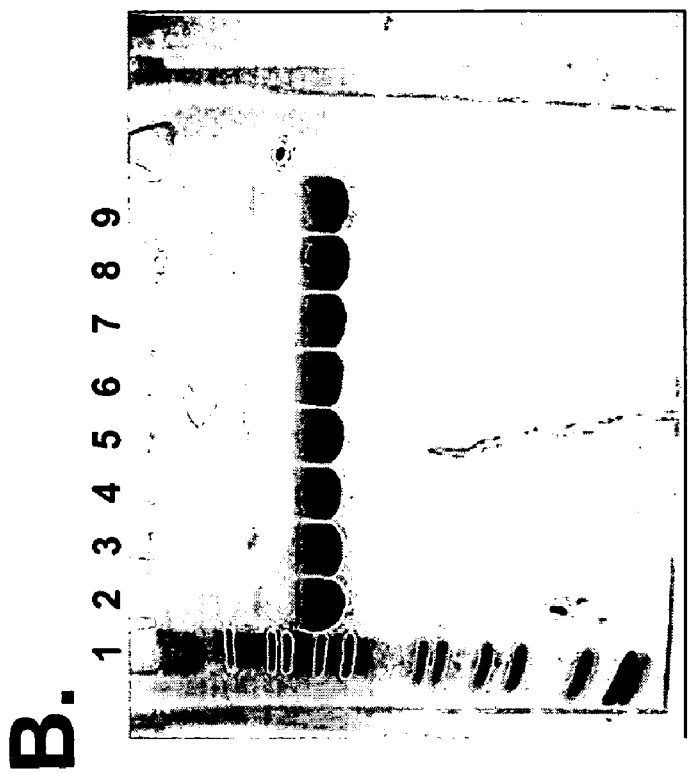
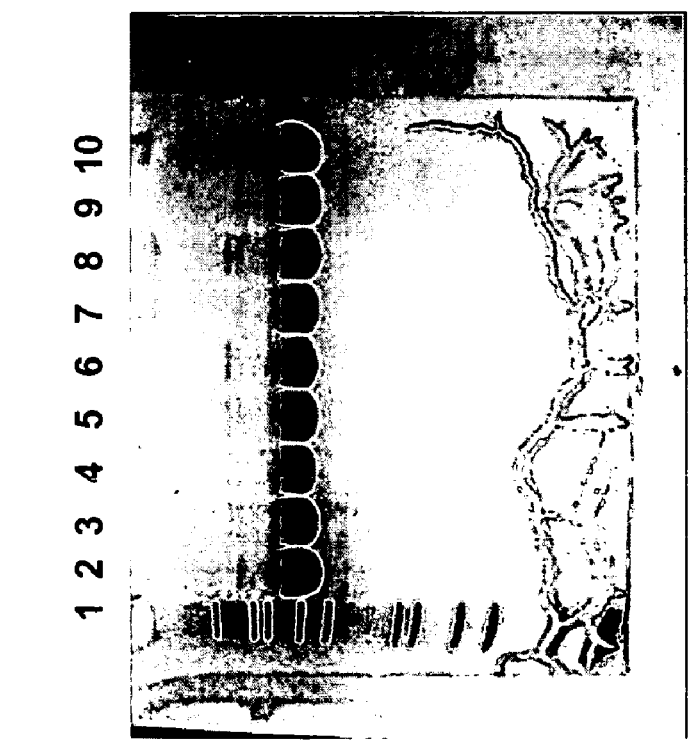
Figure 39

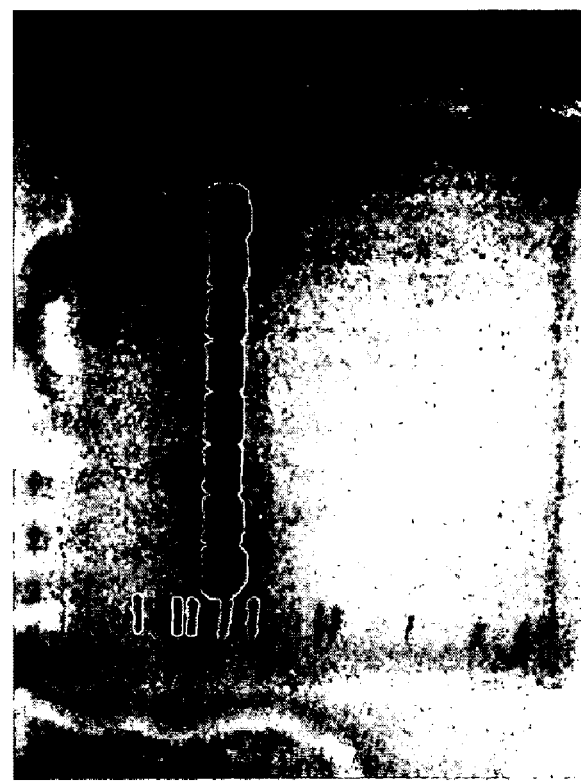
Figure 50

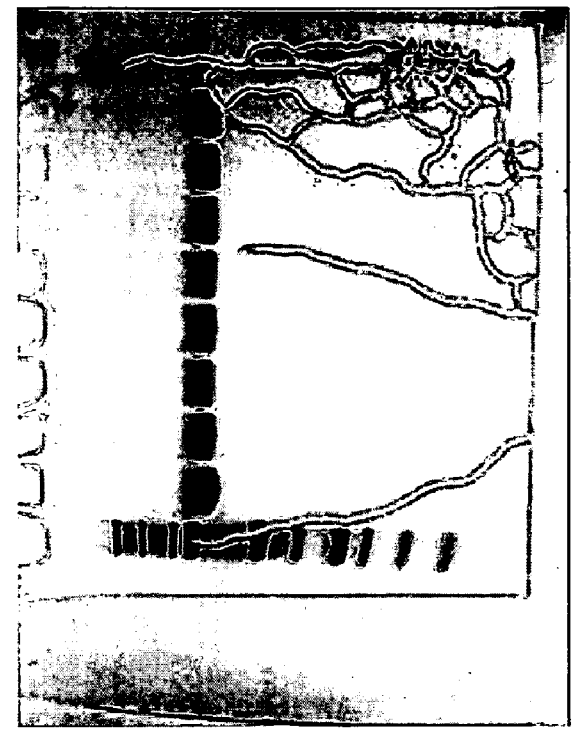
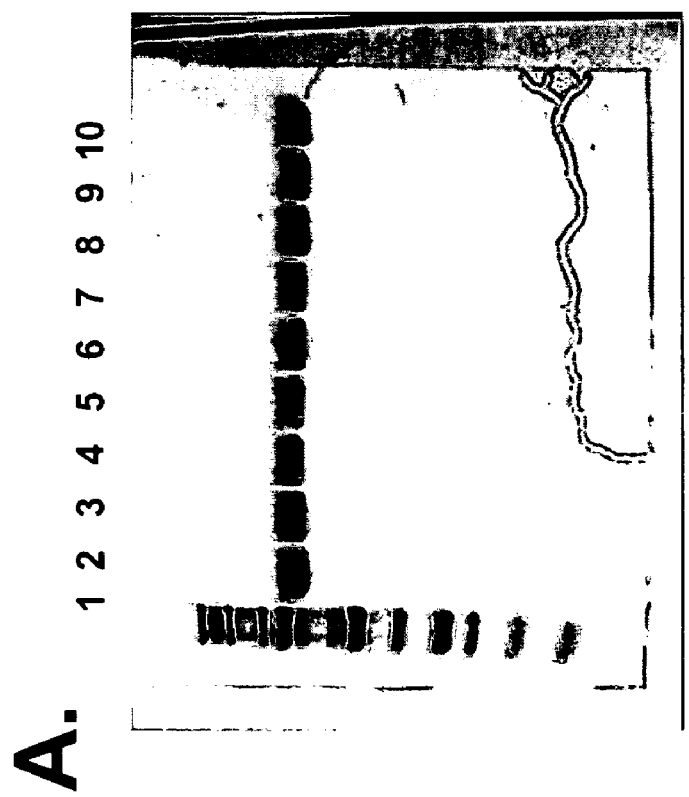
Figure 52

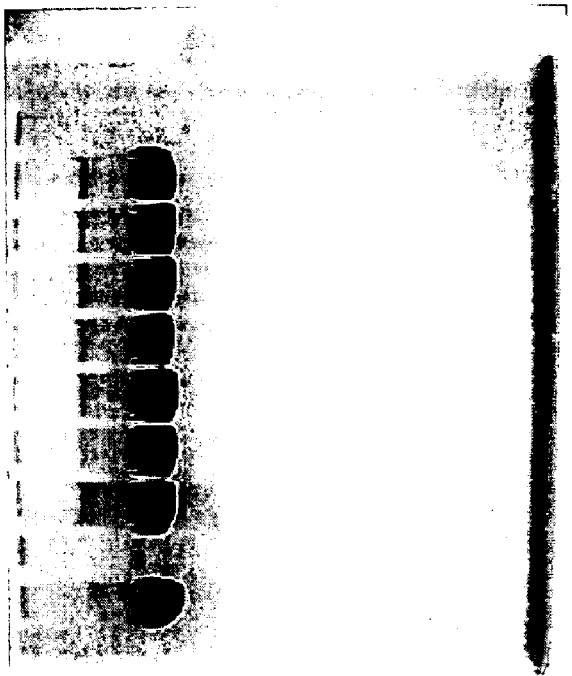
Figure 53

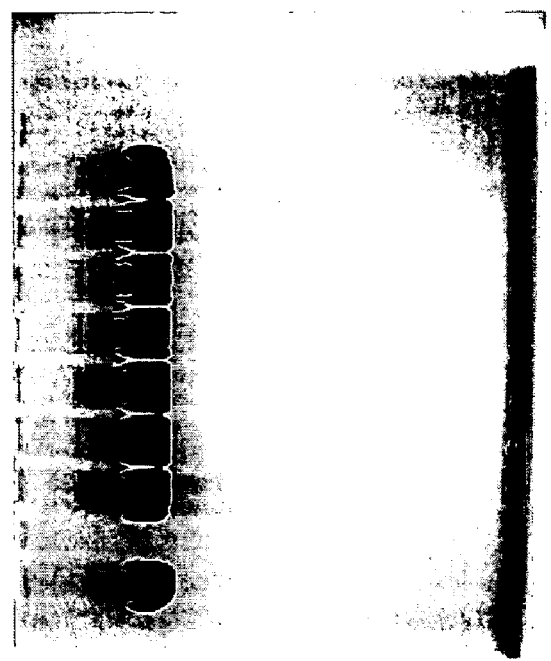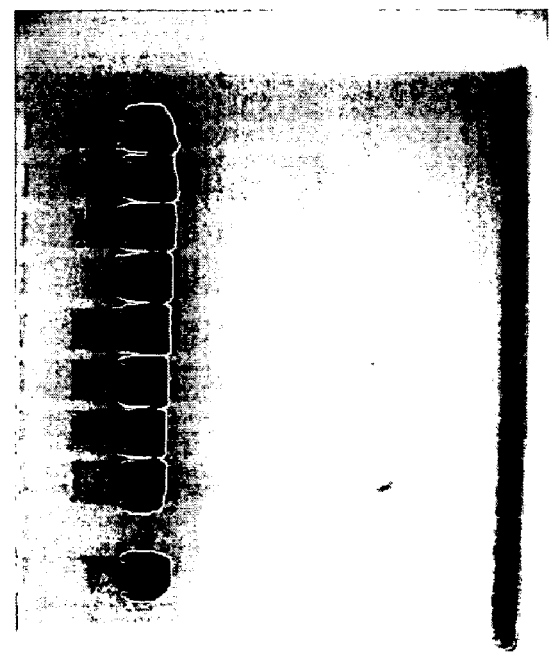
Figure 54

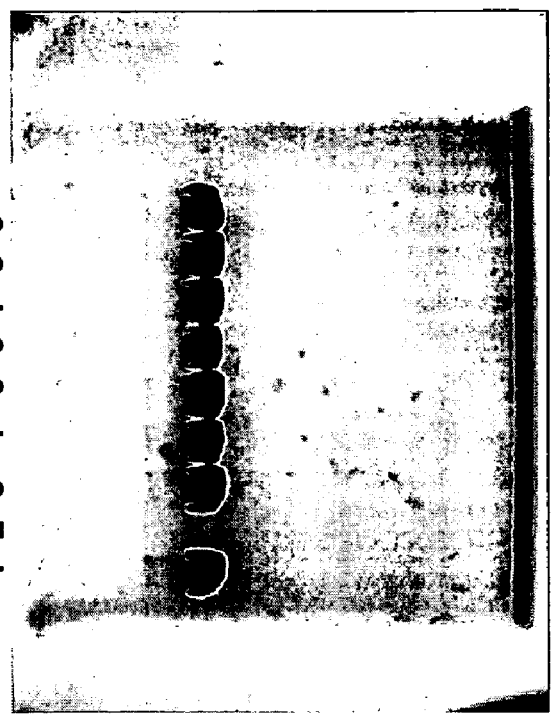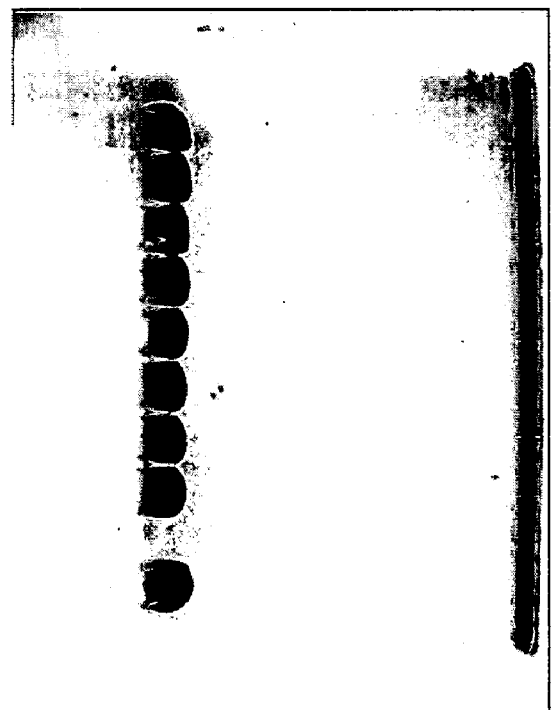
Figure 61

FORMULATIONS OF HUMAN GROWTH HORMONE COMPRISING A NON-NATURALLY ENCODED AMINO ACID AT POSITION 35

CROSS-REFERENCE TO RELATED APPLICATIONS

This application claims priority to U.S. provisional patent application Ser. No. 60/638,616 filed Dec. 22, 2004, U.S. provisional patent application Ser. No. 60/680,617, filed May 13, 2005, and U.S. provisional patent application entitled 60/728,035, filed Oct. 17, 2005, the specifications of which are incorporated herein in their entirety.

FIELD OF THE INVENTION

This invention relates to stabilized human growth hormone (hGH) formulations of hGH polypeptide comprising a non-natural amino acid covalently linked to poly(ethylene glycol) (PEG).

BACKGROUND OF THE INVENTION

Human growth hormone participates in much of the regulation of normal human growth and development. This naturally-occurring single-chain pituitary hormone consists of 191 amino acid residues and has a molecular weight of approximately 22 kDa. hGH exhibits a multitude of biological effects, including linear growth (somatogenesis), lactation, activation of macrophages, and insulin-like and diabetogenic effects, among others (Chawla, R., et al., *Ann. Rev. Med.* 34:519-547 (1983); Isaksson, O., et al., *Ann. Rev. Physiol.,* 47:483-499 (1985); Hughes, J. and Friesen, H., *Ann. Rev. Physiol.,* 47:469-482 (1985)).

The structure of hGH is well known (Goeddel, D., et al., *Nature* 281:544-548 (1979)), and the three-dimensional structure of hGH has been solved by X-ray crystallography (de Vos, A., et al., *Science* 255:306-312 (1992)). The protein has a compact globular structure, comprising four amphipathic alpha helical bundles, termed A-D beginning from the N-terminus, which are joined by loops. Further discussion of hGH including its receptor and variants, and other GH superfamily members is provided in U.S. patent application Ser. No. 11/046,432 entitled "Modifed Human Growth Hormone Polypeptides and Their Uses" and PCT International Patent Application No. PCT/US05/03537 entitled "Modified Human Four Helical Bundle Polypeptides and Their Uses," which are incorporated by reference in their entirety.

Recombinant hGH is used as a therapeutic and has been approved for the treatment of a number of indications. hGH deficiency leads to dwarfism, for example, which has been successfully treated for more than a decade by exogenous administration of the hormone. In addition to hGH deficiency, hGH has also been approved for the treatment of renal failure (in children), Turner's Syndrome, and cachexia in AIDS patients. Recently, the Food and Drug Administration (FDA) has approved hGH for the treatment of non-GH-dependent short stature. hGH is also currently under investigation for the treatment of aging, frailty in the elderly, short bowel syndrome, and congestive heart failure. Target populations for hGH treatment include children with idiopathic short stature (ISS) and adults with GHD-like symptoms.

Recombinant hGH is currently sold as a daily injectable product, with five major products currently on the market: Humatrope™ (Eli Lilly & Co.), Nutropin™ (Genentech), Norditropin™ (Novo-Nordisk), Genotropin™ (Pfizer) and Saizen/Serostim™ (Serono). A significant challenge to using growth hormone as a therapeutic, however, is that the protein has a short in vivo half-life and, therefore, it must be administered by daily subcutaneous injection for maximum effectiveness (MacGillivray, et al., *J. Clin. Endocrinol. Metab.* 81: 1806-1809 (1996)). Considerable effort is focused on means to improve the administration of hGH agonists and antagonists, by lowering the cost of production, making administration easier for the patient, improving efficacy and safety profile, and creating other properties that would provide competitive advantages. For example, Genentech and Alkermes formerly marketed Nutropin Depot™, a depot formulation of hGH, for pediatric growth hormone deficiency. While the depot permits less frequent administration (once every 2-3 weeks rather than once daily), it is also associated with undesirable side effects, such as decreased bioavailability and pain at the injection site and was withdrawn from the market in 2004. Another product, Pegvisomant™ (Pfizer), has also recently been approved by the FDA. Pegvisomant™ is a genetically-engineered analogue of hGH that functions as a highly selective growth hormone receptor antagonist indicated for the treatment of acromegaly (van der Lely, et al., *The Lancet* 358: 1754-1759 (2001). Although several of the amino acid side chain residues in Pegvisomant™ are derivatized with polyethylene glycol (PEG) polymers, the product is still administered once-daily, indicating that the pharmaceutical properties are not optimal. In addition to PEGylation and depot formulations, other administration routes, including inhaled and oral dosage forms of hGH, are under early-stage pre-clinical and clinical development and none have yet received approval from the FDA. Accordingly, there is a need for a polypeptide that exhibits growth hormone activity but that also provides a longer serum half-life and, therefore, more optimal therapeutic levels of hGH and an increased therapeutic half-life.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-

11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *Chem Bio Chem* 3(11):1135-1137; J. W. Chin, et al., (2002), *PNAS United States of America* 99:11020-11024; and, L. Wang, & P. G. Schultz, (2002), *Chem. Comm.*, 1:1-11. All references are incorporated by reference in their entirety. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc.

Human growth hormone formulations may be lyophilized preparations requiring reconstitution or aqueous formulations. Per vial, Protropin™ hGH consists of 5 mg hGH, 40 mg mannitol, 0.1 mg monobasic sodium phosphate, 1.6 mg dibasic sodium phosphate, reconstituted to pH 7.8 (Physician's Desk Reference, Medical Economics Co., Orawell, N.J., p. 1049, 1992). Per vial, Humatrope™ hGH consists of 5 mg hGH, 25 mg mannitol, 5 mg glycine, 1.13 mg dibasic sodium phosphate, reconstituted to pH 7.5 (Physician's Desk Reference, p. 1266, 1992). Examples of aqueous human growth hormone formulations are described in U.S. Pat. Nos. 5,763, 394; 5,981,485; 6,448,225; and U.S. Patent Publication No. 2003/0013653, each of which are incorporated by reference herein.

For a general review for growth hormone formulations, see Pearlman et al., Current Communications in Molecular Biology, eds. D. Marshak and D. Liu, pp. 23-30, Cold Spring Harbor Laboratory Press, Cold Spring Harbor, N.Y., 1989, which is incorporated by reference herein. Other publications of interest regarding stabilization of proteins are as follows.

U.S. Pat. No. 4,297,344, which is incorporated by reference herein, discloses stabilization of coagulation factors II and VIII, antithrombin III, and plasminogen against heat by adding selected amino acids such as glycine, alanine, hydroxyproline, glutamine, and aminobutyric acid, and a carbohydrate such as a monosaccharide, an oligosaccharide, or a sugar alcohol.

U.S. Pat. No. 4,783,441, which is incorporated by reference herein, discloses a method for the prevention of denaturation of proteins such as insulin in aqueous solution at interfaces by the addition of up to 500 ppm surface-active substances comprising a chain of alternating, weakly hydrophilic and weakly hydrophobic zones at pH 6.8-8.0.

U.S. Pat. No. 4,812,557, which is incorporated by reference herein, discloses a method of stabilization of interleukin-2 using human serum albumin.

European Patent Application Publication No. 0 303 746, which is incorporated by reference herein, discloses stabilization of growth promoting hormones with polyols consisting of non-reducing sugars, sugar alcohols, sugar acids, pentaerythritol, lactose, water-soluble dextrans, and Ficoll, amino acids, polymers of amino acids having a charged side group at physiological pH, and choline salts.

European Patent Application Publication No. 0 211 601, which is incorporated by reference herein, discloses the stabilization of growth promoting hormones in a gel matrix formed by a block copolymer containing polyoxyethylene-polyoxypropylene units and having an average molecular weight of about 1,100 to about 40,000.

European Patent Application Publication No. 0 193 917, which is incorporated by reference herein, discloses a biologically active composition for slow release characterized by a water solution of a complex between a protein and a carbohydrate.

International Patent Publication No. WO 89/09614 and Australian patent application No. 30771/89, which are incorporated by reference herein, disclose a stable pharmaceutical formulation containing human growth hormone, glycine, and mannitol. Such a preparation shows improved stability during normal processing and storage in a lyophilized state as well as in the period of use after the reconstitution.

U.S. Pat. No. 5,096,885, which is incorporated by reference herein, discloses a formulation of hGH for lyophilization containing glycine, mannitol, a non-ionic surfactant, and a buffer.

U.S. Pat. No. 4,876,568, which is incorporated by reference herein, discloses that animal growth hormone may be stabilized with various stabilizers to give decreased formation of insolubles and preservation of the soluble activity in aqueous environments. Such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethyl-glycine, aspartic acid or salts thereof, glutamic acid or salts thereof; a polymer of an amino acid having a charged side group at physiological pH may be selected from polylysine, polyaspartic acid, polyglutamic acid, polyarginine, polyhistidine, polyornithine and salts thereof, and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate. U.S. Pat. No. 4,876,568, which is incorporated by reference herein, notes that polyhistidine can be used as a potential stabilizer for animal growth hormone but there is no indication whether it stabilizes an animal growth hormone or human growth hormone. Furthermore, U.S. Pat. No. 4,876,568 mentions that poly-DL-lysine HBr is preferred.

EP 374120, which is incorporated by reference herein, discloses a stabilized preparation of growth hormone comprising a buffered polyol excipient comprising a polyol having three hydroxy groups and a buffer to achieve a pH in a range in which the growth hormone retains its bioactivity for a sufficient period of time. Histidine is mentioned as a buffer for a polyol having three hydroxy groups. Specifically, EP 374120 teaches that histidine hydrochloride may be used as a buffer for buffering a polyol having three hydroxy groups for improving the stability of a growth hormone preparation in the form of a solution comprising a high concentration of growth hormone and a polyol as stabilizer. Furthermore, histidine hydrochloride must be added in an amount of about 3% by weight of the solution corresponding to a concentration of ~0.15M solution of histidine hydrochloride. EP 374120 also teaches that histidine alone does not impart chemical and physical stability to a growth hormone preparation.

Sorensen et al., WO 93/12812, which is incorporated by reference herein, teaches that growth hormone can be stabilized by the presence of histidine or a histidine derivative. If the growth hormone is lyophilized, the composition can also comprise a bulking agent, i.e. sugar alcohols, disaccharides, and mixtures thereof. Sorensen et al., U.S. Pat. No. 5,849,704, which is incorporated by reference herein, discloses a pharmaceutical formulation comprising a growth hormone and histidine or a derivative of histidine as an additive or buffering substance added to provide stability against deamidation, oxidation or cleavage of the peptide bonds in the growth hormone. Also disclosed is that crystallization of growth hormone in the presence of histidine or a derivative thereof gives rise to a higher yield of crystals having higher purity than known methods. Formulations of human growth hormone variants have been described in U.S. Pat. Nos. 6,136,563 and 5,849,535, which are incorporated by reference herein.

hGH undergoes breakdown via several degradative pathways, including deamidation, aggregation, clipping of the peptide backbone, and oxidation of methionine residues. Additional products result from degradation of conjugates of hGH covalently attached to a water soluble polymer such PEG. A pharmaceutical formulation of hGH that provides acceptable control of degradation products, has maintained stability of hGH over a prolonged period of time, and is stable to vigorous agitation (which induces aggregation) would be particularly advantageous.

BRIEF SUMMARY OF THE INVENTION

This invention provides formulations of hGH polypeptides comprising one or more non-naturally encoded amino acids.

In some embodiments, the hGH polypeptide comprises one or more post-translational modifications. In some embodiments, the hGH polypeptide is linked to a linker, polymer, or biologically active molecule. In some embodiments, the hGH polypeptide is linked to a bifunctional polymer, bifunctional linker, or at least one additional hGH polypeptide.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or bonded to a water soluble polymer. In some embodiments, the water soluble polymer comprises a poly(ethylene glycol) moiety. In some embodiments, the invention is a single-dose lyophilized formulation of hGH polypeptide. In some embodiments, the invention is a liquid formulation of hGH polypeptide.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In one embodiment, the pharmaceutical formulation of hGH polypeptide comprising one or more non-naturally encoded amino acids comprises a buffer, at least one a carrier, excipient, or stabilizer, and a pharmaceutical quantity of human growth hormone (hGH).

In another embodiment, the at least one a carrier, excipient, or stabilizer is selected from the group consisting of an antioxidant, an amino acid, a carbohydrate, a chelating agent, a sugar alcohol, a salt-forming counter ion, and a non-ionic surfactant. The present invention also provides methods of treating a patient having a disorder modulated by hGH with an effective amount of the formulation of a hGH molecule of the present invention.

In one embodiment of the present invention, formulations of hGH polypeptide comprising a non-naturally encoded amino acid that minimize formation of undesirable aggregated species or cause chemical changes that reduce biological activity or alter receptor recognition are provided. Such formulations are capable of maintaining activity for appropriate storage times, are readily formulated, and are acceptable for administration to patients.

In one embodiment, the formulation of hGH polypeptide, including but not limited to PEGylated hGH, comprising one or more non-naturally encoded amino acids is a lyophilized formulation that is reconstituted prior to use for subcutaneous injection. The formulations of the present invention may be pharmaceutical formulations, in particular, formulations for subcutaneous administration.

In another embodiment, the invention provides a method for the treatment, prophylactic or therapeutic, of a disorder treatable by the protein formulated, including but not limited to, PEGylated hGH, using the formulations disclosed herein. Such formulations are particularly useful for subcutaneous administration.

Also provided is an article of manufacture comprising a container enclosing a formulation disclosed herein, as well as pre-filled syringes.

BRIEF DESCRIPTION OF THE DRAWINGS

FIG. 1 shows the pH stability analysis of formulation buffers after six weeks at 4° C.

FIG. 5 provides a table summarizing the DSC melting temperatures and changes to $T_m$ for the full matrix.

FIG. 29 shows an SDS-PAGE analysis (non-reduced) of samples stored at 4° C. for 4 weeks. For FIG. 29, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 29, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 37 shows an SDS-PAGE analysis (non-reduced) of samples stored at 25° C. for 1 week. For FIG. 37, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 37, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 39 shows an SDS-PAGE analysis (non-reduced) of samples stored at 25° C. for 2 weeks. For FIG. 39, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 39, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 50 shows an SDS-PAGE analysis (reduced) of samples stored at 40° C. for 1 week. For FIG. 50, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 50, panel B. Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 52 shows an SDS-PAGE analysis (reduced) of samples stored at 40° C. for 2 weeks. For FIG. 52, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 52, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 53 shows an SDS-PAGE analysis (non-reduced) of samples stored at 40° C. for 4 weeks. For FIG. 53, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 53, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 54 shows an SDS-PAGE analysis (reduced) of samples stored at 40° C. for 4 weeks. For FIG. 54, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 54, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

FIG. 61 shows an SDS-PAGE analysis (non-reduced) of control samples in a formulation study (agitation/UV controls). For FIG. 61, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 61, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.

Figure 70:
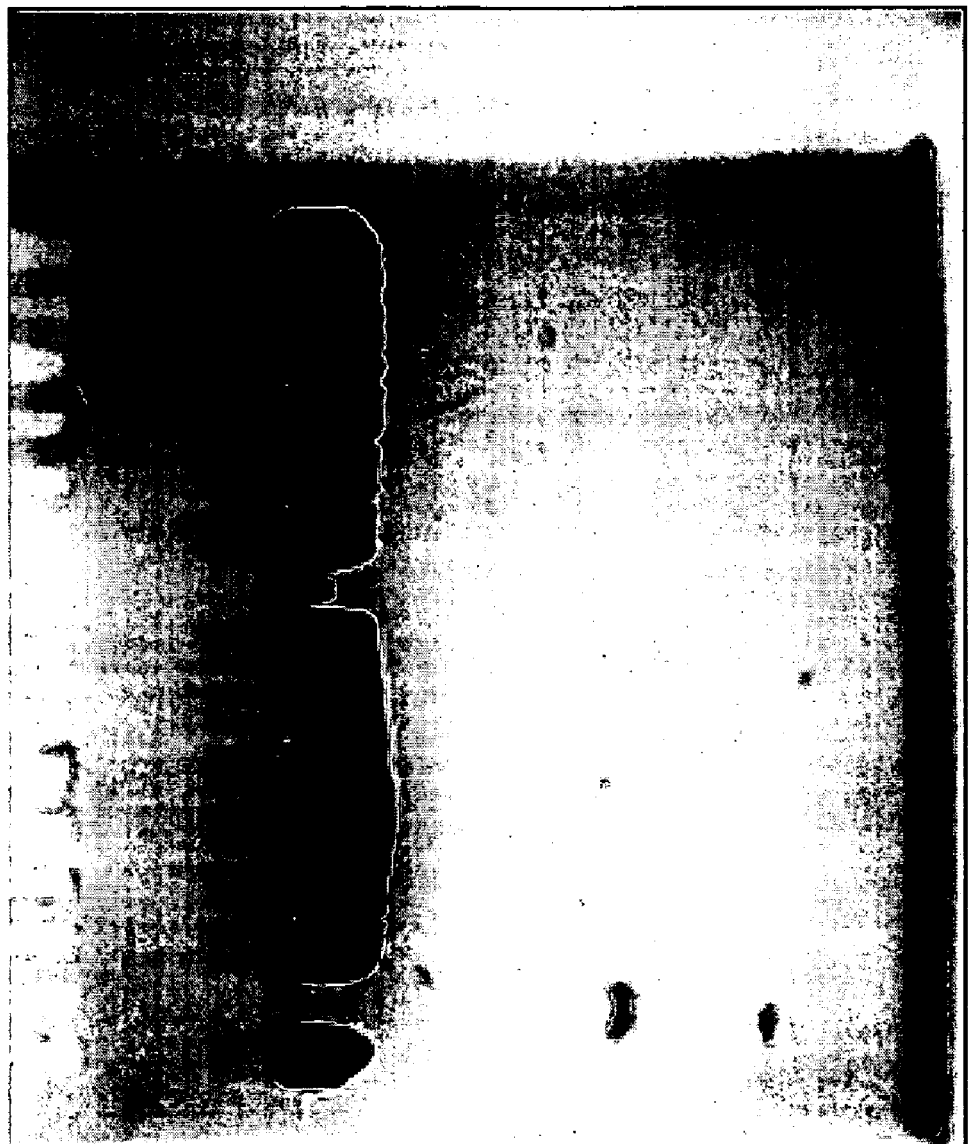

FIG. 70 shows an SDS-PAGE analysis (reduced) of samples that were subject to freeze/thaw conditions (H7MGT-P). Lane 1: PEG-hGH Standard; Lane 2: hGH (1 µg); Lane 3: H7MGT-P 8 mg/mL t=0; Lane 4: H7MGT-P 8 mg/mL F/T 1; Lane 5: H7MGT-P 8 mg/mL F/T 2; Lane 6: H7MGT-P 8 mg/mL F/T 3; Lane 7: H7MGT-P 8 mg/mL F/T 4; Lane 8: H7MGT-P 8 mg/mL F/T 5; Lane 10: H7MGT-P 14 mg/mL t=0; Lane 11: H7MGT-P 14 mg/mL F/T 1; Lane 12: H7MGT-P 14 mg/mL F/T 2; Lane 13: H7MGT-P 14 mg/mL F/T 3; Lane 14: H7MGT-P 14 mg/mL F/T 4; Lane 15: H7MGT-P 14 mg/mL F/T 5.

Figure 71:
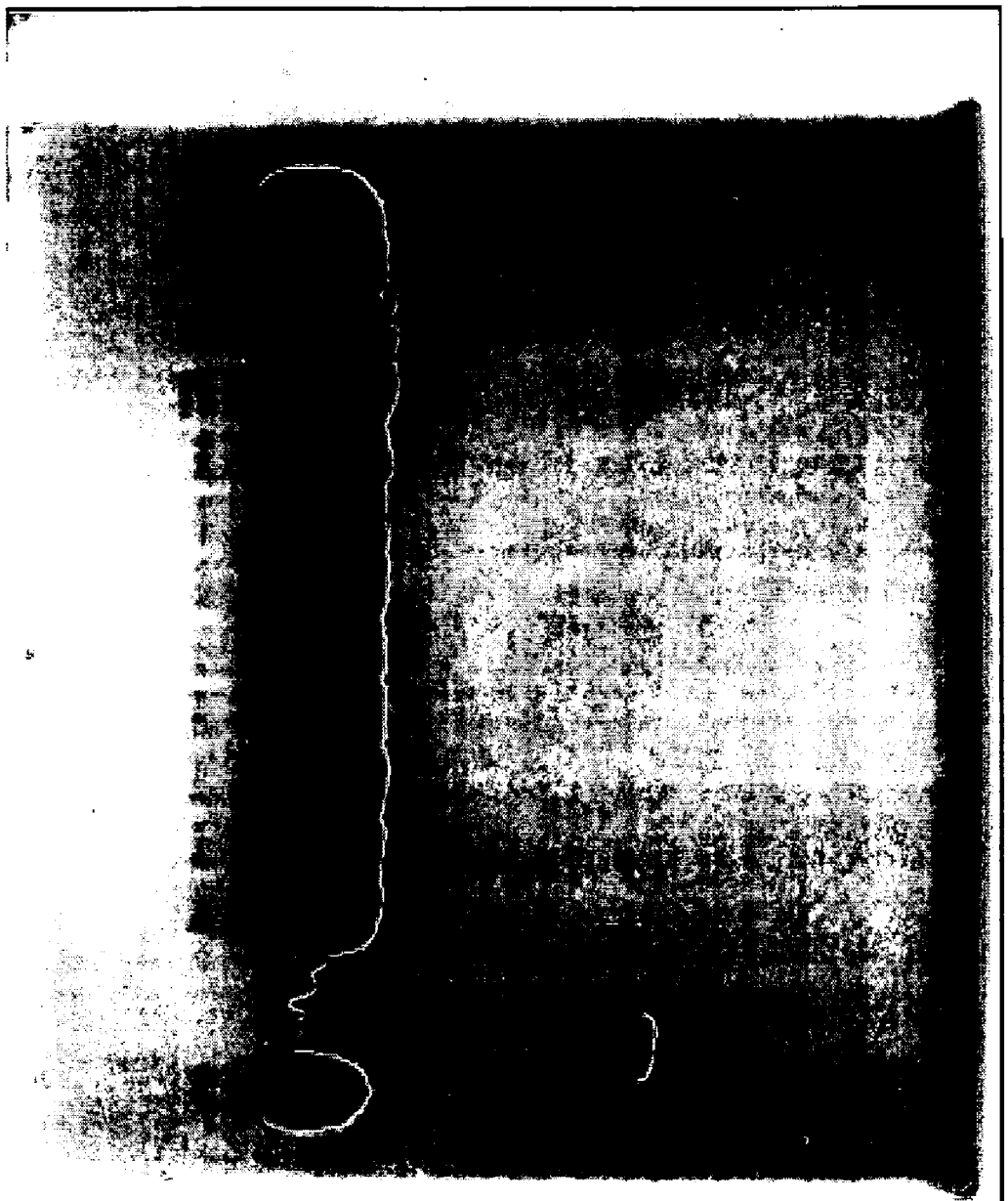

FIG. 71 shows an SDS-PAGE analysis (non-reduced) of control samples and samples that were subject to agitation for 6 hours and UV light for 4 hours. Lane 1: PEG-hGH Standard; Lane 2: hGH (1 µg); Lane 4: Vortex/UV Control H7MT-P 8 mg/mL; Lane 5: Vortex/UV Control H7MT-P 14 mg/mL; Lane 6: Vortex/UV Control H7MGT-P 8 mg/mL; Lane 7: Vortex/UV Control H7MGT-P 14 mg/mL; Lane 8: Vortex H7MT-P 8 mg/mL; Lane 9: Vortex H7MT-P 14 mg/mL; Lane 10: Vortex H7MGT-P 8 mg/mL; Lane 11: Vortex H7MGT-P 14 mg/mL; Lane 12: UV H7MT-P 8 mg/mL; Lane 13: UV H7MT-P 14 mg/mL; Lane 14: UV H7MGT-P 8 mg/mL; Lane 15: UV H7MGT-P 14mg/mL.

Figure 72:
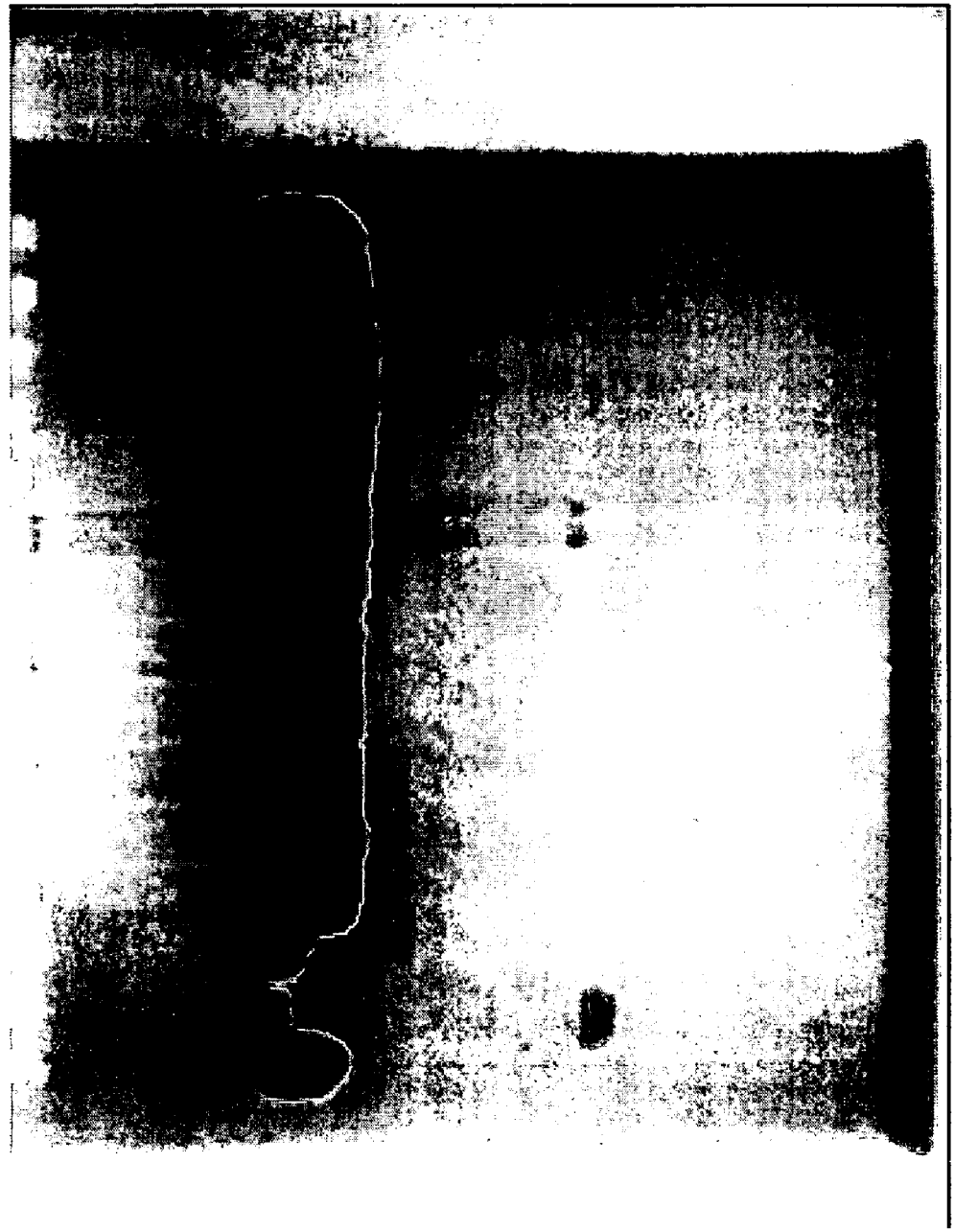

FIG. 72 shows an SDS-PAGE analysis (reduced) of control samples and samples that were subject to agitation for 6 hours and UV light for 4 hours. Lane 1: PEG-hGH Standard; Lane 2: hGH (1 µg); Lane 4: Vortex/UV Control H7MT-P 8 mg/mL; Lane 5: Vortex/UV Control H7MT-P 14 mg/mL; Lane 6: Vortex/UV Control H7MGT-P 8 mg/mL; Lane 7: Vortex/UV Control H7MGT-P 14 mg/mL; Lane 8: Vortex H7MT-P 8 mg/mL; Lane 9: Vortex H7MT-P 14 mg/mL; Lane 10: Vortex H7MGT-P 8 mg/mL* (contaminated); Lane 11: Vortex H7MGT-P 14 mg/mL; Lane 12: UV H7MT-P 8 mg/mL; Lane 13: UV H7MT-P 14 mg/mL; Lane 14: UV H7MGT-P 8 mg/mL; Lane 15: UV H7MGT-P 14mg/mL.

Figure 73:
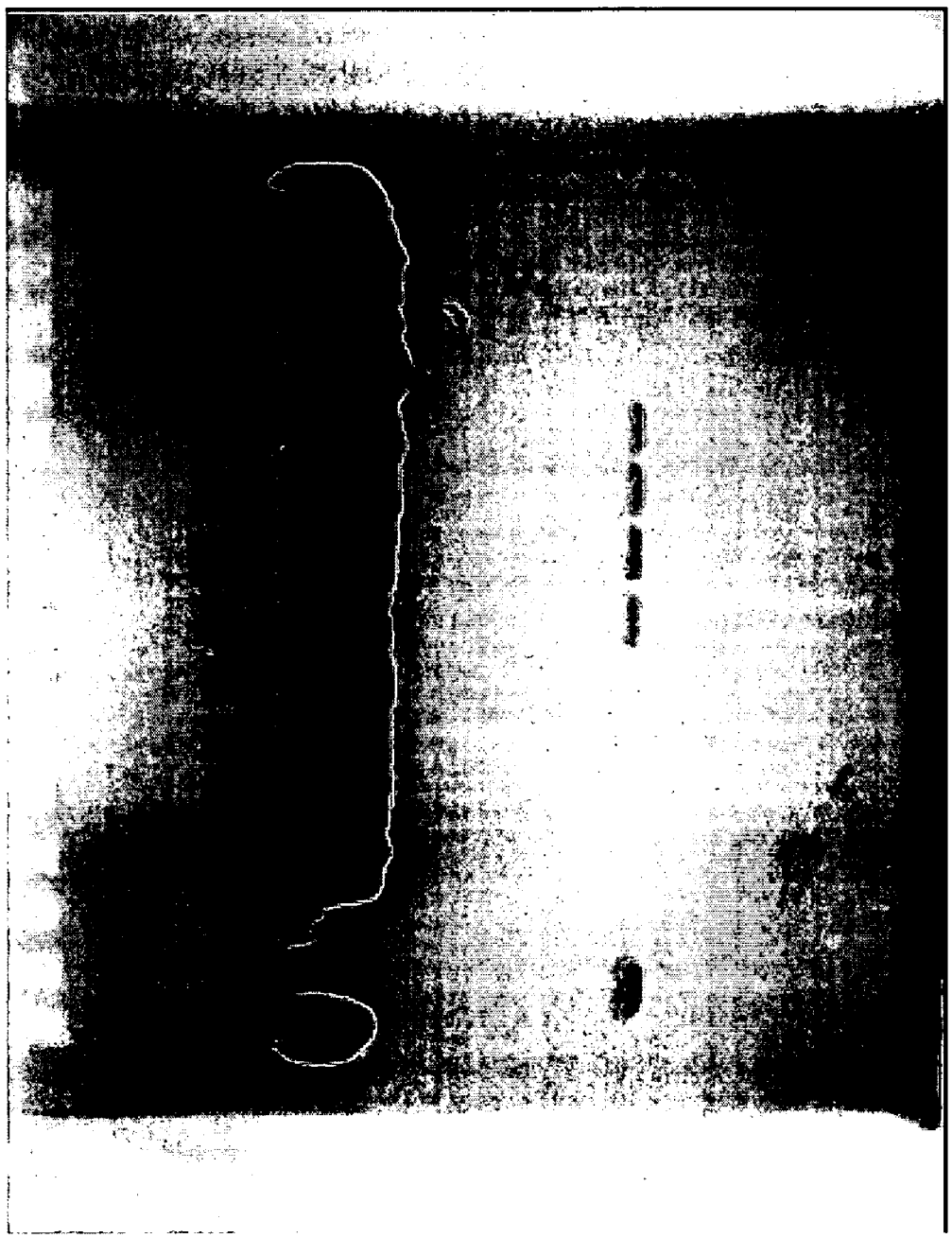

FIG. 73 shows an SDS-PAGE analysis (non-reduced) of samples stored at 4° C. or 40° C. for 1 week and samples that were exposed to thermal unfolding conditions. Lane 1: PEG-hGH Standard; Lane 2: hGH (1 µg); Lane 4: H7MT-P 8 mg/mL 4° C.; Lane 5: H7MT-P 14 mg/mL 4° C.; Lane 6: H7MGT-P 8 mg/mL 4° C.; Lane 7: H7MGT-P 14 mg/mL 4° C.; Lane 8: H7MT-P 8 mg/mL 40° C.; Lane 9: H7MT-P 14 mg/mL 40° C.; Lane 10: H7MGT-P 8 mg/mL 40° C.; Lane 11: H7MGT-P 14 mg/mL 40° C.; Lane 12: H7MT-P 8 mg/mL Thermal-unfolding; Lane 13: H7MT-P 14 mg/mL Thermal-unfolding; Lane 14: H7MGT-P 8 mg/mL Thermal-unfolding; Lane 15: H7MGT-P 14 mg/mL Thermal-unfolding.

Figure 74:
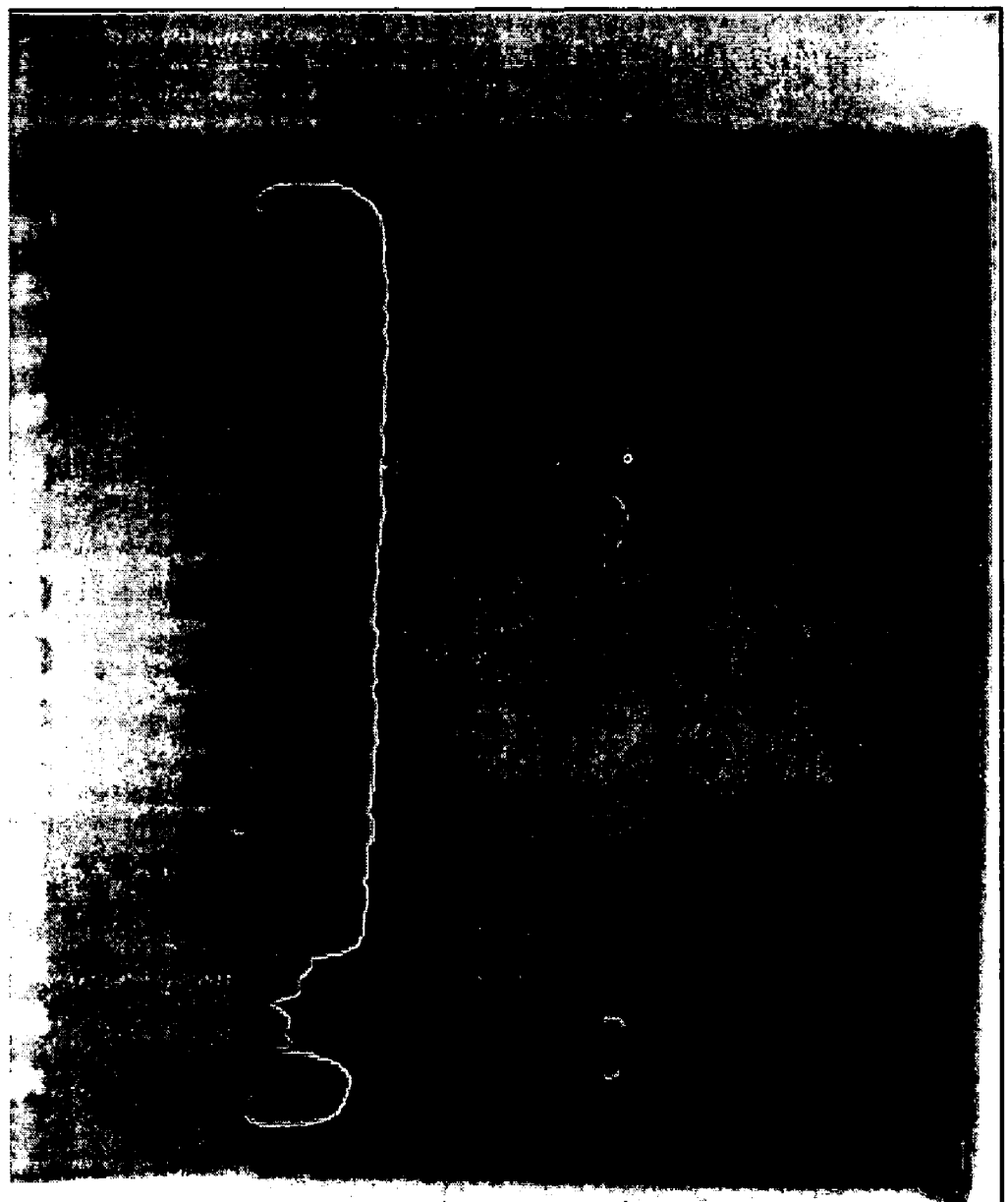

FIG. 74 shows an SDS-PAGE analysis (reduced) of samples stored at 4° C. or 40° C. for 1 week and samples that were exposed to thermal unfolding conditions. Lane 1: PEG-hGH Standard; Lane 2: hGH (1 µg); Lane 4: H7MT-P 8 mg/mL 4° C.; Lane 5: H7MT-P 14 mg/mL 4° C.; Lane 6: H7MGT-P 8 mg/mL 4° C.; Lane 7: H7MGT-P 14 mg/mL 4° C.; Lane 8: H7MT-P 8 mg/mL 40° C.; Lane 9: H7MT-P 14 mg/mL 40° C.; Lane 10: H7MGT-P 8 mg/mL 40° C.; Lane 11: H7MGT-P 14 mg/mL 40° C.; Lane 12: H7MT-P 8 mg/mL Thermal-unfolding; Lane 13: H7MT-P 14 mg/mL Thermal-unfolding; Lane 14: H7MGT-P 8 mg/mL Thermal-unfolding; Lane 15: H7MGT-P 14 mg/mL Thermal-unfolding.

Figure 75:
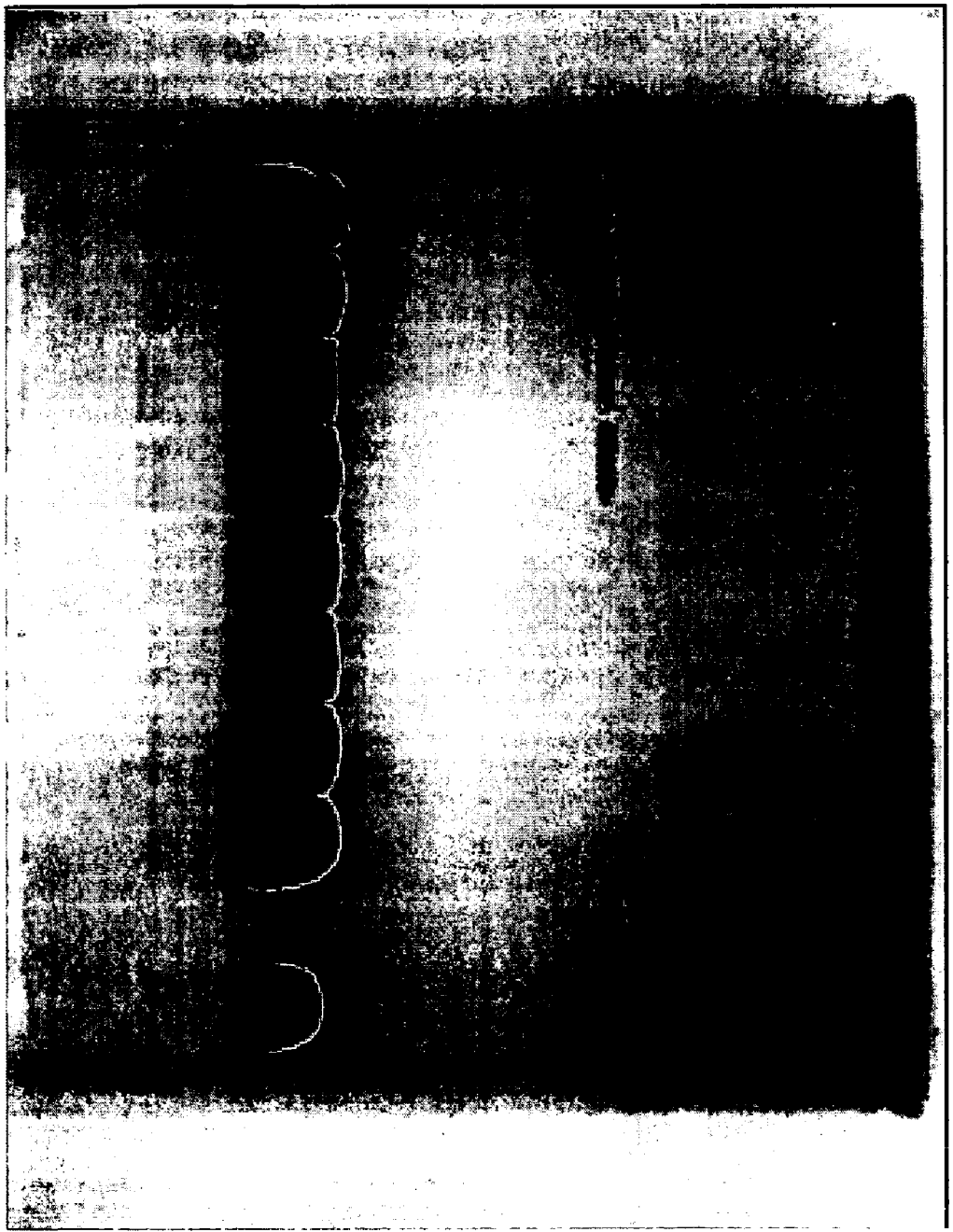

FIG. 75 shows an SDS-PAGE analysis (non-reduced) of samples stored at 4° C. or 40° C. for 2 weeks. Lane 1: PEG-hGH Standard; Lane 2: hGH (1 µg); Lane 3: H7MT-P 8 mg/mL 4° C.; Lane 4: H7MT-P 14 mg/mL 4° C.; Lane 5: H7MGT-P 8 mg/mL 4° C.; Lane 6: H7MGT-P 14 mg/mL 4° C.; Lane 7: H7MT-P 8 mg/mL 40° C.; Lane 8: H7MT-P 14 mg/mL 40° C.; Lane 9: H7MGT-P 8 mg/mL 40° C.; Lane 10: H7MGT-P 14 mg/mL 40° C.

Figure 76:
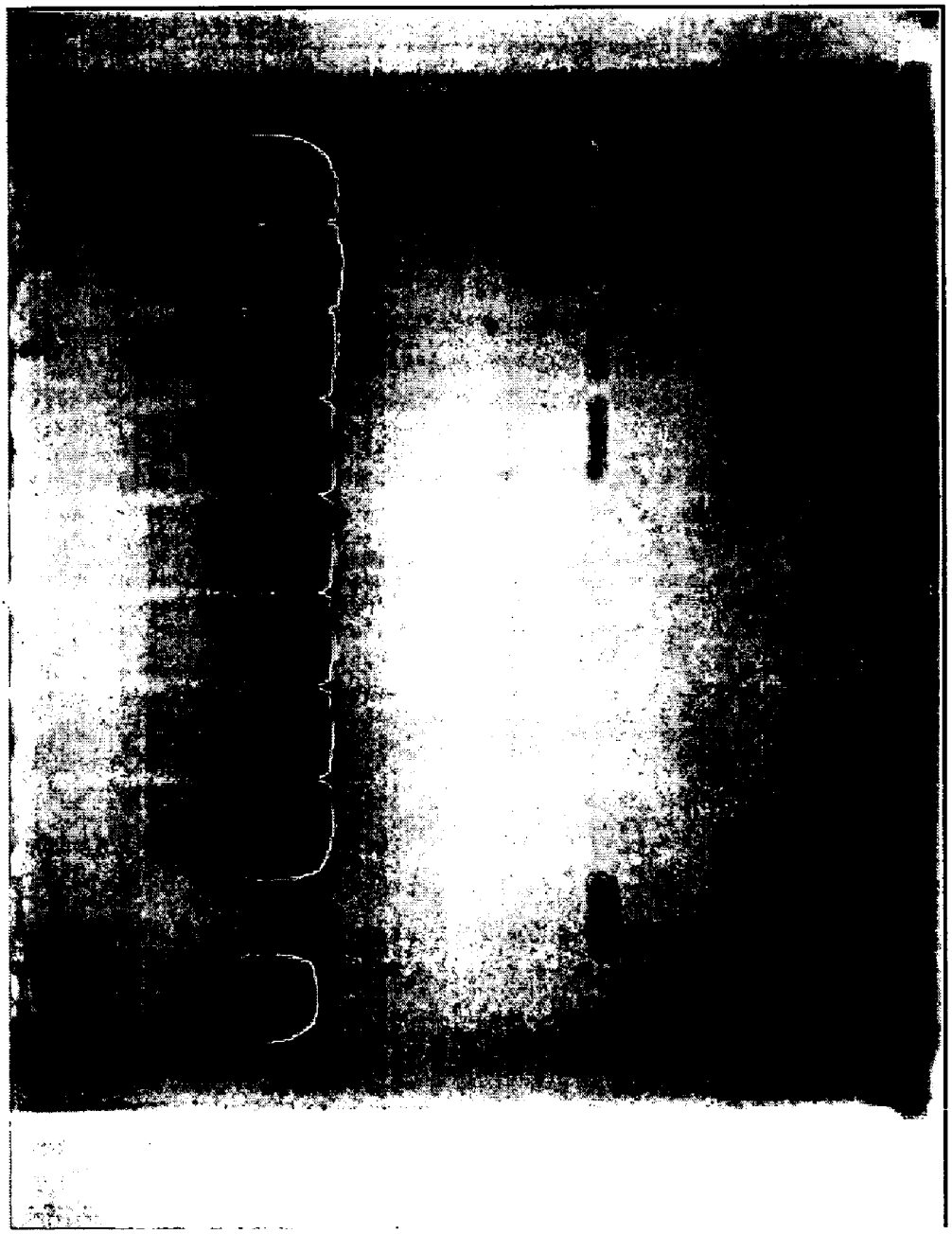

FIG. 76 shows an SDS-PAGE analysis (reduced) of samples stored at 4° C. or 40° C. for 2 weeks. Lane 1: PEG-hGH Standard; Lane 2: hGH (1 µg); Lane 3: H7MT-P 8 mg/mL 4° C.; Lane 4: H7MT-P 14 mg/mL 4° C.; Lane 5: H7MGT-P 8 mg/mL 4° C.; Lane 6: H7MGT-P 14 mg/mL 4° C.; Lane 7: H7MT-P 8 mg/mL 40° C.; Lane 8: H7MT-P 14 mg/mL 40° C.; Lane 9: H7MGT-P 8 mg/mL 40° C.; Lane 10: H7MGT-P 14 mg/mL 40° C.

Figure 77:
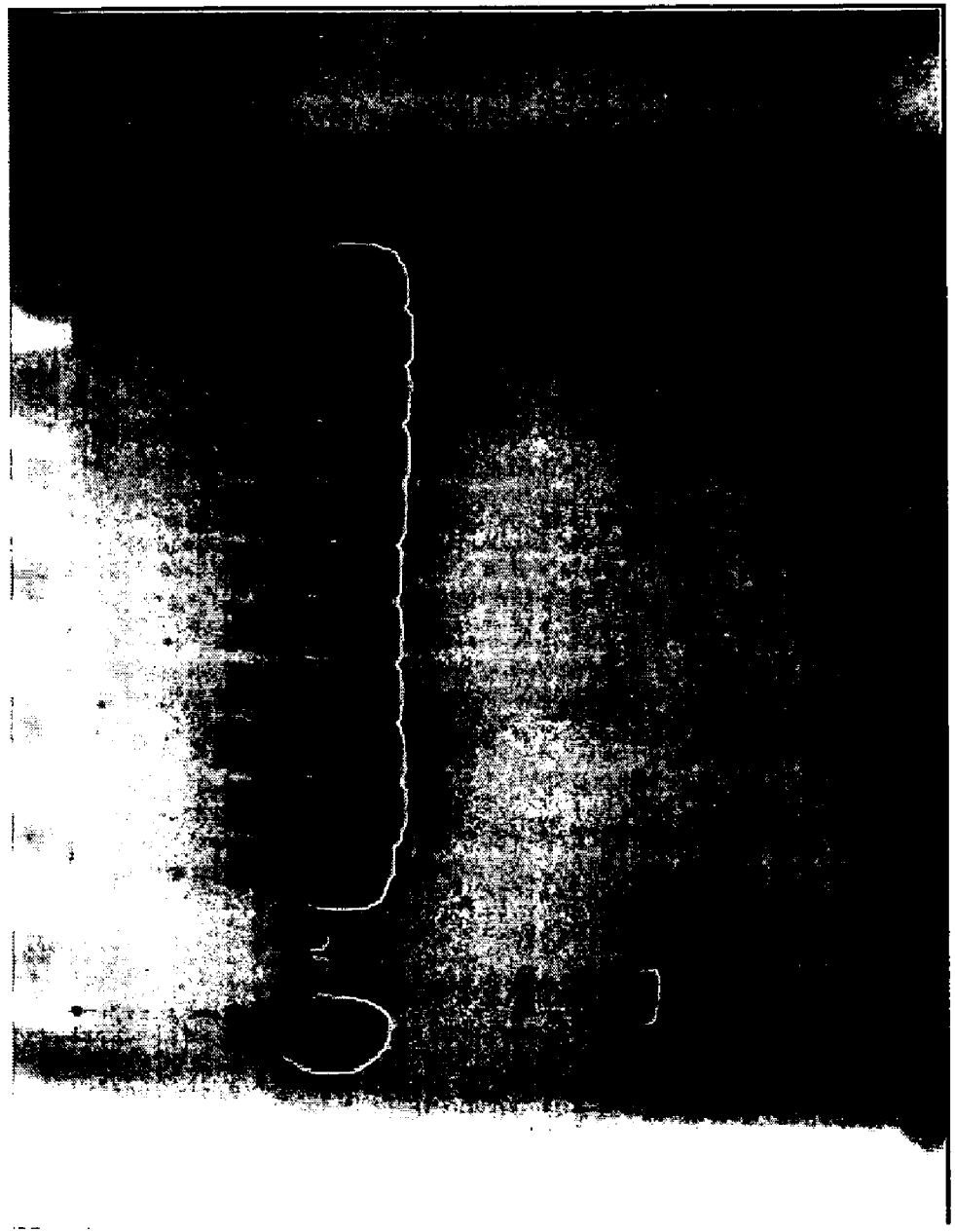

FIG. 77 shows an SDS-PAGE analysis (non-reduced) of samples stored at 4° C. for 4 months. Lane 1: PEG-hGH Standard; Lane 2: hGH (1 µg); Lane 4: P6MT; Lane 5: H6MT; Lane 6: P6GT; Lane 7: P6MS; Lane 8: P6MTMet; Lane 9: P6MT; Lane 10: P7GT; Lane 11: P6MGT; Lane 12: P6MGT-P; Lane 13: P6MT-P; Lane 14: P6GT-P.

Figure 78:
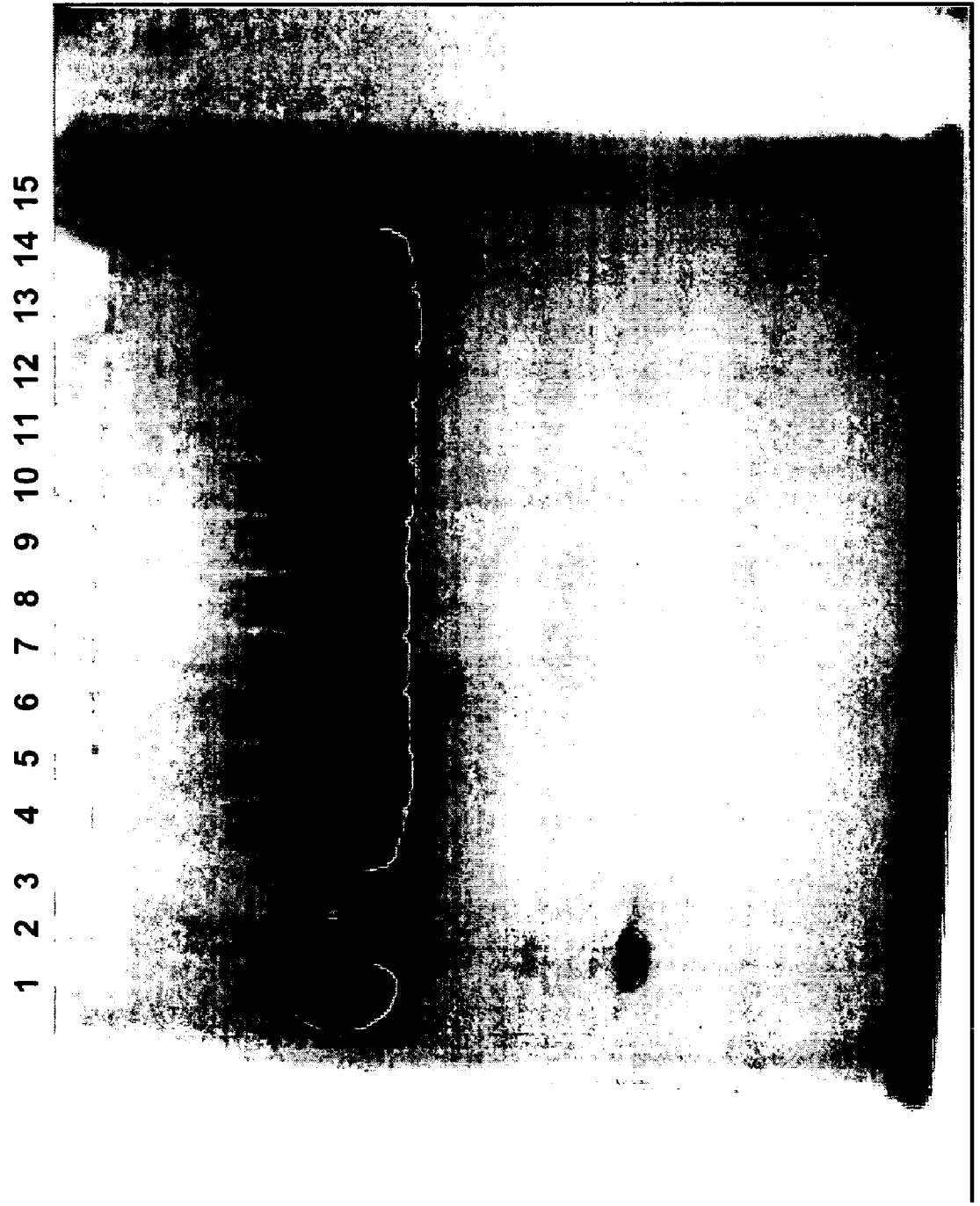

FIG. 78 shoes an SDS-PAGE analysis (reduced) of samples stored at 4° C. for 4 months. Lane 1: PEG-hGH Standard; Lane 2: hGH (1 µg); Lane 4: P6MT; Lane 5: H6MT; Lane 6: P6GT; Lane 7: P6MS; Lane 8: P6MTMet; Lane 9: P6MT; Lane 10: P7GT; Lane 11: P6MGT; Lane 12: P6MGT-P; Lane 13: P6MT-P; Lane 14: P6GT-P.

Figure 79:
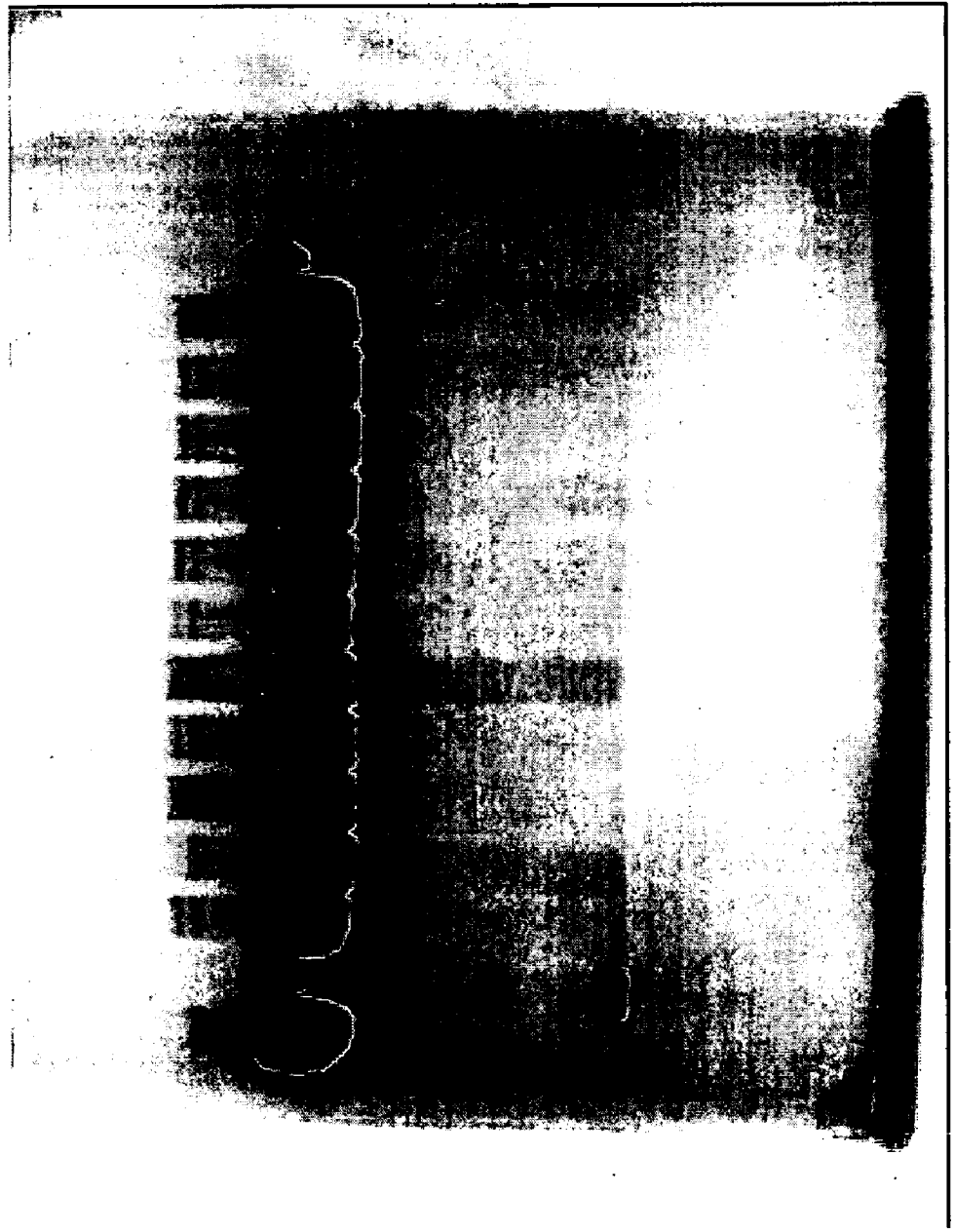

FIG. 79 shows an SDS-PAGE analysis (non-reduced) of samples stored at 25° C. for 4 months. Lane 1: PEG-hGH Standard; Lane 2: hGH (1 µg); Lane 3: P6MT; Lane 4: H6MT; Lane 5: P6GT; Lane 6: P6MS; Lane 7: P6MTMet; Lane 8: P6MT; Lane 9: P7GT; Lane 10: P6MGT; Lane 11: P6MGT-P; Lane 12: P6MT-P; Lane 13: P6GT-P.

Figure 80:
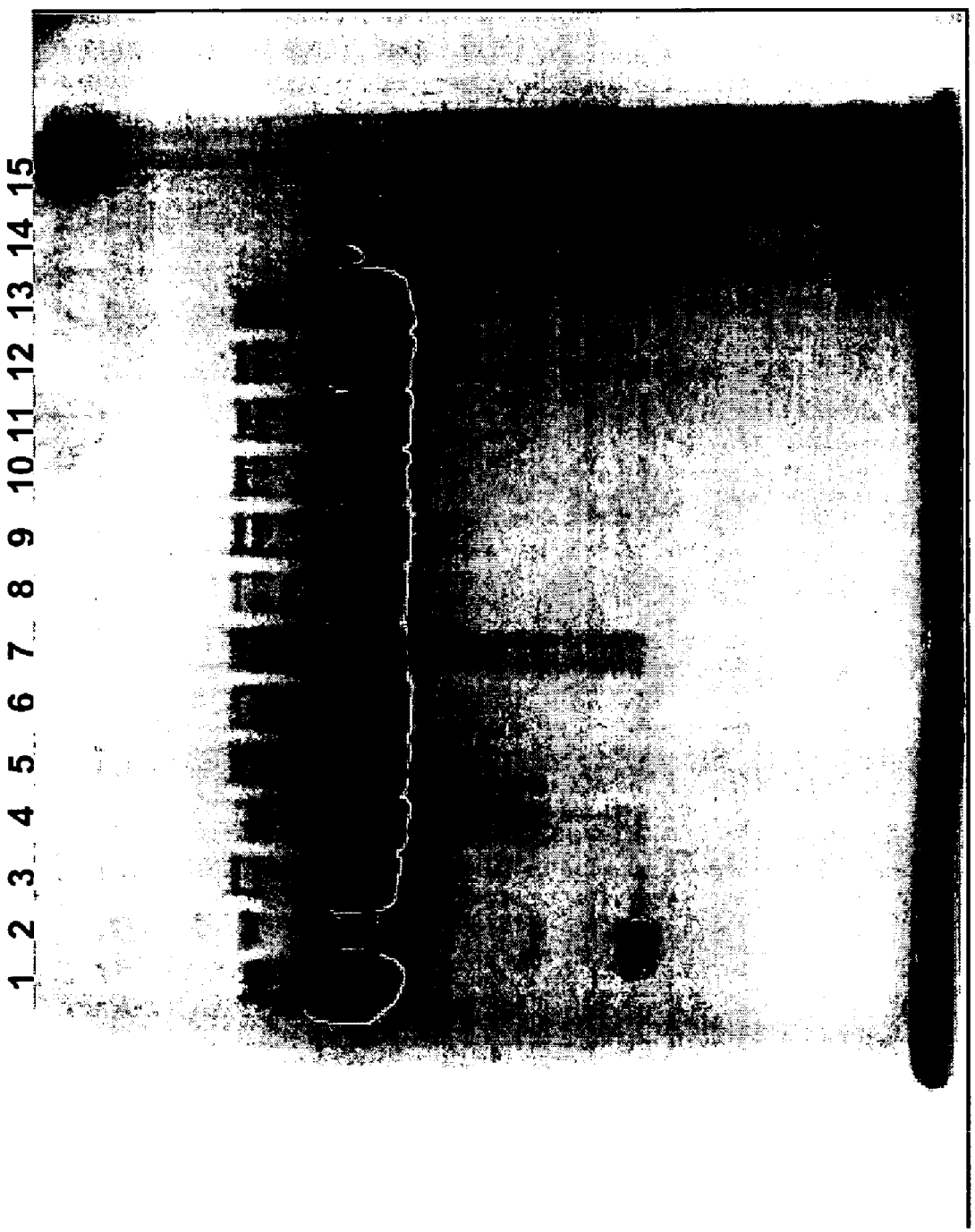

FIG. 80 shows an SDS-PAGE analysis (reduced) of samples stored at 25° C. for 4 months. Lane 1: PEG-hGH Standard; Lane 2: hGH (1 µg); Lane 3: P6MT; Lane 4: H6MT; Lane 5: P6GT; Lane 6: P6MS; Lane 7: P6MTMet; Lane 8: P6MT; Lane 9: P7GT; Lane 10: P6MGT; Lane 11: P6MGT-P; Lane 12: P6MT-P; Lane 13: P6GT-P.

Figure 81:
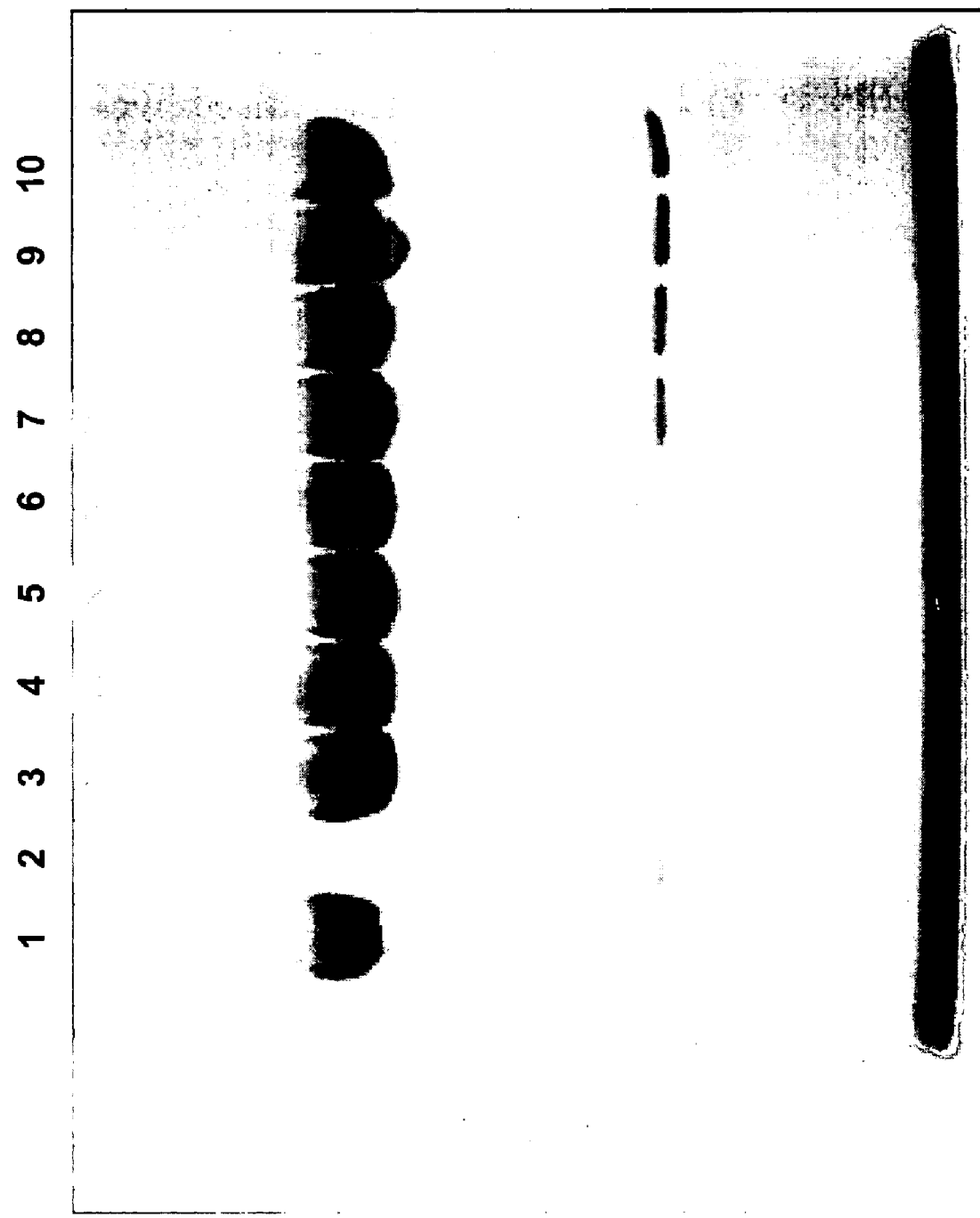

FIG. 81 shows an SDS-PAGE analysis (non-reduced) of samples stored at 4° C. or 40° C. for 4 weeks. Lane 1: PEG-hGH Standard; Lane 2: hGH (0.5 µg); Lane 3: H7MT-P 8 mg/mL 4° C.; Lane 4: H7MT-P 14 mg/mL 4° C.; Lane 5: H7MGT-P 8 mg/mL 4° C.; Lane mg/mL 4° C.; Lane 7: H7MT-P 8 mg/mL 40° C.; Lane 8: H7MT-P 14 mg/mL 40° C.; Lane 9: H7MGT-P 8 mg/mL 40° C.; Lane 10: H7MGT-P 14 mg/mL 40° C.

Figure 82:

FIG. 82 shows an SDS-PAGE analysis (non-reduced) of samples stored at 4° C. or 40° C. for 4 weeks. Lane 1: PEG-hGH Standard; Lane 2: hGH (0.5 µg); Lane 3: H7MT-P 8 mg/mL 4° C.; Lane 4: H7MT-P 14 mg/mL 4° C.; Lane 5: H7MGT-P 8 mg/mL 4° C.; Lane 6: H7MGT-P 14 mg/mL 4° C.; Lane 7: H7MT-P 8 mg/mL 40° C.; Lane 8: H7MT-P 14 mg/mL 40° C.; Lane 9: H7MGT-P 8 mg/mL 40° C.; Lane 10: H7MGT-P 14 mg/mL 40° C.

Figure 83:
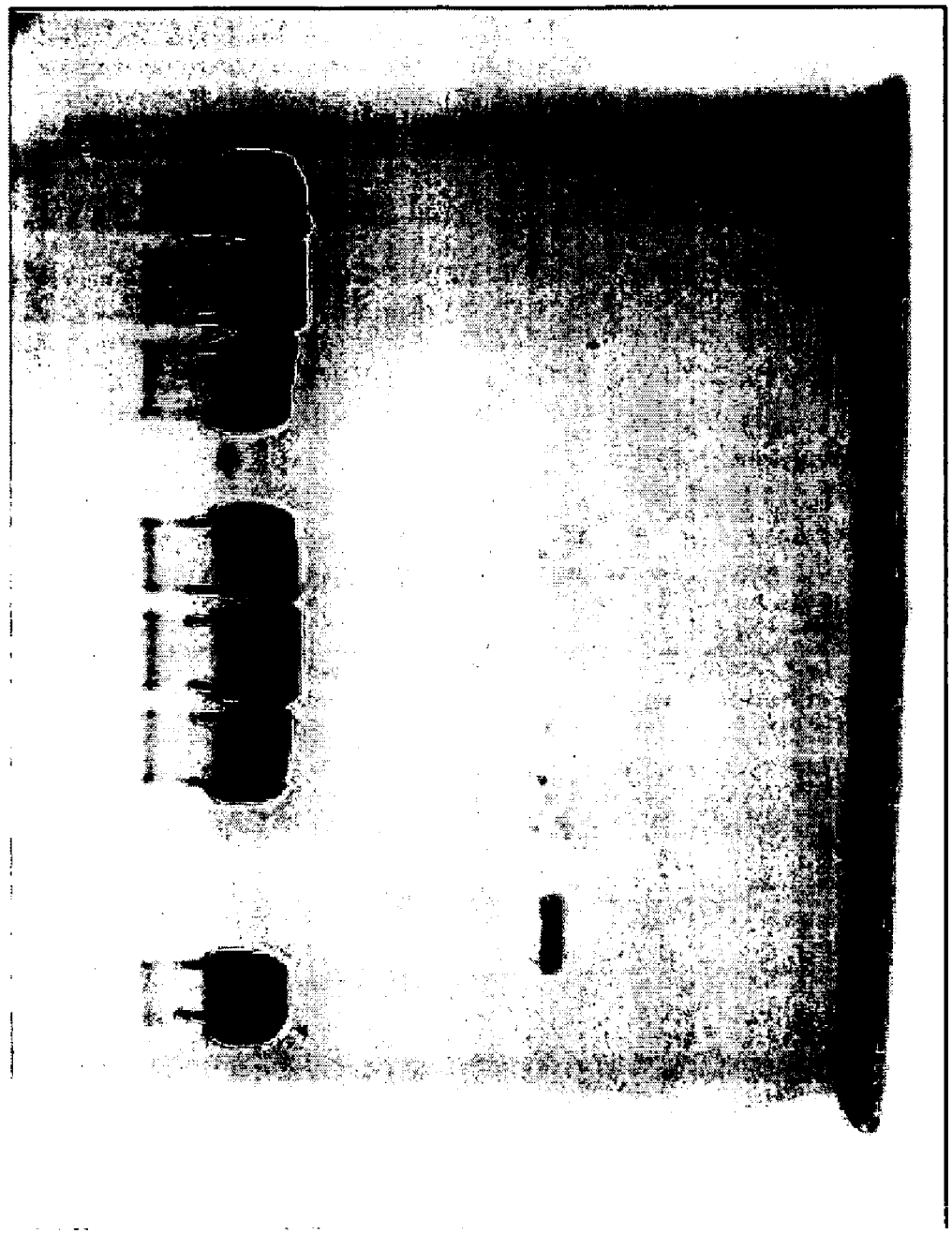

FIG. 83 shows an SDS-PAGE analysis of samples. Lane 1: PEG-hGH Standard (Batch 2); Lane 2: hGH (1 µg); Lane 4: 39.9 mg/mL Non-reduced; Lane 5: 24.3 mg/mL Non-reduced; Lane 6: 1.1 mg/mL Non-reduced; Lane 8: 39.9 mg/mL Reduced; Lane 9: 24.3 mg/mL Reduced; Lane 10: 1.1 mg/mL Reduced.

DEFINITIONS

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "hGH" is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

U.S. patent application Ser. No. 11/046,432 is incorporated by reference in its entirety. Thus, the disclosures provided in paragraphs numbered 79-153, in U.S. patent application Ser. No. 11/046,432 apply fully to the methods, compositions, techniques and strategies for making, purifying, characterizing, and using non-natural amino acids, non-natural amino acid hGH polypeptides and modified non-natural amino acid hGH polypeptides described herein to the same extent as if such disclosures were fully presented herein.

As used herein, "growth hormone" or "GH" shall include those polypeptides and proteins that have at least one biological activity of a human growth hormone, as well as GH analogs, GH isoforms, GH mimetics, GH fragments, hybrid GH proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "hGH polypeptide" encompasses hGH polypeptides comprising one or more amino acid substitutions, additions or deletions.

For the complete full-length naturally-occurring GH amino acid sequence as well as the mature naturally-occurring GH amino acid sequence and naturally occurring mutant, see SEQ ID NO: 1, SEQ ID NO: 2 and SEQ ID NO: 3, respectively, in U.S. patent application Ser. No. 11/046,432, which is incorporated by reference herein. In some embodiments, hGH polypeptides of the invention are substantially identical to these sequences or any other sequence of a growth hormone polypeptide.

The term "hGH polypeptide" also includes the pharmaceutically acceptable salts and prodrugs, and prodrugs of the salts, polymorphs, hydrates, solvates, biologically-active fragments, biologically active variants and stereoisomers of the naturally-occurring hGH as well as agonist, mimetic, and antagonist variants of the naturally-occurring hGH and polypeptide fusions thereof. Fusions comprising additional amino acids at the amino terminus, carboxyl terminus, or both, are encompassed by the term "hGH polypeptide." Exemplary fusions include, but are not limited to, e.g., methionyl growth hormone in which a methionine is linked to the N-terminus of hGH resulting from the recombinant expression, fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13.

Various references disclose modification of polypeptides by polymer conjugation or glycosylation. The term "hGH polypeptide" includes polypeptides conjugated to a polymer such as PEG and may be comprised of one or more additional derivitizations of cysteine, lysine, or other residues. In addition, the hGH polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer conjugation of hGH polypeptides has been reported. See, e.g. U.S. Pat. Nos. 5,849,535, 6,136,563 and 6,608,183, which are incorporated by reference herein. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092, which is incorporated by reference herein, discloses modification of granulocyte colony stimulating factor (G-CSF) and other polypeptides so as to introduce at least one additional carbohydrate chain as compared to the native polypeptide.

The term "hGH polypeptide" also includes glycosylated hGH, such as but not limited to, polypeptides glycosylated at any amino acid position, N-linked or O-linked glycosylated forms of the polypeptide. Variants containing single nucleotide changes are also considered as biologically active variants of hGH polypeptide. In addition, splice variants are also included. The term "hGH polypeptide" also includes hGH polypeptide heterodimers, homodimers, heteromultimers, or homomultimers of any one or more hGH polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

All references to amino acid positions in hGH described herein are based on the position in SEQ ID NO: 2 as listed in U.S. patent application Ser. No. 11/046,432, entitled "Modified Human Growth Hormone Polypeptides and Their Uses,"

which is incorporated by reference herein, unless otherwise specified (i.e., when it is stated that the comparison is based on another hGH sequence such as SEQ ID NO: 1, 3). Those of skill in the art will appreciate that amino acid positions corresponding to positions in SEQ ID NO: 1, 2, 3 listed in U.S. patent application Ser. No. 11/046,432, which is incorporated by reference herein, or any other GH sequence can be readily identified in any other hGH molecule such as hGH fusions, variants, fragments, etc. For example, sequence alignment programs such as BLAST can be used to align and identify a particular position in a protein that corresponds with a position in SEQ ID NO: 1, 2, 3 of U.S. patent application Ser. No. 11/046,432, which is incorporated by reference herein, or other GH sequence. Substitutions, deletions or additions of amino acids described herein in reference to SEQ ID NO: 1, 2, 3 of U.S. patent application Ser. No. 11/046,432, which is incorporated by reference herein, or other GH sequence are intended to also refer to substitutions, deletions or additions in corresponding positions in any other hGH molecule such as hGH fusions, variants, fragments, etc. described herein or known in the art and are expressly encompassed by the present invention.

The term "hGH polypeptide" or "hGH" encompasses hGH polypeptides comprising one or more amino acid substitutions, additions or deletions. hGH polypeptides of the present invention may be comprised of modifications with one or more natural amino acids in conjunction with one or more non-natural amino acid modification. Exemplary substitutions in a wide variety of amino acid positions in naturally-occurring hGH polypeptides have been described, including but not limited to substitutions that modulate one or more of the biological activities of the hGH polypeptide, such as but not limited to, increase agonist activity, increase solubility of the polypeptide, decrease protease susceptibility, convert the polypeptide into an antagonist, etc. and are encompassed by the term "hGH polypeptide."

In some embodiments, the hGH polypeptides further comprise an addition, substitution or deletion that modulates biological activity of the hGH polypeptide. For example, the additions, substitutions or deletions may modulate one or more properties or activities of hGH. For example, the additions, substitutions or deletions may modulate affinity for the hGH polypeptide receptor, modulate (including but not limited to, increases or decreases) receptor dimerization, stabilize receptor dimers, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, hGH polypeptides may comprise protease cleavage sequences, secretion signal sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "hGH polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly(ethylene glycol) or polydextran, or polypeptides of various lengths.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydra zone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein. A "multifunctional polymer" refers to a polymer comprising two or more discrete functional groups that are capable of reacting specifically with other moieties (including but not limited to, amino acid side groups) to form covalent or non-covalent linkages. A bi-functional polymer or multifunctional polymer may be any desired length or molecular weight, and may be selected to provide a particular desired spacing or conformation between one or more molecules linked to the GH, e.g., hGH, molecule.

As used herein, the term "water soluble polymer" refers to any polymer that is soluble in aqueous solvents. Linkage of water soluble polymers to hGH polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding and altered receptor dimerization or multimerization. The water soluble polymer may or may not have its own biological activity. Suitable polymers include, but are not limited to, polyethylene glycol, polyethylene glycol propionaldehyde, mono C1-CIO alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

As used herein, the term "modulated serum half-life" means the positive or negative change in circulating half-life of a modified hGH relative to its non-modified form. Serum half-life is measured by taking blood samples at various time points after administration of hGH, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of hGH, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule.

The term "substantially purified" refers to a hGH polypeptide that may be substantially or essentially free of components that normally accompany or interact with the protein as found in its naturally occurring environment, i.e. a native cell, or host cell in the case of recombinantly produced hGH polypeptides. hGH polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the hGH polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the hGH polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" hGH polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "subject" as used herein, refers to an animal, in some embodiments a mammal, and in other embodiments a human, who is the object of treatment, observation or experiment.

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the modified non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides may be metabolized upon administration to an organism in need to produce a metabolite that is then used to produce a desired effect, including a desired therapeutic effect.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction hGH molecules comprising at least one unnatural amino acid are provided in the invention. In certain embodiments of the invention, the hGH polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein are substituted with an unnatural amino acid.

The present invention provides methods and compositions based on members of the GH supergene family, in particular hGH, comprising at least one non-naturally encoded amino acid. Introduction of at least one non-naturally encoded amino acid into a GH supergene family member such as hGH can allow for the application of conjugation chemistries that involve specific chemical reactions, including, but not limited to, with one or more non-naturally encoded amino acids while not reacting with the commonly occurring 20 amino acids. In some embodiments, the GH supergene family member comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein.

It is well established in the art that PEG can be used to modify the surfaces of biomaterials (see, e.g., U.S. Pat. No. 6,610,281; Mehvar, R., J. Pharmaceut. Sci., 3(1):125-136 (2000) which are incorporated by reference herein).

A discussion of recombinant nucleic acid methods, selector codons, orthogonal tRNAs, orthogonal aminoacyl tRNA synthetases, and non-naturally encoded amino acids with various reactive groups, including but not limited to, carbonyl groups, hydrazine, hydrazide, aminooxy, azide, and alkyne groups, is provided in U.S. patent application Ser. No. 11/046,432 entitled "Modified Human Growth Hormone Polypeptides and Their Uses," which is incorporated by reference in its entirety herein. Cellular uptake and biosynthesis of non-naturally encoded amino acids are also discussed in this application. This application also details sites for incorporation of one or more non-naturally encoded amino acids into hGH and expression of hGH polypeptides. The synthesis of non-natural amino acids containing carbonyl groups such as p-acetyl-(+/−)-phenylalanine and m-acetyl-(+/−)-phenylalanine is described in Zhang, Z., et al., Biochemistry 42: 6735-6746 (2003), which is incorporated by reference herein.

II. Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g., tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology*, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, $(GlcNAc-Man)_2$-Man-GlcNAc-GlcNAc)) to an asparagine by a GlcNAc-asparagine linkage. See Table 1 of U.S. patent application Ser. No. 11/046,432 entitled "Modifed Human Growth Hormone Polypeptides and Their Uses," which is incorporated by reference herein, which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like. U.S. Pat. Nos. 4,963,495 and 6,436,674, which are incorporated herein by reference, detail constructs designed to improve secretion of hGH polypeptides.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.*, 118:8150-8151; Mahal, et al., (1997) *Science*, 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.*, 99:11020-11024; Wang, et al., (2003) *Proc. Natl. Acad. Sci.*, 100:56-61; Zhang, et al., (2003) *Biochemistry*, 42:6735-6746; and, Chin, et al., (2003) *Science*, 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Molecules that may be attached to hGH include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like.

This invention provides formulations of non-natural amino acid polypeptides generated via selective modification of proteins, which involves the genetic incorporation of unnatural amino acids.

III In Vivo Generation of hGH Polypeptides Comprising Non-Genetically-Encoded Amino Acids The hGH polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O—RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O—RSs are also described in U.S. Patent Application Publications 2003/0082575 (Ser. No. 10/126,927) and 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O—RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Additional O-tRNA sequences include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA syn-thetase pairs specific to particular non-naturally encoded amino acids are described in U.S. Patent Application Publication 2003/0082575 (Ser. No. 10/126,927) which is incorporated by reference herein. O—RS and O-tRNA that incorporate both keto- and azide-containing amino acids in S. cerevisiae are described in Chin, J. W., et al., Science 301: 964-967 (2003).

Several other orthogonal pairs have been reported. Glutaminyl (see, e.g., Liu, D. R., and Schultz, P. G. (1999) Proc. Natl. Acad. Sci. U.S.A. 96:4780-4785), aspartyl (see, e.g., Pastrnak, M., et al., (2000) Helv. Chim. Acta 83:2277-2286), and tyrosyl (see, e.g., Ohno, S., et al., (1998) J. Biochem. (Tokyo, Jpn.) 124:1065-1068; and, Kowal, A. K., et al., (2001) Proc. Natl. Acad. Sci. U.S.A. 98:2268-2273) systems derived from S. cerevisiae tRNA's and synthetases have been described for the potential incorporation of unnatural amino acids in E. coli. Systems derived from the E. coli glutaminyl (see, e.g., Kowal, A. K., et al., (2001) Proc. Natl. Acad. Sci. U.S.A. 98:2268-2273) and tyrosyl (see, e.g., Edwards, H., and Schimmel, P. (1990) Mol. Cell. Biol. 10:1633-1641) synthetases have been described for use in S. cerevisiae. The E. coli tyrosyl system has been used for the incorporation of 3-iodo-L-tyrosine in vivo, in mammalian cells. See, Sakamoto, K., et al., (2002) Nucleic Acids Res. 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the hGH polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O—RSs, O-tRNAs, and orthogonal O-tRNA/O—RS pairs that can be used to incorporate a non-naturally encoded amino acid are described in Wang, L., et al., Science 292: 498-500 (2001); Chin, J. W., et al., J. Am. Chem. Soc. 124:9026-9027 (2002); Zhang, Z. et al., Biochemistry 42: 6735-6746 (2003). Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells. Such methods are also detailed in U.S. patent application Ser. No. 11/046,432 entitled "Modifed Human Growth Hormone Polypeptides and Their Uses," which is incorporated by reference herein.

The organisms used in methods generating orthogonal tRNA and RS pairs comprise a variety of organisms and a variety of combinations. For example, the first and the second organisms of the methods can be the same or different. In one embodiment, the organisms are optionally a prokaryotic organism, including but not limited to, Methanococcus jannaschii, Methanobacterium thermoautotrophicum, Halobacterium, Escherichia coli, A. fulgidus, P. furiosus, P. horikoshii, A. pernix, T. thermophilus, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, Methanococcus jannaschii, Methanobacterium thermoautotrophicum, Halobacterium, Escherichia coli, A. fulgidus, Halobacterium, P. furiosus, P. horikoshii, A. pernix, T. thermophilus, or the like. Alternatively, the second organism can be a eukaryotic organism, including but not limited to, a yeast, a animal cell, a plant cell, a fungus, a mammalian cell, or the like. In various embodiments the first and second organisms are different.

V. Location of Non-Naturally-Occurring Amino Acids in hGH Polypeptides

The present invention contemplates incorporation of one or more non-naturally-occurring amino acids into hGH polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids, and/or inserting the non-naturally-occurring amino acid in a location that is not required for activity.

Regions of hGH can be illustrated as follows, wherein the amino acid positions in hGH are indicated in the middle row (SEQ ID NO: 2 of U.S. patent application Ser. No. 11/046, 432, which is incorporated by reference herein):

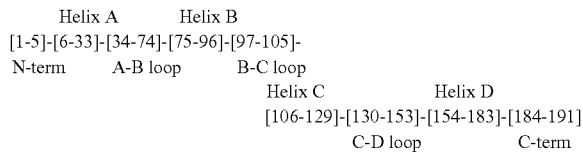

A variety of biochemical and structural approaches can be employed to select the desired sites for substitution with a non-naturally encoded amino acid within the hGH polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a hGH molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of hGH polypeptides can be identified using point mutation analysis, alanine scanning or homolog scanning methods known in the art. See, e.g., Cunningham, B. and Wells, J., *Science,* 244:1081-1085 (1989) (identifying 14 residues that are critical for hGH bioactivity) and Cunningham, B., et al. *Science* 243: 1330-1336 (1989) (identifying antibody and receptor epitopes using homolog scanning mutagenesis). U.S. Pat. Nos. 5,580,723; 5,834,250; 6,013,478; 6,428,954; and 6,451,561, which are incorporated by reference herein, describe methods for the systematic analysis of the structure and function of polypeptides such as hGH by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of hGH polypeptides that contain deletions can also be examined to determine regions of the protein that are likely to be tolerant of substitution with a non-naturally encoded amino acid. See, e.g., Kostyo et al., *Biochem. Biophys. Acta,* 925: 314 (1987); Lewis, U., et al., *J. Biol. Chem.,* 253:2679-2687 (1978) for hGH. In a similar manner, protease digestion and monoclonal antibodies can be used to identify regions of hGH that are responsible for binding the hGH receptor. See, e.g., Cunningham, B., et al. *Science* 243: 1330-1336 (1989); Mills, J., et al., *Endocrinology,* 107:391-399 (1980); Li, C., *Mol. Cell. Biochem.,* 46:31-41 (1982) (indicating that amino acids between residues 134-149 can be deleted without a loss of activity). Once residues that are likely to be intolerant to substitution with non-naturally encoded amino acids have been eliminated, the impact of proposed substitutions at each of the remaining positions can be examined from the three-dimensional crystal structure of the hGH and its binding proteins. See de Vos, A., et al., *Science,* 255:306-312 (1992) for hGH; all crystal structures of hGH are available in the Protein Data Bank (including 3HHR, 1AXI, and 1HWG) (PDB, available on the World Wide Web at rcsb.org), a centralized database containing three-dimensional structural data of large molecules of proteins and nucleic acids. Thus, those of skill in the art can readily identify amino acid positions that can be substituted with non-naturally encoded amino acids.

In some embodiments, the hGH polypeptides of the invention comprise one or more non-naturally occurring amino acids positioned in a region of the protein that does not disrupt the helices or beta sheet secondary structure of the polypeptide.

Exemplary residues of incorporation of a non-naturally encoded amino acid may be those that are excluded from potential receptor binding regions (including but not limited to, Site I and Site II), may be fully or partially solvent exposed, have minimal or no hydrogen-bonding interactions with nearby residues, may be minimally exposed to nearby reactive residues, and may be in regions that are highly flexible (including but not limited to, C-D loop) or structurally rigid (including but not limited to, B helix) as predicted by the three-dimensional crystal structure, secondary, tertiary or quaternary structure of the hGH polypeptide bound or unbound to its receptor.

In some embodiments, one or more non-naturally encoded amino acids are incorporated at any position in one or more of the following regions corresponding to secondary structures in hGH as follows: positions corresponding to 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) from SEQ ID NO: 2. In other embodiments, GH polypeptides, e.g., hGH polypeptides of the invention comprise at least one non-naturally-occurring amino acid substituted for at least one amino acid located in at least one region of GH, e.g., hGH selected from the group consisting regions corresponding to the N-terminus (1-5), the N-terminal end of the A-B loop (32-46); the B-C loop (97-105), the C-D loop (132-149), and the C-terminus (184-191) of SEQ ID NO: 2. In some embodiments, one or more non-naturally encoded amino acids are incorporated at one or more of the following positions of GH, e.g., hGH corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) of SEQ ID NO: 2 or the corresponding amino acids of SEQ ID NO: 1 or 3.

Exemplary sites of incorporation of one or more non-naturally encoded amino acids include sites corresponding to 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187, or any combination thereof from SEQ ID NO: 2 or the corresponding amino acids of SEQ ID NO: 1 or 3.

A subset of exemplary sites for incorporation of one or more non-naturally encoded amino acid include sites corresponding to 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187, or any combination thereof from SEQ ID NO: 2 or the corresponding amino acids of SEQ ID NO: 1 or 3. An examination of the crystal structure of GH, e.g., hGH and its interactions with the GH, e.g., hGH receptor indicates that the side chains of these amino acid residues are fully or partially accessible to solvent and the side chain of a non-naturally encoded amino acid may point away from the protein surface and out into the solvent.

Exemplary positions for incorporation of one or more non-naturally encoded amino acids include sites corresponding to 35, 88, 91, 92, 94, 95, 99, 101, 103, 111, 131, 133, 134, 135, 136, 139, 140, 143, 145, and 155, or any combination thereof from SEQ ID NO: 2 or the corresponding amino acids of SEQ ID NO: 1 or 3. An examination of the crystal structure of GH, e.g., hGH and its interactions with the GH, e.g., hGH receptor indicates that the side chains of these amino acid residues are fully exposed to the solvent and the side chain of the native residue points out into the solvent.

A subset of exemplary sites for incorporation of one or more non-naturally encoded amino acids include sites corresponding to 30, 74, 103, or any combination thereof, from SEQ ID NO: 2 or the corresponding amino acids of SEQ ID NO: 1 or 3. Another subset of exemplary sites for incorporation of one or more non-naturally encoded amino acids include sites corresponding to 35, 92, 143, 145, or any combination thereof, from SEQ ID NO: 2 or the corresponding amino acids of SEQ ID NO: 1 or 3. A further subset of exemplary sites for incorporation of one or more non-naturally encoded amino acids include sites corresponding to 35, 92, 131, 134, 143, 145, or any combination thereof, from SEQ ID NO: 2 or the corresponding amino acids of SEQ ID NO: 1 or 3. Still a further subset of exemplary sites for incorporation of one or more non-naturally encoded amino acids include sites corresponding to 30, 35, 74, 92, 103, 145, or any combination thereof, from SEQ ID NO: 2 or the corresponding amino acids of SEQ ID NO: 1 or 3. Yet a further subset of exemplary sites for incorporation of one or more non-naturally encoded amino acids include sites corresponding to 35, 92, 143, 145, or any combination thereof, from SEQ ID NO: 2 or the corresponding amino acids of SEQ ID NO: 1 or 3. In certain embodiments, sites for incorporation of one or more non-naturally encoded amino acids include a site corresponding to 35 from SEQ ID NO: 2 or the corresponding amino acids of SEQ ID NO: 1 or 3.

In some embodiments, at least one of the non-naturally encoded amino acids incorporated into the GH, e.g., hGH, contains a carbonyl group, e.g., a ketone group. In certain embodiments, at least one of the non-naturally encoded amino acids incorporated into the GH, e.g., hGH is para-acetylphenylalanine. In some embodiments in which the GH, e.g., hGH contains a plurality of non-naturally-encoded amino acids, more than one of the non-naturally-encoded amino acids incorporated into the GH, e.g., hGH is para-acetylphenylalanine. In some embodiments in which the GH, e.g., hGH contains a plurality of non-naturally-encoded amino acids, substantially all of the non-naturally-encoded amino acids incorporated into the GH, e.g., hGH are para-acetylphenylalanine.

In some embodiments, the non-naturally occurring amino acid is linked to a water soluble polymer at one or more positions, including but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 30, 35, 74, 92, 103, 143, 145 (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 35, 92, 143, 145 (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 35, 92, 131, 134, 143, 145, or any combination thereof, from SEQ ID NO: 2 or the corresponding amino acids of SEQ ID NO: 1 or 3. In some embodiments, the non-naturally occurring amino acid is linked to a water soluble polymer at positions including but not limited to, positions corresponding to one or more of these positions: 30, 35, 74, 92, 103, 145, or any combination thereof, from SEQ ID NO: 2 or the corresponding amino acids of SEQ ID NO: 1 or 3. In some embodiments, the non-naturally occurring amino acid is linked to a water soluble polymer at positions including but not limited to, positions corresponding to one or more of these positions: 35, 92, 143, 145, or any combination thereof, from SEQ ID NO: 2 or the corresponding amino acids of SEQ ID NO: 1 or 3. In some embodiments, the non-naturally occurring amino acid is linked to a water-soluble polymer at a position corresponding to, but not limited to, position 35 from SEQ If) NO: 2 or the corresponding amino acids of SEQ ID NO: 1 or 3 is linked to a water-soluble polymer.

In some embodiments the water-soluble polymer(s) linked to the GH, e.g., hGH, include one or more polyethylene glycol molecules (PEGs). The polymer, e.g., PEG, may be linear or branched. Typically, linear polymers, e.g., PEGs, used in the invention can have a MW of about 0.1 to about 100 kDa, or about 1 to about 60 kDa, or about 20 to about 40 kDa, or about 30 kDa. Typically, branched polymers, e.g., PEGs, used in the invention can have a MW of about 1 to about 100 kDa, or about 30 to about 50 kDa, or about 40 kDa. Polymers such as PEGs are described further herein. In certain embodiments, the linkage between the GH, e.g., hGH and the water-soluble polymer, e.g., PEG, is an oxime bond.

Certain embodiments of the invention encompass compositions that include a GH, e.g., hGH, linked to at least one water-soluble polymer by a covalent bond, where the covalent bond is an oxime bond. In some embodiments, the water-soluble polymer is a PEG, e.g., a linear PEG. In some embodiments encompassing at least one linear PEG linked by an oxime bond to a GH, e.g., hGH, the PEG can have a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In some embodiments encompassing at least one branched PEG linked by an oxime bond to a GH, e.g., hGH, the PEG can have a MW of about 1 to about 100 kDa or about 30 to about 50 kDa, or about 40 kDa. In certain embodiments encompassing a branched PEG linked by an oxime bond to a GH, e.g., hGH, the PEG has a MW of about 40 kDa. In some embodiments, the GH is a GH, e.g., hGH and in certain of these embodiments, the GH, e.g., hGH has a sequence that is at least about 80% identical to SEQ ID NO: 2; in some embodiments the GH, e.g., hGH has a sequence that is the sequence of SEQ ID NO: 2. In some embodiments, the GH, e.g., hGH, contains at least one non-naturally-encoded amino acid; in some of these embodiments, at least one oxime bond is between the non-naturally-encoded amino acid and at least one water-soluble polymer. In some embodiments, the non-naturally-encoded amino acid contains a carbonyl group, such as a ketone group; in some embodiments, the non-naturally-encoded amino acid is para-acetylphenylalanine. In some embodiments, the para-acetylphenylalanine is substituted at a position corresponding to position 35 of SEQ ID NO: 2.

Thus, in some embodiments, the invention provides a GH, e.g., hGH, linked to at least one water-soluble polymer, e.g., a PEG, by a covalent bond, where the covalent bond is an oxime bond. In certain embodiments, the water-soluble polymer is a PEG and the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments, the water-soluble polymer is a PEG that is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, where the GH, e.g., hGH contains a non-naturally encoded amino acid, where the GH is linked to at least one water-soluble polymer, e.g., a PEG, by a covalent bond, and where the covalent bond is an oxime bond between the non-naturally encoded amino acid and the water-soluble polymer, e.g., PEG. In some embodiments, the non-naturally-encoded amino acid is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, where the GH, e.g., hGH contains a non-naturally encoded amino acid that is a carbonyl-containing non-naturally encoded amino acid, where the GH is linked to at least one water-soluble polymer, e.g., a PEG, by a covalent bond, and where the covalent bond is an oxime bond between the non-naturally encoded carbonyl-containing amino acid and the water-soluble polymer, e.g., PEG. In some embodiments, the non-naturally-encoded carbonyl-containing amino acid is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, that contains a non-naturally encoded amino acid that includes a ketone group, where the GH is linked to at least one water-soluble polymer, e.g., a PEG, by a covalent bond, and where the covalent bond is an oxime bond between the non-naturally encoded amino acid containing a ketone group and the water-soluble polymer, e.g., PEG. In some embodiments, the non-naturally-encoded amino acid containing a ketone group is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, that contains a non-naturally encoded amino acid that is a para-acetylphenylalanine, where the GH linked to at least one water-soluble polymer, e.g., a PEG, by a covalent bond, and where the covalent bond is an oxime bond between the para-acetylphenylalanine and the water-soluble polymer, e.g., PEG. In some embodiments, the para-acetylphenylalanine is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In certain embodiments the invention provides a GH, e.g., hGH that includes SEQ ID NO: 2, and where the GH, e.g., hGH is substituted at a position corresponding to position 35 of SEQ ID NO: 2 with a para-acetylphenylalanine that is linked by an oxime linkage to a linear PEG of MW of about 30 kDa.

In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 30, 35, 74, 92, 103, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 131, 134, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 30, 35, 74, 92, 103, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 143, 145, or any combination thereof, from SEQ ID NO: 2 or the corresponding amino acids of SEQ ID NO: 1 or 3 In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to position 35 from SEQ ID NO: 2 or the corresponding amino acids of SEQ ID NO: 1 or 3. In embodiments in which the PEG is a linear PEG, the PEG can have a MW of about 0.1 to about 100 kDa, or about 1 to about 60 kDa, or about 20 to about 40 kDa, or about 30 kDa.

In some embodiments, the invention provides a hormone composition that includes a GH, e.g., hGH, linked via an oxime bond to at least one PEG, e.g., a linear PEG, where the GH, e.g., hGH includes the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 30, 35, 74, 92, 103, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 131, 134, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 30, 35, 74, 92, 103, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to position 35 from SEQ ID NO: 2 or the corresponding amino acids of SEQ ID NO: 1 or 3. In embodiments in which the PEG is a linear PEG, the PEG can have a MW of about 0.1 to about 100 kDa, or about 1 to about 60 kDa, or about 20 to about 40 kDa, or about 30 kDa.

In some embodiments, the invention provides a GH, e.g., hGH, where the GH, e.g., hGH contains at least one non-naturally encoded amino acid, where the GH is linked to a plurality of water-soluble polymers, e.g., a plurality of PEGs, by covalent bonds, where one or more of the covalent bond is an oxime bond between at least one of the non-naturally encoded amino acid and the water-soluble polymer, e.g., PEG. The GH, e.g., hGH, may be linked to about 2-100 water-soluble polymers, e.g., PEGs, or about 2-50 water-soluble polymers, e.g., PEGs, or about 2-25 water-soluble polymers, e.g., PEGs, or about 2-10 water-soluble polymers, e.g., PEGs, or about 2-5 water-soluble polymers, e.g., PEGs, or about 5-100 water-soluble polymers, e.g., PEGs, or about 5-50 water-soluble polymers, e.g., PEGs, or about 5-25 water-soluble polymers, e.g., PEGs, or about 5-10 water-soluble polymers, e.g., PEGs, or about 10-100 water-soluble polymers, e.g., PEGs, or about 10-50 water-soluble polymers, e.g., PEGs, or about 10-20 water-soluble polymers, e.g., PEGs, or about 20-100 water-soluble polymers, e.g., PEGs, or about 20-50 water-soluble polymers, e.g., PEGs, or about 50-100 water-soluble polymers, e.g., PEGs. The one or more non-naturally-encoded amino acids may be incorporated into the GH, e.g., hGH, at any position described herein. In some embodiments, at least one non-naturally-encoded amino acid is incorporated into the GH, e.g., hGH, at a position corresponding to position 35 of SEQ ID NO: 2. In some embodiments, the non-naturally encoded amino acids include at least one non-naturally encoded amino acid that is a carbonyl-containing non-naturally encoded amino acid, e.g., a ketone-containing non-naturally encoded amino acid such as a para-acetylphenylalanine. In some embodiments, the GH, e.g., hGH, includes a para-acetylphenylalanine. In some embodiments, the para-acetylphenylalanine is incorporated into the GH, e.g., hGH, at a position corresponding to position 35 of SEQ ID NO: 2, where the para-acetylphenylalanine is linked to one of the polymers, e.g., one of the PEGs, by an oxime bond. In some embodiments, at least one of the water-soluble polymers, e.g., PEGs, is linked to the GH, e.g., hGH, by a covalent bond to at least one of the non-naturally-encoded amino acids. In some embodiments, the covalent bond is an oxime bond. In some embodiments, a plurality of the water-soluble polymers, e.g., PEGs, are linked to the GH, e.g., hGH, by covalent bonds to a plurality of the non-naturally-encoded amino acids. In some embodiments, at least one the covalent bonds is an oxime bond; in some embodiments, a plurality of the covalent bonds are oxime bonds; in some embodiments, substantially all of the bonds are oxime bonds. The plurality of water-soluble polymers, e.g., PEG, may be linear, branched, or any combination thereof. In embodiments that incorporate one or more linear PEGs, the linear PEGs have a MW of about 0.1 to about 100 kDa, or about 1 to about 60 kDa, or about 20 to about 40 kDa, or about 30 kDa. In embodiments that incorporate one or more branched PEGs, the branched PEGs have a MW of about 1 to about 100 kDa, or about 30 to about 50 kDa, or about 40 kDa. It will be appreciated that embodiments employing a plurality of water-soluble polymers, e.g., PEGs, will, in general, employ such polymers at lower MWs than embodiments in which a single PEG is used. Thus, in some embodiments, the overall MW of the plurality of PEGs is about 0.1-500 kDa, or about 0.1-200 kDa, or about 0.1-100 kDa, or about 1-1000 kDa, or about 1-500 kDa, or about 1-200 kDa, or about 1-100 kDa, or about 10-1000 kDa, or about 10-500 kDa, or about 10-200 kDa, or about 10-100 kDa, or about 10-50 kDa, or about 20-1000 kDa, or about 20-500 kDa, or about 20-200 kDa, or about 20-100 kDa, or about 20-80 kDa, or about 20-60 kDa, about 5-100 kDa, about 5-50 kDa, or about 5-20 kDa.

Human GH antagonists include, but are not limited to, those with substitutions at: 1, 2, 3, 4, 5, 8, 9, 11, 12, 15, 16, 19, 22, 103, 109, 112, 113, 115, 116, 119, 120, 123, and 127 or an addition at position 1 (i.e., at the N-terminus), or any combination thereof (SEQ ID NO:2, or the corresponding amino acid in SEQ ID NO: 1, 3, or any other GH sequence).

A wide variety of non-naturally encoded amino acids can be substituted for, or incorporated into, a given position in a hGH polypeptide. In general, a particular non-naturally encoded amino acid is selected for incorporation based on an examination of the three dimensional crystal structure of a hGH polypeptide with its receptor, a preference for conservative substitutions (i.e., aryl-based non-naturally encoded amino acids, such as p-acetylphenylalanine or O-propargyl-tyrosine substituting for Phe, Tyr or Trp), and the specific conjugation chemistry that one desires to introduce into the hGH polypeptide (e.g., the introduction of 4-azidophenylalanine if one wants to effect a Huisgen [3+2]cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance that comprises a second reactive group.

In some cases, the non-naturally encoded amino acid substitution(s) will be combined with other additions, substitutions or deletions within the hGH polypeptide to affect other biological traits of the hGH polypeptide. In some cases, the other additions, substitutions or deletions may increase the stability (including but not limited to, resistance to proteolytic degradation) of the hGH polypeptide or increase affinity of the hGH polypeptide for its receptor. In some cases, the other additions, substitutions or deletions may increase the solubility (including but not limited to, when expressed in E. coli or other host cells) of the hGH polypeptide. In some embodiments additions, substitutions or deletions may increase the polypeptide solubility following expression in *E. coli* or other recombinant host cells. In some embodiments sites are selected for substitution with a naturally encoded or non-natural amino acid in addition to another site for incorporation of a non-natural amino acid that results in increasing the polypeptide solubility following expression in *E. coli* or other recombinant host cells. In some embodiments, the hGH polypeptides comprise another addition, substitution or deletion that modulates affinity for the hGH polypeptide receptor, modulates (including but not limited to, increases or decreases) receptor dimerization, stabilizes receptor dimers, modulates circulating half-life, modulates release or bioavailabilty, facilitates purification, or improves or alters a particular route of administration. A number of such alterations are described in U.S. patent application Ser. No. 11/046,432 entitled "Modifed Human Growth Hormone Polypeptides and Their Uses," which is incorporated by reference herein in its entirety. Similarly, hGH polypeptides can comprise protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification or other traits of the polypeptide.

In some embodiments, the substitution of a non-naturally encoded amino acid generates an GH, e.g., hGH antagonist. A subset of exemplary sites for incorporation of one or more non-naturally encoded amino acid include: 1, 2, 3, 4, 5, 8, 9, 11, 12, 15, 16, 19, 22, 103, 109, 112, 113, 115, 116, 119, 120, 123, 127, or an addition before position 1 (SEQ ID NO: 2, or the corresponding amino acid in SEQ ID NO: 1, 3, or any other GH sequence). In some embodiments, GH, e.g., hGH antagonists comprise at least one substitution in the regions 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) that cause GH to act as an antagonist. In other embodiments, the exemplary sites of incorporation of a non-naturally encoded amino acid include residues within the amino terminal region of helix A and a portion of helix C. In another embodiment, substitution of G120 with a non-naturally encoded amino acid such as p-azido-L-phenylalanine or O-propargyl-L-tyrosine. In other embodiments, the above-listed substitutions are combined with additional substitutions that cause the GH, e.g., hGH polypeptide to be an GH, e.g., hGH antagonist. For instance, a non-naturally encoded amino acid is substituted at one of the positions identified herein and a simultaneous substitution is introduced at G120 (e.g., G120R, G120K, G120W, G120Y, G120F, or G120E). In some embodiments, the GH, e.g., hGH antagonist comprises a non-naturally encoded amino acid linked to a water soluble polymer that is present in a receptor binding region of the ;GH, e.g., hGH molecule.

In some cases, 1, 2, 3, 4, 5, 6, 7, 8, 9, 10, or more amino acids are substituted with one or more non-naturally-encoded amino acids. In some cases, the GH, e.g., hGH polypeptide further includes 1, 2, 3, 4, 5, 6, 7, 8, 9, 10, or more substitutions of one or more non-naturally encoded amino acids for naturally-occurring amino acids. For example, in some embodiments, one or more residues in the following regions of GH, e.g., hGH are substituted with one or more non-naturally encoded amino acids: 1-5 (N-terminus); 32-46 (N-terminal end of the A-B loop); 97-105 (B-C loop); and 132-149 (C-D loop); and 184-191 (C-terminus). In some embodiments, one or more residues in the following regions of GH, e.g., hGH are substituted with one or more non-naturally encoded amino acids: 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus). In some cases, the one or more non-naturally encoded residues are linked to one or more lower molecular weight linear or branched PEGs (approximately ~5-20 kDa in mass or less), thereby enhancing binding affinity and comparable serum half-life relative to the species attached to a single, higher molecular weight PEG.

In some embodiments, up to two of the following residues of GH, e.g., hGH are substituted with one or more non-naturally-encoded amino acids at position: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187. In some cases, any of the following pairs of substitutions are made: K38X* and K140X*; K41X* and K145X*; Y35X* and E88X*; Y35X* and F92X*; Y35X* and Y143X*; F92X* and Y143X* wherein X* represents a non-naturally encoded amino acid. Preferred sites for incorporation of two or more non-naturally encoded amino acids include combinations of the following residues: 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187. Particularly preferred sites for incorporation of two or more non-naturally encoded amino acids include combinations of the following residues: 35, 88, 91, 92, 94, 95, 99, 101, 103, 111, 131, 133, 134, 135, 136, 139, 140, 143, 145, and 155.

Preferred sites for incorporation in GH, e.g., hGH of two or more non-naturally encoded amino acids include combinations of the following residues: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e. at the carboxyl terminus of the protein) or any combination thereof from SEQ ID NO: 2.

V. Expression in Non-Eukaryotes and Eukaryotes

To obtain high level expression of a cloned hGH polynucleotide, one typically subclones polynucleotides encoding a hGH polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. Molecular Cloning, A Laboratory Manual (2001) and Ausubel et al. Current Protocols in Molecular Biology (1999).

Bacterial expression systems for expressing hGH polypeptides of the invention are available in, including but not limited to, *E. coli, Bacillus* sp., *Pseudomonas fluorescens, Pseudomonas aeruginosa, Pseudomonas putida,* and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the hGH polypeptides of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O—RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 μg/liter, at least 50 μg/liter, at least 75 μg/liter, at least 100 μg/liter, at least 200 μg/liter, at least 250 μg/liter, or at least 500 μg/liter, at least 1 mg/liter, at least 2mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

Expression systems, vectors, host cells, culturing conditions and medium, and isolation from host cells of hGH polypeptides are further described in U.S. patent application Ser. No. 11/046,432 entitled "Modifed Human Growth Hormone Polypeptides and Their Uses," which is incorporated by reference herein.

V. General Purification Methods

The hGH polypeptides of the present invention are normally purified after expression in recombinant systems. The hGH polypeptide may be purified from host cells by a variety of methods known to the art. hGH polypeptides produced in bacterial host cells may be poorly soluble or insoluble (in the form of inclusion bodies). Amino acid substitutions may readily be made in the hGH polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using techniques known to those of ordinary skill in the art, including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the hGH polypeptides. When handling inclusion bodies of hGH polypeptide, it is advantageous to minimize the homogenization time on repetitions in order to maximize the yield of inclusion bodies without loss due to factors such as solubilization, mechanical shearing or proteolysis.

Insoluble or precipitated hGH polypeptide may then be solubilized using any of a number of suitable solubilization agents known to the art. The hGH polypeptide may be solubilized with urea or guanidine hydrochloride. The volume of the solubilized hGH polypeptide should be minimized so that large batches may be produced using conveniently manageable batch sizes. This factor may be significant in a large-scale commercial setting where the recombinant host may be grown in batches that are thousands of liters in volume. In addition, when manufacturing hGH polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the hGH polypeptide inclusion bodies in place of the harsher denaturing agent guanidine hydrochloride. The use of urea significantly reduces the risk of damage to stainless steel equipment utilized in the manufacturing and purification process of hGH polypeptide while efficiently solubilizing the hGH polypeptide inclusion bodies.

In the case of soluble hGH protein, the hGH may be secreted into the periplasmic space or into the culture medium. In addition, soluble hGH may be present in the cytoplasm of the host cells. It may be desired to concentrate soluble hGH prior to performing purification steps. Standard techniques known to those of ordinary skill in the art may be used to concentrate soluble hGH from, for example, cell lysates or culture medium. In addition, standard techniques known to those of ordinary skill in the art may be used to disrupt host cells and release soluble hGH from the cytoplasm or periplasmic space of the host cells.

When hGH polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved hGH polypeptide may be purified from the cleaved fusion sequence by methods known to those of ordinary skill in the art. Such methods will be determined by the identity and properties of the fusion sequence and the hGH polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

The hGH polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The hGH polypeptide may be separated from the precipitated DNA using standard methods known to those of ordinary skill in the art, including, but not limited to, centrifugation or filtration. Removal of host nucleic acid molecules is an important factor in a setting where the hGH polypeptide is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human hGH polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the hGH polypeptide of the present invention includes separating deamidated and clipped forms of the hGH polypeptide variant from the intact form.

Any of the following exemplary procedures can be employed for purification of hGH polypeptides of the invention: affinity chromatography; anion- or cation-exchange chromatography (using, including but not limited to, DEAE SEPHAROSE); chromatography on silica; high performance liquid chromatography (HPLC), reverse phase HPLC (RP-HPLC); gel filtration chromatography (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach IRL Press at Oxford, Oxford, England; Scopes, (1993) Protein Purification: Principles and Practice 3rd Edition* Springer Verlag, N.Y.; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.,* 268: 14065-14070; Kreitman and Pastan (1993) *Bioconjug. Chem.,* 4: 581-585; and Buchner, et al., (1992) *Anal. Biochem.,* 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of hGH polypeptide, the hGH polypeptide thus produced may be misfolded and thus lacks or has reduced biological activity. The bioactivity of the protein may be restored by "refolding". In general, misfolded hGH polypeptide is refolded by solubilizing (where the hGH polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. hGH polypeptide may be refolded using standard methods known in the art, such as those described in U.S. Pat. Nos. 4,511,502, 4,511,503, and 4,512,922, which are incorporated by reference herein. The hGH polypeptide may also be cofolded with other proteins to form heterodimers or heteromultimers.

After refolding or cofolding, the hGH polypeptide may be further purified. Purification of hGH may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, hGH may be exchanged into different buffers and/or concentrated by any of a variety of methods known to those of ordinary skill in the art, including, but not limited to, diafiltration and dialysis. hGH that is provided as a single purified protein may be subject to aggregation and precipitation.

The purified hGH may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the hGH, the hGH is sufficiently pure for use as a pharmaceutical product or for further processing, such as conjugation with a water soluble polymer such as PEG. Certain hGH molecules may be used as therapeutic agents in the absence of other active ingredients or proteins (other than excipients, carriers, and stabilizers, serum albumin and the like), or they may be complexed with another protein or a polymer.

Any one of a variety of isolation steps may be performed on the cell lysate, extract, culture medium, inclusion bodies, periplasmic space of the host cells, cytoplasm of the host cells, or other material, comprising hGH polypeptide or on any hGH polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristalic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the hGH polypeptide may be reduced and denatured by first denaturing the resultant purified hGH polypeptide in urea, followed by dilution into TRIS buffer containing a reducing agent (such as DTT) at a suitable pH. In another embodiment, the hGH polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured hGH polypeptide mixture may then be further isolated or purified.

As stated herein, the pH of the first hGH polypeptide mixture may be adjusted prior to performing any subsequent isolation steps. In addition, the first hGH polypeptide mixture or any subsequent mixture thereof may be concentrated using techniques known in the art. Moreover, the elution buffer comprising the first hGH polypeptide mixture or any subsequent mixture thereof may be exchanged for a buffer suitable for the next isolation step using techniques known to those of ordinary skill in the art.

Ion Exchange Chromatography Ion exchange chromatography may be performed. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE®

High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the hGH polypeptide at any stage of the purification process to isolate substantially purified hGH polypeptide.

The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding hGH over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, having an hGH binding pH range of about 2.5 to about 6.0. Alternatively, the strong cation exchanger may have an hGH binding pH range of about pH 2.5 to about pH 5.5. The cation exchange matrix may be a strong cation exchanger having an hGH binding pH of about 3.0. Alternatively, the cation exchange matrix may be a strong cation exchanger, having an hGH binding pH range of about 6.0 to about 8.0. The cation exchange matrix may be a strong cation exchanger having an hGH binding pH range of about 8.0 to about 12.5. Alternatively, the strong cation exchanger may have an hGH binding pH range of about pH 8.0 to about pH 12.0.

Prior to loading the hGH, the cation exchange matrix may be equilibrated, for example, using several column volumes of a dilute, weak acid, e.g., four column volumes of 20 mM acetic acid, pH 3. Following equilibration, the hGH may be added and the column may be washed one to several times, prior to elution of substantially purified hGH, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified hGH may be eluted by contacting the cation exchanger matrix with a buffer having a sufficiently low pH or ionic strength to displace the hGH from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes. Moreover, suitable buffers known to those of skill in the art may include, but not limited to, citrate, phosphate, formate, HEPES, and MES buffers ranging in concentration from at least about 5 mM to at least about 100 mM.

Following adsorption of the hGH to the cation exchanger matrix, substantially purified hGH may be eluted by contacting the matrix with a buffer having a sufficiently high pH or ionic strength to displace the hGH from the matrix. The pH of the elution buffer may range from about pH 8.0 to about pH 12.5. More specifically, the elution buffer may range from about pH 8.0 to about pH 12.0. Suitable buffers for use in high pH elution of substantially purified hGH include, but are not limited to, citrate, phosphate, formate, acetate, HEPES, and MES buffers ranging in concentration from at least about 5 mM to at least about 100 mM. In addition, a buffer having 0.1 M potassium borate, 0.6 M potassium chloride, 0.1 mM EDTA, pH 8.7 may be used. Substantially purified hGH may also be eluted using standard buffers, such as a bicine buffer which includes about 50 to 100 mM bicine, about 75 mM bicine; 25 to about 100 mM sodium chloride, about 50 mM sodium chloride, and about 0.05 to about 0.5 EDTA, about 0.1 mM EDTA, pH 7.5.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the hGH polypeptide to isolate substantially purified hGH polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG 1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the hGH polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

hGH may be isolated or purified, for example, using a SOURCE RP column, with an acetonitrile gradient.

Hydrophobic Interaction Chromatography Purification Techniques Hydrophobic interaction chromatography (HIC) may be performed on the hGH polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate)

matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the hGH polypeptide, the column may then washed using standard buffers and conditions to remove unwanted materials but retaining the hGH polypeptide on the HIC column. The hGH polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the hGH molecules. The eluant may then be concentrated, for example, by filtration such as diafiltration or ultrafiltration. Diafiltration may be utilized to remove the salt used to elute the hGH polypeptide.

Isolation steps using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first hGH polypeptide mixture or any subsequent mixture thereof, to remove any excess salts and to replace the buffer with a suitable buffer for the next isolation step or even formulation of the final drug product.

The yield of hGH polypeptide, including substantially purified hGH polypeptide, may be monitored at each step described herein using techniques known to those of ordinary skill in the art. Such techniques may also be used to assess the yield of substantially purified hGH polypeptide following the last isolation step. For example, the yield of hGH polypeptide may be monitored using any of several reverse phase high pressure liquid chromatography columns, having a variety of alkyl chain lengths such as cyano RP-HPLC, $C_{18}$RP-BPLC; as well as cation exchange HPLC and gel filtration HPLC.

Purity may be determined using standard techniques, such as SDS-PAGE, or by measuring hGH polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of hGH polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The hGH polypeptide fractions which are within the IPC limits are pooled.

DEAE Sepharose (GE Healthcare) material consists of diethylaninoethyl (DEAE)-groups which are covalently bound to the surface of Sepharose beads. The binding of hGH polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and hGH polypeptide is eluted with a buffer with increased ionic strength. The column is packed with DEAE Sepharose fast flow. The column volume is adjusted to assure a hGH polypeptide load in the range of 3-10 mg hGH polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, hGH polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays.

A wide variety of methods and procedures can be used to assess the yield and purity of a hGH protein one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art. Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

Procedures including, but not limited to, those listed herein for isolation and purification may also be used in formulation studies to assess the stability of hGH polypeptides of the invention, the stability of PEGylated forms of hGH polypeptides, and progress of the PEGylation reaction.

VII. Expression in Alternate Systems

Several strategies have been employed to introduce unnatural amino acids into proteins in non-recombinant host cells, mutagenized host cells, or in cell-free systems. These systems are also suitable for use in making the hGH polypeptides comprising a non-naturally encoded amino acid. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide*, *J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.*, 428:68 (1998); J. C. van Hest, K. L. Kuck and D. A. Tirrell, *J. Am. Chem. Soc.*, 122:1282 (2000); and, K. L. Kiick and D. A. Tirrell, Tetrahedron, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature*, 192: 1227-1232 (1961); Hoffmann, K., Bohn, H. *Studies on polypeptides. XXXVI. The effect of pyrazole-imidazole replacements on the S-protein activating potency of an S-peptide fragment, J. Am Chem*, 88(24):5914-5919 (1966); Kaiser, E. T. *Synthetic approaches to biologically active peptides and*

*proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183): 243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enzyme active sites, Science,* 226 (4674):505-511 (1984); Neet, K. E., Nanci A, Koshland, D. E. *Properties of thiol-subtilisin, J Biol. Chem,* 243(24):6392-6401 (1968); Polgar, L. et M. L. Bender. *A new enzyme containing a synthetically formed active site. Thiol-subtilisin. J. Am Chem Soc,* 88:3153-3154 (1966); and, Pollack, S. J., Nakayama, G. Schultz, P. G. *Introduction of nucleophiles and spectroscopic probes into antibody combining sites, Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagenesis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{CCCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Lu et al. in Mol Cell. October 2001; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, Science, 268:439 (1995); and, D. A. Dougherty, Curr. Opin. Chem. Biol., 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, J. Biol. Chem., 271:19991 (1996); the incorporation of biotinylated amino acids to identify surface-exposed residues in ion channels, see, e.g., J. P. Gallivan, H. A. Lester and D. A. Dougherty, Chem. Biol., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, Nat. Neurosci., 4:239 (2001).

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998).

It may also be possible to obtain expression of a hGH polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering*, 74:309-316 (2001); Kim, D. M. and J. R. Swartz, *Biotechnology Letters*, 22, 1537-1542, (2000); Kim, D. M., and J. R. Swartz, *Biotechnology Progress*, 16, 385-390, (2000); Kim, D. M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of hGH polypeptides comprising a non-naturally encoded amino acid includes the mRNA-peptide fusion technique. See, e.g., R. Roberts and J. Szostak, *Proc. Natl Acad. Sci.* (USA) 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of hGH polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl Acad. Sci.* (USA) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

VIII Macromolecular Polymers Coupled to hGH Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to hGH polypeptides of the present invention to modulate biological properties of the hGH polypeptide, and/or provide new biological properties to the hGH molecule. These macromolecular polymers can be linked to the hGH polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated hGH polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating-PEG:hGH polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of hGH polypeptide used for therapy gives an acceptable rate of change and maintains the desired change at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the hGH polypeptide by the formula:

$$XO-(CH_2CH_2O)_n-CH_2CH_2-Y$$

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a hGH polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the hGH polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the hGH polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of the PEG may be of a wide range, including but not limited to, between about 100 Da and about 100,000 Da or more. The molecular weight of the PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the PEG is between about 100 Da and 50,000 Da. In some embodiments, the molecular weight of the PEG is between about 100 Da and 40,000 Da. In some embodiments, the molecular weight of the PEG is between about 1,000 Da and 40,000 Da. In some embodiments, the molecular weight of the PEG is between about 5,000 Da and 40,000 Da. In some embodiments, the molecular weight of the PEG is between about 10,000 Da and 40,000 Da. Branched chain PEGs, including but not limited to, PEG molecules with each chain having a MW ranging from 1-100 kDa (including but not limited to, 1-50 kDa or 5-20 kDa) can also be used. The molecular weight of the branched chain PEG may be, including but not limited to, between about 1,000 Da and about 100,000 Da or more. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and 50,000 Da. In some embodiments, the molecular weight of the branched chain PEG is between about 1,000 Da and 40,000 Da. In some embodiments, the molecular weight of the branched chain PEG is between about 5,000 Da and 40,000 Da. In some embodiments, the molecular weight of the branched chain PEG is between about 5,000 Da and 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acid. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the hGH polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula $-CH_2CH_2O-(CH_2CH_2O)_n-CH_2CH_2-$, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and 50,000 Da. In some embodiments, the molecular weight of PEG is between about 100 Da and 40,000 Da. In some embodiments, the molecular weight of PEG is between about 1,000 Da and 40,000 Da. In some embodiments, the molecular weight of PEG is between about 5,000 Da and 40,000 Da. In some embodiments, the molecular weight of PEG is between about 10,000 Da and 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(—PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932, 462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

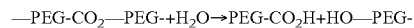

—PEG-CO$_2$—PEG-+H$_2$O→PEG-CO$_2$H+HO—PEG-

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and 50,000 Da. In some embodiments, the molecular weight of each chain of the polymer backbone is between about 100 Da and 40,000 Da. In some embodiments, the molecular weight of each chain of the polymer backbone is between about 1,000 Da and 40,000 Da. In some embodiments, the molecular weight of each chain of the polymer backbone is between about 5,000 Da and 40,000 Da. In some embodiments, the molecular weight of each chain of the polymer backbone is between about 10,000 Da and 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

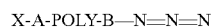

X-A-POLY-B—N=N=N wherein:
N=N=N is an azide moiety;
B is a linking moiety, which may be present or absent;
POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, including but not limited to, between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10, including but not limited to, 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Purification of the crude product can usually be accomplished by methods known in the art including, but are not limited to, precipitation of the product followed by chromatography, if necessary.

Water soluble polymers can be linked to the hGH polypeptides of the invention. The water soluble polymers may be linked via a non-naturally encoded amino acid incorporated in the hGH polypeptide or any functional group or substituent of a non-naturally encoded or naturally encoded amino acid, or any functional group or substituent added to a non-naturally encoded or naturally encoded amino acid. Alternatively, the water soluble polymers are linked to a hGH polypeptide incorporating a non-naturally encoded amino acid via a naturally-occurring amino acid (including but not limited to, cysteine, lysine or the amine group of the N-terminal residue). In some cases, the hGH polypeptides of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the hGH polypeptides of the invention further comprise 1, 2, 3, 4, 5, 6, 7, 8, 9, 10, or more naturally-encoded amino acid(s) linked to water soluble polymers. In some cases, the hGH polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the hGH polypeptide relative to the unconjugated form.

The number of water soluble polymers linked to a hGH polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of hGH is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a hGH polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

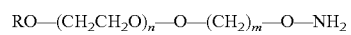

RO—(CH$_2$CH$_2$O)$_n$—O—(CH$_2$)$_m$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

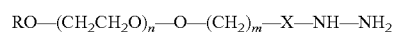

RO—(CH$_2$CH$_2$O)$_n$—O—(CH$_2$)$_m$—X—NH—NH$_2$ where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

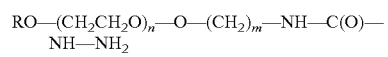

RO—(CH$_2$CH$_2$O)$_n$—O—(CH$_2$)$_m$—NH—C(O)—NH—NH$_2$ where R is a simple alkyl (methyl, ethyl, propyl, etc.), m is 2-10 and n is 100-1,000.

In another embodiment of the invention, a hGH polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

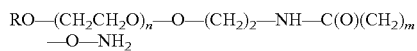

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

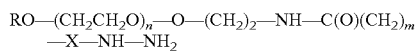

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

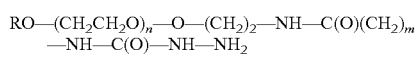

where R is a simple alkyl (methyl, ethyl, propyl, etc.), m is 2-10 and n is 100-1,000.

In another embodiment of the invention, a hGH polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa. Each chain of the branched PEG may have a MW ranging from 5-20 kDa.

In another embodiment of the invention, a hGH polypeptide comprising a non-naturally encoded amino acid is modified with a PEG derivative having a branched structure. For instance, in some embodiments, the hydrazine- or hydrazide-terminal PEG derivative will have the following structure:

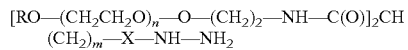

where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

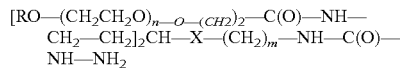

where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

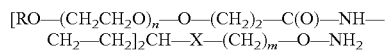

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the hGH polypeptide can modulate the binding of the hGH polypeptide to the hGH polypeptide receptor at Site 1. In some embodiments, the linkages are arranged such that the hGH polypeptide binds the hGH polypeptide receptor at Site 1 with a $K_d$ of about 400 nM or lower, with a $K_d$ of 150 nM or lower, and in some cases with a $K_d$ of 100 nM or lower, as measured by an equilibrium binding assay, such as that described in Spencer et al., *J. Biol. Chem.*, 263:7862-7867 (1988) for hGH.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)). All references and patents cited are incorporated by reference herein.

PEGylation (i.e., addition of any water soluble polymer) of hGH polypeptides containing a non-naturally encoded amino acid, such as p-azido-L-phenylalanine, is carried out by any convenient method. For example, hGH polypeptide is PEGylated with an alkyne-terminated mPEG derivative. Briefly, an excess of solid mPEG(5000)—O—CH$_2$—C≡CH is added, with stirring, to an aqueous solution of p-azido-L-Phe-containing hGH polypeptide at room temperature. Typically, the aqueous solution is buffered with a buffer having a pK$_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated hGH polypeptide variants from free mPEG(5000)—O—CH$_2$—C≡CH and any high-molecular weight complexes of the PEGylated hGH polypeptide which may form when unblocked PEG is activated at both ends of the molecule, thereby crosslinking hGH polypeptide variant molecules. The conditions during hydrophobic interaction chromatography are such that free mPEG(5000)—O—CH$_2$—C≡CH flows through the column, while any crosslinked PEGylated hGH polypeptide variant complexes elute after the desired forms, which contain one hGH polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

If necessary, the PEGylated hGH polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, Ariz. in PROTEIN PURIFICATION METHODS, A PRACTICAL APPROACH (Harris & Angal, Eds.) IRL Press 1989, 293-306). The purity of the hGH-PEG conjugate can be assessed by proteolytic degradation (including but not limited to, trypsin cleavage) followed by mass spectrometry analysis. Pepinsky RB, et al., *J. Pharmcol. & Exp. Ther.* 297(3):1059-66 (2001).

A water soluble polymer linked to an amino acid of a hGH polypeptide of the invention can be further derivatized or substituted without limitation.

Other PEG Derivatives and General PEGylation Techniques

Azide-containing, alkyne-containing, and phosphine-containing PEG derivatives are described in U.S. patent application Ser. No. 11/046,432, entitled "Modifed Human Growth Hormone Polypeptides and Their Uses".

Other exemplary PEG molecules that may be linked to hGH polypeptides, as well as PEGylation methods include those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229, 108, EP 402,378, WO 92/16555, WO 94/04193, WO 94/14758, WO 94/17039, WO 94/18247, WO 94/28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof. U.S. patent application Ser. No. 11/046, 432 entitled "Modified Human Growth Hormone Polypeptides and Their Uses," which is incorporated by reference, provides further discussion of PEG and forms thereof.

IX. Measurement of Potency, Functional In Vivo Half-Life, and Pharmacokinetic Parameters An important aspect of the invention is the prolonged biological half-life that is obtained by construction of the hGH polypeptide with or without conjugation of the polypeptide to a water soluble polymer moiety. The rapid decrease of hGH polypeptide serum concentrations has made it important to evaluate biological responses to treatment with conjugated and non-conjugated hGH polypeptide and variants thereof. The conjugated and non-conjugated hGH polypeptide and variants thereof of the present invention may have prolonged serum half-lives also after subcutaneous or i.v. administration, making it possible to measure by, e.g. ELISA method or by a primary screening assay. ELISA or RIA kits from either BioSource International (Camarillo, Calif.) or Diagnostic Systems Laboratories (Webster, Tex.) may be used. Measurement of in vivo biological half-life is carried out as described herein.

The potency and functional in vivo half-life of an hGH polypeptide comprising a non-naturally encoded amino acid can be determined according to the protocol described in Clark, R., et al., *J. Biol. Chem.* 271(36):21969-21977 (1996).

Pharmacokinetic parameters for a hGH polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a hGH polypeptide comprising a non-naturally encoded amino acid not conjugated to a water soluble polymer and about 4 days for a hGH polypeptide comprising a non-naturally encoded amino acid and conjugated to a water soluble polymer. Pharmacokinetic data for hGH polypeptides is well-studied in several species and can be compared directly to the data obtained for hGH polypeptides comprising a non-naturally encoded amino acid. See Mordenti J., et al., *Pharm. Res.* 8(11): 1351-59 (1991), which is incorporated by reference herein, for studies related to hGH.

Pharmacokinetic parameters can also be evaluated in a primate, e.g., cynomolgus monkeys. A single injection may be administered either subcutaneously or intravenously, and serum hGH levels are monitored over time.

The specific activity of hGH polypeptides in accordance with this invention can be determined by various assays known in the art. The biological activity of the hGH polypeptide muteins, or fragments thereof, obtained and purified in accordance with this invention can be tested by methods described or referenced herein or known to those of ordinary skill in the art.

X. Administration and Pharmaceutical Compositions

The polypeptides or proteins of the invention (including but not limited to, hGH, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a hGH polypeptide modified to include one or more unnatural amino acids to a natural amino acid hGH polypeptide), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

hGH polypeptides of the invention, including but not limited to PEGylated hGH, may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The hGH polypeptide, including but not limited to PEGylated hGH, comprising a non-naturally encoded amino acid may be used alone or in combination with other suitable components such as a pharmaceutical carrier.

The hGH polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of hGH can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, and/or any other pharmaceutically delivered protein), along with formulations in current use, provide preferred routes of administration and formulation for the polypeptides of the invention.

The viscosity and formulation profiles of the polypeptide composition may allow administration with a small gauge needle by using smaller plunger pressures compared to conventional formulations. Smaller gauge needles including, but not limited to, 27, 28, 29, 30, or 31 gauge needles may be used to administer the polypeptide composition of the present invention to subjects. U.S. Pat. No. 6,875,432, which is incorporated by reference herein, discusses the viscosity of protein formulations and problems associated with viscosity of protein formulations for subcutaneous administration. Small gauge needles are an advantage due to reduced pain of injection which improves patient compliance with dosing regimens. Smaller plunger pressures needed for injecting render the hGH polypeptide, including but not limited to PEGylated hGH, easier to administer with short injection duration. Types of needles include, but are not limited to, pen needles, thin walled, normal walled, and luer needles.

Viscosity may be measured by standard techniques known to those of ordinary skill in the art. "Viscosity" may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. If one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density:

$$\text{Absolute Viscosity} = \text{Kinematic Viscosity} \times \text{Density}$$

The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human hGH polypeptides of the invention can be administered directly to a mammalian subject. Administration is by any of the routes normally used for introducing hGH polypeptide to a subject. The hGH polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampules and vials. hGH polypeptides of the invention can be prepared in a mixture in a unit dosage injectable form (including but not limited to, solution, suspension, or emulsion) with a pharmaceutically acceptable carrier or excipient. hGH polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the present invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include, but are not limited to, buffers containing succinate, phosphate, borate, HEPES, citrate, histidine or histidine derivatives, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, histidine or histidine derivatives, methionine, asparagine, arginine, glutamate, or lysine; monosaccharides, disaccharides, and other carbohydrates, including but not limited to, trehalose, sucrose, glucose, mannose, or dextrins; chelating agents including but not limited to, EDTA; divalent metal ions including but not limited to, zinc, cobalt, or copper; sugar alcohols including but not limited to, mannitol or sorbitol; salt-forming counter ions including but not limited to, sodium; and/or nonionic surfactants including but not limited to Tween™ (including but not limited to, Tween 80 (polysorbate 80) and Tween 20 (polysorbate 20; PS20)), Pluronics™ and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated hGH against one or more stresses including but not limited to stress that results from agitation. Some of the above may be referred to as "bulking agents." Some may also be referred to as "tonicity modifiers." Additional carriers include, but are not limited to, ammonium sulfate (($NH_4$)$_2SO_4$). Ammonium sulfate (($NH_4$)$_2$ $SO_4$) may be used in a formulation of the present invention at a range of about 0.1 mM to about 200 mM, including but not limited to, 200 mM, 190 mM, 180 mM, 170 mM, 160 mM, 150 mM, 140 mM, 130 mM, 120 mM, 110 mM, 100 mM, 95 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 15 mM, 10 mM, 5 mM, 1 mM, 0.9 mM, 0.8 mM, 0.7 mM, 0.6 mM, 0.5 mM, 0.4 mM, 0.3 mM, 0.2 mM, and 0.1 mM. Histidine may be used in a formulation of the present invention at a range of about 0.1 mM to about 200 mM, including but not limited to, 200 mM, 190 mM, 180 mM, 170 mM, 160 mM, 150 mM, 140 mM, 130 mM, 120 mM, 110 mM, 100 mM, 95 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 15 mM, 10 mM, 5 mM, 1 mM. 0.9 mM, 0.8 mM, 0.7 mM, 0.6 mM, 0.5 mM, 0.4 mM, 0.3 mM, 0.2 mM, and 0.1 mM. In some embodiments, Histidine is between about 5 mM and about 30 mM in the formulation.

A buffer of a formulation of the present invention may be in a range of about 0.1 mM to about 200 mM, including but not limited to, 200 mM, 190 mM, 180 mM, 170 mM, 160 mM, 150 mM, 140 mM, 130 mM, 120 mM, 110 mM, 100 mM, 95 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 19 mM, 18 mM, 17mM, 16mM, 15 mM, 14 mM, 13 mM, 12 mM, 11 mM, 10 mM, 9 mM, 8 mM, 7 mM, 6 mM, 5 mM, 4 mM, 3 mM, 2 mM, 1 mM, 0.9 mM, 0.8 mM, 0.7 mM, 0.6 mM, 0.5 mM, 0.4 mM, 0.3 mM, 0.2 mM, and 0.1 mM. In some embodiments, the buffer is at a concentration of about 0.1 mM to about 200 mM. In some embodiments, the buffer is at a concentration of about 1 mM to about 75 mM. In some embodiments, the buffer is at a concentration of about 1 mM to about 20 mM. In some embodiments, the buffer is at a concentration of about 5 mM to about 30 mM. The buffer of a formulation of the present invention may provide a pH range from about pH 4.0 to about pH 8.5, including but not limited to, pH 8.5, pH 8.0, pH 7.5, pH 7.0, pH 6.5, pH 6.0, pH 5.5, pH 5.0, pH 4.5 and pH 4.0. The pH is any tenth pH value within those enumerated above; for example, pH 8.5, pH 8.4, pH 8.3, pH 8.2, pH 8.1, pH 8.0, pH 7.9, pH 7.8, pH 7.7, pH 7.6, pH 7.5, pH 7.4, pH 7.3, pH 7.2, pH 7.1, pH 7.0, pH 6.9, pH 6.8, pH 6.7, pH 6.6, pH 6.5, pH 6.4, pH 6.3, pH 6.2, pH 6.1, pH 6.0, pH 5.9, pH 5.8, pH 5.7, pH 5.6, pH 5.5, pH 5.4, pH 5.3, pH 5.2, pH 5.1, pH 5.0, pH 4.9, pH 4.8, pH 4.7, pH 4.6, pH 4.5, pH 4.4, pH 4.3, pH 4.2, pH 4.1, and pH 4.0. In some embodiments, the pH is between about pH 6.0 and about pH 7.3. In some embodiments, the pH is between about pH 5.5 and about 8.0. In some embodiments, the pH is between about 4.0 and about 8.5. In some embodiments, the pH is between about 4.0 and about 7.5. In some embodiments, the pH is between about 6.0 and about 7.5.

An amino acid of a formulation of the present invention may be in a range of about 0.1 g/L to 100 g/L, including but not limited to, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/L, 35 g/L, 30 g/L, 25 g/L, 20 g/L, 19 g/L, 18 g/L, 17 g/L, 16 g/L, 15 g/L, 14 g/L, 13 g/L, 12 g/L, 11 g/L, 10 g/L, 9 g/L, 8 g/L, 7 g/L, 6 g/L, 5 g/L, 4 g/L, 3 g/L, 2 g/L, 1 g/L, 0.9 g/L, 0.8 g/L, 0.7 g/L, 0.6 g/L, 0.5 g/L, 0.4 g/L, 0.3 g/L, 0.2 g/L, and 0.1 g/L. In some embodiments, the amino acid is between about 0.1 g/L and 60 g/L. In some embodiments, the amino acid is between about 0.1 g/L and 100 g/L. In some embodiments, the amino acid is between about 1 g/L and 50 g/L. In some embodiments, the amino acid is between about 5 g/L and 25 g/L.

A sugar alcohol of a formulation of the present invention may be in a range of about 0.1 g/L to 100 g/L, including but not limited to, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/L, 35 g/L, 30 g/L, 25 g/L, 20 g/L, 19 g/L, 18 g/L, 17 g/L, 16 g/L, 15 g/L, 14 g/L, 13 g/L, 12 g/L, 11 g/L, 10 g/L, 9 g/L, 8 g/L, 7 g/L, 6 g/L, 5 g/L, 4 g/L, 3 g/L, 2 g/L, 1 g/L, 0.9 g/L, 0.8 g/L, 0.7 g/L, 0.6 g/L, 0.5 g/L, 0.4 g/L, 0.3 g/L, 0.2 g/L, and 0.1 g/L. In some embodiments, the sugar alcohol is between about 0.1 g/L and about 60 g/L. In some embodiments, the sugar alcohol is between about 0.1 g/L and about 100 g/L. In some embodiments, the sugar alcohol is between about 1 g/L and about 50 g/L. In some embodiments, the sugar alcohol is between about 2 g/L and about 25 g/L.

A carbohydrate of a formulation of the present invention may be in a range of about 0.1 g/L to 100 g/L, including but not limited to, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/L, 35 g/L, 30 g/L, 25 g/L, 20 g/L, 19 g/L, 18 g/L, 17 g/L, 16 g/L, 15 g/L, 14 g/L, 13 g/L, 12 g/L, 11 g/L, 10 g/L, 9 g/L, 8 g/L, 7 g/L, 6 g/L, 5 g/L, 4 g/L, 3 g/L, 2 g/L, 1 g/L, 0.9 g/L, 0.8 g/L, 0.7 g/L, 0.6 g/L, 0.5 g/L, 0.4 g/L, 0.3 g/L, 0.2 g/L, and 0.1 g/L. In some embodiments, the carbohydrate is at about 0.1 g/L to about 100 g/L. In some embodiments, the carbohydrate is at about 1 g/L to about 50 g/L. In some embodiments, the carbohydrate is at about 2 g/L to about 25 g/L. In some embodiments, the carbohydrate is at about 0.1 g/L to about 50 g/L.

A disaccharide of a formulation of the present invention may be in a range of about 0.1 g/L to 100 g/L, including but not limited to, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/L, 35 g/L, 30 g/L, 25 g/L, 20 g/L, 19 g/L, 18 g/L, 17 g/L, 16 g/L, 15 g/L, 14 g/L, 13 g/L, 12 g/L, 11 g/L, 10 g/L, 9 g/L, 8 g/L, 7 g/L, 6 g/L, 5 g/L, 4 g/L, 3 g/L, 2 g/L, 1 g/L, 0.9 g/L, 0.8 g/L, 0.7 g/L, 0.6 g/L, 0.5 g/L, 0.4 g/L, 0.3 g/L, 0.2 g/L, and 0.1 g/L. In some embodiments, the disaccharide is between about 0.1 g/L and about 50 g/L.

A monosaccharide of a formulation of the present invention may be in a range of about 0.1 g/L to 100 g/L, including but not limited to, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/L, 35 g/L, 30 g/L, 25 g/L, 20 g/L, 19 g/L, 18 g/L, 17 g/L, 16 g/L, 15 g/L, 14 g/L, 13 g/L, 12 g/L, 11 g/L, 10 g/L, 9 g/L, 8 g/L, 7 g/L, 6 g/L, 5 gL, 4 g/L, 3 g/L, 2 g/L, 1 g/L, 0.9 g/L, 0.8 g/L, 0.7 g/L, 0.6 g/L, 0.5 g/L, 0.4 g/L, 0.3 g/L, 0.2 g/L, and 0.1 g/L.

A non-ionic surfactant of a formulation of the present invention may be in a range of about 0.01% to about 10%, including but not limited to, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.0085%, 0.008%, 0.0075%, 0.007%, 0.0065%, 0.006%, 0.0055%, 0.005%, 0.0045%, 0.004%, 0.0035%, 0.003%, 0.0025%, 0.002%, 0.0015% 0.001%, 0.0009%, 0.0008%, 0.0007%, 0.0006%, 0.0005%, 0.0004%, 0.0003%, 0.0002%, and 0.0001%. In some embodiments, the non-ionic surfactant is at about 0.0001% to about 10%. In some embodiments, the non-ionic surfactant is at about 0.01% to about 10%. In some embodiments, the non-ionic surfactant is at about 0.1% to about 5%. In some embodiments, the non-ionic surfactant is at about 0.1% to about 1%. In some embodiments, the non-ionic surfactant is at about 0.0001% to about 1%.

The pharmaceutical quantity of hGH in a formulation of the present invention may be in a range of about 0.1 mg to about 50 mg, including but not limited to, 50 mg, 49 mg, 48 mg, 47 mg, 46 mg, 45 mg, 44 mg, 43 mg, 42 mg, 41 mg, 40 mg, 39 mg, 38 mg, 37 mg, 36 mg, 35 mg, 34 mg, 33 mg, 32 mg, 31 mg, 30 mg, 29.5 mg, 29 mg, 28.5 mg, 28 mg, 27.5 mg, 27 mg, 26.5 mg, 26 mg, 25.5 mg, 25 mg, 24.5 mg, 24 mg, 23.5 mg, 23 mg, 22.5 mg, 22 mg, 21.5 mg, 21 mg, 20.5 mg, 20 mg, 19.5 mg, 19 mg, 18.5 mg, 18 mg, 17.5 mg, 17 mg, 16.5 mg, 16 mg, 15.5 mg, 15 mg, 14.5 mg, 14 mg, 13.5 mg, 13 mg, 12.5 mg, 12 mg, 11.5 mg, 11 mg, 10.5 mg, 10 mg, 9.5 mg, 9 mg, 8.5 mg, 8 mg, 7.5 mg, 7.0 mg, 6.5 mg, 6.0 mg, 5.5 mg, 5.0 mg, 4.5 mg, 4.0 mg, 3.5 mg, 3.0 mg, 2.5 mg, 2.0 mg, 1.5 mg, 1.0 mg, 0.9 mg, 0.8 mg, 0.7 mg, 0.6 mg, 0.5 mg, 0.4 mg, 0.3 mg, 0.2 mg, and 0.1 mg. In some embodiments, the pharmaceutical quantity of hGH in a formulation is between about 2 mg and about 30 mg. In some embodiments, the pharmaceutical quantity of hGH in a formulation is between about 2 mg and about 25 mg. In some embodiments, the pharmaceutical quantity of hGH in a formulation is between about 0.1 mg and about 30 mg. In some embodiments, the pharmaceutical quantity of hGH in a formulation is between about 0.1 mg and about 8 mg. In some embodiments, the pharmaceutical quantity of hGH in a formulation is between about 0.5 mg and about 8 mg. In some embodiments, the pharmaceutical quantity of hGH in a formulation is between about 0.5 mg and about 6 mg. In some embodiments, the pharmaceutical quantity of hGH in a formulation is between about 1 mg and about 5 mg.

hGH polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamnate (Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. USA*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped hGH polypeptides can be prepared by methods described in, e.g., DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the hGH polypeptide of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available hGH polypeptide products approved for use in humans. Generally, a PEGylated hGH polypeptide of the invention can be administered by any of the routes of administration described above.

XI. Therapeutic Uses of hGH Polypeptides of the Invention

The hGH polypeptides of the invention are useful for treating a wide range of disorders.

The hGH agonist polypeptides of the invention may be useful, for example, for treating growth deficiency, immune disorders, and for stimulating heart function. Individuals with growth deficiencies include, e.g., individuals with Turner's Syndrome, GH-deficient individuals (including children), children who experience a slowing or retardation in their normal growth curve about 2-3 years before their growth plate closes (sometimes known as "short normal children"), and individuals where the insulin-like growth factor-I (IGF-I) response to GH has been blocked chemically (i.e., by glucocorticoid treatment) or by a natural condition such as in adult patients where the IGF-I response to GH is naturally reduced. The hGH polypeptides of the invention may be useful for treating individuals with the following conditions: pediatric growth hormone deficiency, idiopathic short stature, adult growth hormone deficiency of childhood onset, adult growth hormone deficiency of adult onset, or secondary growth hormone deficiency. Adults diagnosed with growth hormone deficiency in adulthood may have had a pituitary tumor or radiation. Conditions including but not limited to, metabolic syndrome, head injury, obesity, osteoporosis, or depression may result in growth hormone deficiency-like symptoms in adults.

An agonist hGH variant may act to stimulate the immune system of a mammal by increasing its immune function, whether the increase is due to antibody mediation or cell mediation, and whether the immune system is endogenous to the host treated with the hGH polypeptide or is transplanted from a donor to the host recipient given the hGH polypeptide (as in bone marrow transplants). "Immune disorders" include any condition in which the immune system of an individual has a reduced antibody or cellular response to antigens than normal, including those individuals with small spleens with reduced immunity due to drug (e.g., chemotherapeutic) treatments. Examples individuals with immune disorders include, e.g., elderly patients, individuals undergoing chemotherapy or radiation therapy, individuals recovering from a major illness, or about to undergo surgery, individuals with AIDS, Patients with congenital and acquired B-cell deficiencies such as hypogammaglobulinemia, common varied agammaglobulinemia, and selective immunoglobulin deficiencies (e.g., IgA deficiency, patients infected with a virus such as rabies with an incubation time shorter than the immune response of the patient; and individuals with hereditary disorders such as diGeorge syndrome.

hGH antagonist polypeptides of the invention may be useful for the treatment of gigantism and acromegaly, diabetes and complications (diabetic retinopathy, diabetic neuropathy) arising from diabetes, vascular eye diseases (e.g., involving proliferative neovascularization), nephropathy, and GH-responsive malignancies.

Vascular eye diseases include, e.g., retinopathy (caused by, e.g., prematurity or sickle cell anemia) and macular degeneration.

GH-responsive malignancies include, e.g., Wilm's tumor, sarcomas (e.g., osteogenic sarcoma), breast, colon, prostate, and thyroid cancer, and cancers of tissues that express GH receptor mRNA (i.e., placenta, thymus, brain, salivary gland, prostate, bone marrow, skeletal muscle, trachea, spinal cord, retina, lymph node and from Burkitt's lymphoma, colorectal carcinoma, lung carcinoma, lymphoblastic leukemia, and melanoma).

The GH, e.g., hGH agonist polypeptides of the invention may be useful, for example, for treating chronic renal failure, growth failure associated with chronic renal insufficiency (CRI), short stature associated with Turner Syndrome, pediatric Prader-Willi Syndrome (PWS), HIV patients with wasting or cachexia, children born small for gestational age (SGA), obesity, and osteoporosis.

Average quantities of the hGH may vary and in particular should be based upon the recommendations and prescription of a qualified physician. The exact amount of hGH is a matter of preference subject to such factors as the exact type of condition being treated, the condition of the patient being treated, as well as the other ingredients in the composition. The amount to be given may be readily determined by one of ordinary skill in the art based upon therapy with hGH.

Pharmaceutical compositions of the invention may be manufactured in conventional manner.

XII. Articles of Manufacture

In another embodiment of the invention, an article of manufacture is provided which contains the formulation of the present invention and provides instructions for its use. The article of manufacture comprises a container. The article of manufacture may contain the formulation of the present invention, including but not limited to, lyophilized, liquid, spray dried, frozen or other forms thereof, and instructions for its preparation or reconstitution, if required. Suitable containers include, but are not limited to, for example, bottles, vials, syringes, auto-injection devices, and test tubes. The container may be formed from a variety of materials such as glass or plastic. The container holds the formulation and the label on, or associated with, the container may indicate directions for reconstitution of the lyophilized formulation, if required, and/or use. For example, the label may indicate that the formulation is reconstituted to specific protein concentrations. The label may further indicate that the formulation is useful or intended for subcutaneous administration. The container holding the formulation may be a single-use or a multi-use vial. In one embodiment, the container holding the formulation is a single-use vial. The article of manufacture may further comprise a second container comprising a suitable diluent. In one embodiment, the suitable diluent is sterile water or bacteriostatic water for injection, USP. Upon mixing of a diluent and the lyophilized formulation, if required, the final protein concentration in the formulation may generally be between about 2 mg/ml and about 50 mg/ml. Upon mixing of a diluent and the lyophilized formulation, if required, the final protein concentration in the formulation may generally be between about 2 mg/ml and about 25 mg/ml. The final protein concentration in the formulation may generally be between about 2 mg/ml and about 25 mg/ml. In one embodiment, the final protein concentration is about 8 mg/ml. The article of manufacture may further include other materials desirable from a commercial and user standpoint, including other buffers, diluents, filters, needles, syringes, and package inserts with instructions for use.

EXAMPLES

The following examples are offered to illustrate, but not to limit the claimed invention.

Example 1

Materials and Methods for Formulations for Met-Y35pAF hGH

This example describes a formulations study that identified and evaluated suitable conditions and excipients that preserve the protein structure and activity of Met-Y35pAF hGH during storage before conjugation with PEG. Liquid formulations of hGH are frozen formulations which contain (1) 2.5 g/L sodium bicarbonate, 20 g/L glycine, 2 g/L mannitol, 2 g/L lactose, at pH 7.3; or 2) sodium citrate, 20 g/L glycine, 5 g/L mannitol, at pH 6.0. An estimated dose of 0.5-4 mg/ml of PEG-hGH is added as an active ingredient. These formulations are currently stored at −20° C. Development of a single-dose lyophilized formulation of PEGylated hGH comprising a non-naturally encoded amino acid or liquid formulation of PEGylated hGH comprising a non-naturally encoded amino acid is desired.

Methods

Several methods were implemented to characterize the physical and chemical stability of Met-Y35pAF hGH. These methods may be used in the formulations study with PEGylated hGH.

SDS-PAGE with a Reducing Gel (SDS-PAGE-R) provided separations of hGH based exclusively on molecular weight allowing any potential degradation products to be visualized, since this technique results in all disulfide bonds being completely cleaved and causes the polypeptides to be completely unfolded. SDS-PAGE with a Non-reducing Gel (SDS-PAGE-NR) provided separation of molecules based on molecular weight, allowing the identification of potential dimers of hGH since the protein is unfolded without a reducing agent, thus leaving disulfide bonds intact.

Differential Scanning Calorimetry (DSC) was used to measure the ΔH (enthalpy) of unfolding due to heat denaturation. This technique evaluated the effects of different solution conditions and excipients on protein stability which was reflected in either an increase or decrease in the overall melting temperature ($T_m$) of the protein. Another technique used was Reverse Phase HPLC (RP-HPLC) to separate molecules on the basis of relative hydrophobicities. Specifically, this method was used to separate hGH based on subtle differences in hydrophobicity and retention behavior associated with structural modifications such as deamidation and oxidation.

Matrix and Solutions

A Formulations Matrix of forty-eight combinations was designed with either U.S.P. (U.S. Pharmacopeia) grade or high analytical grade excipients. The matrix, sample preparation, and procedures used were as follows (Table 1):

| | Excipients* | A 20 mM Sodium Acetate pH 4.5 | B 20 mM Sodium Citrate pH 6.0 | C 50 mM Histidine pH 6.5 | D 50 mM Sodium Phosphate pH 7.0 | E 50 mM Sodium Bicarbonate pH 7.3 | F 50 mM HEPES pH 7.5 |
|---|---|---|---|---|---|---|---|
| 1 | No additions | | | | | | |
| 2 | 15 mM Trehalose | | | | | | |
| 3 | 15 mM Sucrose | | | | | | |
| 4 | 15 mM Mannitol | | | | | | |
| 5 | 75 mM $(NH_4)_2SO_4$ | | | | | | |
| 6 | 250 mM Glycine | | | | | | |
| 7 | 250 mM Arginine | | | | | | |
| 8 | 100 mM Glutamate | | | | | | |

Stocks of all excipients were sterile filtered, dated and stored at 4° C. Sugars were made as 100 mM stocks, $(NH_4)SO_4$ as 1 M stock, and amino acids at the following stock concentrations: 1M Glycine, 666 mM Arginine, or 1M Glutamate.

The specific buffers were prepared the day of experiment as 250 mM to 1M stocks (sterile filtered and dated), and excipients were added to the final concentration, sterile filtered and stored at 4° C.

Sample Preparation

The sample of methionyl-hGH with the non-natural amino acid p-acetyl-phenylalanine substituted at position 35 (MetY35pAF cB1) in WHO buffer was allocated into 6 different vials at 4.425 mg/ml and frozen at −80° C. until the day of the study. On the day of experiment, MetY35pAF was buffer exchanged into the specific buffer at 4° C. by dialysis in 0.1-0.5 mL Slide-a-lyzers. Approximately 800 µl of 425 mg/ml Met-Y35pAF hGH was dialyzed in 250 mL buffer for at least four hours, and the dialysis buffer was changed (250 mL) for overnight dialysis. Using 500 mL provided a 10,000,000-fold dilution of WHO buffer excipients.

Samples were removed from dialysis and concentrations were measured. Each sample was diluted to the appropriate concentration. For DSC, the desired final concentration was 0.75 mg/ml (450 ul volume). For RP-HPLC, the final concentration was 2 mg/ml (30 ul volume). Ten samples were analyzed on RP-HPLC for each individual group of the matrix. Enough sample to allow for four time points (3 days, 1 week, 2 weeks, and I months) was stored in a tube at 4° C. Enough sample for 5 freeze/thaw cycles was stored in a vial at −80° C. There may have been one or two additional freeze/thaw cycles prior to the number of freeze/thaw cycles (1, 2, 3, 4 and 5 cycles) completed as part of this study. The sample for the 0 time point at 4° C. was immediately placed in an HPLC vial.

For SDS-PAGE-R, 30 ug (0.015 mL @ 2 mg/mL) of material was used in the analysis. Samples were aliquoted into three vials as indicated for RP-HPLC.

For SDS-PAGE-NR, 30 ug (0.015 mL @ 2 mg/mL) of material was used in the analysis. Samples were aliquoted into three vials as indicated for RP-HPLC. In all cases, any remaining sample was immediately frozen at −80° C.

Example 2

Results of Formulation Study for Met-Y35pAF hGH

Buffer pH

The pH of all formulation buffers was analyzed after six weeks at 4° C. It was found that the pH of all buffers chosen was stable over a six week period, with the exception of the sodium bicarbonate buffer (Group E) as shown in FIG. 1. The pH of Group E increased over time.

SDS-PAGE-R and SDS-PAGE-NR

Figure 2:
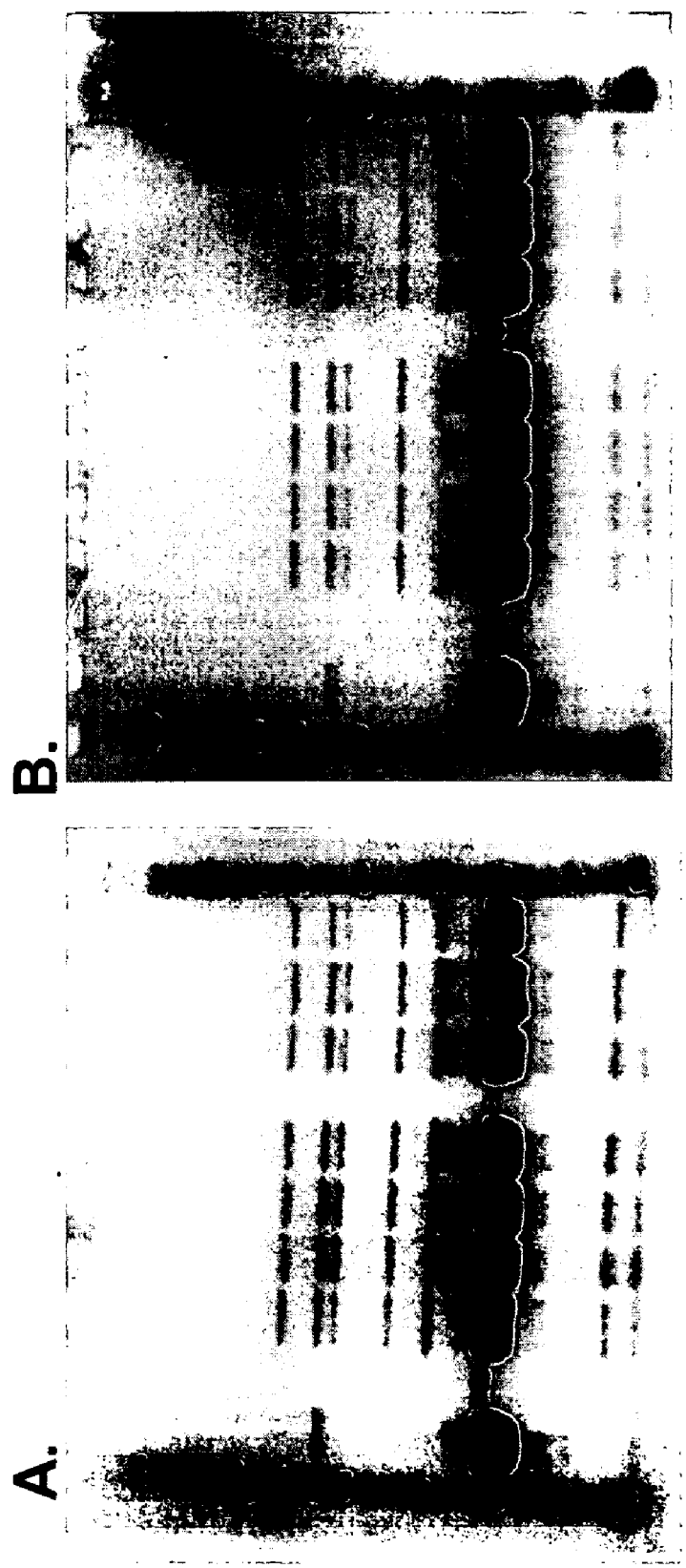
FIG. 2 shows SDS-PAGE reducing (FIGS. 2C and 2D) and non-reducing gels (FIGS. 2A and 2B) of Met Y35pAF hGH. Gels in FIGS. 2A and 2B are loaded as follows: Lane 1: MW, Lane 2: WHO hGH, Lane 3: WHO hGH 1%; Lane 4: A1; Lane 5: A2; Lane 6: A3; Lane 7: A4; Lane 8: A5; Lane 9: A6; Lane 10: A7; Lane 11: A8; Lane 12: MW. Gels in FIGS. 2C and 2D are loaded as follows: Lane 1: MW, Lane 2: WHO hGH, Lane 3: WHO hGH 1%; Lane 4: B1; Lane 5: B2; Lane 6: B3; Lane 7: B4; Lane 8: B5; Lane 9: B6; Lane 10: B7; Lane 11: B8; Lane 12: MW.

Analysis of samples with SDS-PAGE reducing and non-reducing gels showed no change either after four weeks (1 month) at 4° C. or during five freeze/thaw cycles. No dimer formation or degradation products were found by this method. Reducing gels for group A (at t=0, t=4 weeks at 4° C.) are shown as FIGS. 2C and 2D, and non-reducing gels for group B (at t=0, t=4 weeks at 4° C.) are shown as FIGS. 2A and 2B.

Differential Scanning Calorimetry (DSC)

The effects of buffer and excipient on thermal stability of MetY35pAF hGH are shown as FIGS. 3-8. FIGS. 3A-F shows overlaid thermoprofiles of formulation groups A-F. FIG. 5 provides a table summarizing the DSC melting temperatures and changes to $T_m$ for the full matrix. Thermoprofiles from B7 and F2 of the matrix are shown in FIGS. 4A-B.

Figure 3:
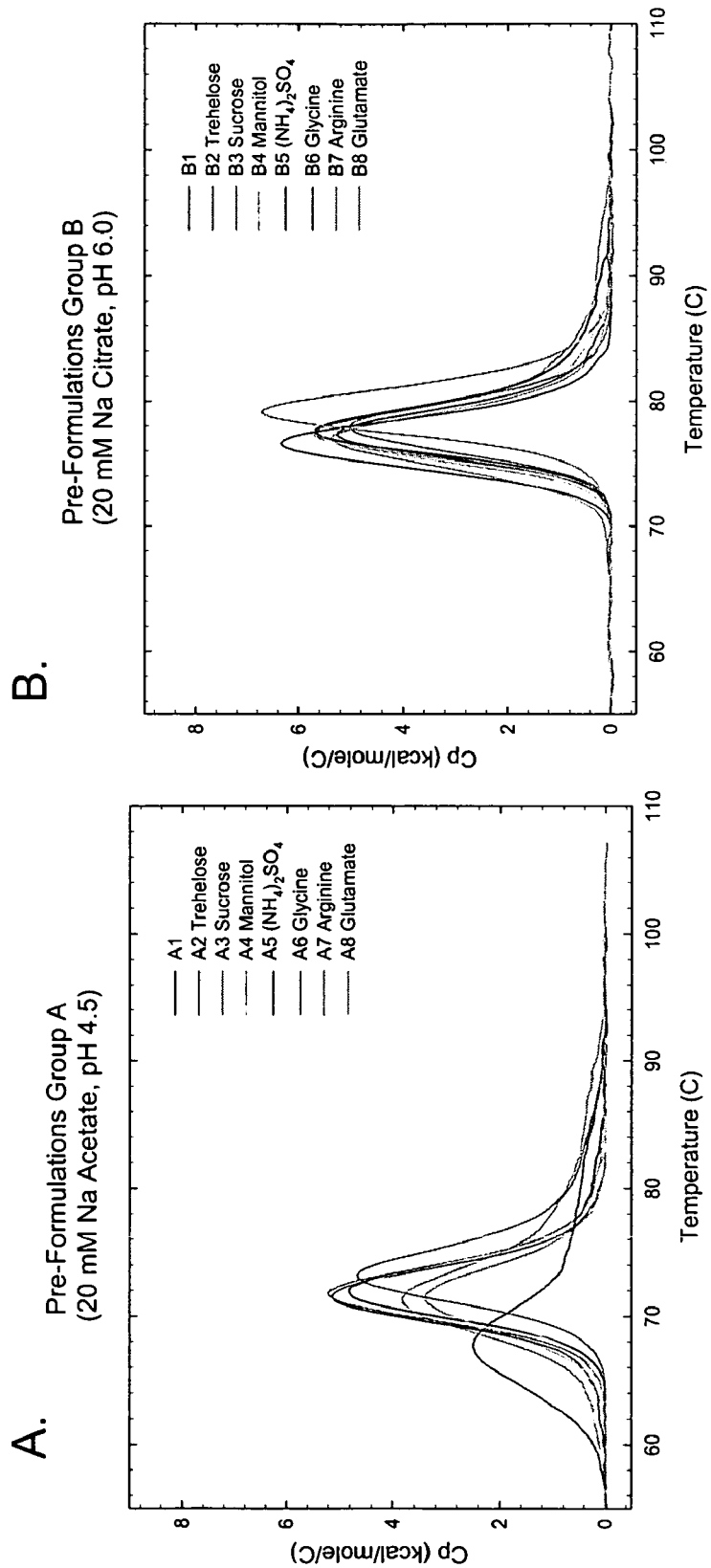
FIGS. 3A-F shows Differential Scanning Calorimetry (DSC) thermoprofiles of formulation groups A-F.
Figure 3:
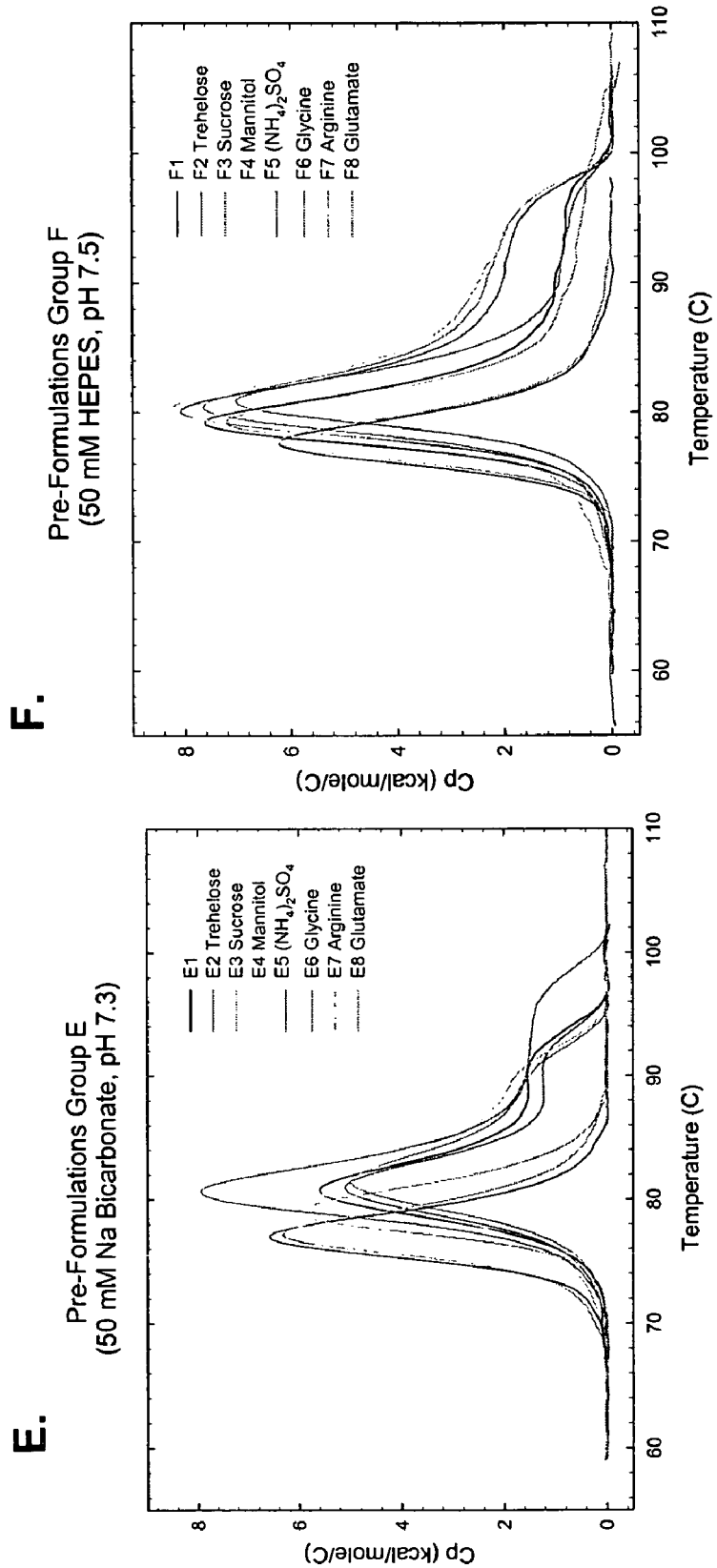
Figure 4:
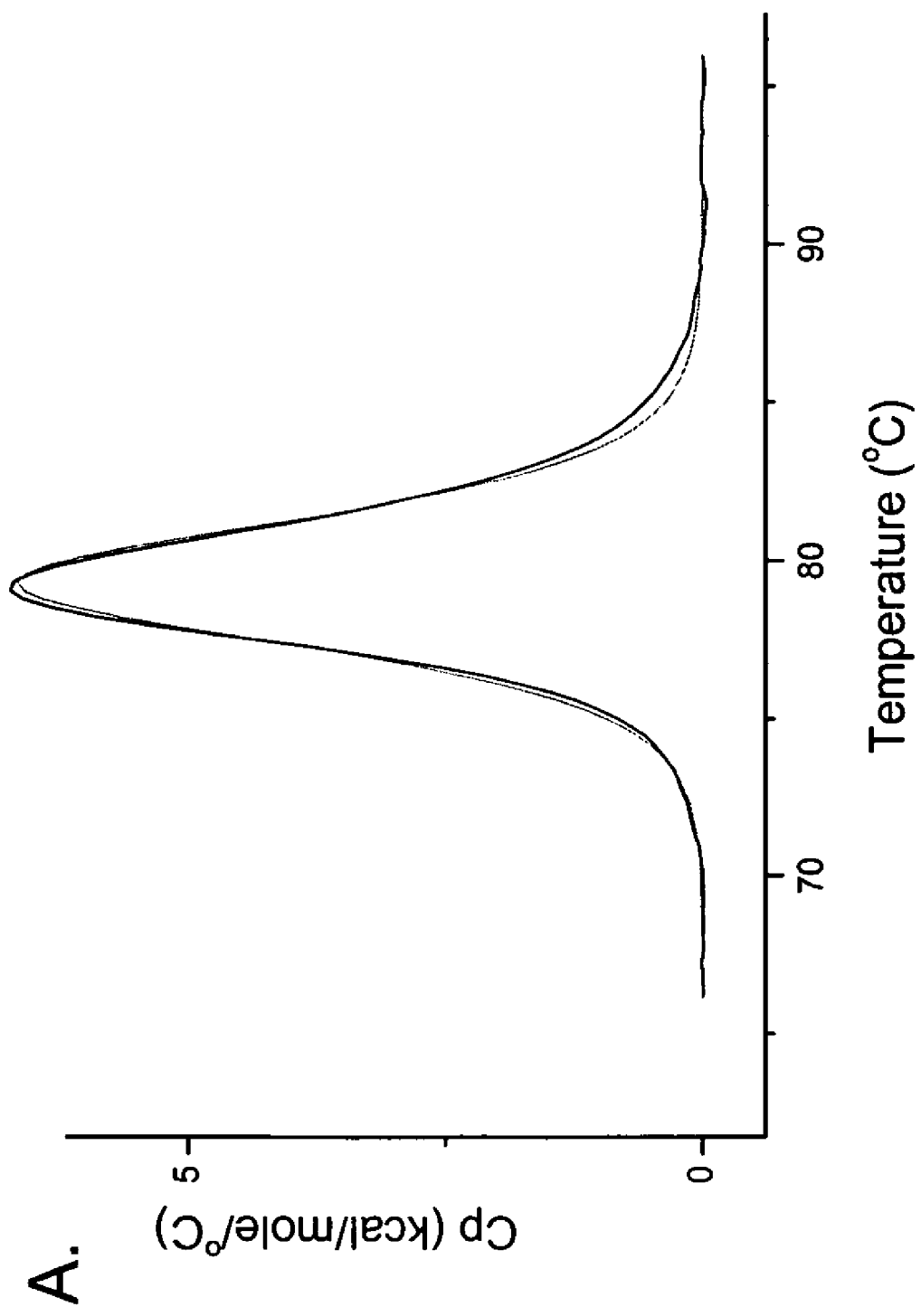
FIG. 4 shows DSC thermoprofiles from groups B7 (FIG. 4A) and F2 (FIG. 4B) of the matrix.
Figure 4:
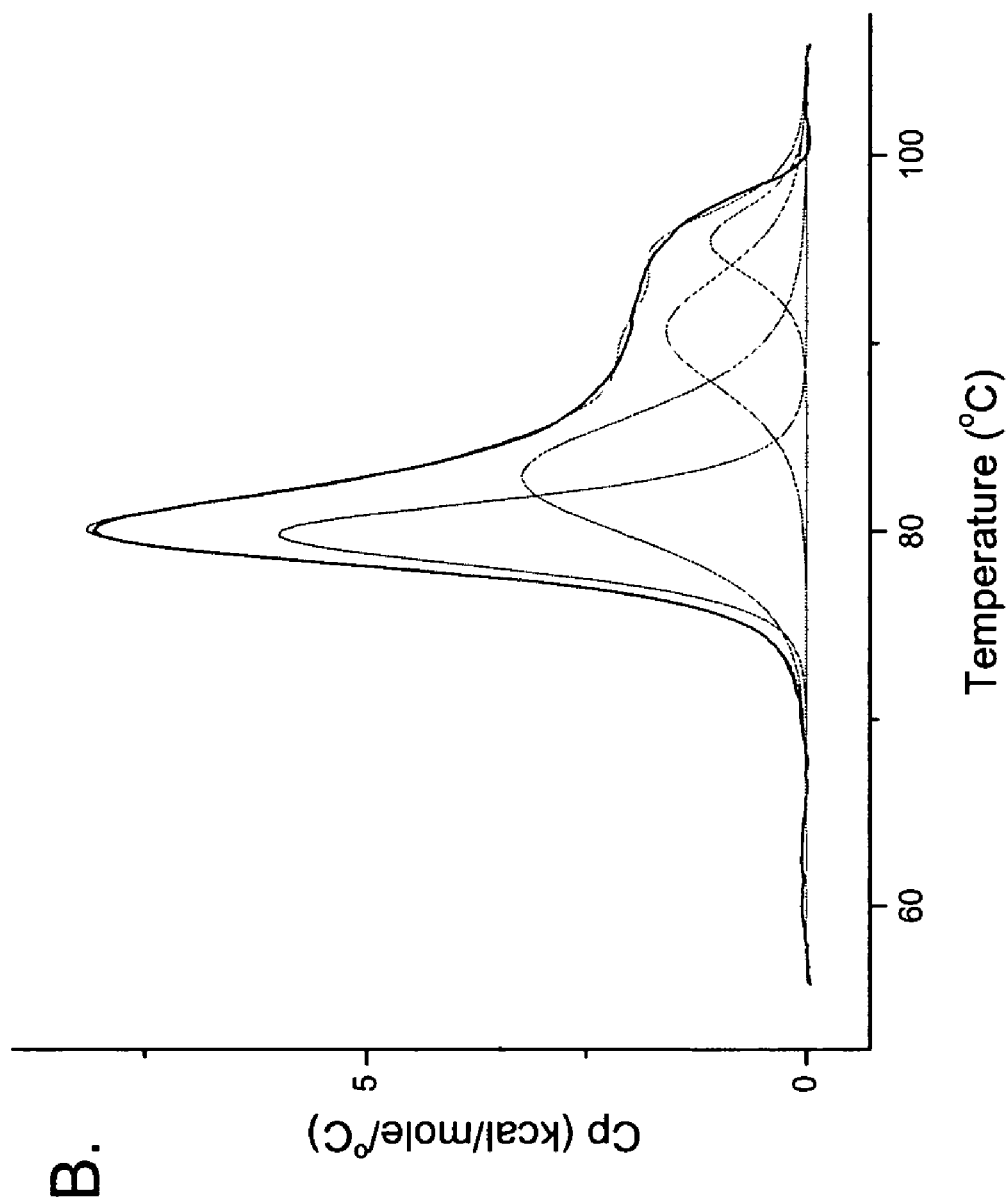
Figure 6:
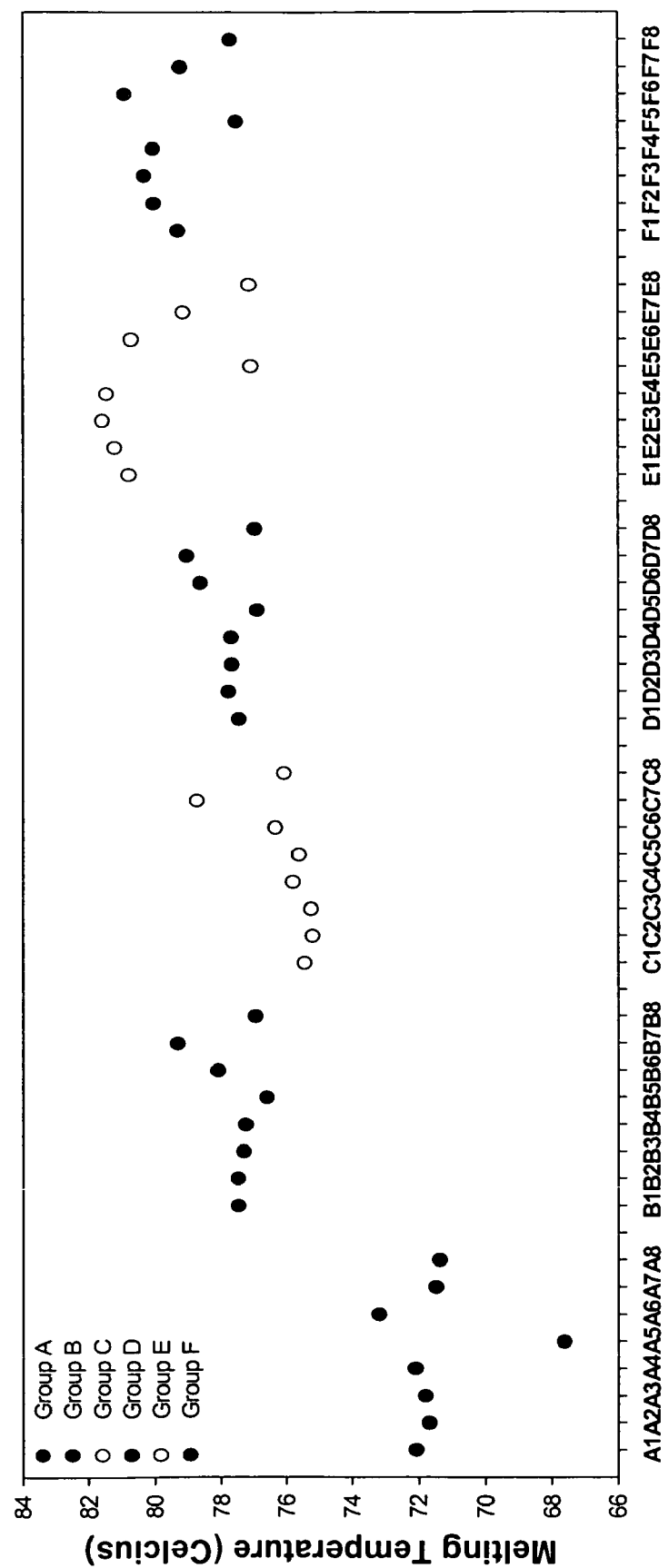
FIG. 6 shows a summary of the DSC melting temperatures for the full matrix.

Buffer A demonstrated the lowest $T_m$, as shown in FIGS. 5 and 6. Arginine raised the $T_m$ in Groups B and C, as shown in B7 and C7 of the matrix on FIGS. 5 and 6. At higher pHs (i.e.

pH>7.0), MetY35pAF hGH exhibited greater thermostability; however additional subpopulations were seen that have much higher melting temperatures and broader curves as shown in FIGS. 3 and 4. These subpopulations may exhibit greater stability or aggregation tendencies. Amino acids, in particular Arg and Glu, as well as $(NH_4)_2SO_4$ decreased the $T_m$ at higher pHs. Sugars did not have an effect on the overall $T_m$.

Figure 7:
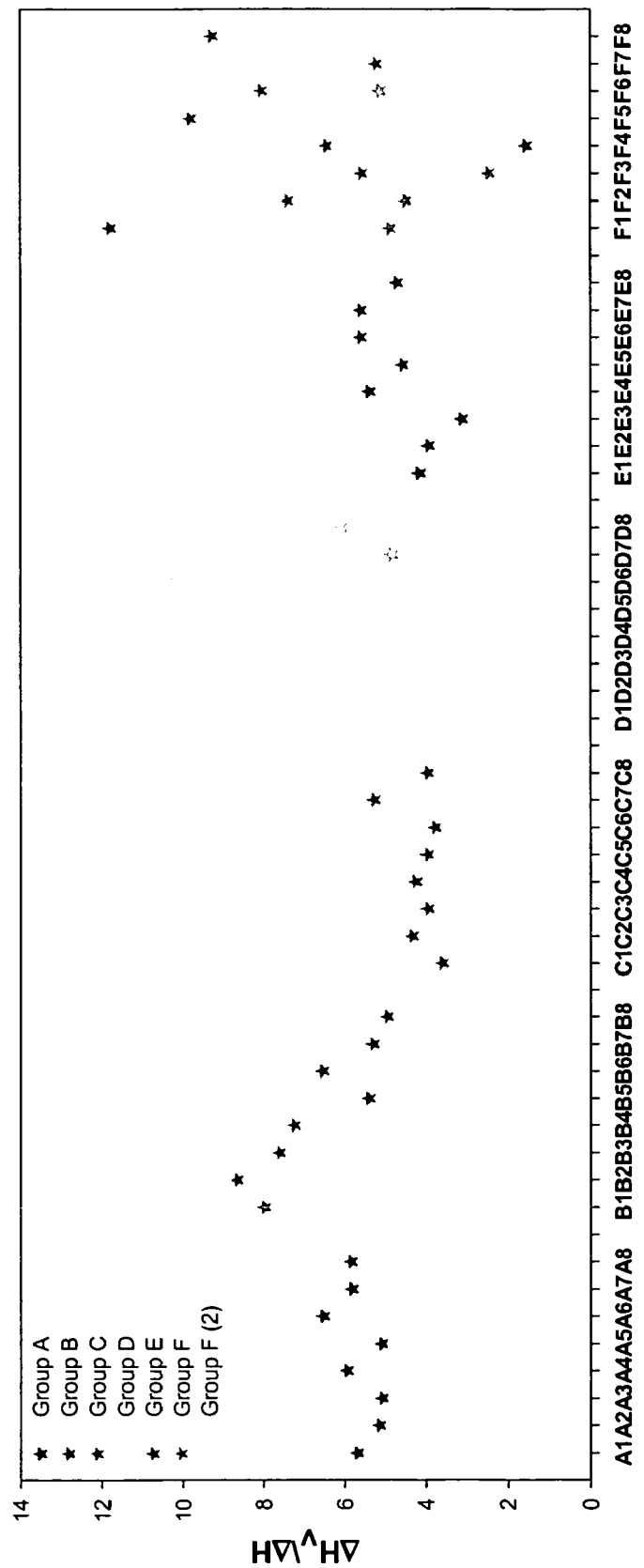
FIG. 7 shows an analysis of the ratio of $\Delta H_v/\Delta H$ for the formulation groups.
Figure 8:
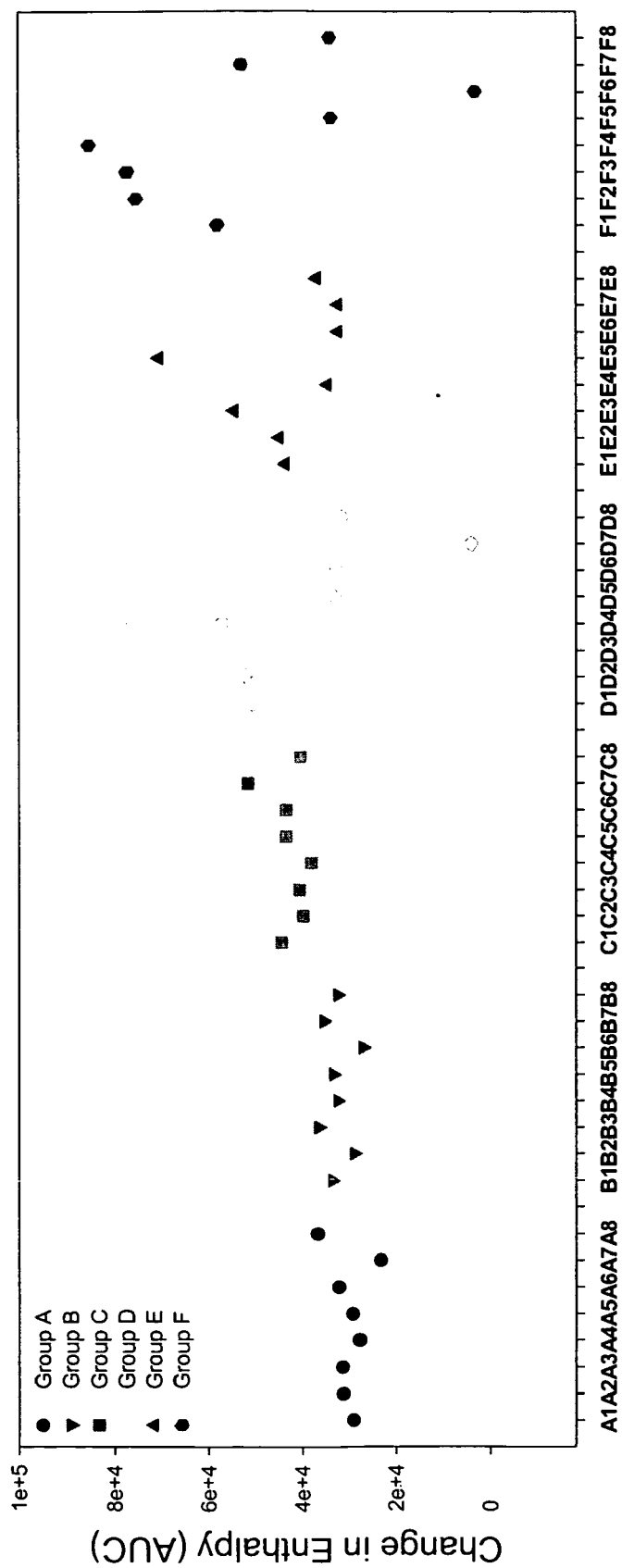
FIG. 8 shows an analysis of the change in enthalpy (AUC) of each sample.
Figure 9A:
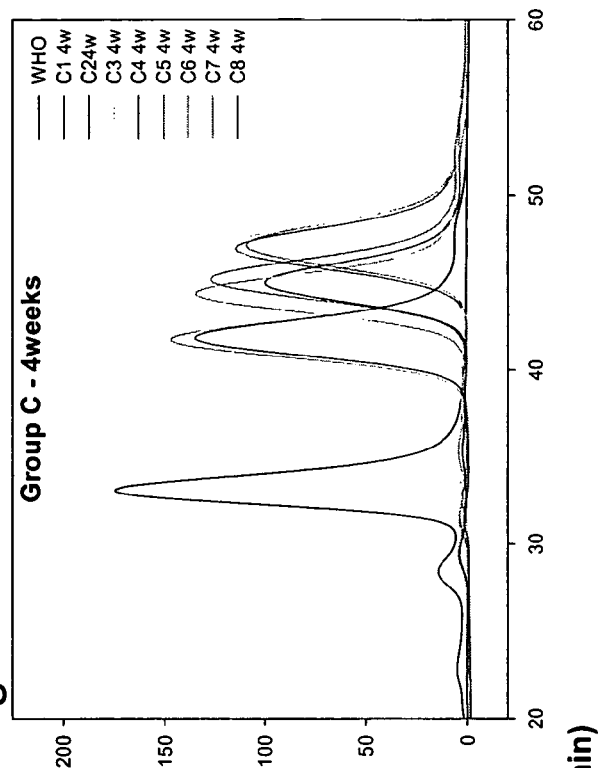
FIGS. 9A-D shows RP-HPLC datasets of samples in Group B, C, E, and F compared to the WHO hGH standard.
Figure 9B:
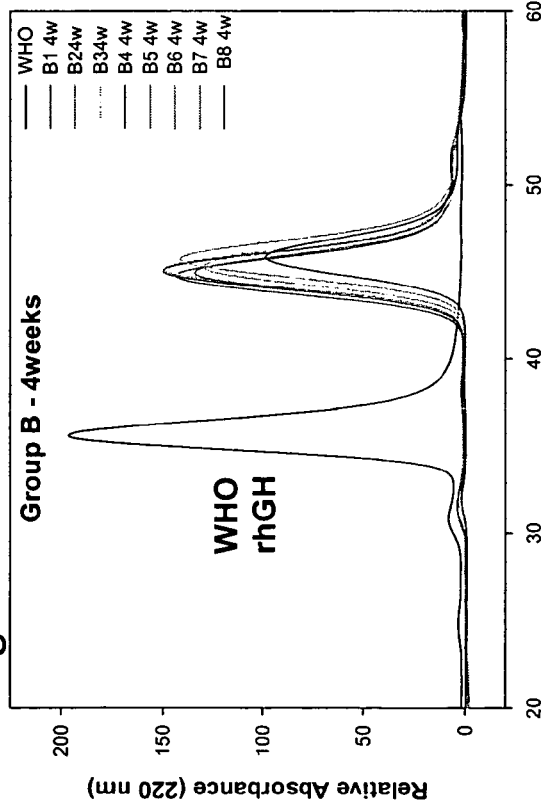
Figure 9C:
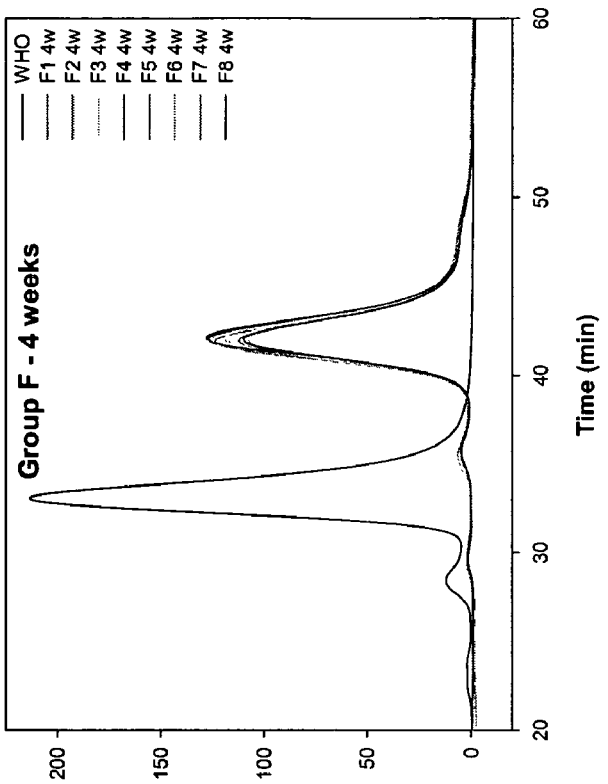
Figure 9D:
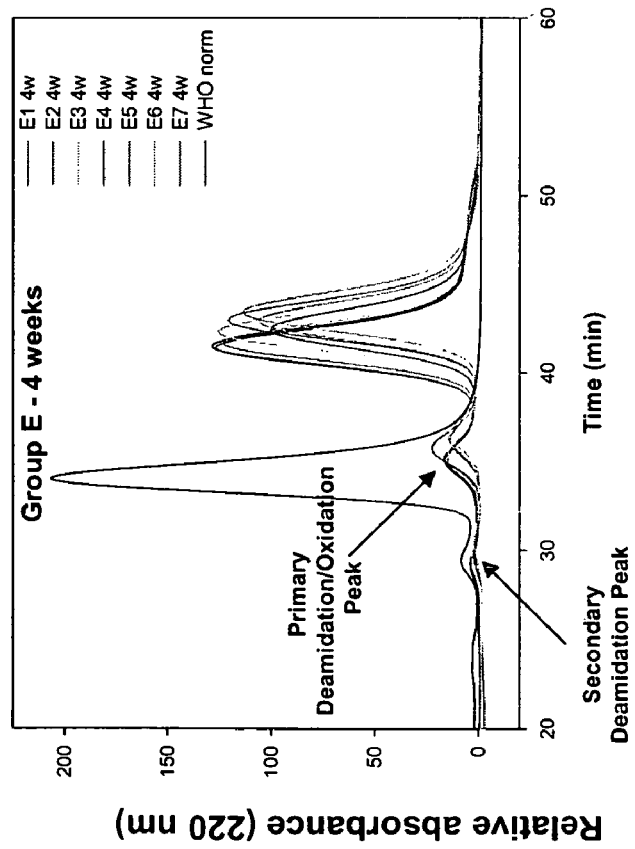

The ratio of $\Delta H_v/\Delta H$ was analyzed for all groups as shown in FIG. 7. Recombinant hGH is known to exhibit a $\Delta H_v/\Delta H>4$. Variations in this ratio were observed; these values demonstrate that the unfolding of MetY35pAF is irreversible. As the pH increased, additional subpopulations were identified (the ratio for a 2nd subpopulation of Group F was also plotted at pH 7.5 on FIG. 7). The change in enthalpy (AUC) of each sample was similar as shown in FIG. 8, except at higher pHs. Differences in $\Delta H$ at higher pHs may be due to missed broad transitions, accounting for a lower AUC. $\Delta H$ (AUC of the fit) was plotted for every group to ensure similar values were obtained within each group.

Reverse Phase HPLC (RP-HPLC)

Figure 10:
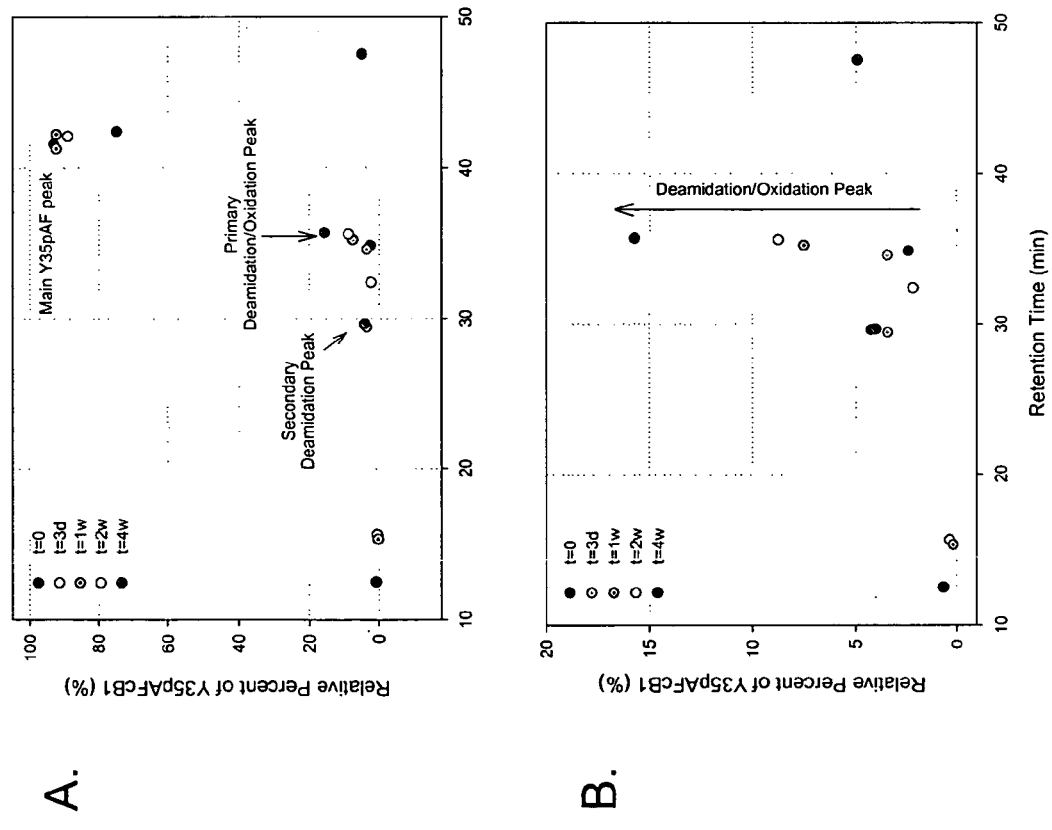
FIG. 10A shows an analysis of the different Y35pAF peaks for Group E5 (Relative percent of all peaks were plotted at each time point to visualize any and all changes to the main MetY35pAF hGH peak)
FIG. 10B shows a zoom of the primary deamination/oxidation peak (Zoomed in Deamidation Peak—increase in deamidation over time (t=0 to 4 weeks). RP-HPLC Analysis ws performed using Agilent Chemstation Software.
Figure 11:
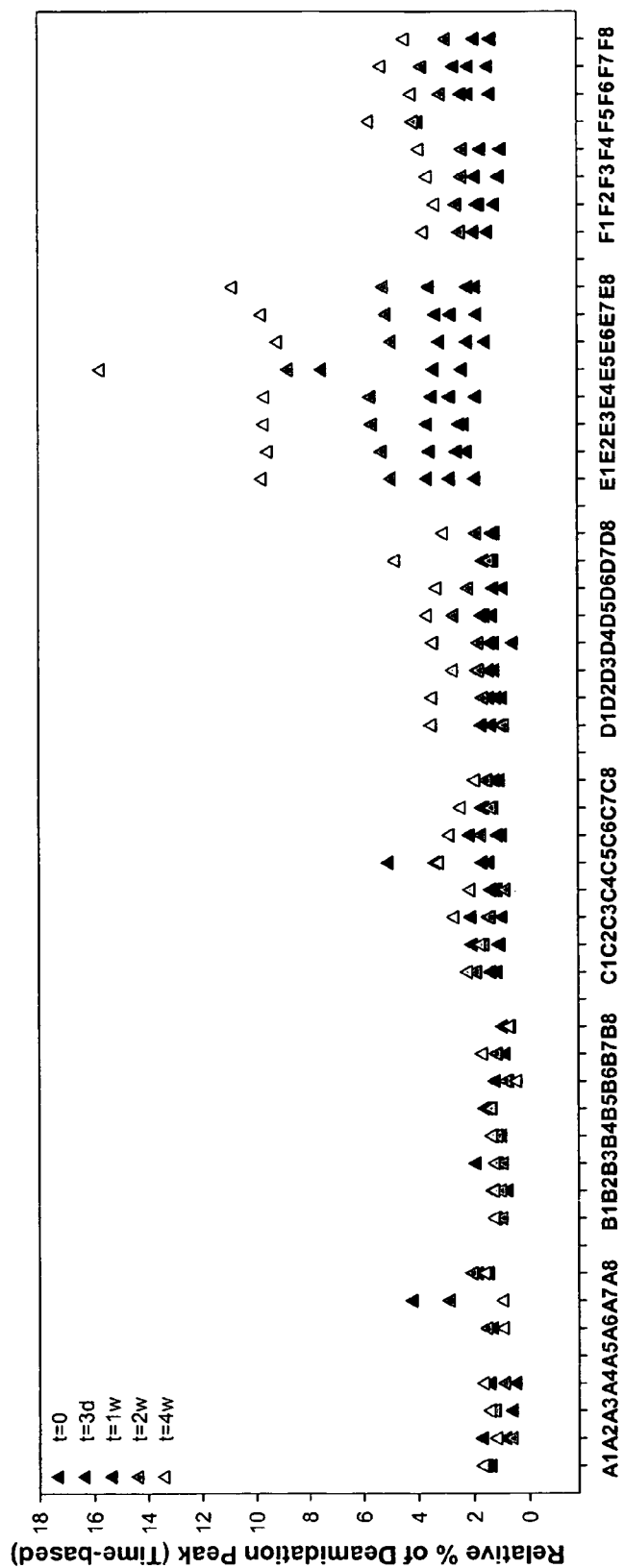
FIG. 11 shows an analysis of the primary deamidation/oxidation peak across the matrix. (Analysis of the Met Y35pAF hGH Over 4 weeks @ 4° C.)
Figure 12:
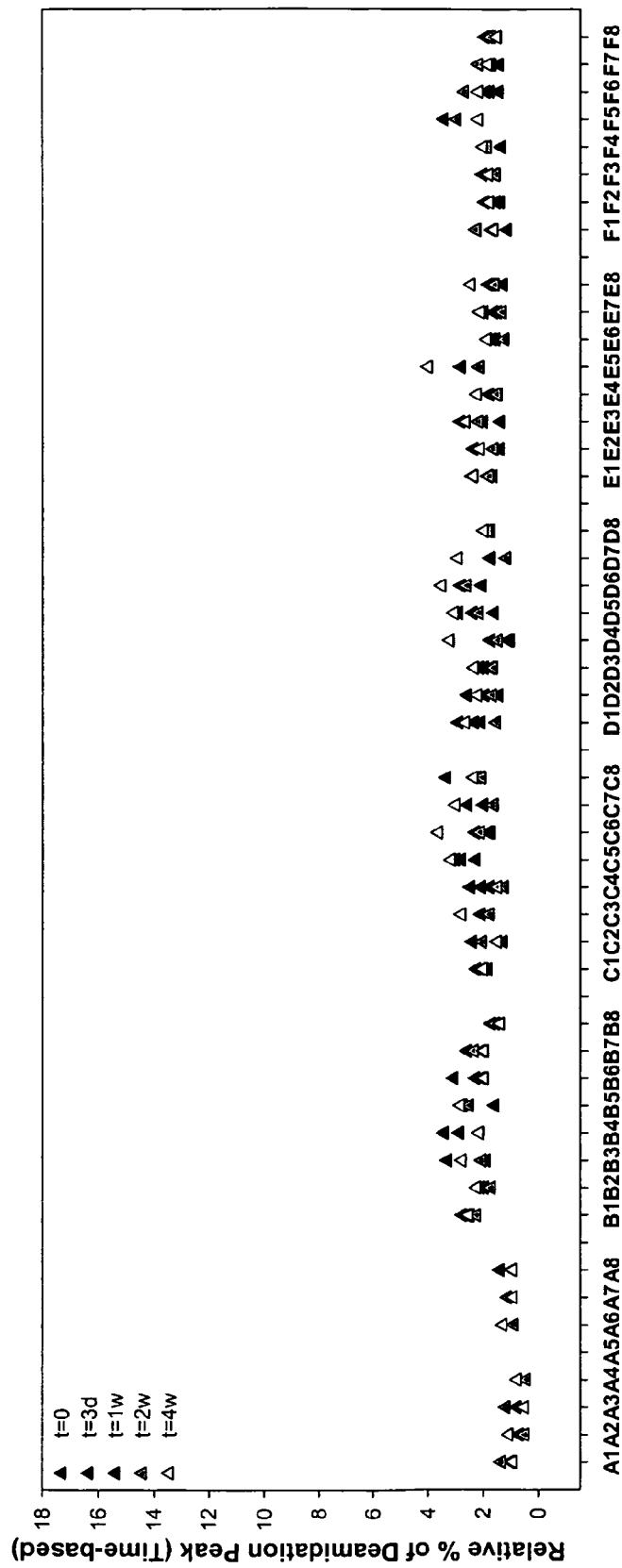
FIG. 12 shows an analysis of the secondary deamidation/oxidation peak with the formulation groups. (Analysis of the Met Y35pAF hGH Over 4 weeks @ 4° C.)
Figure 13:
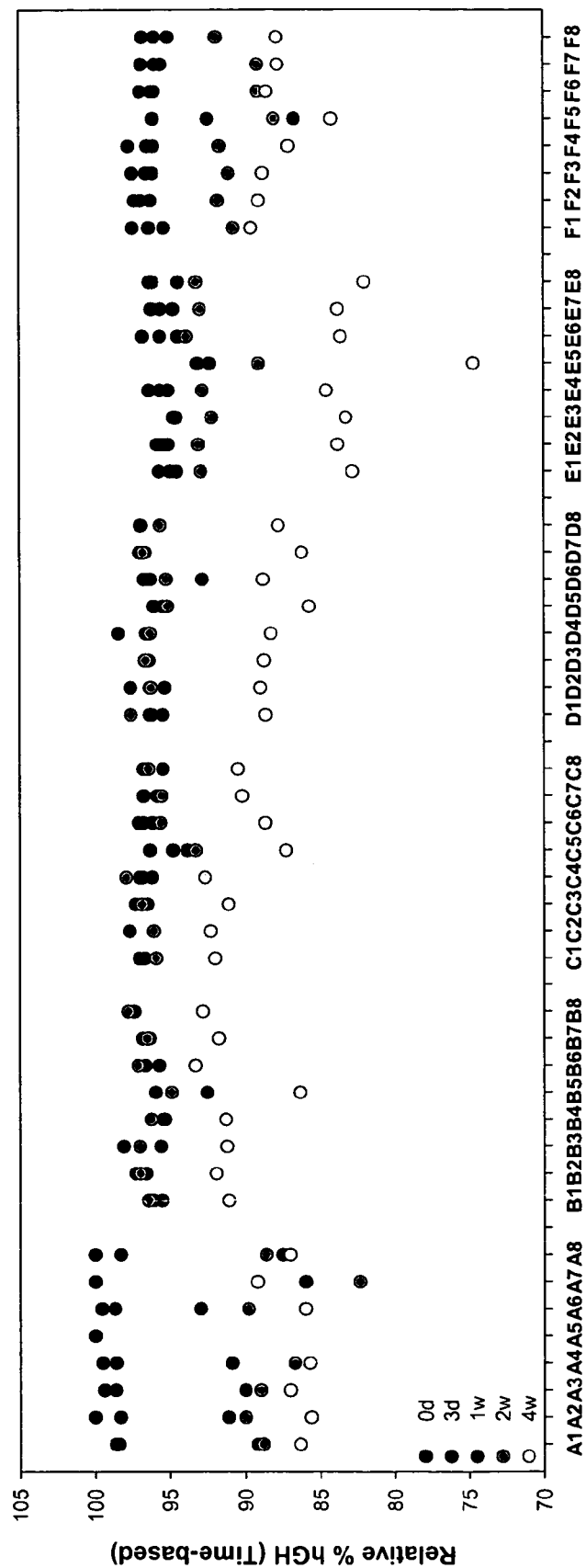
FIG. 13 shows an analysis of the main GH peak for the formulation groups. (Analysis of the Met Y35pAF hGH Over 4 weeks @ 4° C.)

RP-HPLC was used to analyze the purity and chemical degradation of MetY35pAF hGH during storage at 4° C. for four weeks. Datasets for Groups B, C, E and F each comparing MetY35pAF hGH with the WHO hGH standard are shown in FIGS. 9A-D. FIG. 10A illustrates the use of Agilent Chemstation software in analyzing the different peaks present in group E5 (the main peak, primary deamidation/oxidation peak, and the secondary deamidation peak). The primary deamidation/oxidation peak increased over time with Group E as shown in FIGS. 10B and 11; also, higher pHs exhibited greater amounts of deamidation/oxidation than lower pHs. FIG. 12 shows that the secondary deamidation/oxidation peak demonstrated less variability over time with all formulations groups. The main GH peak decreased over time for all formulations groups as shown in in FIG. 13, though groups B and C exhibited less change compared to the other groups. Group A exhibited very little deamidation, but the main GH peak did decrease over time and additional peaks, other than known deamidation/oxidation peaks, did develop over time. The data of Group A did, however, demonstrate that MetY35pAF is fairly stable from 0 to 3 days at this pH, which is critical since the PEGylation reaction takes place at pH 4.0 over one to two days.

Figure 14:
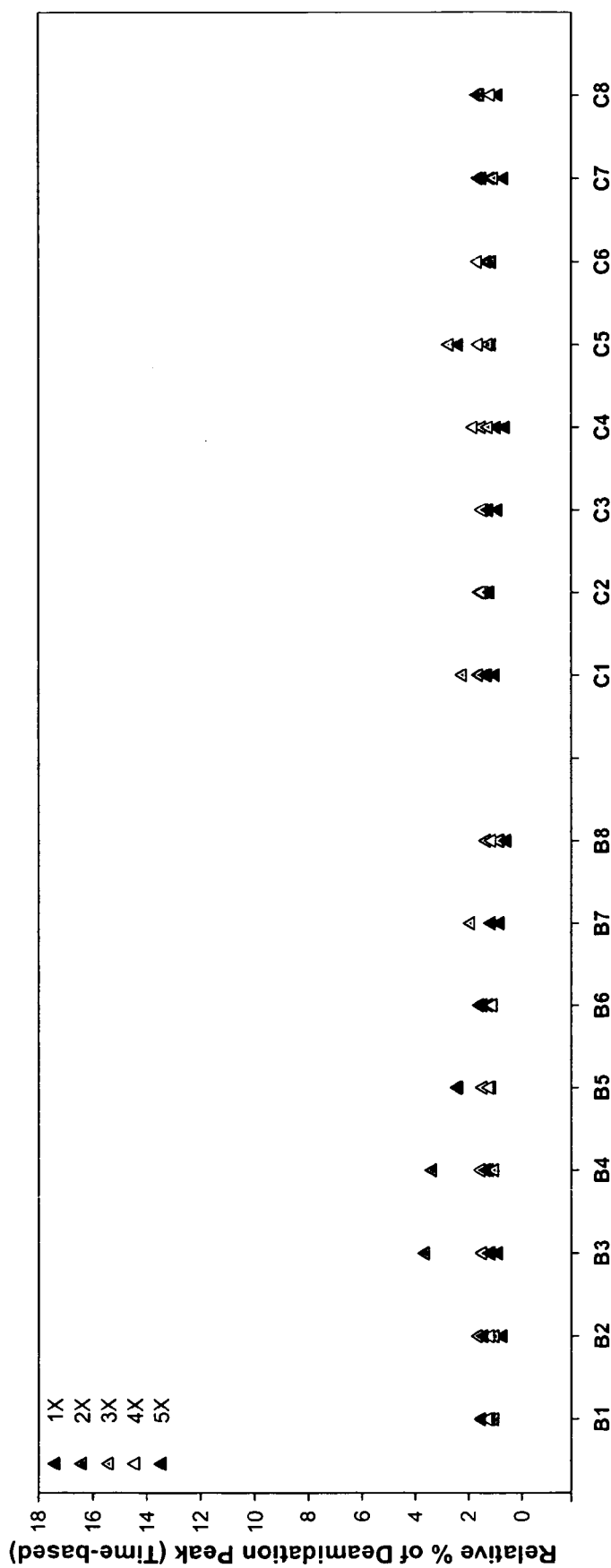
FIG. 14 shows RP-HPLC analysis of the primary deamidation/oxidation peak in samples that had undergone freeze-thaw cycles with formulation groups B and C. (Analysis of Met Y35pAF hGH Peak over 5 Freeze/Thaw Cycles)
Figure 15:
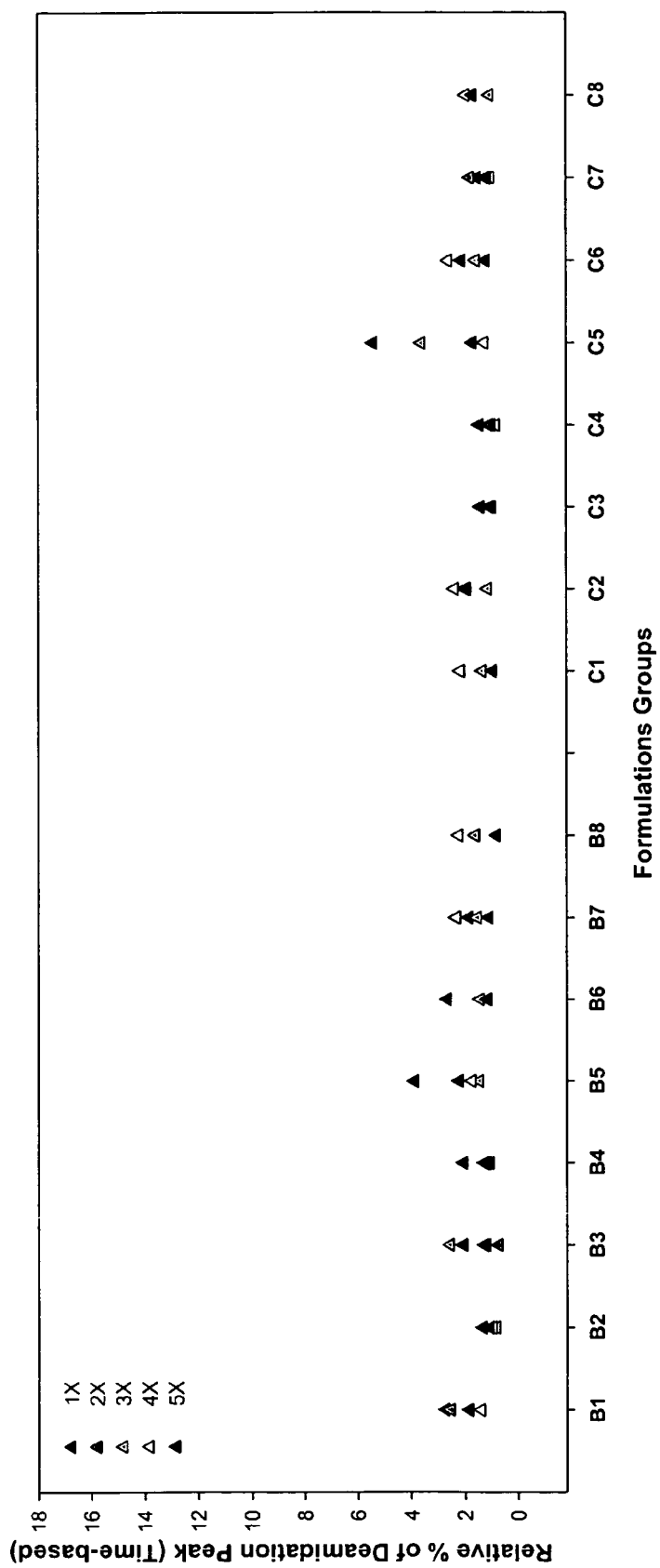
FIG. 15 shows RP-HPLC analysis of the secondary deamidation peak in samples that had undergone freeze-thaw cycles with formulation groups B and C. (Analysis of Met Y35pAF hGH over 5 Freeze/Thaw Cycles)
Figure 16:
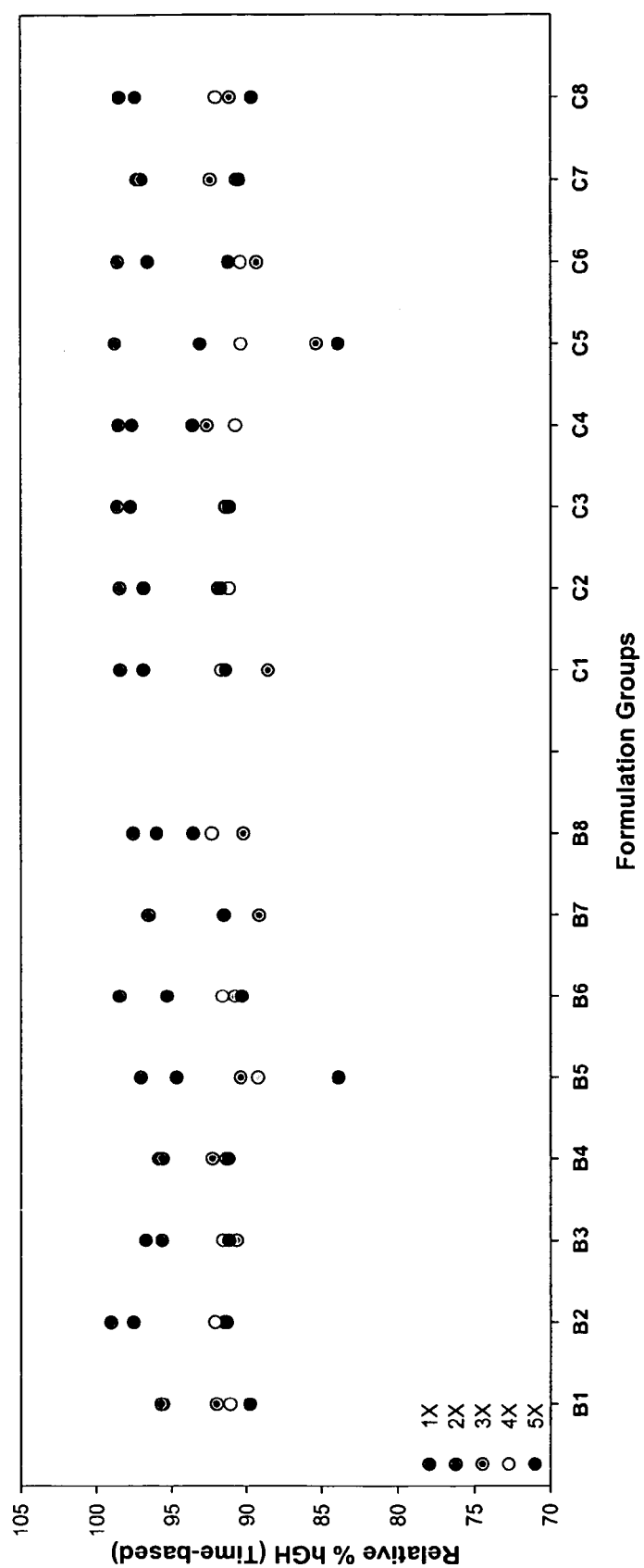
FIG. 16 shows RP-HPLC analysis of the main GH peak in samples that had undergone freeze-thaw cycles with formulation groups B and C. (Analysis of Met Y35pAF hGH over 5 Freeze/Thaw Cycles)

RP-HPLC was also used to analyze the samples that had undergone freeze-thaw cycles. Individual groups within B and C appeared similar as shown in FIG. 14 (primary deamidation/oxidation peak) and FIG. 15 (secondary deamidation peak). After two freeze/thaw cycles, the main GH peak decreased as shown in FIG. 16, indicating freeze/thaw effects. However, one or two freeze/thaw cycles did occur with this sample prior to the initiation of this formulations study.

Summary of Findings

It is well established that hGH exhibits a highly flexible structure at lower pH, and hGH forms a very rigid structure at higher pH (Kasimova et al. J. Mol. Biol. 2002 318:679-695).

Of the buffers tested, it was found that Buffer B (20 mM sodium citrate) at pH 6.0 performed best for chemical and thermodynamic stability of MetY35pAF hGH. The addition of Arginine at pH 6.0 increased the thermostability of MetY35pAF hGH. At this time, sugars did not have any positive or negative effect on MetY35pAF hGH; however, sugars may be important for pH shifts pre- and post-PEGylation events. The oxime linkage over time is also likely to be more stable at pH 6.0 than at a higher pH such as pH 7.5.

Example 3

The stability profile of PEG-hGH is examined with key formulation parameters under accelerated stability conditions, major degradation products are identified, and stability indicating assays are confirmed. The main objective of single-dose formulation development is to optimize the formulation for sufficient storage stability minimally at refrigerated temperature and may have sufficient storage stability when stored at ambient temperature. In addition to the lyophilized formulation development, additional studies are investigating the sensitivity to light exposure and agitation, development of the RP-HPLC method distinguishing the PEGylated hGH from the non-PEGylated form, structural analysis, and other studies. Successful lyophilized formulations normally show the following attributes: stability in solution for handling during formulation and fill-finish, good stability during freeze-drying, good storage stability, native structure in the dried state (if relevant), no obvious sample collapse or melt back, optimum moisture content level, high glass transition temperature, rugged cake structure, efficient drying cycle, minimum injection associated pain, and dissolves in water-filled injectable within one minute when reconstituted. In some embodiments, the optimum moisture content level is <3% water for a lyophilized formulation. In preferred embodiments, the optimum moisture content level is <1% water for a lyophilized formulation.

The formulation variables are determined. The stability of lyophilized formulation candidates are examined at 40° C., ambient temperature, and refrigerated temperature with weekly time points for up to 4 weeks, 6 weeks, and 2 months. Also, the stability of lyophilized formulation candidates are examined at ambient temperature and refrigerated temperature for up to 3, 4, and 6 month increments. The stability of the reconstituted form of each formulation during storage at 2-8° C. for a week is also be tested. Analytical methods include the SDS-PAGE method described above, SEC-HPLC, Ion-exchange HPLC, RP-HPLC, and other structural analyses.

Basic parameters useful for optimizing lyophilization cycle for most stable formulations are determined. For example, collapse temperature (or glass transition temperature), annealing temperature, and other important physical properties of frozen formulations are determined. A test lyophilization process is run to confirm that ideal cake can be obtained with the optimized cycle.

Example 4

Reverse Phase High Performance Liquid Chromatography (RP-HPLC)

Reverse Phase High Performance Liquid Chromatography (RP-HPLC) is a technique that separates molecules on the basis of relative hydrophobicities. Samples are passed over a stationary phase of silica covalently bonded to hydrocarbon chains. The molecules of interest are retarded by the stationary phase and eluted with an isocratic solvent. The chromatographic elution time is characteristic for a particular molecule. This method separates hGH based on subtle differences in hydrophobicity and retention behavior associated with structural modifications such as deamidation.

C4 RP-HPLC was used to assess relative purity and potential chemical degradation (deamidation and oxidation) of recombinant human growth hormone (hGH). This method was used to support identification and purity assessment of hGH. Some partial degradation products of hGH were observed using this technique. References for this technique include, European Pharmacopoeia 2002, p. 193; British Pharmacopoeia 2001, p. 1938-1939; and "A Reversed-Phase High Performance Liquid Chromatographic Method for Characterization of Biosynthetic Human Growth Hormone" by R. M. Riggin et al. Analytical Biochemistry 167, 199-209 (1987).

Equipment for this procedure included, the following or equivalents thereof: UV/Vis Spectrophotometer (Agilent 8453 or equivalent); 50 ul quartz cuvette; PD-10, Nap-10, or Nap 5 desalting columns (depending on sample volume; Amersham Biosciences Nap5 column 17-0853-02 or equivalent); 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent); clean 1 and 2 L glass bottles; a column such as Vydac C4 214TP54, a C4-silica reversed phase HPLC column with a dimension of 4.6×250 mm, particle size of 5 μ and pore size of 300 Å; and High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software).

Reagents for this procedure included solid chemicals that were analytical grade or better and solvents that were HPLC grade or better, unless otherwise noted. Examples of such chemicals include TRIS—Tromethamine, U.S.P. grade, Spectrum TR149, or equivalent; N-propanol, HPLC grade, 99.9%, Sigma Aldrich 34871, or equivalent; and Amnoniuno Bicarbonate, Ultra>99.5%, Fluka # 09830, or equivalent. Additional solutions include: Buffer for Deamidation Control (30 mM Ammonium Bicarbonate, pH 9.0) and mobile phase solution. For the buffer for deamidation control, 2.37 g of Ammonium bicarbonate was dissolved in 0.95 L Milli-Q $H_2O$, pH to 9.0 with NaOH, and the volume was brought up to 1 L with Milli-Q $H_2O$. The resulting buffer was sterile filtered using 0.22 μm PES filters (Corning #431098, or equivalent). For the Mobile phase solution (50 mM Tris-HCl, pH 7.5 and 29% n-propanol)), 6.05 g Tromethamine (USP grade, Spectrum # TR149, or equivalent) was dissolved in 0.95 L Milli-Q $H_2O$. The solution was brought to pH 7.5 with HCl, and the volume brought up to 1 L with Milli-Q $H_2O$. The two solvents (TRIS and propanol) were mixed, and the mixture was sterile filtered using 0.22 μm PES filters (Corning #431098, or equivalent).

Samples for use as standards in RP-HPLC include World Health, Organization (WHO) hGH (Cat. # 98/574) reconstituted to 1.9-2.1 mg/ml with 1.0 ml of water. Other hGH reference standards may be used at 1.9-2.1 mg/ml concentration. For the resolution solution, the hGH standard is buffer exchanged into 30 mM Ammonium Bicarbonate, pH 9.0 buffer using a PD-10, Nap-10, or Nap-5 desalting column (depending on sample volume). The standard was concentrated using a 0.5 mL Vivaspin concentrator to 1.9-2.1 mg/ml, incubated at 37° C. for 24 hours, and then stored at −80° C. until use. Test material was diluted to 2.0 mg/ml protein concentration for analysis. Sample concentrations were measured using standard techniques.

Procedure

The instrument was set-up with the following conditions: 1) Column: Vydac C4 214TP54 column; 2) Pump Setup—gradient: isocratic; flow rate: 0.5 ml/min; duration: 90 min; Max Pressure: 200 bar; 3) Autosampler Temperature: 4° C.; 4) Injector Setup—Injection: Standard Injection; Injection Volume: 20 μl; Draw Speed: 100 μl/min; Needle Wash: 100 ul with water; Injection Speed: 100 μl/min; Stop Time: As pump; 5) DAD Signals—Table 2; Peak Width>0.1 min; Slit: 4 nm; Stop Time: 75 min;

TABLE 2

| Sample | Bw | Reference | Bw | Units |
|--------|----|-----------|----|-------|
| 220    | 4  | 600       | 100 | nm   |
| 276    | 4  | 600       | 100 | nm   |
| 214    | 8  | 600       | 100 | nm   |
| 220    | 4  | 600       | 100 | nm   |

6) Column Thermostat—Temperature: 45° C.; Store: Temperature; 7) Preliminary Integration Events—Slope Sensitivity: 0.1; Peak Width: 0.5; Area Reject: 1.0; Height Reject: 1.0; Integration ON: 10 min.

The column was equilibrated with 10 column volumes (41.5 ml=83 min at 0.5 ml/min) of the mobile phase. 20 μl of the standard was injected using the autosampler, and the HPLC program was run. If the retention time of the WHO standard was not between 33-35 minutes, or the other standard was not between 37-40 minutes, the mobile phase composition was adjusted, the column was re-equilibrated, and the standard was re-run. Suggested adjustments included adding less than 5 ml of 50 mM Tris-HCl pH 7.5 per liter of mobile phase if retention time was less than 33 minutes, and less than 2 ml of n-propanol if retention time greater than 35. Since evaporation of the propanol may occur, a standard was run on each day that samples were tested, and buffers were adjusted accordingly.

20 μl of the resolution solution was injected, and the HPLC program was run. Desamido-hGH appeared as a small peak at a retention time of about 0.85 relative to the principal peak. The test was not valid unless the resolution between the peaks corresponding to hGH and desamido-hGH was at least 1.0 and the symmetry factor of the hGH peak was 0.8 to 1.8. 20 μl of the test article was injected, and the HPLC program was run. Samples were run in triplicate. Average retention times were reported.

Modifications to various conditions and/or parameters may be required to analyze PEGylated hGH and other forms. Modifications to RP-HPLC are known to those of ordinary skill in the art.

Data Analysis

The average retention time of the test article was compared with the standard. The average purity of the test article was calculated: Integration area of the main peak/integration areas of all peaks)×100%. Any peak(s) due to the solvent were disregarded.

Figure 17:
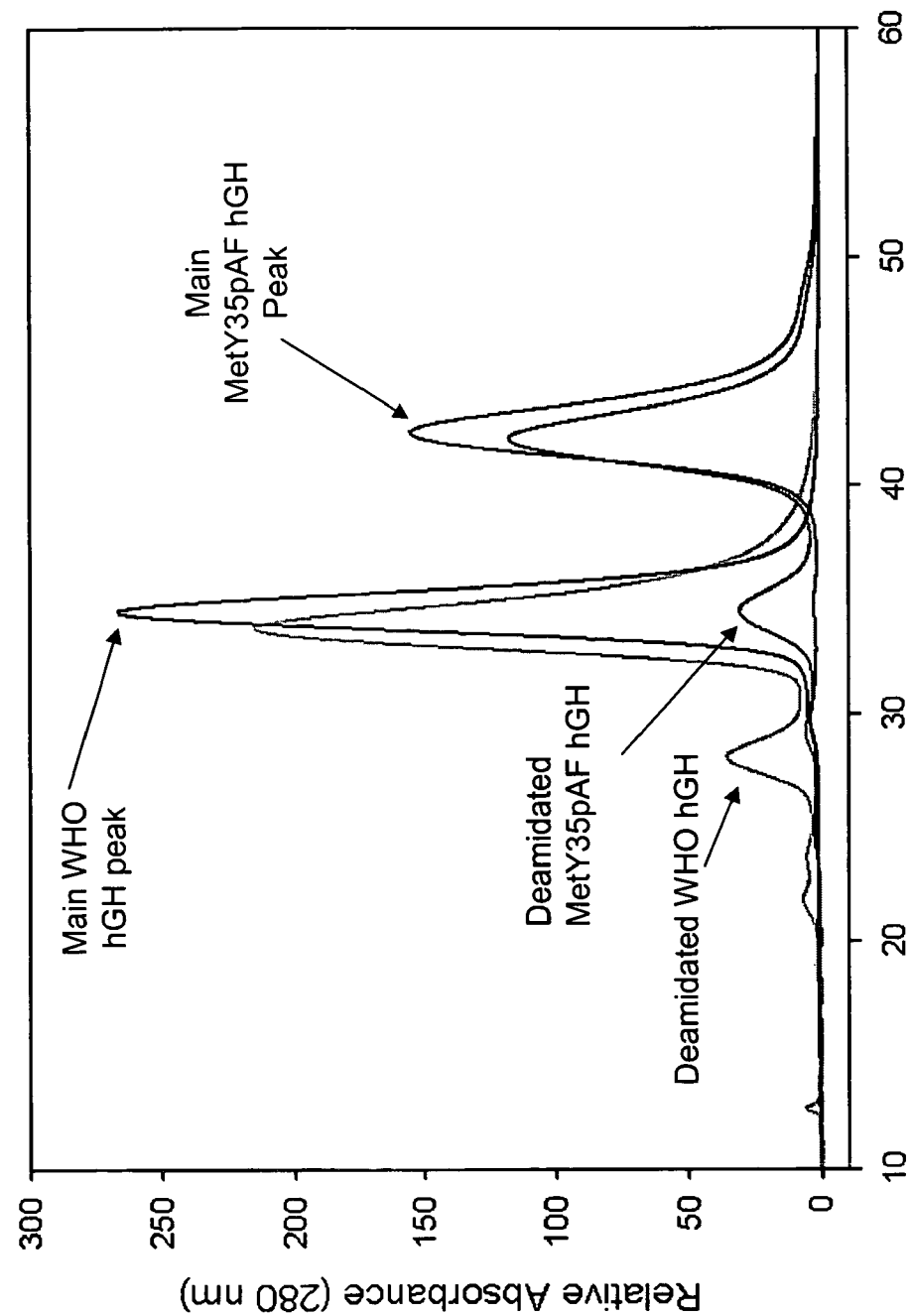
FIG. 17 shows results from an analysis by RP-HPLC.

Results from RP-HPLC for MetY35pAF hGH with the WHO hGH standard are provided in Table 3 and FIG. 17. Specifications such as the retention time difference between the test article and the reference standard and purity may vary with different molecules or forms of a molecule (i.e. Y35pAF hGH compared to metY35pAF hGH).

TABLE 3

|      | Ret Time (min) | Area | % Area | Symmetry | Resolution |
|------|----------------|------|--------|----------|------------|
| WHO  |                |      |        |          |            |
| Main Peak | 34.4 | 36576 | 99.3 | 0.86 |  |

TABLE 3-continued

| | Ret Time (min) | Area | % Area | Symmetry | Resolution |
|---|---|---|---|---|---|
| Deamidated WHO | | | | | |
| Deam. Peak | 28.069 | 4920 | 11.05 | | |
| Main peak MetY35pAF | 33.746 | 38180 | 85.76 | | 1.54 |
| Main peak | 42.307 | 31432 | 96.08 | 0.69 | |
| Deamidated MetY35pAF | | | | | |
| Deamid. peak | 34.461 | 5225 | 16.67 | | |
| Main peak MetY35pAF(2) | 42.034 | 24534 | 78.28 | | 1.72 |
| Main peak | 41.938 | 30304 | 96.19 | 0.69 | |
| Deamidated MetY35pAF (2) | | | | | |
| Deamid. peak | 34.209 | 5039 | 16.74 | | |
| Main peak | 41.495 | 23716 | 78.82 | | 1.69 |

Example 5

Size Exclusion Chromatography

Size-exclusion high performance liquid chromatography (SEC-HPLC) is a technique using the stationary phase as a porous matrix which is permeated by mobile phase molecules. Sample molecules small enough to enter the pore structure are retarded, while larger molecules are excluded and therefore rapidly carried through the column. Thus, size exclusion chromatography provides separation of molecules by size and the chromatographic elution time is characteristic for a particular molecule.

SEC-HPLC was used to assess recombinant human growth hormone (hGH) potency. SEC-HPLC was a method to determine the percentage of monomer (PEGylated and non-PEGylated) hGH. Dimer and other high molecular weight proteins were observable using this technique. Thus, this technique separates monomer from dimer and other higher molecular weight substances in the sample, as well as PEGylated and non-PEGylated forms. References for this technique, include, but are not limited to, European Pharmacopoeia 2002, p. 193; British Pharmacopoeia 2001, p. 1941; and "High-Performance Size-Exclusion Chromatographic Determination of the Potency of Biosynthetic Human Growth Hormone Products" by R. M. Riggin et al. Journal of Chromatography 435(1988), p. 307-318.

Equipment for this procedure included, the following or equivalents thereof: a UV/Vis Spectrophotometer (Agilent 8453 or equivalent); 50 ul quartz cuvette; 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent); clean 1 and 2 L glass bottles; a column such as Tosohaas TSK Super SW3000 18675 and Super SW Guard Column 18762, a silica-based size exclusion HPLC column with a dimension of 4.6×300 mm, particle size of 4 Mm and pore size of 250 Å along with a guard column having a dimension of 4.6×35 mm and 4 µ particle size); and High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), Refractive Index detector (RID) and Chemstation chromatography software).

Reagents for this procedure included solid chemicals that were analytical grade or better and solvents that were HPLC grade or better, unless otherwise noted. Examples of such chemicals include, Monobasic Sodium Phosphate, Spectrum U.S.P. grade S0130, or equivalent; Dibasic Sodium Phosphate, Spectrum U.S.P. grade S0140, or equivalent; 2-propanol, Fisher HPLC grade A451-4, or equivalent. Additional solutions include: mobile phase solution (97% of 63 mM sodium phosphate pH 7.0; 3% of 2-propanol) and solution A. To make mobile phase solution, 26.8 g of dibasic sodium phosphate was dissolved in 1 L Milli-Q $H_2O$, and 13.79 g monobasic sodium phosphate was dissolved in 1 L Mill-Q $H_2O$. The two solutions were mixed to give a sodium phosphate buffer of pH 7.0. The 100 mM sodium phosphate, pH 7.0 buffer was diluted to 63 mM with Mill-Q $H_2O$. 970 mL of 63 mM sodium phosphate pH 7.0 was mixed with 30 mL of 2-propanol (or other appropriate volumes to obtain 97% of 63 mM sodium phosphate pH 7.0, 3% of 2-propanol). The resulting buffer was sterile filtered using 0.22 µm PES filters (Corning #431098, or equivalent). Solution A is 25 mM Sodium Phosphate, pH 7.0. 250 mL of 100 mM sodium phosphate, pH 7.0 buffer was diluted with 750 mL Milli-Q $H_2O$. The resulting buffer was sterile filtered using 0.22 µm PES filters (Corning #431098, or equivalent).

Samples for use as standards in SEC-HPLC include World Health, Organization (WHO) hGH (Cat. # 98/574) reconstituted with 1.0 ml of water and diluted to 0.9-1.1 mg/ml. Other hGH reference standards may be used at 0.9-1.1 mg/ml concentration. For the resolution solution, the hGH standard was incubated at 50° C. for 12-24 hours, dissolved in solution A, then diluted to 1 mg/ml with solution A, and stored at −80° C. until use. The test material was diluted to 1.0 mg/ml with Solution A. Sample concentrations were measured using standard techniques.

Procedure

The instrument was set-up with the following conditions: 1) Column: TSK Super SW3000 18675 and Guard Column 18762 Auto sampler; 2) Temperature: room temperature; 3) Pump Setup—gradient: isocratic; flow rate: 0.3 ml/min; duration: 25 min; Max Pressure: 120 bar; 4) Injector setup—Injection: Standard Injection; Injection Volume: 20 µl; Draw Speed: 100 µµl/min; Injection Speed: 100 µl/min; Needle wash: 100 ul $H_2O$; Stop Time: As pump; 4) DAD Signals—Table 4; Peak Width>0.05 min; Slit: 2 nm; Stop Time: As pump;

TABLE 4

| Sample | Bw | Reference | Bw | Units |
|---|---|---|---|---|
| 214 | 4 | 600 | 100 | nm |
| 276 | 4 | 600 | 100 | nm |
| 220 | 8 | 600 | 100 | nm |
| 280 | 4 | 600 | 100 | nm |
| 250 | 8 | 600 | 100 | nm |

5)RID Signal—Temperature: 35° C.; Response Time: >0.2 min 4 s, standard; 6) Column Thermostat: Temperature: 23° C.; Store: Temperature.

The column was equilibrated with 10 column volumes (50 ml=166 minutes at 0.3 ml/minutes) of the mobile phase, and the RID was purged for 20 minutes before injecting the samples. 20 µl of the resolution solution was injected. In the chromatogram obtained, 1) the main non-PEGylated peak eluted at a retention time of approximately 13-13.5 minutes, 2) the peaks corresponding to the hGH dimer eluted at a retention time of approximately 12.2-12.6 minutes, and 3) the higher molecular weight proteins (non-PEGylated) eluted at relative retention time of 7.4-8.0 minutes. The main PEGylated peak eluted at a retention time of approximately 8.3-8.8 minutes. 20 μl of the standard was injected, and the HPLC program was run. 20 μl of the test article was injected, and the HPLC program was run. Samples were run in triplicate. Average retention times were recorded.

Modifications to various conditions and/or parameters may be required to further characterize PEGylated hGH or other forms. Modifications to SEC-HPLC are known to those of ordinary skill in the art.

Data Analysis

The Retention Time of the hGH test article is compared with the standard. For purity determinations of non-PEGylated hGH, the integrated main peak areas of the hGH test article and the standard is compared, and the percentage of monomer in the hGH test article is calculated: (peak area of hGH sample/peak area of standard)×100%. The percentage of dimer and/or higher aggregates in the hGH test article is also calculated. For purity determinations of PEGylated hGH, the integrated main peak areas of the PEGylated hGH sample and the standard is compared, and the percentage of PEGylated monomer in PEGylated-hGH sample is calculated by: (peak area of PEGylated hGH sample/peak area of standard)×100%. The percentage of PEGylated dimer, higher aggregates, and non-PEGylated monomer in the hGH test article are calculated also. Alternatively, purity is determined for non-PEGylated hGH or PEGylated hGH by: (Integration area of the main peak of hGH sample/integration areas of all peaks of hGH sample)×100%. Any peak(s) due to the solvent were disregarded. Purity determinations are also calculated using absolute mass or direct peak area rather than by percent of a reference standard.

Specifications: The retention time difference between the hGH test article and the standard is approximately <±30 seconds. For dimer and higher molecular weight proteins, in the chromatogram obtained with the test article, the sum of the areas of any peak with a retention time less than that of the principal peak is not greater than 4.0% or 6.0% of the total area of the peaks, respectively. Any peak(s) due to the solvent are disregarded.

Figure 18:
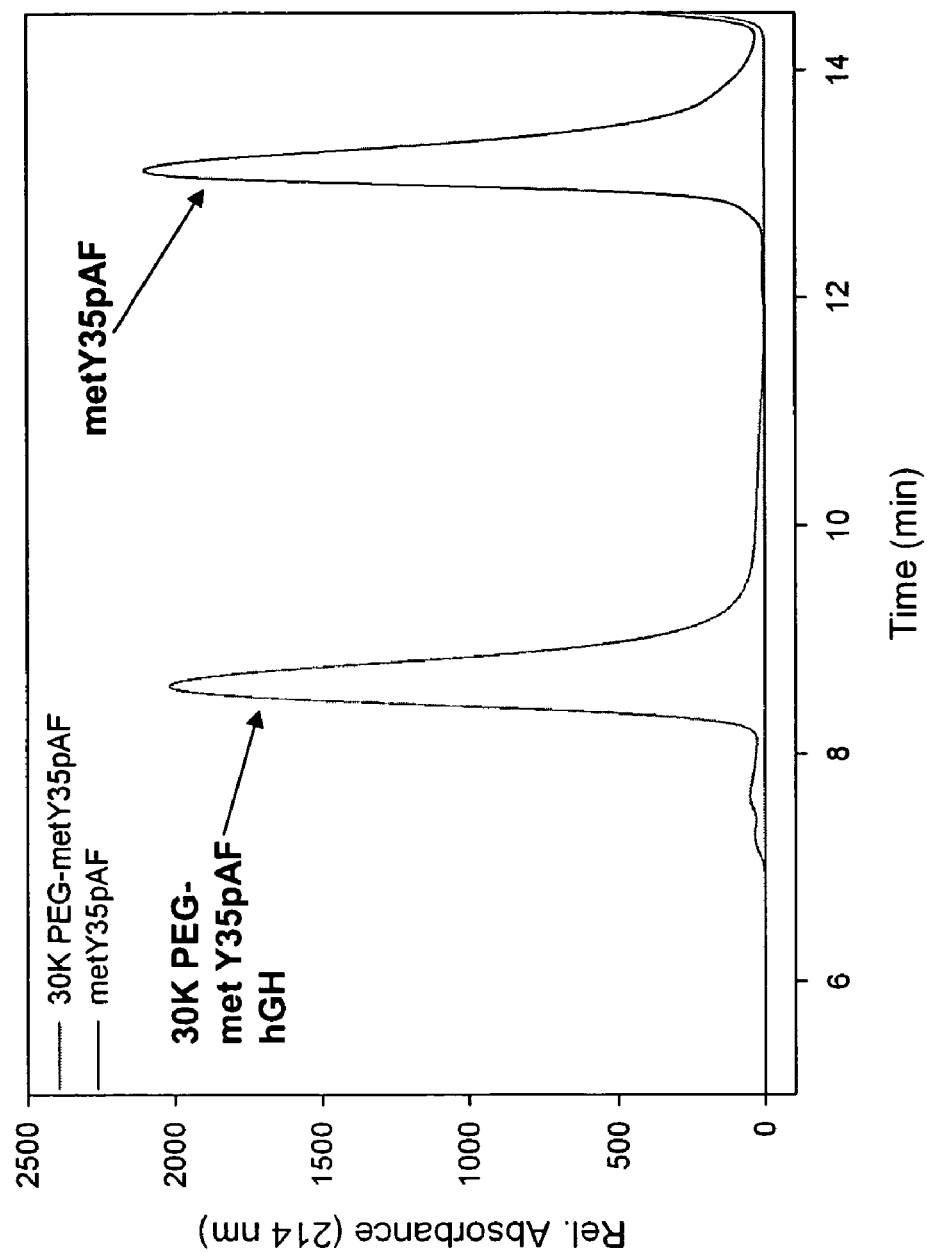
FIG. 18 shows results from an analysis by SEC-HPLC.

FIG. 18 shows SEC-HPLC data from 30K PEG-metY35pAF and metY35pAF.

Example 6

Cation-Exchange High Performance Liquid Chromatography (cIEX-HPLC)

Cation-exchange high performance liquid chromatography (cIEX-HPLC) is a technique that relies on charge-charge interactions between a protein and the charges immobilized on the resin. Cation exchange chromatography takes advantage of the positively charged ions of a protein that bind to the negatively charged resin. A common structural modification of hGH is deamidation of asparagine (Asn) residues, and this cIEX-HPLC method permits the separation of deamidated and deamidation intermediates of PEGylated and non-PEGylated hGH.

The following method was used to assess relative purity and potential chemical degradation (i.e. deamidation) of recombinant human growth hormone (hGH). This method was used to support identification and purity assessment of PEGylated and non-PEGylated hGH. Some partial degradation products of hGH were observable using this technique.

Equipment for this procedure included, the following or equivalents thereof: UV/Vis Spectrophotometer (Agilent 8453 or equivalent); 50 ul quartz cuvette; 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent); clean 1 and 2 L glass bottles; a column such as PolyCAT A 4.6×200 mm, 5 μ, 1000 Å (204CT0510) and PolyCAT A guard column, 4.6×10 mm, 5 μ, 1000 Å (JGCCT0510); and High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), Refractive Index detector (RID) and Chemstation chromatography software).

Reagents for this procedure included solid chemicals that were analytical grade or better and solvents that were HPLC grade or better, unless otherwise noted. Examples of such chemicals include, Ammonium Acetate, Spectrum HPLC grade A2149, or equivalent; Acetonitrile, Fisher HPLC grade A998, or equivalent, Ammonium Bicarbonate. Additional solutions include: Mobile phase A (40% Acetonitrile, $H_2O$); Mobile phase B (40% Acetonitrile, 500 mM Ammonium Acetate, pH 4.5) and Buffer for Deamidation Control (30 mM Ammonium Bicarbonate, pH 9.0). For Mobile phase A buffer, 400 mL HPLC grade Acetonitrile was mixed with 600 ml sterile filtered Milli-Q $H_2O$, and the resulting mixture was sterile filtered using 0.22 μm PES filters (Corning #431098), or equivalent). For Mobile phase B buffer, 38.54 g ammonium acetate was dissolved in 970 mL Milli-Q $H_2O$. The solution was brought to pH 4.5 with glacial acetic acid, and then the volume brought up to 1000 mL volume with Milli-Q $H_2O$. The buffer was sterile filtered using 0.22 μm PES filters (Corning #431098). 100 mL Milli-Q $H_2O$, 400 mL HPLC grade Acetonitrile, and 500 mL 500 mM Ammonium Acetate, pH 4.5 were mixed. For the Buffer for Deamidation Control, 2.37 g of Ammonium bicarbonate was dissolved in 0.95 L Milli-Q $H_2O$, and the pH was brought to 9.0 with NaOH. The volume was then brought up to 1 L with Milli-Q $H_2O$. The resulting buffer was sterile filtered using 0.22 μm PES filters (Corning #431098, or equivalent).

Samples for use as standards in cIEX-HPLC included World Health, Organization (WHO) hGH (Cat. # 98/574) reconstituted with 1.0 ml of water and diluted to 0.9-1.1 mg/ml. Other hGH reference standards may be used at 0.9-1.1 mg/ml concentration. For the resolution solution, hGH standard(s) were buffer exchanged into 30 mM Ammonium Bicarbonate, pH 9.0 buffer using a PD-10, Nap-10, or Nap-5 desalting column (depending on sample volume). The standard was concentrated using a 0.5 mL Vivaspin concentrator to 0.9-1.1 mg/ml, incubated at 37° C. for 24 hours, and then stored at −80° C. until use. The test article was diluted to 1.0 mg/ml. A deamidated resolution standard was included. Alternatively, the test article and standards are diluted over a range of concentrations. Sample concentrations were measured using standard techniques.

Procedure

The instrument was set-up with the following conditions: 1) Column: PolyCAT A 204CT0510 and JGCCT0510; 2) Auto sampler Temperature: 4° C.; 3) Pump Setup—gradient: 50 50-250 mM Ammonium Acetate pH 4.5;

TABLE 5

| Time | Mobile Phase A | Mobile Phase B | Flow (ml/min) | Pressure (bar) |
|---|---|---|---|---|
| 0 | 90 | 10 | 0.5 | 140 |
| 14 | 90 | 10 | 0.5 | 140 |
| 79 | 50 | 50 | 0.5 | 140 |
| 19.5 | 50 | 50 | 0.75 | 140 |
| 80 | 0 | 100 | 1 | 140 |
| 115 | 0 | 100 | 1 | 140 |
| 115.5 | 90 | 10 | 1 | 140 |
| 150 | 90 | 10 | 1 | 140 |
| 150.5 | 90 | 10 | 0.5 | 140 |
| 153 | 90 | 10 | 0.5 | 140 |

4) Injector Setup—Injection: Standard Injection; Injection Volume: 15 µl; Draw Speed: 50 µl/min; Injector Speed: 50 µl/min; Needle wash: 15 ul H$_2$O; Stop Time: As pump; 5) DAD Signals—Table 5; Peak Width: >0.1 min; Slit: 4 nm; Stop Time: As pump;

TABLE 5

| Sample | Bw | Reference | Bw | Units |
|---|---|---|---|---|
| 280 | 4 | 600 | 100 | nm |
| 276 | 4 | 600 | 100 | nm |
| 214 | 8 | 600 | 100 | nm |
| 220 | 4 | 600 | 100 | nm |
| 250 | 8 | 600 | 100 | nm |

6) Column Thermostat: Temperature: 20° C.; Store: Temperature.

The column was equilibrated with 10 column volumes of 90% mobile phase A and 10% mobile phase B. 15 µl of the resolution solution was injected. In the chromatogram obtained, the main non-PEGylated peak elutes at a retention time of approximately 64-67 minutes, the non-PEGylated deamidated peak elutes at a retention time of approximately 62-65 minutes, the main PEGylated peak elutes at a retention time of approximately 43-46 minutes, and the PEGylated deamidated peak elutes at a retention time of approximately 41-44 minutes. 15 µl of the standard was injected, and the HPLC program was run. 15 µl of the test article was injected, and the HPLC program was run. Samples were run in triplicate. Average retention times were reported.

Modifications to various conditions and/or parameters may be required to analyze PEGylated hGH and other forms. Modifications to cIEX-HPLC are known to those of ordinary skill in the art. Additional reference standards include, but are not limited to, in-process pY35pAF for in-process release of bulk pY35pAF, purified pY35pAF for quantifying residual free pY35pAF in PEGylated-pY35pAF, and purified PEG-pY35pAF.

Data Analysis

The retention times of the hGH test article with the standard were compared and purity determinations of non-PEGylated hGH and PEGylated hGH calculated. Purity may be determined by calculations such as: (Integration area of the main peak of hGH sample/integration areas of all peaks of hGH sample)×100%. Any peak(s) due to the solvent were disregarded.

Figure 19:
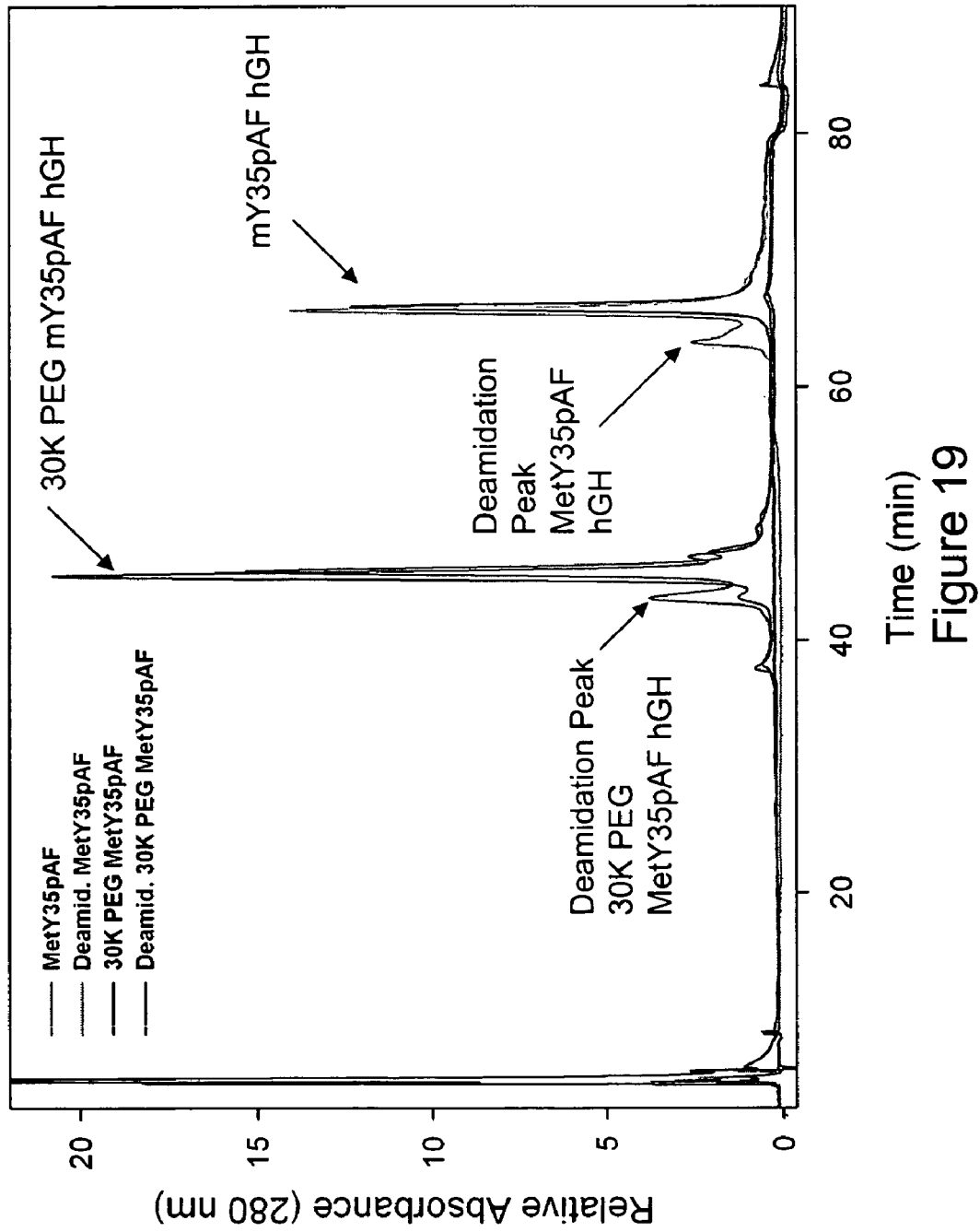
FIG. 19 shows results from an analysis by cIEX-HPLC.

Table 6 and FIG. 19 show cIEX-HPLC analysis of 30K PEGmY35pAF hGH and mY35pAF hGH.

TABLE 6

| | Deamid 30K PEG mY35pAF | Rel. % | 30K PEG mY35pAF | Rel. % | Deamid mY35pAF | Rel % | mY35pAF | Rel % |
|---|---|---|---|---|---|---|---|---|
| mY35pAF | | | | | | | 66.26 | 100 |
| Deamid mY35pAF | | | | | 63.48 | 18.5 | | 81.4 |
| 30K PEG mY35pAF | 43.37 | 5.3 | 45.07 | 72.1 | | | | |
| Deamid 30K PEG mY35pAF | 43.32 | 21.1 | 45.42 | 64.9 | | | | |

Example 7

This example describes the synthesis of p-Acetyl-D,L-phenylalanine (pAF) and m-PEG-hydroxylamine derivatives.

The racemic pAF was synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures were completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which was stirred at room temperature (RT) for 1 hour, methoxy-polyethylene glycol amine (m-PEG-NH$_2$, 7.5 g, 0.25 mmol, Mt. 30 K, from Bio-Vectra) and Diisopropylethylamine (0.1 mL, 0.5 mmol) were added. The reaction was stirred at RT for 48 hours, and then was concentrated to about 100 mL. The mixture was added dropwise to cold ether (800 mL). The t-Boc-protected product precipitated out and was collected by filtering, washed by ether 3×100 mL. It was further purified by re-dissolving in DCM (100 mL) and precipitating in ether (800 mL) twice. The product was dried in vacuum yielding 7.2 g (96%), confirmed by NMR and Nihydrin test.

The deBoc of the protected product (7.0 g) obtained above was carried out in 50% TFA/DCM (40 mL) at 0° C. for 1 hour and then at RT for 1.5 hour. After removing most of TFA in vacuum, the TFA salt of the hydroxylamine derivative was converted to the HCl salt by adding 4N HCl in dioxane (1 mL) to the residue. The precipitate was dissolved in DCM (50 mL) and re-precipitated in ether (800 mL). The final product (6.8 g, 97%) was collected by filtering, washed with ether 3×100 mL, dried in vacuum, stored under nitrogen. Other PEG (5K, 20K) hydroxylamine derivatives were synthesized using the same procedure.

Example 8

This example describes expression and purification methods used for hGH polypeptides comprising a non-natural amino acid. Host cells have been transformed with orthogonal tRNA, orthogonal aminoacyl tRNA synthetase, and hGH constructs.

A small stab from a frozen glycerol stock of the transformed DH10B(fis3) cells were first grown in 2 ml defined medium (glucose minimal medium supplemented with leucine, isoleucine, trace metals, and vitamins) with 100 μg/ml ampicillin at 37° C. When the $OD_{600}$ reached 2-5, 60 μl was transferred to 60 ml fresh defined medium with 100 μg/ml ampicillin and again grown at 37° C. to an $OD_{600}$ of 2-5. 50 ml of the culture was transferred to 2 liters of defined medium with 100 μg/ml ampicillin in a 5 liter fermenter (Sartorius BBI). The fermenter pH was controlled at pH 6.9 with potassium carbonate, the temperature at 37° C., the air flow rate at 5 lpm, and foam with the polyalkylene defoamer KFO F119 (Lubrizol). Stirrer speeds were automatically adjusted to maintain dissolved oxygen levels $\geq$30% and pure oxygen was used to supplement the air sparging if stirrer speeds reached their maximum value. After 8 hours at 37° C., the culture was fed a 50× concentrate of the defined medium at an exponentially increasing rate to maintain a specific growth rate of 0.15 $hour^{-1}$. When the $OD_{600}$ reached approximately 100, a racemic mixture of para-acetyl-phenylalanine was added to a final concentration of 3.3 mM, and the temperature was lowered to 28° C. After 0.75 hour, isopropyl-b-D-thiogalactopyranoside was added to a final concentration of 0.25 mM. Cells were grown an additional 8 hour at 28° C., pelleted, and frozen at −80° C. until further processing.

The His-tagged mutant hGH proteins were purified using the ProBond Nickel-Chelating Resin (Invitrogen, Carlsbad, Calif.) via the standard His-tagged protein purification procedures provided by Invitrogen's instruction manual, followed by an anion exchange column.

The purified hGH was concentrated to 8 mg/ml and buffer exchanged to the reaction buffer (20 mM sodium acetate, 150 mM NaCl, 1 mM EDTA, pH 4.0). MPEG-Oxyamine powder was added to the hGH solution at a 20:1 molar ratio of PEG:hGH. The reaction was carried out at 28° C. for 2 days with gentle shaking. The PEG-hGH was purified from un-reacted PEG and hGH via an anion exchange column.

Example 9

Purity Analysis by SDS-PAGE

The following method was used to evaluate the purity of PEG-recombinant hGH conjugates by SDS-PAGE, followed by total protein staining. Any charged molecule such as a protein will migrate when placed in an electric field. The velocity of migration of a protein in an electric field depends on the strength of the electric field, the net electric charge on the protein, and the frictional resistance. The frictional resistance is the function of the size and shape of the protein. When denatured in the presence of excess SDS, most proteins bind SDS in a constant weight ratio such that they have essentially identical charge densities and migrate in polyacrylamide gels according to protein size. Proteins separated by gel electrophoresis can be detected by Coomassie Brilliant Blue staining.

Equipment for this procedure included, the following or equivalents thereof: XCell Surelock Mini-Cell (Invitrogen), heat block set to +70-80° C., power supply (up to 200V), microcentrifuge (such as Beckman Coulter Microfuge 18 or 22R), and reciprocal shaker. Reagents included NuPAGE MOPS SDS Running Buffer (20×, Invitrogen PN NP0001); NuPAGE MES SDS Running Buffer (20×, Invitrogen PN NP0002); NuPAGE LDS Sample Buffer (4×, Invitrogen PN NP0007); NuPAGE Sample Reducing Agent (10×, Invitrogen PN NP0009); 12% Bis-Tris NuPAGE precast gel, 1.0 mm×10-well (Invitrogen PN NP0341BOX); 4-12% Bis-Tris NuPAGE precast gel, 1.0 mm×10-well (Invitrogen PN NP0321BOX); Pre-Stained Molecular Weight Marker (See-Blue Plus2, Invitrogen PN LC5925); MilliQ-quality $H_2O$ or equivalent; SimplyBlue SafeStain (Invitrogen PN LC6065) or equivalent; reference standard (WHO rhGH standard; calibration solutions for rhGH (Y35pAF-pB2/pB3, 2 mg/ml); calibration solutions for the pEG-rhGH conjugate (PEG30-pY35pAF-01, 2 mg/mL). Protein concentrations of the standards and the test article were measured using standard techniques known in the art.

Analysis of PEGylated rhGH Product

10 μg of the reference standard (RS, e.g. calibration solution PEG30-pY35pAF-01) was prepared under non-reducing and reducing conditions. 10 ug of PEG30-pY35pAF-01 (2 mg/mL) was added to 4× LDS and MilliQ $H_2O$ to obtain a final 28 μl sample in 1× LDS. For reduced conditions, 10 μg of reference standard was added to 4× LDS, 10× Reducing Agent, and MilliQ $H_2O$ to obtain a 28 μl sample in 1× LDS and 1× Reducing Agent. Similarly, 10 μg of PEGylated rhGH test articles were also prepared under non-reduced and reduced conditions. The PEG-rhGH test articles and PEG-rhGH reference standards were not heated, but were snap centrifuged prior to loading on 4-12% Bis-Tris NuPAGE precast gels prepared with 1× MES SDS Running Buffer according to manufacturer's instructions. The gels were loaded in the order of Pre-Stained Molecular Weight Marker, 10 μg reference standard, blank lane (recommended to minimize potential carryover effects), followed by the test articles with a maximum setting of 200V for 35 minutes. The gels were incubated in di-$H_2O$, stained with shaking using SimplyBlue or an equivalent, and destained with water.

The electropherogram of the PEG-rhGH test article should conform to the electropherogram obtained with the PEG-rhGH reference standard. Any bands that do not match the reference standard may be degradation products or aggregates. Higher molecular weight bands may represent aggregates, and lower molecular weight bands may represent polypeptide that is no longer conjugated to PEG.

Example 10

Purity and Chemical Degradation Analysis of rhGH by CEX-HPLC/IEX-HPLC

The following method was used to assess relative purity and potential chemical degradation (i.e. deamidation) of PEGylated recombinant human growth hormone (rhGH) by cation-exchange high performance liquid chromatography (CEX-HPLC). CEX-HPLC is a technique that relies on charge-charge interactions between a protein and the charges immobilized on the resin. Cation exchange chromatography takes advantage of the positively charged ions of a protein that bind to the negatively charged resin. A common structural modification of rhGH deamidation of asparagine (Asn) residues, and this CEX-HPLC method permits the separation of deamidated and deamidation intermediates of PEGylated and nonPEGylated rhGH. This method was used to support identification and purity assessment of PEGylated rhGH. Some partial degradation products of rhGH are observable using this technique.

Equipment for this procedure included, the following or equivalents thereof: UV/Vis Spectrophotometer (Agilent 8453 or equivalent); 50 µl quartz cuvette; 0.5 mL Vivaspin concentrators (if needed; Vivascience 10,000 MWCO, PES, VS0102 or equivalent); PD-10, NAP-10, or NAP-5 column (GE Healthcare, Cat. #17-0851-01, 17-0853-01, 17-0854-01); HPLC vials and caps (Alltech 100 µl screw cap polypropylene vials #12962, TFE liner caps #73048, open hole screw caps #73044, or equivalent); clean 1 and 2 L glass bottles; column—PolyCAT A 4.6×200 mm, 5 µ, 1000 Å (PolyLC, 204CT0510) and PolyCAT A guard column, 4.6×10 mm, 5 µ, 1000 Å (PolyLC, JGCCT0510); high-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software).

Reagents for this procedure included water (Milli-Q quality or equivalent) and solid chemicals are analytical grade or better and solvents are HPLC grade or better, unless otherwise noted. Storage of reagents and procedural steps occurred at room temperature, unless otherwise indicated. Examples of such chemicals include Ammonium Acetate,. Spectrum A2149, HPLC grade, or equivalent; Acetonitrile, Fisher A998, HPLC grade, or equivalent; Ammonium Bicarbonate, Fluka # 09830, Ultra>99.5%, or equivalent; Glacial Acetic Acid, Fisher # 64-19-7, HPLC grade, or equivalent; Sodium Citrate Dihydrate, Spectrum S0165, USP grade, or equivalent; Glycine, Spectrum AM125 or equivalent; Mannitol, Spectrum MA165, or equivalent; 6N HCl, Mallinckrodt 2662-46, or equivalent.

Mobile phase A buffer was 50 mM Ammonium Acetate, pH 4.25, 40% Acetonitrile (AcCN), and Mobile Phase B buffer was 500 mM Ammonium Acetate, pH 4.25, 40% AcCN. Additional reagents prepared were 10% acetic acid; Buffer for Deamidation: 30 mM Ammonium Bicarbonate, pH 9.0; and Sample Dilution Buffer: 20 mM Sodium Citrate, 20 g/L Glycine, 5 g/L Mannitol, pH 6.0, each sterile filtered using 0.22 µm PES filters (Coming #431098, or equivalent).

World Health Organization (WHO) rhGH (Cat. # 98/574) was used as a non-PEGylated hGH standard. It was reconstituted in 1.0 ml of water and diluted to 1.1 mg/ml using dilution buffer. 10% (v/v) of 10% acetic acid was added to bring the pH between pH 3.8-4.3 with a final concentration of 1.0 mg/ml (acceptable range 0.9-1.1 mg/ml). Another non-PEGylated hGH standard, the calibration solution Y35pAF-pB2/pB3, was prepared in a similar fashion. A PEGylated hGH standard, calibration solution PEG30-pY35pAF-01, was also prepared in a similar fashion.

For the PEGylated Resolution Solution, the PEG30-pY35pAF-01 calibration solution was buffer exchanged into 30 mM Ammonium Bicarbonate, pH 9.0 buffer using a PD-10, Nap-10, or NAP-5 desalting column. The standard was concentrated using a 0.5 mL Vivaspin concentrator to approximately 2 mg/ml (acceptable range 1.9-2.1 mg/ml), and the sample was incubated at 37° C. for 24 hours. The sample or portion of the sample needed was diluted to 1.1 mg/ml using dilution buffer, and 10% (v/v) of 10% acetic acid was added to bring pH between pH 3.8-4.3 with a final concentration of 1.0 mg/ml (acceptable range 0.9-1.1 mg/ml).

The test article was diluted to 1.1 mg/ml using dilution buffer and 10% (v/v) of 10% acetic acid was added to bring pH between pH 3.8-4.3 with a final concentration of 1.0 mg/ml (acceptable range 0.9-1.0 mg/ml). Protein concentrations of the standards and the test article were measured using standard techniques known in the art.

Procedure

The instrument was set-up with the following conditions: 1) Column: PolyCAT A 204CT0510 and JGCCT0510; 2) Auto sampler Temperature: room temperature; 3) Pump Setup: step gradient: 81.5-108.5 mM Ammonium Acetate pH 4.25 (7-13% B), followed by 108.5-500 mM Ammonium Acetate pH 4.25 (13-100% B); 4) Table 7;

TABLE 7

| Time | Mobile Phase A | Mobile Phase B | Flow (ml/min) | Pressure (bar) |
|---|---|---|---|---|
| 0 | 100 | 0 | 1.0 | 140 |
| 10 | 100 | 0 | 1.0 | 140 |
| 11 | 93 | 7 | 1.0 | 140 |
| 91 | 87 | 13 | 1.0 | 140 |
| 102 | 0 | 100 | 1.0 | 140 |
| 118 | 0 | 100 | 1.0 | 140 |
| 119 | 100 | 0 | 1.0 | 140 |
| 151 | 100 | 10 | 1 | 140 |

5) Injector Setup—Injection: Standard Injection; Injection Volume: 25 µl; Draw Speed: 50 µl/min; Injector Speed: 50 µl/min; Needle wash: 15 µl H$_2$O; Stop Time: As pump; 6) DAD signals: Table 8;

TABLE 8

| Sample | Bw | Reference | Bw | Units |
|---|---|---|---|---|
| 280 | 4 | 600 | 100 | nm |
| 276 | 4 | 600 | 100 | nm |
| 214 | 8 | 600 | 100 | nm |
| 220 | 4 | 600 | 100 | nm |
| 250 | 8 | 600 | 100 | nm |

Peak Width: >0.1 min; Slit: 4 nm; Stop Time: as pump; 7) Column Thermostat: Temperature: 30° C.; record the temperature.

The column was equilibrated with 10-15 column volumes of 100% mobile phase A. 20-50 µl of the PEGylated calibration solution PEG30-pY35pAF-01 was injected. The main PEGylated peak eluted at a retention time of 56.97 min (±0.5 min). Next, 25-50 µl of the WHO or calibration solution Y35pAF-pB2/pB3 was injected and the HPLC program was run. The main non-PEGylated peak eluted at a retention time of 98.54 min (±0.5 min), a relative retention time of 1.73±0.01 to the main PEGylated peak.

25-50 µl of the PEGylated resolution solution was then injected. In the chromatogram obtained, the main PEGylated peak eluted at a retention time of 56.97 min (±0.5 min), and the PEGylated deamidated peak eluted at a retention time of 0.79±0.02 relative to the main peak (45.23±0.3 min; (current conditions result in a resolution of 2.3±0.02).

25-50 µl of the PEGylated test article was then injected, and the HPLC program was run. The samples were run in triplicate, and average retention times were noted. Chromatograms were generated with absorbance (280 nm).

Data Analysis

The retention time of the PEGylated rhGH test article was compared with the calibration solution PEG30-pY35pAF-01. The average purity of the test article was calculated using: (Integration area of the main peak/integration areas of all peaks)×100%. Any peak(s) due to the solvent were disregarded.

Example 11

Purity Determination of rhGH by SEC-HPLC

This procedure was used to assess the purity of recombinant human growth hormone (rhGH) and PEGylated rhGH by size-exclusion high performance liquid chromatography (SEC-HPLC). This test separates monomer from dimer and other related substances of higher molecular weight in the sample, as well as PEGylated and nonPEGylated samples. SEC-HPLC is a technique using the stationary phase as a porous matrix which is permeated by mobile phase molecules. Sample molecules small enough to enter the pore structure are retarded, while larger molecules are excluded and therefore rapidly carried through the column. Thus, size exclusion chromatography means separation of molecules by size and the chromatographic elution time is characteristic for a particular molecule. This procedure is used to determine the percentage of monomer (PEGylated and unPEGylated) rhGH. Dimer and other high molecular weight proteins are observable using this technique. An example of SEC-HPLC integration is shown as FIG. 20 with the y-axis as absorbance (214 nm) and the x-axis as time (minutes).

References for this technique include European Pharmacopoeia 2002, p. 193; British Pharmacopoeia 2001, p. 1941; "High-Performance Size-Exclusion Chromatographic Determination of the Potency of Biosynthetic Human Growth Hormone Products" by R. M. Riggin et al. Journal of Chromatography 435(1988), p. 307-318.

Equipment for this procedure included, the following or equivalents thereof: UV/Vis Spectrophotometer (Agilent 8453 or equivalent); 50 ul quartz cuvette; 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent); clean 1 and 2 L glass bottles; Column—Tosohaas TSK Super SW3000 18675 and Super SW Guard Column 18762, a silica-based size exclusion HPLC column with a dimension of 4.6×300 mm, particle size of 4 μm and pore size of 250 Å along with a guard column having a dimension of 4.6×35 mm and 4 μ particle size; High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), Refractive Index detector (RID) and Chemstation chromatography software).

Reagents for this procedure included water (Milli-Q quality or equivalent) and solid chemicals are analytical grade or better and solvents are HPLC grade or better, unless otherwise noted. The storage of reagents and procedural steps occurred at room temperarture, unless otherwise indicated. Examples of such chemicals included Monobasic Monohydrate Sodium Phosphate, Spectrum U.S.P. grade S0130, or equivalent; Dibasic Heptahydrate Sodium Phosphate, Spectrum U.S.P. grade S0140, or equivalent; 2-propanol, Fisher HPLC grade A451-4, or equivalent.

Mobile phase buffer was 97% of 63 mM sodium phosphate pH 7.0, 3% of 2-propanol. Solution A was 25 mM Sodium Phosphate, pH 7.0. Both were sterile filtered using 0.22 μm PES filters (Coming #431098, or equivalent).

World Health Organization (WHO) rhGH (Cat. # 98/574) was used as a non-PEGylated hGH standard. It was reconstituted with 1.0 ml of water and diluted to 1 mg/ml concentration (acceptable range 0.9-1.1 mg/ml) in WHO buffer. Another non-PEGylated hGH standard, calibration solution Y35pAF-pB2/pB3, was prepared in a similar fashion and diluted with 20 mM sodium citrate, 2% glycine, 0.5% mannitol, pH 6. A PEGylated hGH standard, calibration solution PEG30-pY35pAF-01, was also prepared in a similar fashion and diluted with 20 mM sodium citrate, 2% glycine, 0.5% mannitol, pH 6. For the Resolution Solution, the PEG30-pY35pAF-02 higher molecular weight standard was brought to 1 mg/ml concentration (acceptable range 0.9-1.1 mg/ml). This solution contains approximately 33% PEG-PEG-GH, 66.5% PEG-GH): Test material was diluted to approximately 1.0 mg/ml with Solution A (acceptable range 0.9-1.1 mg/ml). All sample concentrations were measured using standard techniques known in the art. The dilution of samples may be performed with any suitable buffer.

Procedure

The instrument was set-up with the following conditions: 1) Column: TSK Super SW3000 18675 and Guard Column 18762; 2) Pump Setup—gradient: isocratic; flow rate: 0.3 ml/min; duration: 25 min; Max Pressure: 120 bar; 3) Injector Setup—Injection: Standard Injection; Injection Volume: 10 μl; Draw Speed: 100 μl/min; Injection Speed: 100 μl/min; Needle wash: 100 ul $H_2O$; Stop Time: As pump; 4) DAD Signals: Table 9;

TABLE 9

| Sample | Bw | Reference | Bw | Units |
|---|---|---|---|---|
| 214 | 4 | 600 | 100 | nm |
| 276 | 4 | 600 | 100 | nm |
| 220 | 8 | 600 | 100 | nm |
| 280 | 4 | 600 | 100 | nm |
| 250 | 8 | 600 | 100 | nm |

Peak Width: >0.05 min; Slit: 2 nm; Stop Time: as pump; 5) RID Signal—Temperature: 35° C.; Response Time: >0.2 min 4 s, standard; 6) Column Thermostat: Temperature: 23° C.; record the temperature.

The column was equilibrated with 10 column volumes (50 ml=166 min at 0.3 ml/min) of the mobile phase, and the RID was purged for at least 20 minutes before injecting samples. DAD and RI detectors were autobalanced before sample runs.

20 μl of the calibration solution Y35pAF-pB2/pB3 (or WHO standard) was injected, and the HPLC program was run. In the chromatogram obtained, the main unPEGylated peak eluted at a retention time of approximately 12.96 (±0.05) min. The higher molecular weight unPEGylated rhGH dimer eluted at a retention time of 0.94±0.02 relative to the main peak. Higher molecular weight aggregates eluted at retention times of 7.3-8.0 min.

20 μl of the calibration solution PEG30-pY35pAF-01 was injected. The main pegylated peak eluted at a retention time of approximately 8.33 (±0.08) min (relative retention time of 0.64 to the unPEGylated rhGH). Higher molecular weight PEGylated rhGH aggregates eluted at times grater than 8.0 min.

20 μl of the resolution solution was injected and the HPLC program was run. The main PEGylated peak elutes at a retention time of 8.28 min, and the higher molecular weight species eluted at 7.54 min, a relative retention time of 0.9 (±0.05) relative to the main PEGylated peak.

20 μl of the test article was injected, and the HPLC program was run. Samples were run in triplicate and average retention times were noted. The retention time of the rhGH test article was compared with the rhGH standard(s).

The SEC-HPLC data from the test article was compared to data obtained from the reference standards. To determine the purity of PEGylated rhGH, the integrated main peak areas of the PEGylated rhGH sample was compared with the total peak area, and the percentage of PEGylated monomer in PEG-rhGH sample was calculated by: (main peak area of PEG-rhGH sample/total peak area )×100%. The percentage of PEGylated dimer, higher aggregates, and nonPEGylated monomer were calculated in the PEGylated hGH test article. Any peak(s) due to the solvent were disregarded. Peaks eluting in the chromatogram prior to the main PEGylated hGH peak represent higher molecular weight species. Such higher molecular weight species may include but are not limited to dimers (such as PEG-PEG-hGH and other possible dimers) or soluble aggregates. Peaks eluting after the main PEGylated hGH peak represent lower molecular weight species. Such lower molecular weight species may include but are not limited to non-PEGylated monomer and clipped forms of PEGylated hGH.

Example 12

Purity and Chemical Degradation Analysis of PEG-hGH by RP-HPLC

The following method was used to assess relative purity and potential chemical degradation (i.e. oxidation) of PEGylated recombinant human growth hormone (PEG-hGH) by reverse phase high performance liquid chromatography (RP-HPLC). RP-HPLC is a technique that separates molecules on the basis of relative hydrophobicities. Samples are passed over a stationary phase of silica covalently bonded to hydrocarbon chains. The molecules of interest are retarded by the stationary phase and eluted with an isocratic solvent. The chromatographic elution time is characteristic for a particular molecule. This method separates PEG-hGH from nonPEGylated hGH, as well as isoforms based on subtle differences in hydrophobicity and retention behavior associated with structural modifications such as oxidation. This method was used to support identification and purity assessment of PEG-hGH. Some partial degradation products of rhGH are observable using this technique. An example of RP-HPLC integration is shown as FIG. 21 with the y-axis as absorbance (214 nm) and the x-axis as time (minutes).

Equipment for this procedure included, the following or equivalents thereof: UV/Vis Spectrophotometer (Agilent 8453 or equivalent); 50 μl quartz cuvette; 0.5 mL Vivaspin concentrators (if needed; Vivascience 10,000 MWCO, PES, VS0102 or equivalent); HPLC vials and caps (Alltech 100 μl screw cap polypropylene vials #12962, TFE liner caps #73048, open hole screw caps #73044, or equivalent); clean 1 and 2 L glass bottles; Column—J. T. Baker Wide Pore Butyl, 250×4.6 mm (cat# 7116-00); High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software).

Reagents for this procedure included water (Milli-Q quality or equivalent) and solid chemicals are analytical grade or better and solvents are HPLC grade or better, unless otherwise noted. Storage of reagents and procedural steps occurred at room temperature, unless otherwise indicated. Examples of such chemicals include, Acetonitrile, Fisher A998, HPLC grade, or equivalent; Trifluoroacetic Acid, Halocarbon UN2699, Biograde, or equivalent; Sodium Phosphate, Spectrum MA1654, USP grade, or equivalent; Glycine, Spectrum AM125 or equivalent; Mannitol, Spectrum MA165, or equivalent; Trehalose, Fluka 90208, or equivalent; 10N Sodium Hydroxide, or equivalent. Mobile Phase A was 0.1% TFA in $H_2O$, and Mobile phase B was 0.1% TFA in Acetonitrile.

One of the nonPEGylated standards was World Health Organization (WHO) rhGH (Cat. # 98/574). It was reconstituted with 1.0 ml of water and diluted to 1.0 mg/ml (acceptable, range 0.9-1.1 mg/ml) with WHO buffer. Another nonPEGylated standard, calibration solution Y35pAF-pB2/pB3, was prepared in a similar fashion and diluted with 20 mM sodium citrate, 2% glycine, 0.5% mannitol, pH 6. Calibration solution PEG30-pY35pAF-01, a PEGylated standard, was also prepared in a similar fashion and diluted with 20 mM sodium citrate, 2% glycine, 0.5% mannitol, pH 6. For the PEGylated Resolution Solution, PEG30-pY35pAF-01 was incubated with 0.1% $H_2O_2$ for 24 hours at 4° C. to oxidize PEG30-pY35pAF-01. To obtain between 5% and 20% oxidized PEG30-pY35pAF-01, this incubation time with $H_2O_2$ may vary between 4-24 hours. Catalase (20 mg/ml stock) can be added to stop the oxidation reaction if needed.

The test article was diluted to 1.0 mg/ml using dilution buffer (acceptable range 0.9-1.0 mg/ml). The sample dilution buffer may be any suitable buffer. Standards and test article protein concentrations were measured using standard techniques known in the art.

Procedure

The instrument was set-up with the following conditions: 1) Column: J. T. Baker Wide Pore Butyl, 250×4.6 mm (cat# 7116-00); 2) Auto sampler—Temperature: 4° C.; 3) Pump Setup: Table 10;

TABLE 10

| Time (min) | Flow (mL/min) | % B |
|---|---|---|
| 0.0 | 1.0 | 31.0 |
| 17.5 | 1.0 | 64.5 |
| 17.75 | 1.0 | 100 |
| 18.75 | 1.0 | 100 |
| 19.0 | 1.0 | 31.0 |
| 25.0 | 1.0 | 31.0 |

4) Injector Setup—Injection: Standard Injection; Injection Volume: 10 μl; Draw Speed: 100 μl/min; Injector Speed: 100 μl/min; Needle wash: 20 μl $H_2O$; Stop Time: As pump; 5) DAD Signals: Table 11;

TABLE 11

| Sample | Bw | Reference | Bw | Units |
|---|---|---|---|---|
| 214 | 4 | 600 | 100 | nm |
| 276 | 4 | 600 | 100 | nm |
| 280 | 16 | 600 | 100 | nm |
| 220 | 4 | 600 | 100 | nm |
| 250 | 8 | 600 | 100 | nm |

Peak Width: >0.1 min; Slit: 4 nm; Stop Time: as pump; 6) Column Thermostat: Temperature: RT; record the temperature.

New columns were flushed with 10CV of distilled HPLC-grade water to remove the shipping solvent. The column was cleaned with 10-15 column volumes (CV) of 0.1% TFA in 60% isopropanol in MillQ $H_2O$, and 10-15 CV $H_2O$. This can be followed by 5 CV of 50:50 DMSO:$H_2O$ if necessary; otherwise the column was equilibrated with mobile phase A.

The column was equilibrated with 10-15 column volumes of 100% mobile phase A. 10 μl of the PEGylated calibration solution PEG30-pY35pAF-01 was injected. The main pegylated peak eluted at a retention time of 17.05 min (±0.5 min).

10 μl of the WHO or calibration solution Y35pAF-pB2/pB3 was injected, and the HPLC program run. The main nonPEGylated peak elutes at a retention time of 19.04 min (±0.5 min), a relative retention time of 1.1±0.05 to the main PEGylated peak.

10 μl of the PEGylated resolution solution was injected. In the chromatogram obtained, the main PEGylated peak eluted at a retention time of 17.12 min (±0.5 min), and the PEGylated oxidized peak eluted at a retention time of 0.93±0.02 relative to the main peak (15.94±0.3 min and a resolution of 2.97±0.05).

10 μl of the PEGylated test article was injected, and the HPLC program was run. Samples were run in triplicate and average retention times noted.

The retention time (using $A_{214}$) of the PEGylated rhGH test article was compared with the calibration solution PEG30-pY35pAF-01. The average purity of the test article (using $A_{214}$) was calculated using: (Integration area of the main peak/integration areas of all peaks)×100%. Any peak(s) due to the solvent were disregarded.

Example 13

A summary of the methods used in formulations development is shown as Table 12. Long-term storage, basic, or acidic conditions can result in the following product-related impurities: Deamidated hGH—Asn149, Asn152; Oxidized hGH—Met14, Met125; Isomerized hGH—Asp130; Dehydrated hGH—Asp130; desPhe/des-Phe-Pro—Phe1, Pro2 (non-enzymatic cleavage); Dimer (covalent and non-covalent species); Clipped hGH (cleavage between Thr142 and Tyr143). Additional methods such as moisture analysis, pH and bioassays including, but not limited to, proliferation assays are used to evaluate formulations for PEGylated hGH comprising a non-naturally encoded amino acid.

SDS-PAGE, SEC-HPLC, and cIEX-HPLC show key degradation products. cIEX-HPLC may show cyclic imide, iso-asp (Isomerized hGH-Asp130), and deamidation intermediates.

Example 14

Lyophilized Formulation Study

Purified PEGylated hGH samples comprising a non-naturally encoded amino acid in 20 mM sodium citrate, 2% glycine, 0.5% mannitol, pH 6 were dialyzed into a buffer from the formulations matrix (Table 13) prior to stability analysis. A reaction between the non-naturally encoded amino acid (para-acetylphenylalanine) substituted for a tyrosine at position 35 of hGH and mPEG-oxyamine formed an oxime bond between hGH and PEG. The samples were then lyophilized and stored at 4, 25, and 40° C. After storage of the lyophilized samples for various lengths of time (0, 1 week, 2 weeks, 4 weeks, 6 weeks, 2 months, and 3 months), the samples were reconstituted in water to 2 mg/ml and characteristics such as moisture content (Karl Fisher), pH and concentration were observed post reconstitution using standard techniques known to one of ordinary skill in the art. The methods described in Examples 9-13 were used to analyze the PEGylated hGH for degradation products. Sodium phosphate and sodium succinate were included in the formulations matrix. Additional analyses include time points at 4 months and 6 months.

TABLE 12

| Current Methods | Structure/Stability | Deamidation | Oxidation | Clipped | Isomerization | desPhe/desPhe-Pro | Higher MW species | DePEGylated ahGH |
|---|---|---|---|---|---|---|---|---|
| SDS PAGE GEL | | | | X | | | X | X |
| IEF GEL | | X | X | | | | | X |
| SEC-HPLC | | | | | | | X | X |
| RP-HPLC | | | X | | | | | X |
| CEX-HPLC | | X | | | X | X | (X) | X |
| Analytical Ultracentrifugation for accelerated study | | | | | | | X | |
| Dynamic Light Scattering for accelerated study | | | | | | | X | |
| FTIR | X | | | | | | | |

TABLE 13

FORMULATIONS MATRIX

| Formulation ID | Buffer | pH | Bulking Agent | Stabilizer | Antioxidant | Surfactant |
|---|---|---|---|---|---|---|
| P6MT | 10 mM Phosphate | 6 | 4% Mannitol | 2% Trehalose | none | 0.01% PS20 |
| S4MT | 10 mM Succinate | 4 | 4% Mannitol | 2% Trehalose | none | 0.01% PS20 |
| S5MT | 10 mM Succinate | 5 | 4% Mannitol | 2% Trehalose | none | 0.01% PS20 |
| S5GT | 10 mM Succinate | 5 | 2.5% Glycine | 2% Trehalose | none | 0.01% PS20 |
| H6MT | 10 mM Histidine | 6 | 4% Mannitol | 2% Trehalose | none | 0.01% PS20 |
| P6GT | 10 mM Phosphate | 6 | 2.5% Glycine | 2% Trehalose | none | 0.01% PS20 |
| P6MA | 10 mM Phosphate | 6 | 4% Mannitol | 4.4% Arginine | none | 0.01% PS20 |
| P6MS | 10 mM Phosphate | 6 | 4% Mannitol | 2% Sucrose | none | 0.01% PS20 |
| P6MTMet | 10 mM Phosphate | 6 | 4% Mannitol | 2% Trehalose | 1 mM Methionine | 0.01% PS20 |
| P7MT | 10 mM Phosphate | 7 | 4% Mannitol | 2% Trehalose | none | 0.01% PS20 |
| P7GT | 10 mM Phosphate | 7 | 2.5% Glycine | 2% Trehalose | none | 0.01% PS20 |
| P6MGT | 10 mM Phosphate | 6 | 2% Mannitol, 1.25% Glycine | 2% Trehalose | none | 0.01% PS20 |
| P6MGT-P | 10 mM Phosphate | 6 | 2% Mannitol, 1.25% Glycine | 2% Trehalose | none | |
| P6MT-P | 10 mM Phosphate | 6 | 4% Mannitol | 2% Trehalose | none | |
| P6GT-P | 10 mM Phosphate | 6 | 2.5% Glycine | 2% Trehalose | none | |

Results

Moisture Content, pH, and concentration results are shown in Tables 14-32.

TABLE 14

MOISTURE, CONCENTRATION, pH POST RECONSTITUTION; T = 0

| Formulation ID | Conc. (mg/mL) | pH | % Moisture |
|---|---|---|---|
| P6MT | 2.1 | 6.20 | 0.849 |
| S4MT | 2.0 | 4.04 | 0.587 |
| S5MT | 2.0 | 5.02 | 0.662 |
| S5GT | 2.1 | 5.10 | 0.495 |
| H6MT | 2.1 | 5.93 | 0.790 |
| P6GT | 2.2 | 6.13 | 0.442 |
| P6MA | 2.1 | 6.43 | 1.558 |
| P6MS | 2.2 | 6.11 | 0.454 |
| P6MTMet | 2.1 | 6.15 | 0.713 |
| P7MT | 1.9 | 6.97 | 0.828 |
| P7GT | 2.1 | 6.94 | 0.928 |
| P6MGT | 2.0 | 6.14 | 1.038 |
| P6MGT-P | 2.0 | 6.15 | 4.328 |
| P6MT-P | 2.0 | 6.05 | 1.522 |
| P6GT-P | 2.1 | 6.10 | 0.884 |

TABLE 15

MOISTURE CONTENT

| Formulation ID | % Moisture (t = 0) | % Moisture (2 months) |
|---|---|---|
| P6MT | 0.849 | 0.796 |
| H6MT | 0.790 | 0.714 |
| P6GT | 0.442 | 1.035 |
| P6MS | 0.454 | 0.301 |
| P6MTMet | 0.713 | 0.693 |
| P7MT | 0.828 | 0.687 |
| P7GT | 0.928 | 0.670 |
| P6MGT | 1.038 | 1.447 |
| P6MGT-P | 4.328 | 1.552 |
| P6MT-P | 1.522 | 1.495 |
| P6GT-P | 0.884 | 0.751 |

TABLE 16

CONCENTRATION, pH POST RECONSTITUTION; T = 1 week; 4° C.

| Formulation ID | Conc. (mg/mL) | pH |
|---|---|---|
| P6MT | 1.7 | 6.03 |
| S4MT | 1.7 | 3.97 |
| S5MT | 1.7 | 4.94 |
| S5GT | 1.8 | 5.03 |
| H6MT | 1.9 | 5.88 |
| P6GT | 2.0 | 5.95 |
| P6MA | 1.8 | 6.33 |
| P6MS | 1.8 | 6.09 |
| P6MTMet | 1.8 | 5.95 |
| P7MT | 1.6 | 6.93 |
| P7GT | 1.8 | 6.89 |
| P6MGT | 1.7 | 6.07 |
| P6MGT-P | 1.7 | 5.97 |
| P6MT-P | 1.9 | 5.93 |
| P6GT-P | 1.9 | 5.94 |

TABLE 17

CONCENTRATION, pH
POST RECONSTITUTION; T = 2 week; 4° C.

| Formulation ID | Conc. (mg/mL) | pH |
|---|---|---|
| P6MT | 1.7 | 6.05 |
| S4MT | 1.7 | 4.09 |
| S5MT | 1.6 | 5.04 |
| S5GT | 1.8 | 5.10 |
| H6MT | 1.8 | 5.98 |
| P6GT | 1.9 | 6.05 |
| P6MA | 1.7 | 6.44 |
| P6MS | 1.8 | 6.17 |
| P6MTMet | 1.8 | 6.04 |
| P7MT | 1.6 | 6.95 |
| P7GT | 1.8 | 6.91 |
| P6MGT | 1.7 | 6.08 |
| P6MGT-P | 1.8 | 6.03 |
| P6MT-P | 1.8 | 6.10 |
| P6GT-P | 1.7 | 6.10 |

TABLE 18

CONCENTRATION, pH
POST RECONSTITUTION; T = 4 week; 4° C.

| Formulation ID | Conc. (mg/mL) | pH |
|---|---|---|
| P6MT | 1.6 | 6.18 |
| S4MT | 1.6 | 3.98 |
| S5MT | 1.6 | 4.98 |
| S5GT | 1.6 | 5.11 |
| H6MT | 1.7 | 5.98 |
| P6GT | 1.8 | 6.08 |
| P6MA | 1.8 | 6.46 |
| P6MS | 1.7 | 6.21 |
| P6MTMet | 1.8 | 6.18 |
| P7MT | 1.6 | 7.04 |
| P7GT | 1.7 | 6.96 |
| P6MGT | 1.5 | 6.12 |
| P6MGT-P | 1.5 | 6.13 |
| P6MT-P | 1.6 | 6.13 |
| P6GT-P | 1.6 | 6.11 |

TABLE 19

CONCENTRATION, pH
POST RECONSTITUTION; T = 6 week; 4° C.

| Formulation ID | Conc. (mg/mL) | pH |
|---|---|---|
| P6MT | 1.7 | 6.21 |
| S5MT | 1.7 | 5.10 |
| S5GT | 1.7 | 5.13 |
| H6MT | 1.7 | 6.05 |
| P6GT | 1.8 | 6.12 |
| P6MS | 1.7 | 6.16 |
| P6MTMet | 1.8 | 6.16 |
| P7MT | 1.5 | 7.01 |
| P7GT | 1.8 | 6.94 |
| P6MGT | 1.5 | 6.18 |
| P6MGT-P | 1.6 | 6.17 |
| P6MT-P | 1.7 | 6.14 |
| P6GT-P | 1.6 | 6.18 |

TABLE 20

CONCENTRATION, pH
POST RECONSTITUTION; T = 2 month; 4° C.

| Formulation ID | Conc. (mg/mL) | pH |
|---|---|---|
| P6MT | 1.8 | 6.15 |
| H6MT | 1.7 | 5.99 |
| P6GT | 2.0 | 6.15 |
| P6MS | 1.8 | 6.15 |
| P6MTMet | 1.8 | 6.15 |
| P7MT | 1.5 | 7.03 |
| P7GT | 1.7 | 6.89 |
| P6MGT | 1.7 | 6.09 |
| P6MGT-P | 1.6 | 6.05 |
| P6MT-P | 1.7 | 6.08 |
| P6GT-P | 1.7 | 6.07 |

TABLE 21

CONCENTRATION, pH
POST RECONSTITUTION; T = 3 month; 4° C.

| Formulation ID | Conc. (mg/mL) | pH |
|---|---|---|
| P6MT | 1.7 | 6.16 |
| H6MT | 1.9 | 6.03 |
| P6GT | 2.2 | 6.14 |
| P6MS | 1.9 | 5.90 |
| P6MTMet | 1.9 | 6.10 |
| P7MT | 1.5 | 7.00 |
| P7GT | 1.9 | 6.93 |
| P6MGT | 1.7 | 6.16 |
| P6MGT-P | 1.7 | 6.17 |
| P6MT-P | 1.8 | 6.11 |
| P6GT-P | 1.7 | 6.11 |

TABLE 22

CONCENTRATION, pH
POST RECONSTITUTION; T = 1 week; 25° C.

| Formulation ID | Conc. (mg/mL) | pH |
|---|---|---|
| P6MT | 1.7 | 6.18 |
| S4MT | 1.7 | 4.03 |
| S5MT | 1.7 | 5.00 |
| S5GT | 1.7 | 5.08 |
| H6MT | 1.8 | 5.90 |
| P6GT | 1.9 | 6.03 |
| P6MA | 1.8 | 6.42 |
| P6MS | 1.7 | 6.15 |
| P6MTMet | 1.7 | 6.06 |
| P7MT | 1.6 | 6.96 |
| P7GT | 1.7 | 6.89 |
| P6MGT | 1.6 | 6.08 |
| P6MGT-P | 1.6 | 6.01 |
| P6MT-P | 1.6 | 6.07 |
| P6GT-P | 1.7 | 6.05 |

TABLE 23

CONCENTRATION, pH
POST RECONSTITUTION; T = 2 week; 25° C.

| Formulation ID | Conc. (mg/mL) | pH |
|---|---|---|
| P6MT | 1.7 | 6.14 |
| S4MT | 1.6 | 4.07 |

TABLE 23-continued

CONCENTRATION, pH
POST RECONSTITUTION; T = 2 week; 25° C.

| Formulation ID | Conc. (mg/mL) | pH |
|---|---|---|
| S5MT | 1.6 | 5.04 |
| S5GT | 1.7 | 5.11 |
| H6MT | 1.8 | 5.96 |
| P6GT | 2.0 | 6.06 |
| P6MA | 1.9 | 6.43 |
| P6MS | 1.9 | 6.18 |
| P6MTMet | 1.9 | 6.04 |
| P7MT | 1.6 | 6.94 |
| P7GT | 1.8 | 6.91 |
| P6MGT | 1.6 | 6.06 |
| P6MGT-P | 1.7 | 6.07 |
| P6MT-P | 1.7 | 6.10 |
| P6GT-P | 1.7 | 6.08 |

TABLE 24

CONCENTRATION, pH
POST RECONSTITUTION; T = 4 week; 25° C.

| Formulation ID | Conc. (mg/mL) | pH |
|---|---|---|
| P6MT | 1.6 | 6.20 |
| S4MT | 1.5 | 4.02 |
| S5MT | 1.7 | 5.08 |
| S5GT | 1.7 | 5.16 |
| H6MT | 1.7 | 6.02 |
| P6GT | 1.7 | 6.16 |
| P6MA | 1.7 | 6.43 |
| P6MS | 1.6 | 6.20 |
| P6MTMet | 1.8 | 6.21 |
| P7MT | 1.5 | 7.03 |
| P7GT | 1.6 | 6.98 |
| P6MGT | 1.4 | 6.18 |
| P6MGT-P | 1.6 | 6.17 |
| P6MT-P | 1.7 | 6.17 |
| P6GT-P | 1.6 | 6.16 |

TABLE 25

CONCENTRATION, pH
POST RECONSTITUTION; T = 6 week; 25° C.

| Formulation ID | Conc. (mg/mL) | pH |
|---|---|---|
| P6MT | 1.7 | 6.21 |
| S5MT | 1.6 | 5.08 |
| S5GT | 1.8 | 5.15 |
| H6MT | 1.8 | 6.05 |
| P6GT | 1.8 | 6.14 |
| P6MS | 1.8 | 6.24 |
| P6MTMet | 1.8 | 6.18 |
| P7MT | 1.6 | 7.00 |
| P7GT | 1.7 | 6.93 |
| P6MGT | 1.7 | 6.13 |
| P6MGT-P | 1.7 | 6.15 |
| P6MT-P | 1.7 | 6.23 |
| P6GT-P | 1.7 | 6.18 |

TABLE 26

CONCENTRATION, pH
POST RECONSTITUTION; T = 2 month; 25° C.

| Formulation ID | Conc. (mg/mL) | pH |
|---|---|---|
| P6MT | 1.7 | 6.14 |
| H6MT | 1.8 | 5.94 |
| P6GT | 1.9 | 6.10 |
| P6MS | 1.8 | 6.15 |
| P6MTMet | 1.8 | 6.07 |
| P7MT | 1.5 | 6.92 |
| P7GT | 1.8 | 6.88 |
| P6MGT | 1.5 | 6.09 |
| P6MGT-P | 1.7 | 6.13 |
| P6MT-P | 1.7 | 6.12 |
| P6GT-P | 1.7 | 6.08 |

TABLE 27

CONCENTRATION, pH
POST RECONSTITUTION; T = 3 month; 25° C.

| Formulation ID | Conc. (mg/mL) | pH |
|---|---|---|
| P6MT | 1.8 | 6.17 |
| H6MT | 2.1 | 5.94 |
| P6GT | 2.0 | 6.12 |
| P6MS | 1.9 | 6.15 |
| P6MTMet | 1.9 | 6.15 |
| P7MT | 1.7 | 6.98 |
| P7GT | 1.8 | 6.92 |
| P6MGT | 1.7 | 6.15 |
| P6MGT-P | 1.7 | 6.14 |
| P6MT-P | 1.7 | 6.10 |
| P6GT-P | 1.8 | 6.14 |

TABLE 28

CONCENTRATION, pH
POST RECONSTITUTION; T = 1 week; 40° C.

| Formulation ID | Conc. (mg/mL) | pH |
|---|---|---|
| P6MT | 1.8 | 6.18 |
| S4MT | 1.7 | 4.01 |
| S5MT | 1.8 | 5.02 |
| S5GT | 1.9 | 5.07 |
| H6MT | 1.8 | 5.92 |
| P6GT | 2.0 | 6.09 |
| P6MA | 1.8 | 6.39 |
| P6MS | 1.9 | 6.16 |
| P6MTMet | 1.7 | 6.11 |
| P7MT | 1.6 | 6.98 |
| P7GT | 1.6 | 6.93 |
| P6MGT | 1.8 | 6.11 |
| P6MGT-P | 1.7 | 6.09 |
| P6MT-P | 1.6 | 6.12 |
| P6GT-P | 1.7 | 6.07 |

TABLE 29

CONCENTRATION, pH
POST RECONSTITUTION; T = 2 week; 40° C.

| Formulation ID | Conc. (mg/mL) | pH |
|---|---|---|
| P6MT | 1.6 | 6.15 |
| S4MT | 1.7 | 4.02 |

TABLE 29-continued

CONCENTRATION, pH
POST RECONSTITUTION: T = 2 week; 40° C.

| Formulation ID | Conc. (mg/mL) | pH |
|---|---|---|
| S5MT | 1.7 | 5.00 |
| S5GT | 1.8 | 5.11 |
| H6MT | 1.8 | 5.93 |
| P6GT | 1.9 | 6.15 |
| P6MA | 1.9 | 6.41 |
| P6MS | 1.9 | 6.07 |
| P6MTMet | 1.8 | 6.11 |
| P7MT | 1.6 | 6.95 |
| P7GT | 1.9 | 6.90 |
| P6MGT | 1.7 | 6.17 |
| P6MGT-P | 1.8 | 6.15 |
| P6MT-P | 1.8 | 6.15 |
| P6GT-P | 1.8 | 6.15 |

TABLE 30

CONCENTRATION, pH
POST RECONSTITUTION; T = 4 week; 40° C.

| Formulation ID | Conc. (mg/mL) | pH |
|---|---|---|
| P6MT | 1.6 | 6.25 |
| S4MT | 1.5 | 3.97 |
| S5MT | 1.6 | 5.06 |
| S5GT | 1.6 | 5.11 |
| H6MT | 1.6 | 6.01 |
| P6GT | 1.7 | 6.25 |
| P6MA | 1.7 | 6.42 |
| P6MS | 1.7 | 6.28 |
| P6MTMet | 1.6 | 6.23 |
| P7MT | 1.5 | 7.01 |
| P7GT | 1.6 | 6.98 |
| P6MGT | 1.5 | 6.25 |
| P6MGT-P | 1.5 | 6.20 |
| P6MT-P | 1.5 | 6.24 |
| P6GT-P | 1.6 | 6.22 |

TABLE 31

CONCENTRATION, pH
POST RECONSTITUTION; T = 6 week; 40° C.

| Formulation ID | Conc. (mg/mL) | pH |
|---|---|---|
| P6MT | 1.7 | 6.24 |
| S5MT | 1.6 | 5.11 |
| S5GT | 1.7 | 5.17 |
| H6MT | 1.8 | 6.00 |
| P6GT | 1.9 | 6.17 |
| P6MS | 1.8 | 6.24 |
| P6MTMet | 2.5 | 6.15 |
| P7MT | 1.5 | 6.98 |
| P7GT | 1.8 | 6.94 |
| P6MGT | 1.5 | 6.28 |
| P6MGT-P | 1.7 | 6.23 |
| P6MT-P | 1.7 | 6.19 |
| P6GT-P | 1.7 | 6.22 |

TABLE 32

CONCENTRATION, pH
POST RECONSTITUTION; T = 2 month; 40° C.

| Formulation ID | Conc. (mg/mL) | pH |
|---|---|---|
| P6MT | 1.7 | 6.19 |
| H6MT | 1.9 | 5.99 |
| P6GT | 1.9 | 6.21 |
| P6MS | 1.8 | 6.19 |
| P6MTMet | 1.7 | 6.18 |
| P7MT | 1.5 | 6.97 |
| P7GT | 1.7 | 6.90 |
| P6MGT | 1.6 | 6.15 |
| P6MGT-P | 1.6 | 6.22 |
| P6MT-P | 1.7 | 6.20 |
| P6GT-P | 1.7 | 6.18 |

Figure 22:
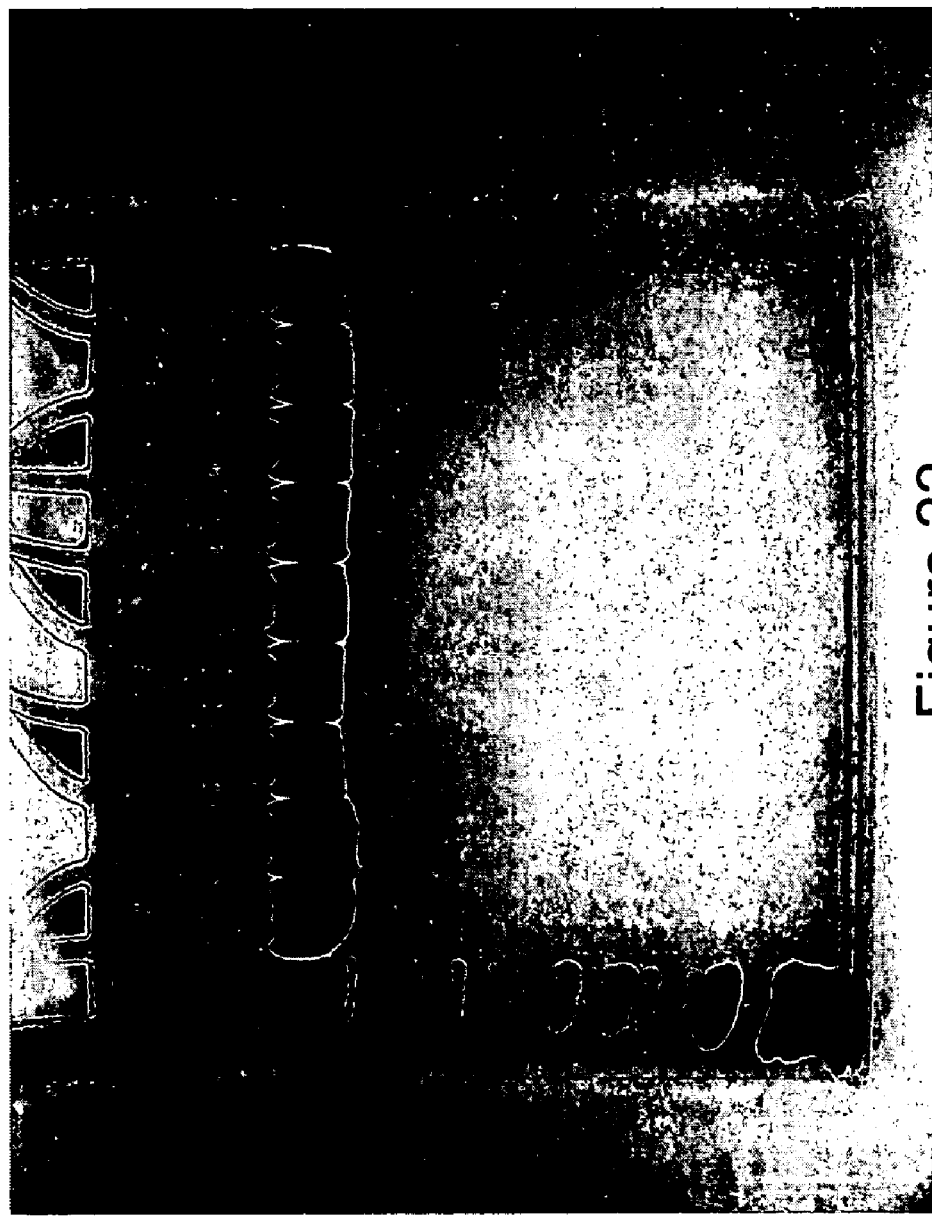
FIG. 22 shows an SDS-PAGE analysis (reduced) of control samples in a formulation study (t=0). Lane 1: Mark 12; Lane 2: Ref. Std; Lane 3: P6MT; Lane 4: S4MT; Lane 5: S5MT; Lane 6: S5GT; Lane 7: H6MT; Lane 8: P6GT; Lane 9: P6MA; Lane 10: P6MS.
Figure 23:
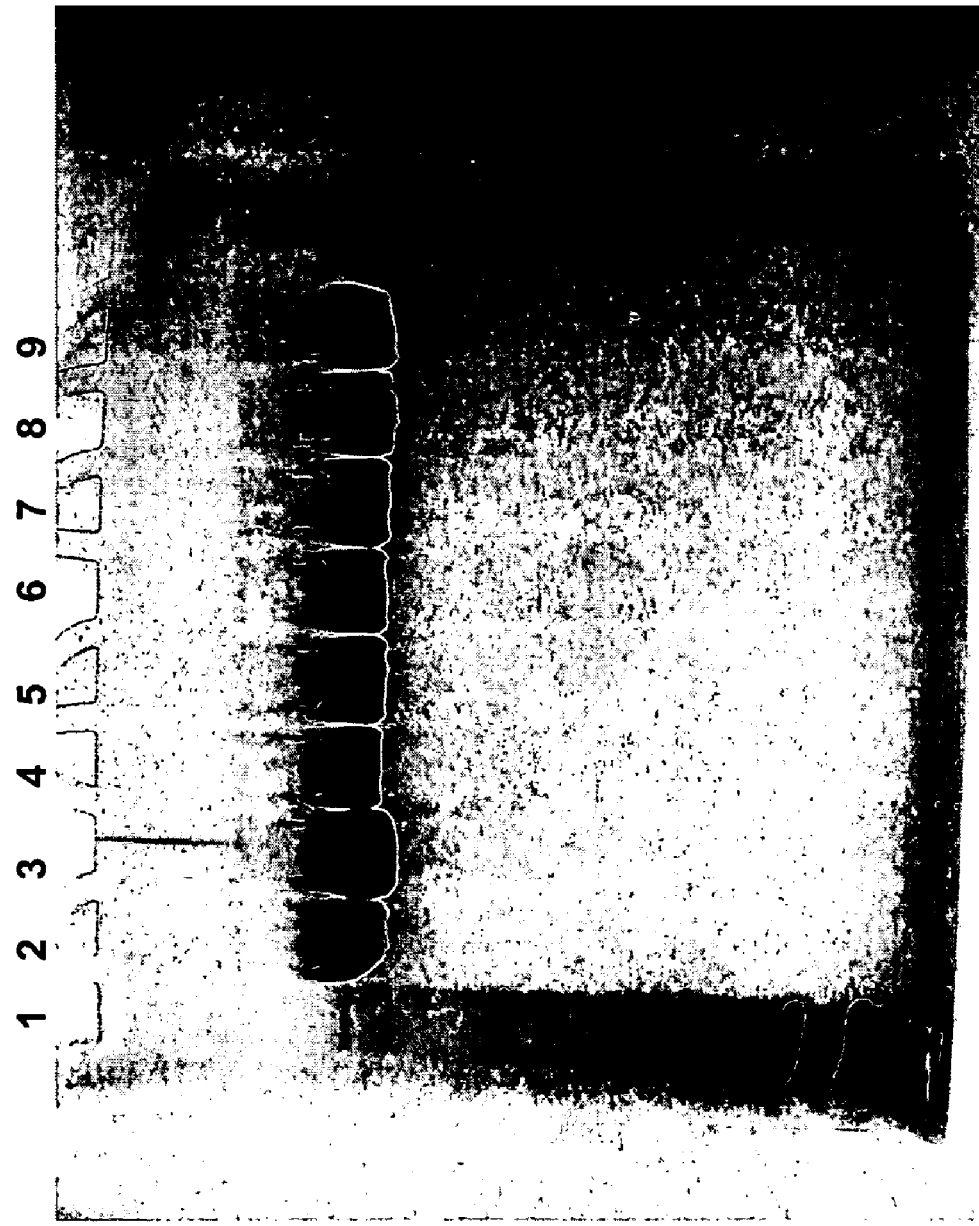
FIG. 23 shows an SDS-PAGE analysis (reduced) of control samples in a formulation study (t=0). Lane 1: Mark 12; Lane 2: Ref. Std; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 24:
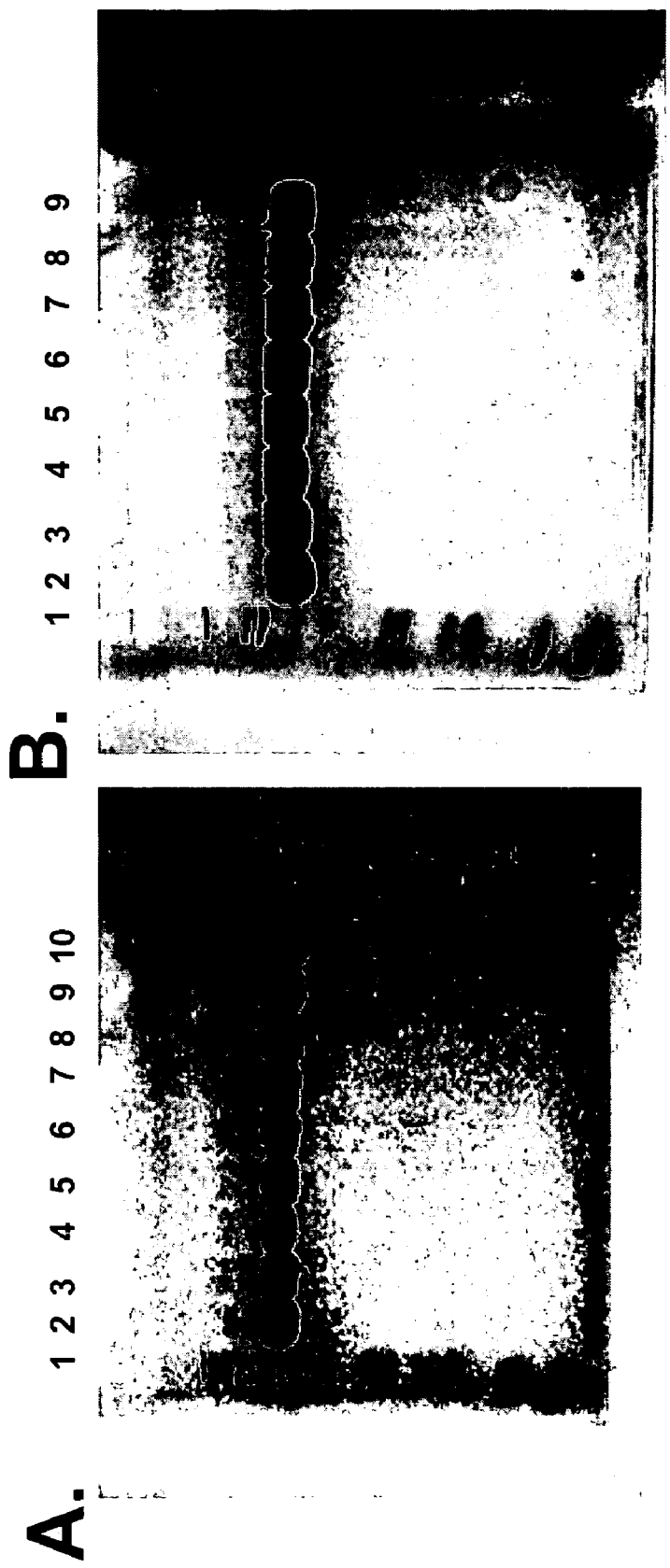
FIG. 24 shows an SDS-PAGE analysis (non-reduced) of control samples in a formulation study (t=0). For FIG. 24, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 24, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 25:
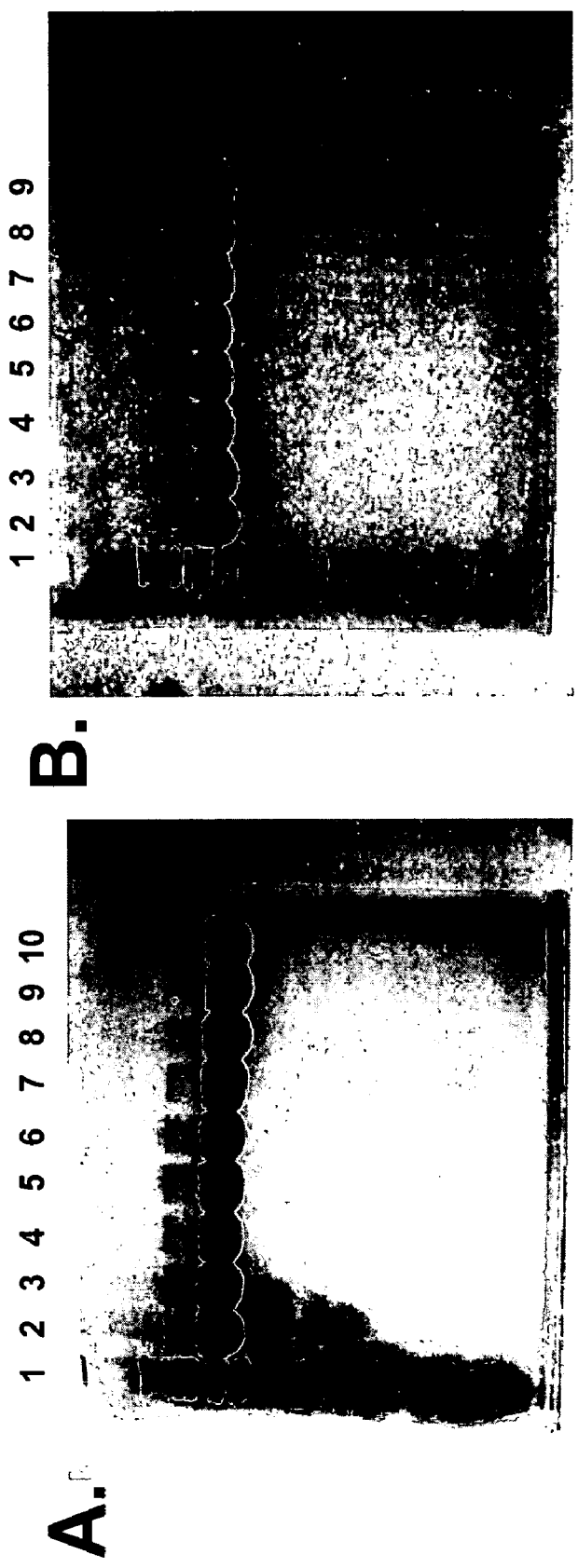
FIG. 25 shows an SDS-PAGE analysis (non-reduced) of samples stored at 4° C. for 1 week. For FIG. 25, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 25, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 26:
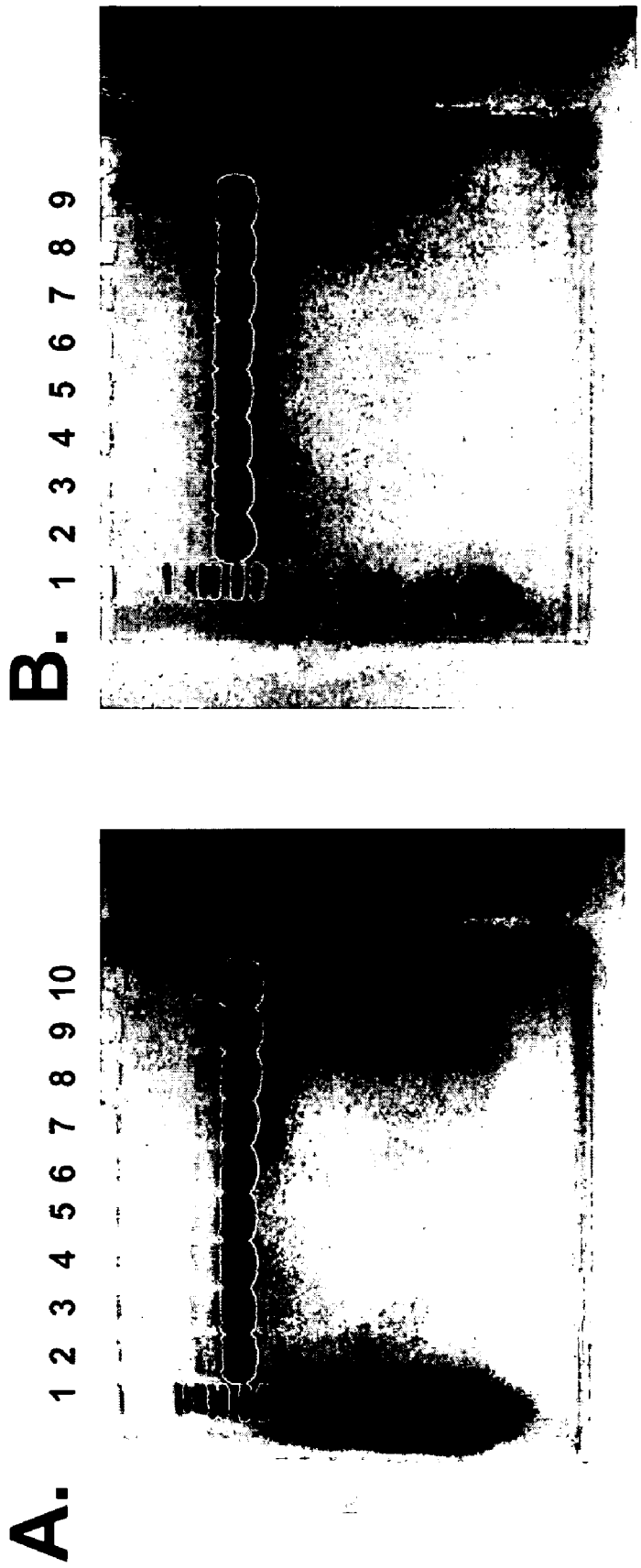
FIG. 26 shows an SDS-PAGE analysis (reduced) of samples stored at 4° C. for 1 week. For FIG. 26, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 26, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 27:
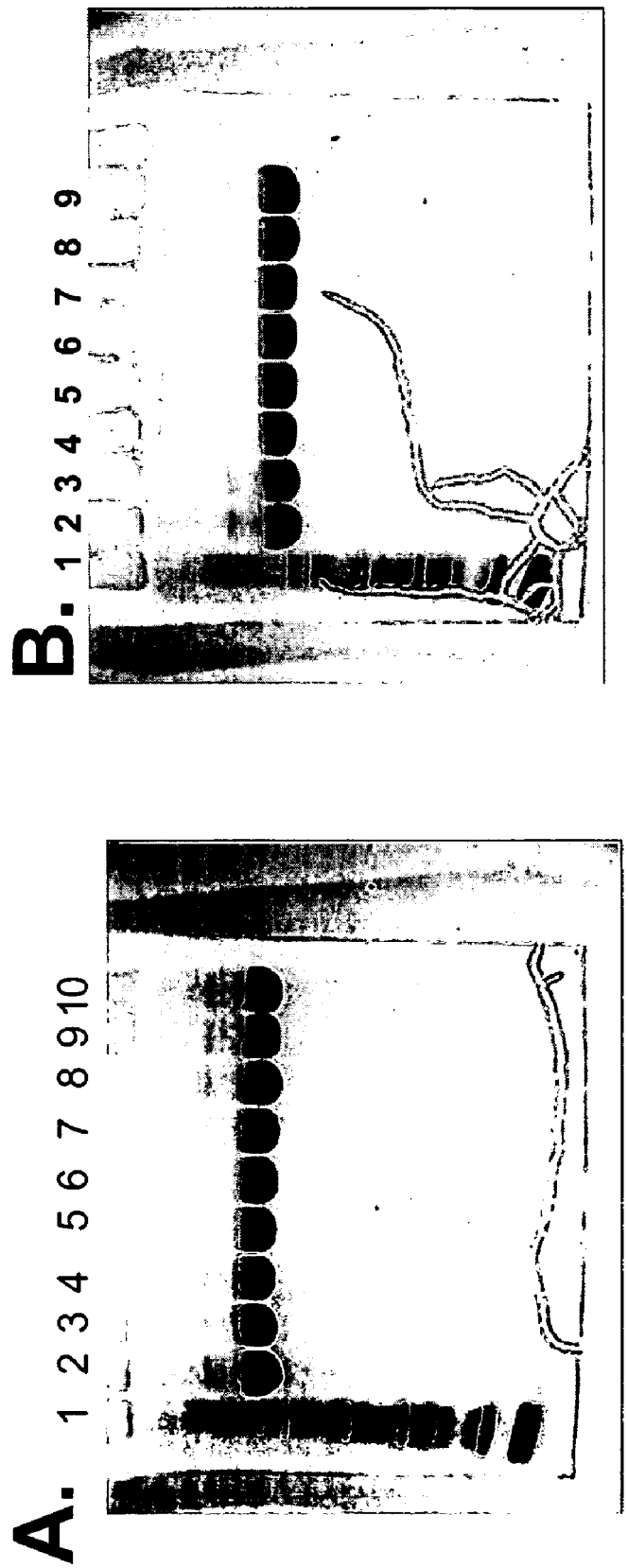
FIG. 27 shows an SDS-PAGE analysis (non-reduced) of samples stored at 4° C. for 2 weeks. For FIG. 27, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 27, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 28:
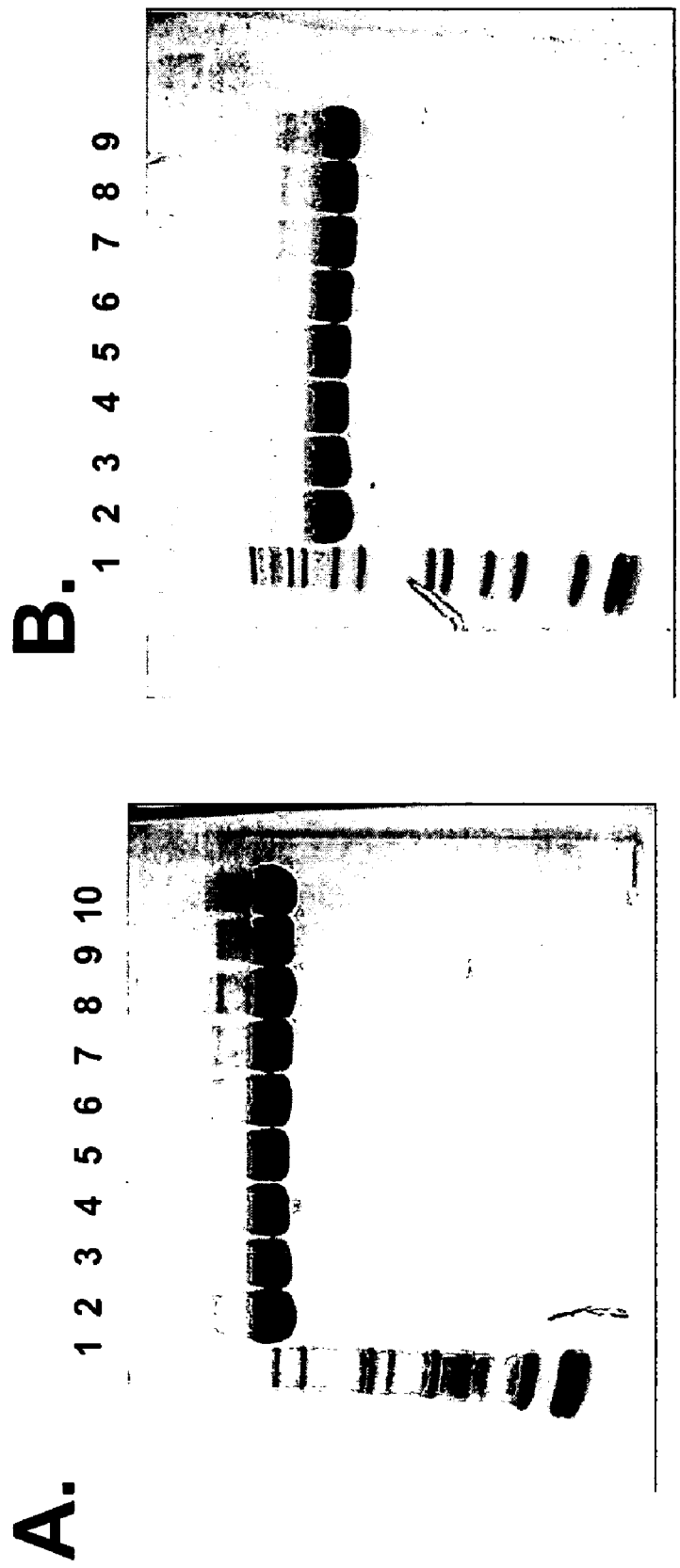
FIG. 28 shows an SDS-PAGE analysis (reduced) of samples stored at 4° C. for 2 weeks. For FIG. 28, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 28, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 30:
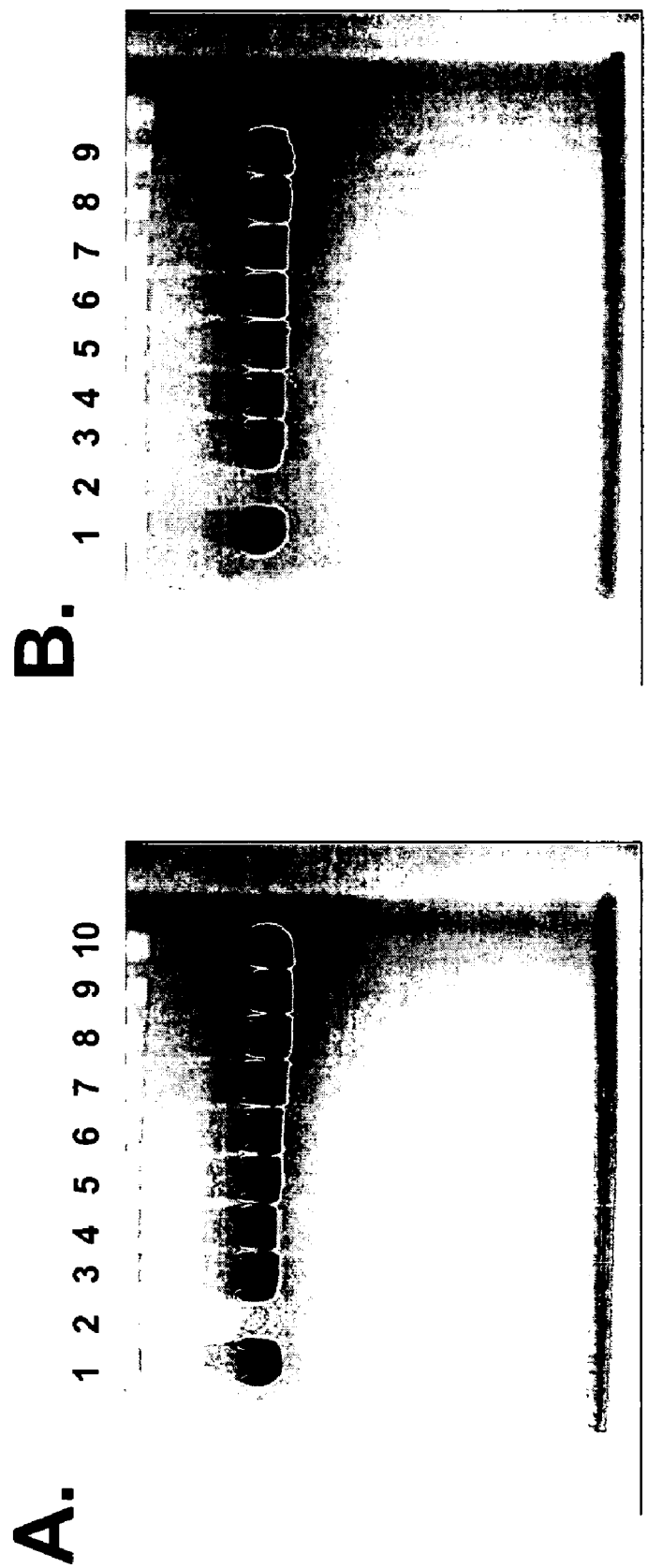
FIG. 30 shows an SDS-PAGE analysis (reduced) of samples stored at 4° C. for 4 weeks. For FIG. 30, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 30, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 31:
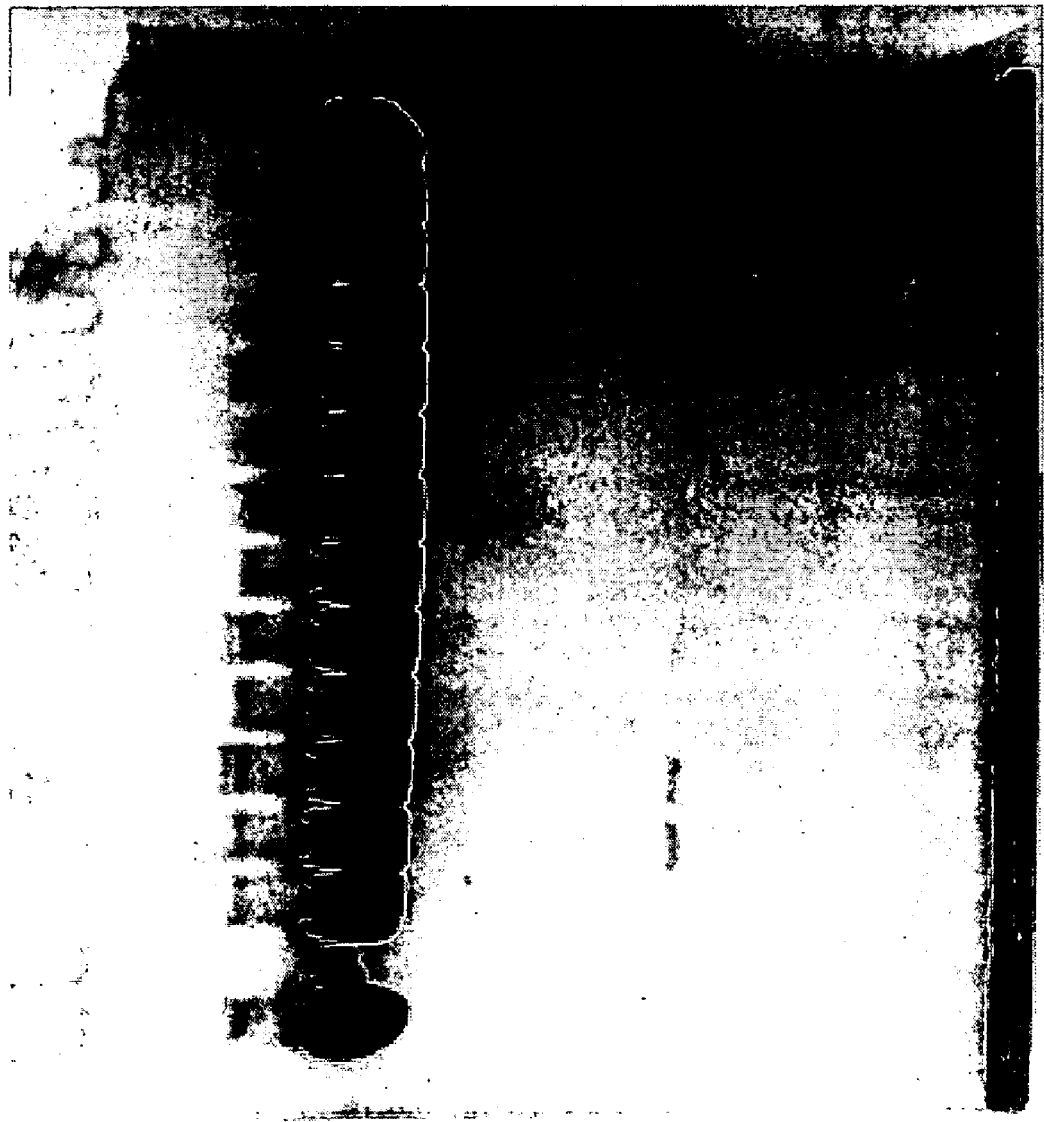
FIG. 31 shows an SDS-PAGE analysis (non-reduced) of samples stored at 4° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 32:
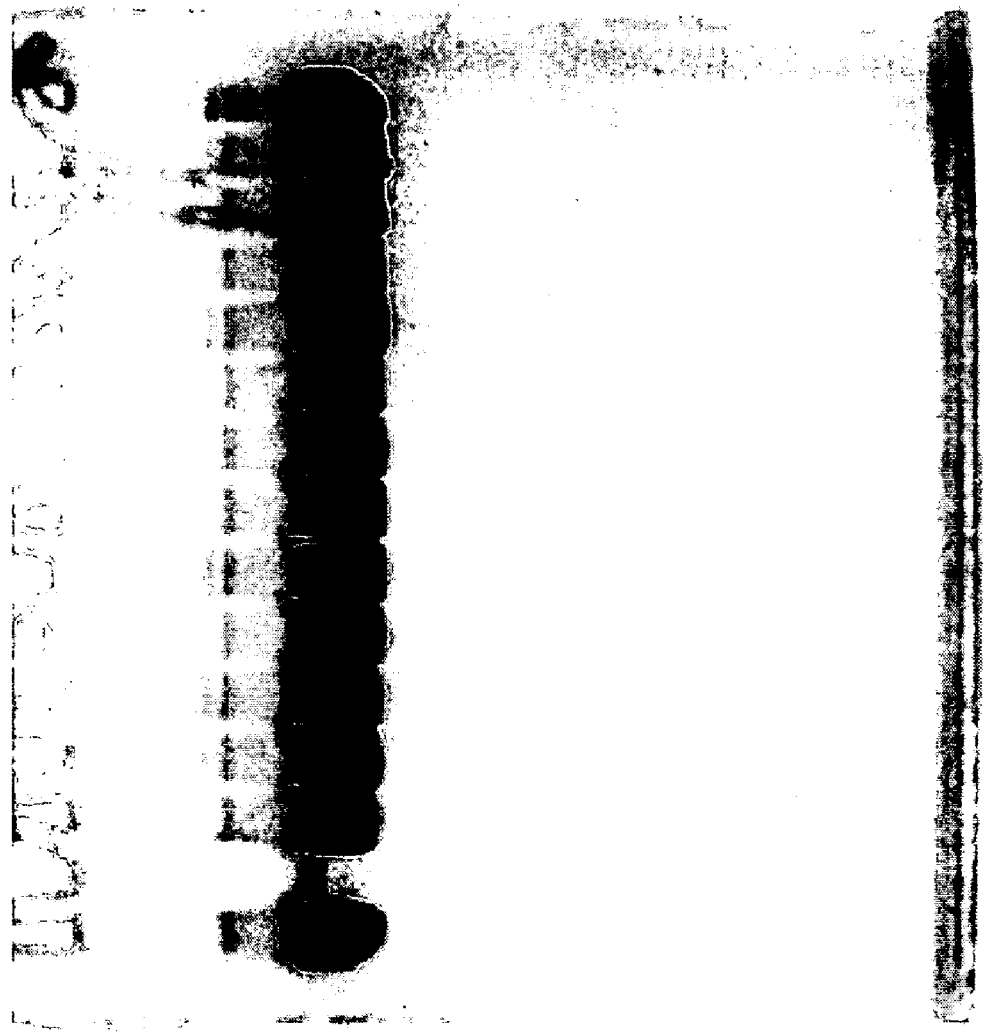
FIG. 32 shows an SDS-PAGE analysis (reduced) of samples stored at 4° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 33:
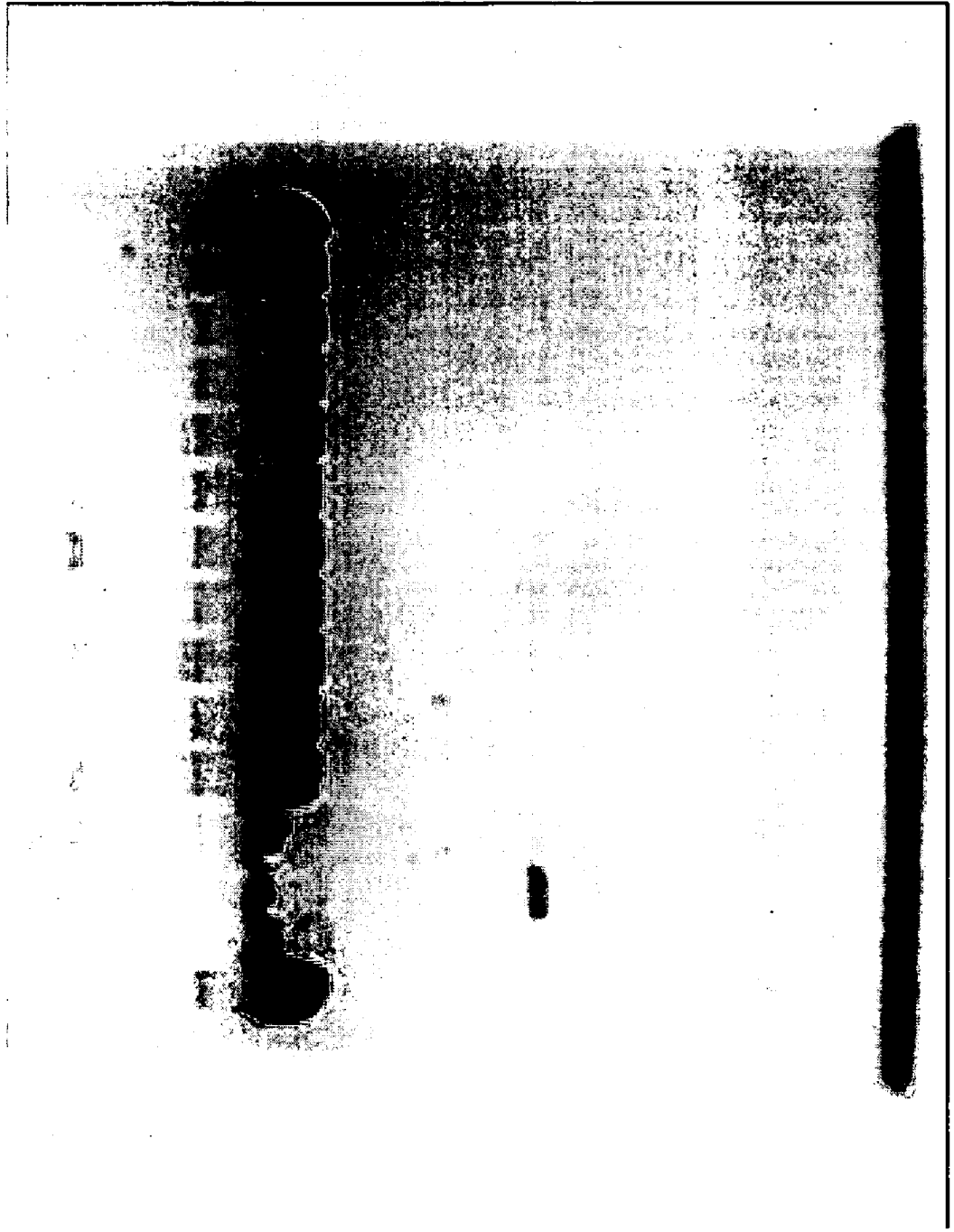
FIG. 33 shows an SDS-PAGE analysis (non-reduced) of samples stored at 4° C. for 2 months. Lane 1: PEG-hGH Standard; Lane 3: hGH (1 µg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 34:
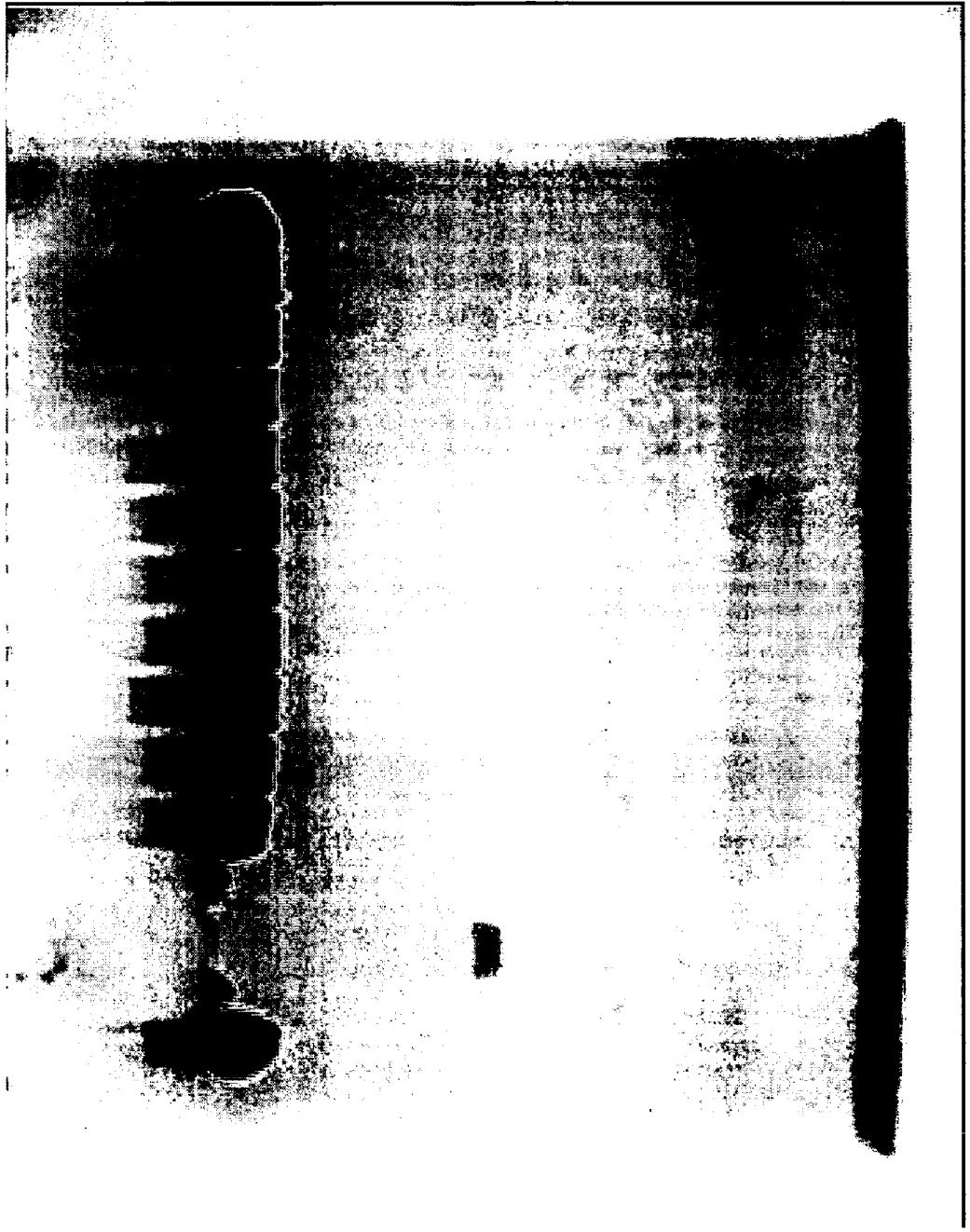
FIG. 34 shows an SDS-PAGE analysis (reduced) of samples stored at 4° C. for 2 months. Lane 1: PEG-hGH Standard; Lane 3: hGH (1 µg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 35:
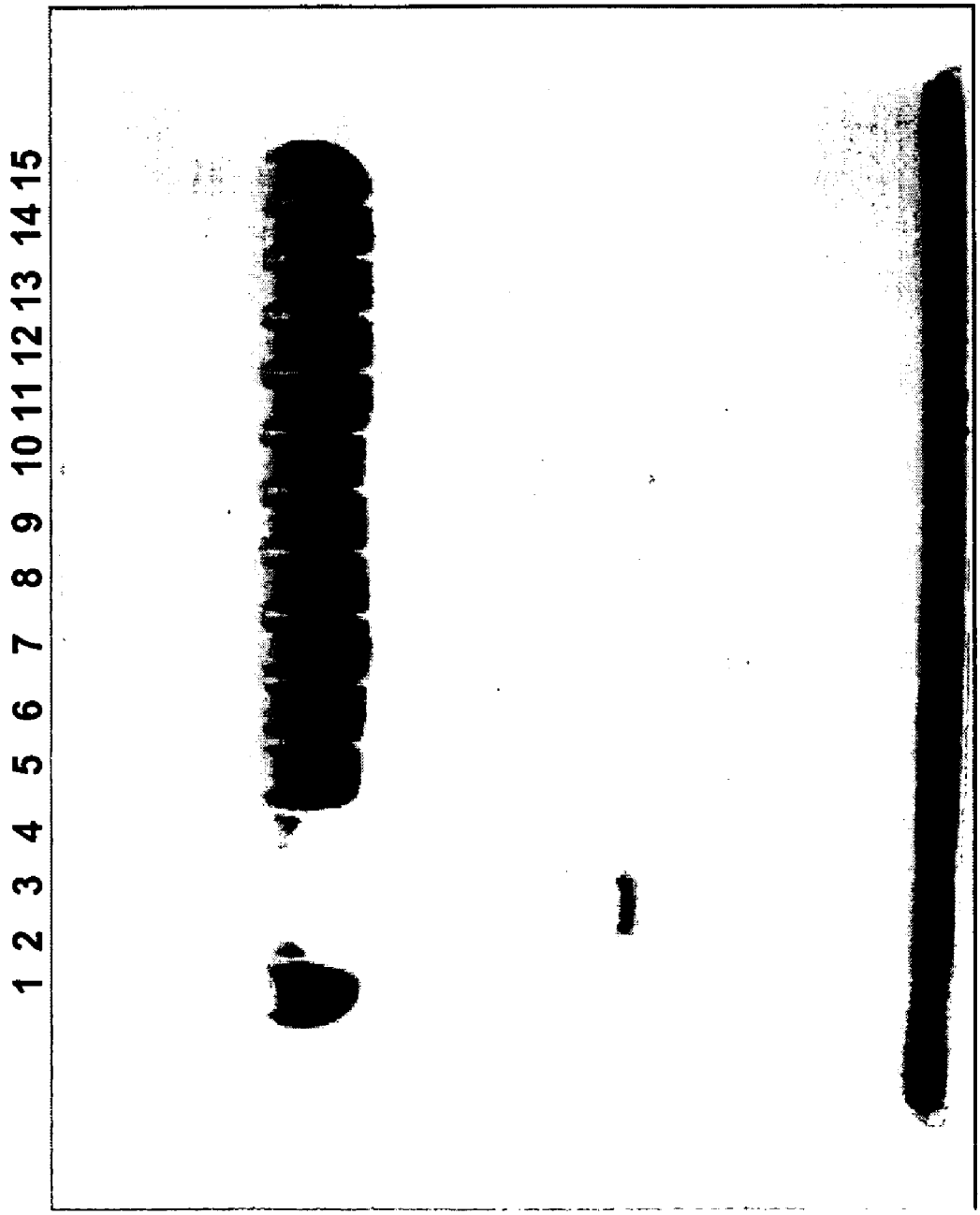
FIG. 35 shows an SDS-PAGE analysis (non-reduced) of samples stored at 4° C. for 3 months. Lane 1: PEG-hGH Standard; Lane 3: hGH (1 µg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 36:
FIG. 36 shows an SDS-PAGE analysis (reduced) of samples stored at 4° C. for 3 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet* (contamination); Lane 10: P6MT; Lane 11: P7GT; Lane 12: P6MGT; Lane 13: P6MGT-P; Lane 14: P6MT-P; Lane 15: P6GT-P.
Figure 38:
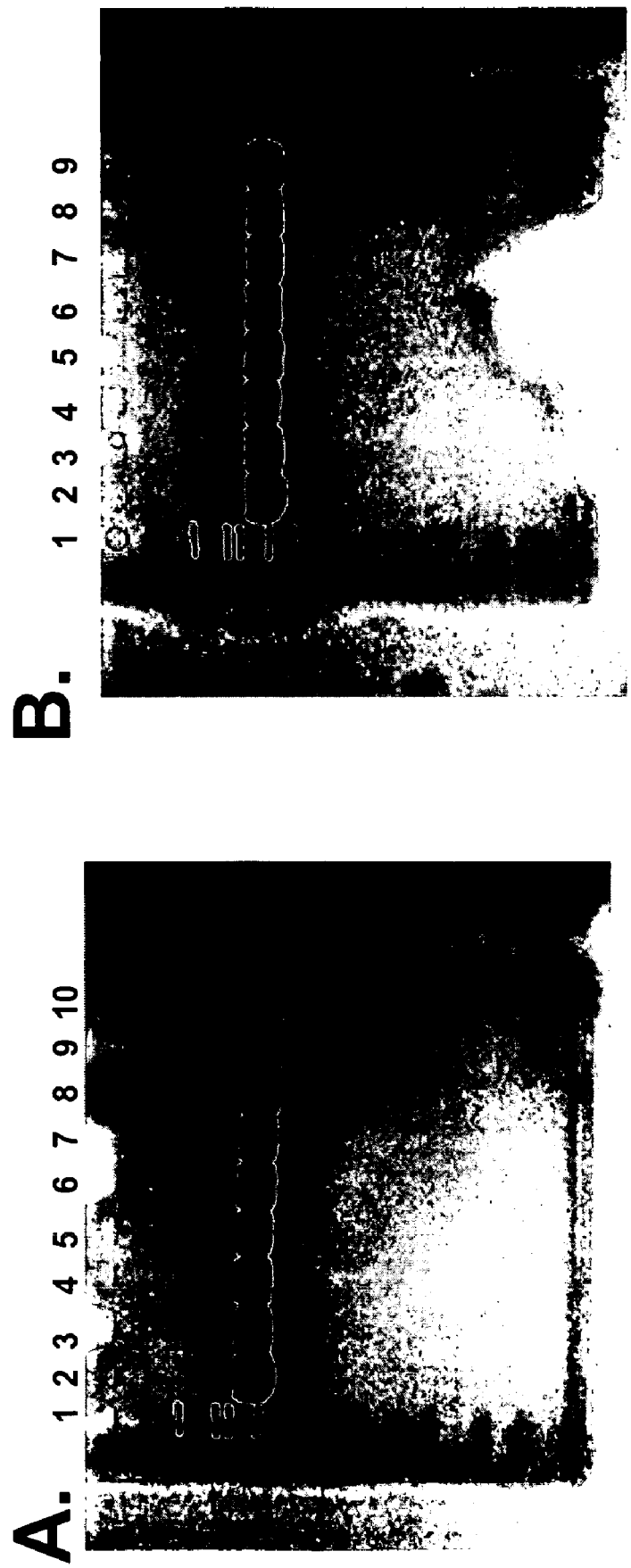
FIG. 38 shows an SDS-PAGE analysis (reduced) of samples stored at 25° C. for 1 week. For FIG. 38, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 38, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 40:
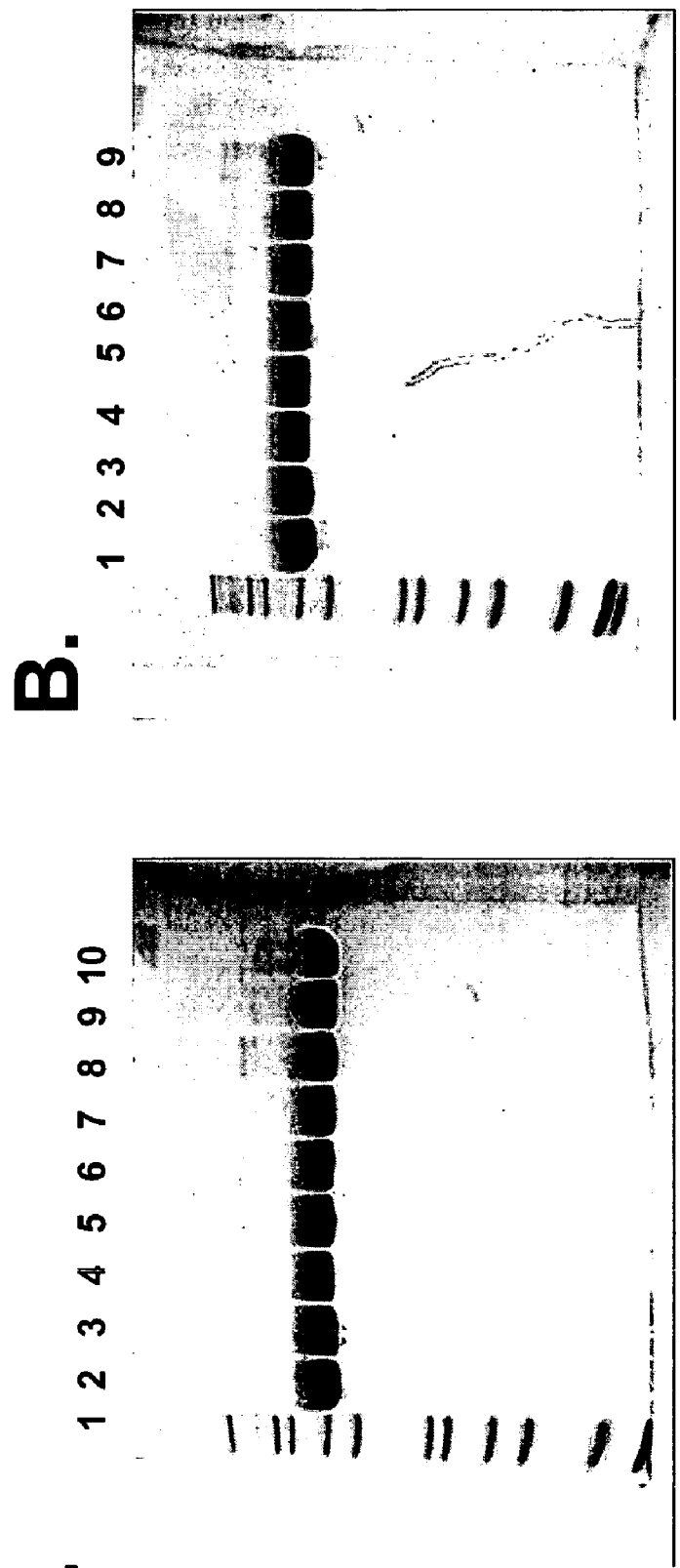
FIG. 40 shows an SDS-PAGE analysis (reduced) of samples stored at 25° C. for 2 weeks. For FIG. 40, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 40, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 41:
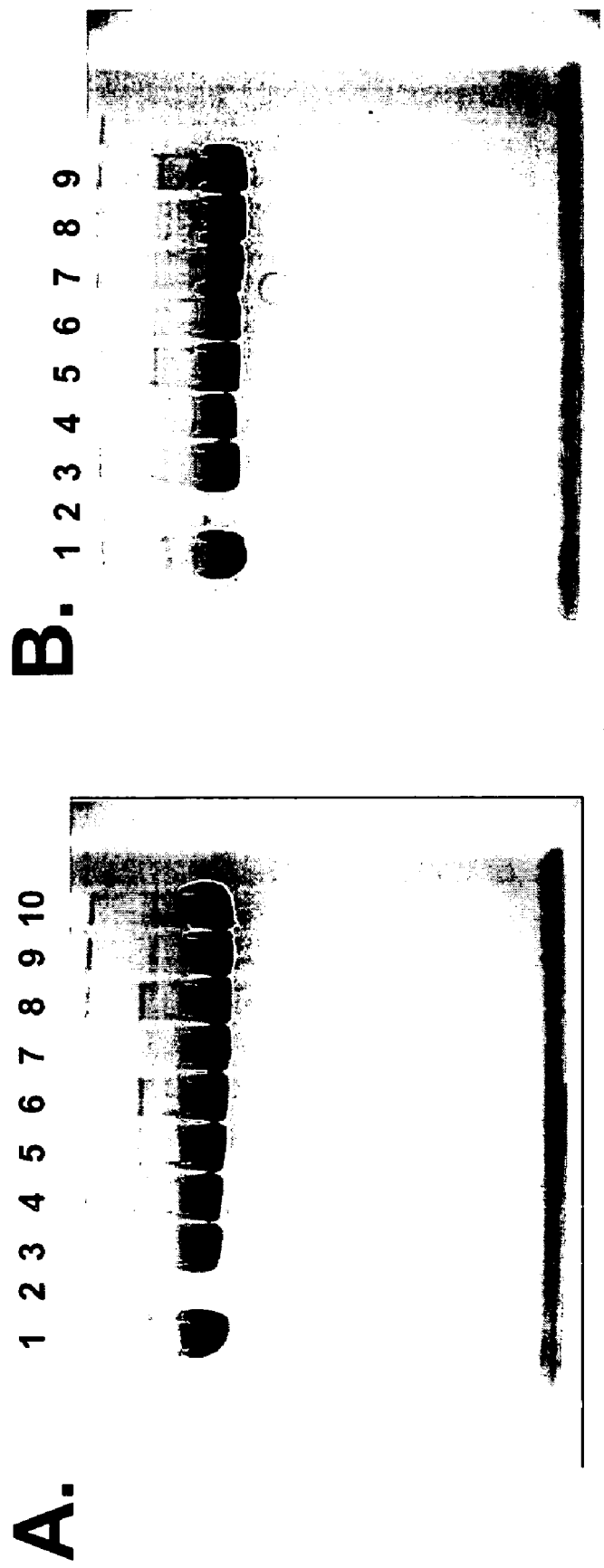
FIG. 41 shows an SDS-PAGE analysis (non-reduced) of samples stored at 25° C. for 4 weeks. For FIG. 41, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 41, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 42:
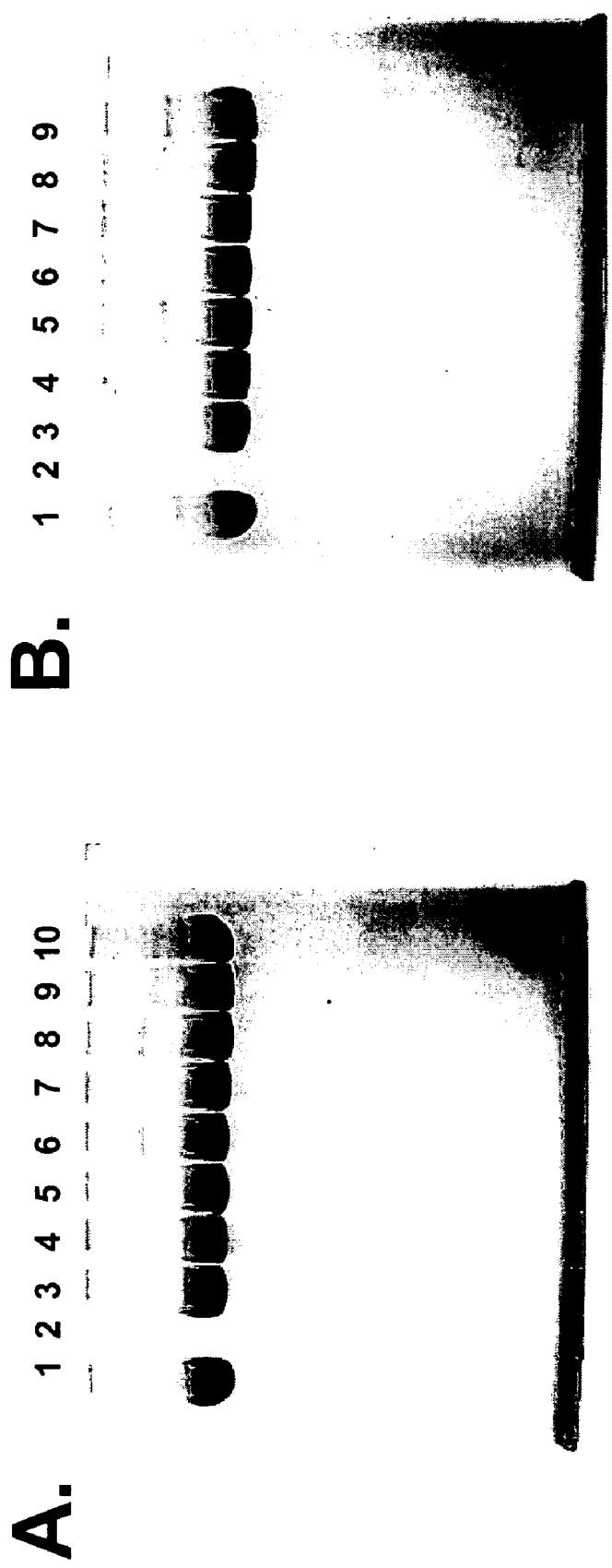
FIG. 42 shows an SDS-PAGE analysis (reduced) of samples stored at 25° C. for 4 weeks. For FIG. 42, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 42, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 43:
FIG. 43 shows an SDS-PAGE analysis (non-reduced) of samples stored at 25° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 44:
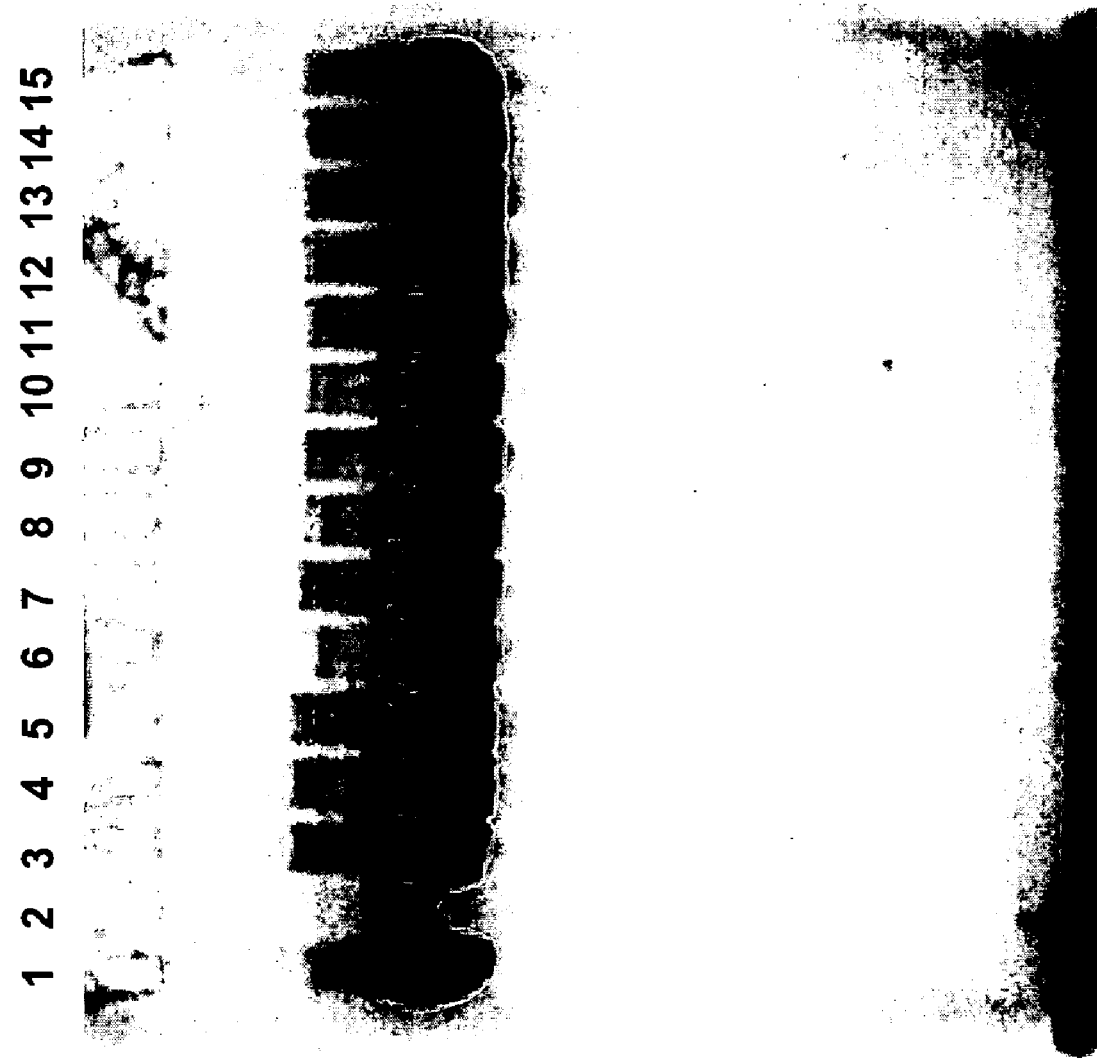
FIG. 44 shows an SDS-PAGE analysis (reduced) of samples stored at 25° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 45:
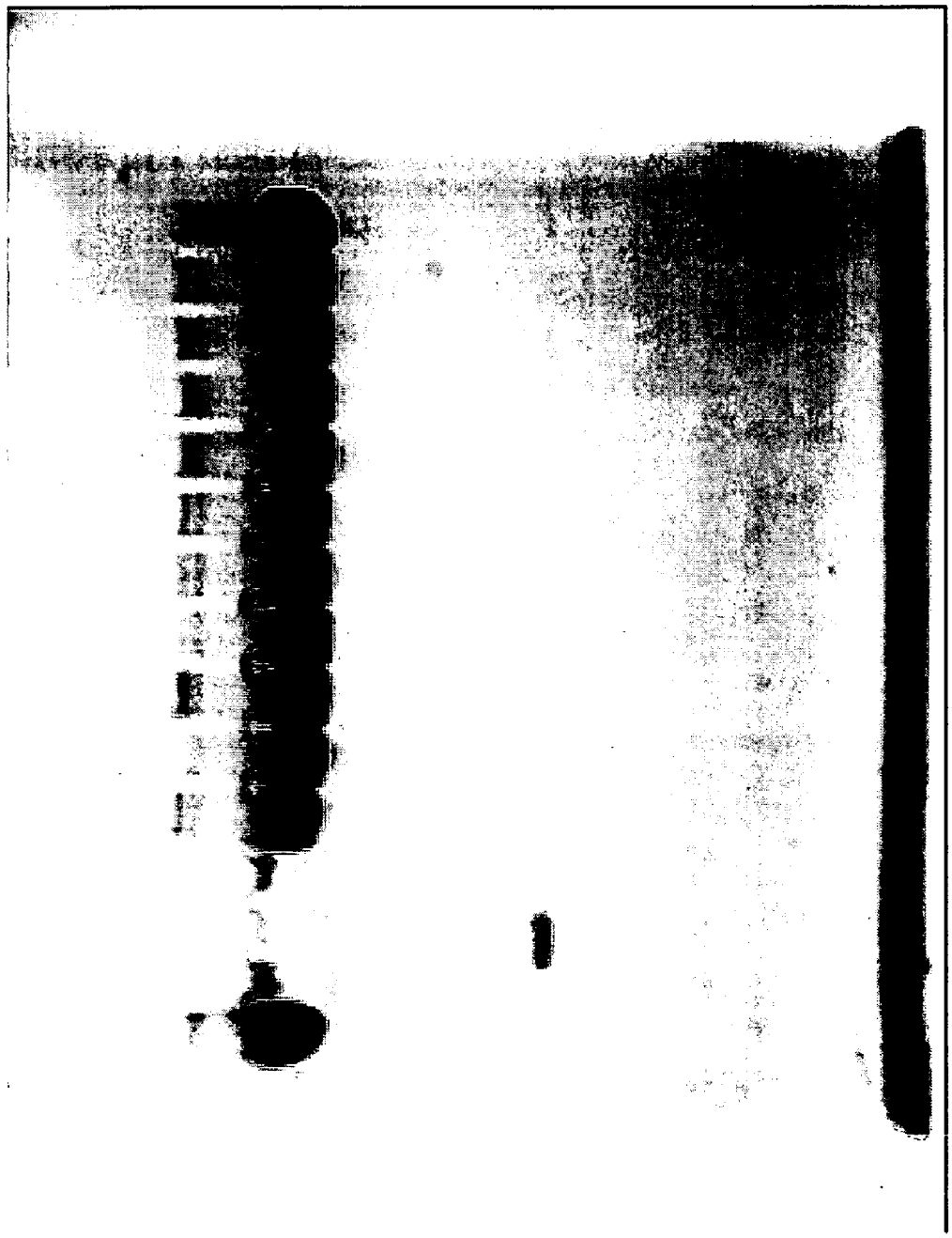
FIG. 45 shows an SDS-PAGE analysis (non-reduced) of samples stored at 25° C. for 2 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 46:
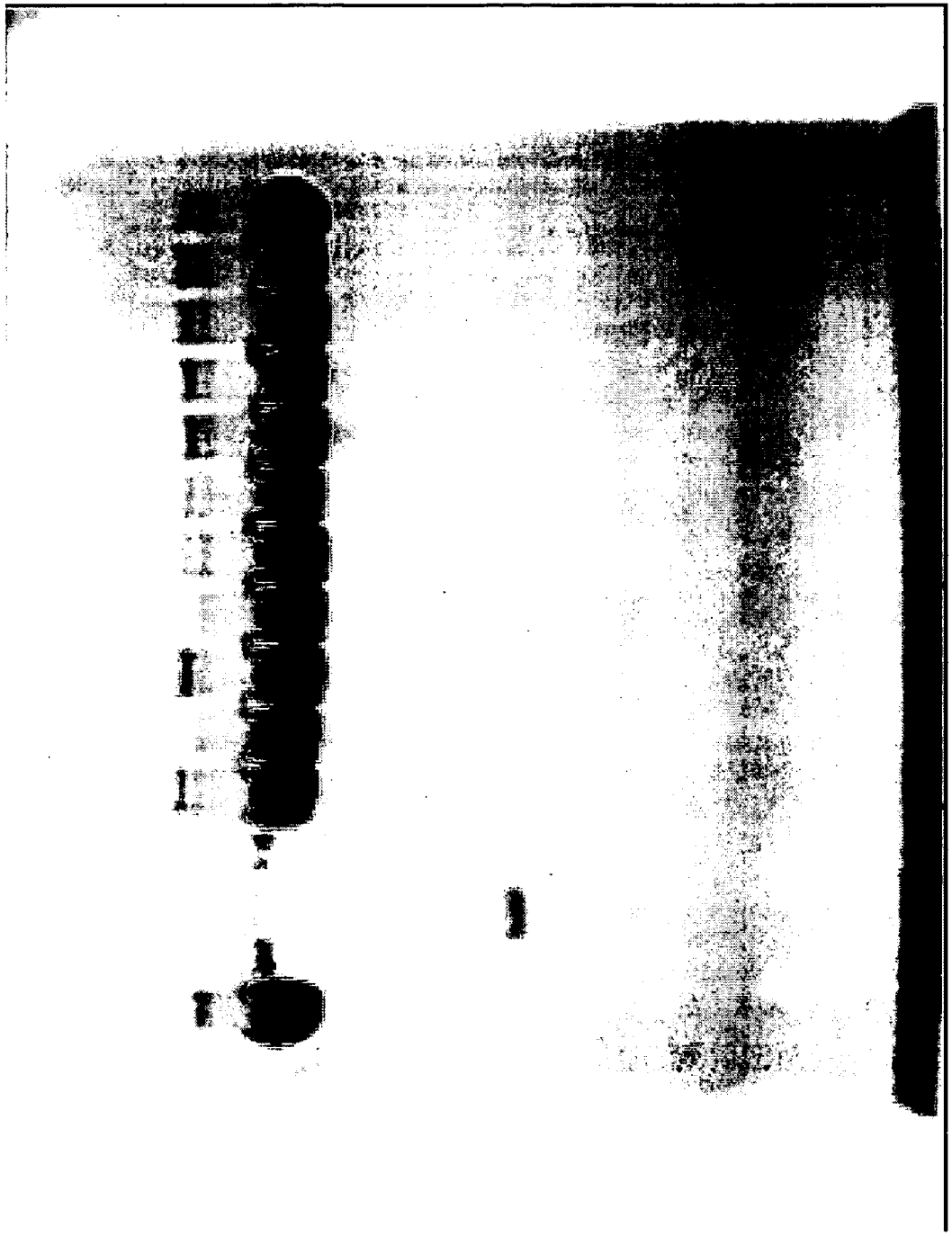
FIG. 46 shows an SDS-PAGE analysis (reduced) of samples stored at 25° C. for 2 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 47:
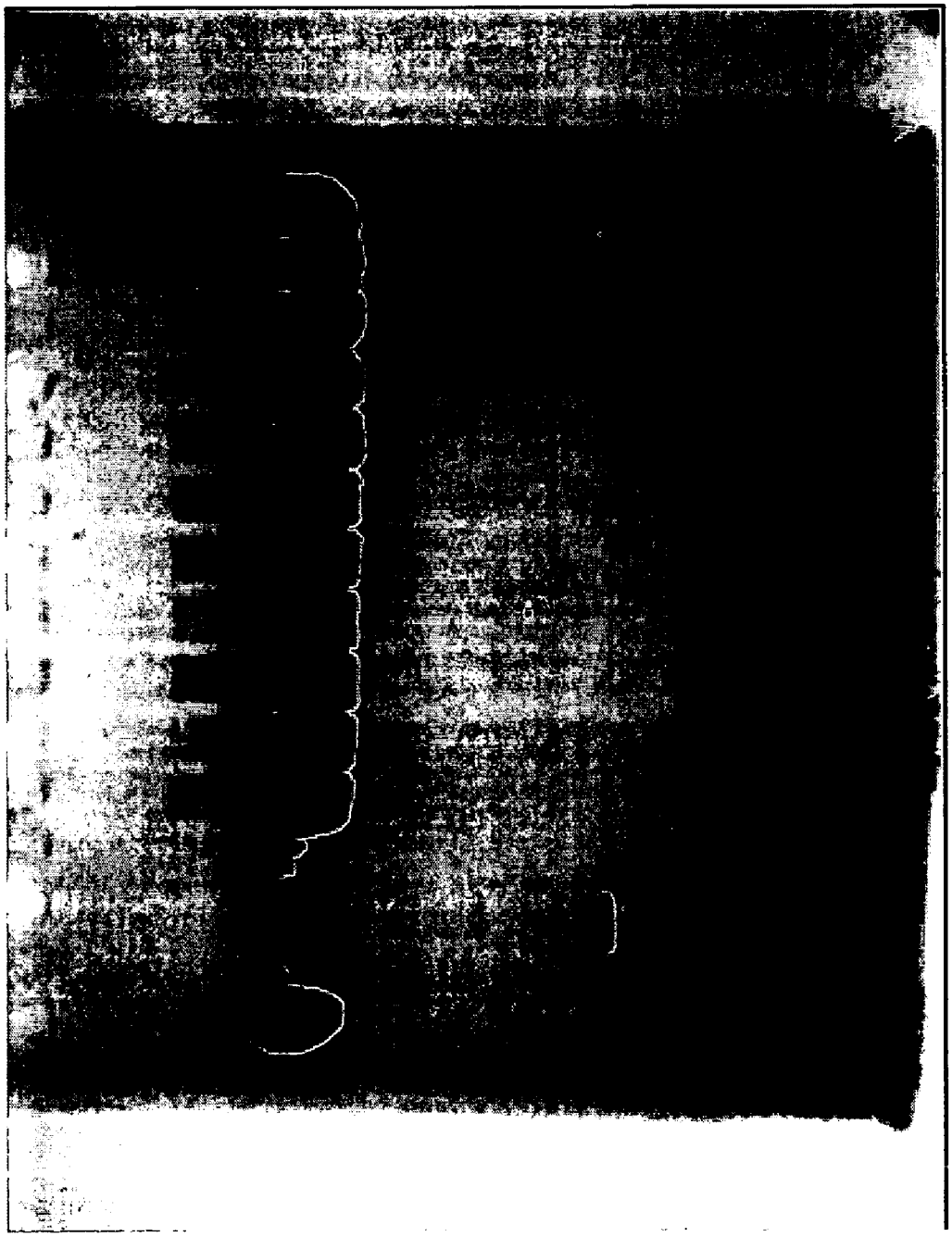
FIG. 47 shows an SDS-PAGE analysis (non-reduced) of samples stored at 25° C. for 3 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 48:
FIG. 48 shows an SDS-PAGE analysis (reduced) of samples stored at 25° C. for 3 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 49:
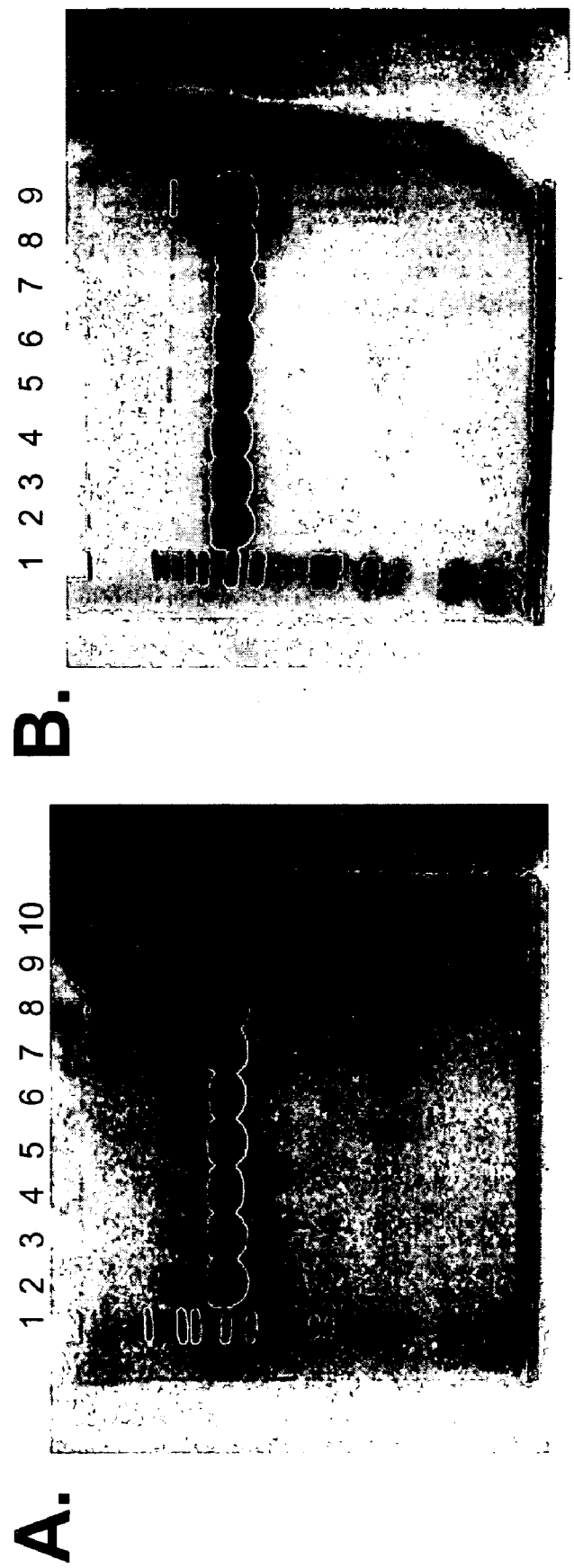
FIG. 49 shows an SDS-PAGE analysis (non-reduced) of samples stored at 40° C. for 1 week. For FIG. 49, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 49, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 51:
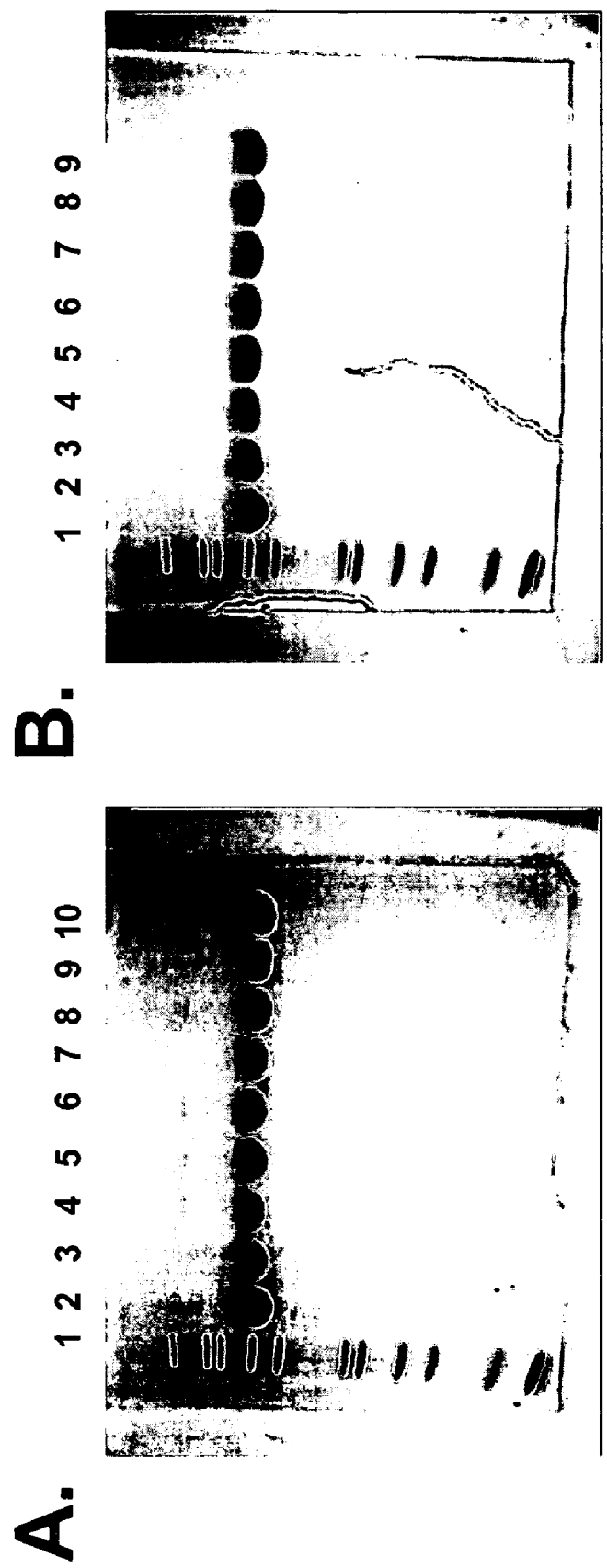
FIG. 51 shows an SDS-PAGE analysis (non-reduced) of samples stored at 40° C. for 2 weeks. For FIG. 51, panel A, Lane 1: Mark 12 Standard; Lane 2: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 51, panel B, Lane 1: Mark 12 Standard; Lane 2: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 55:
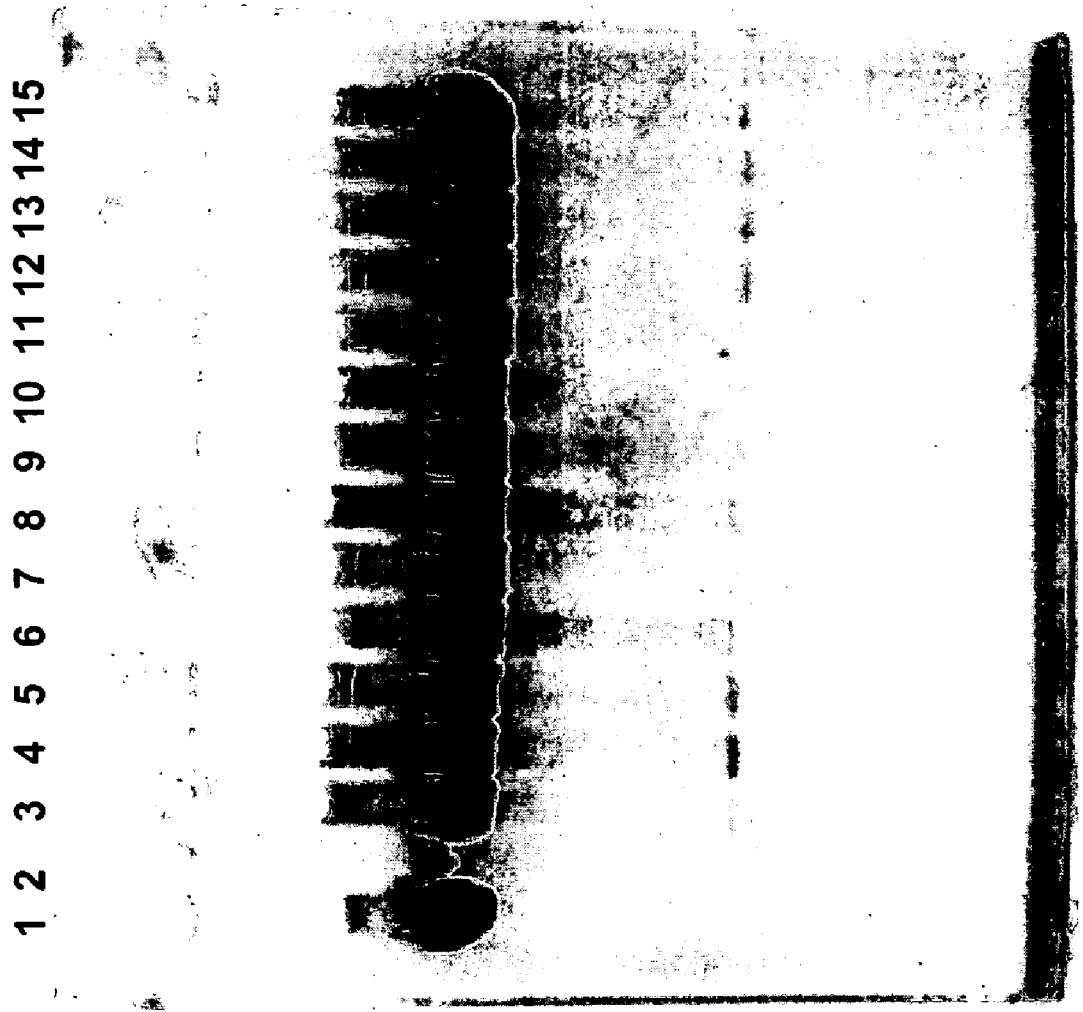
FIG. 55 shows an SDS-PAGE analysis (non-reduced) of samples stored at 40° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 56:
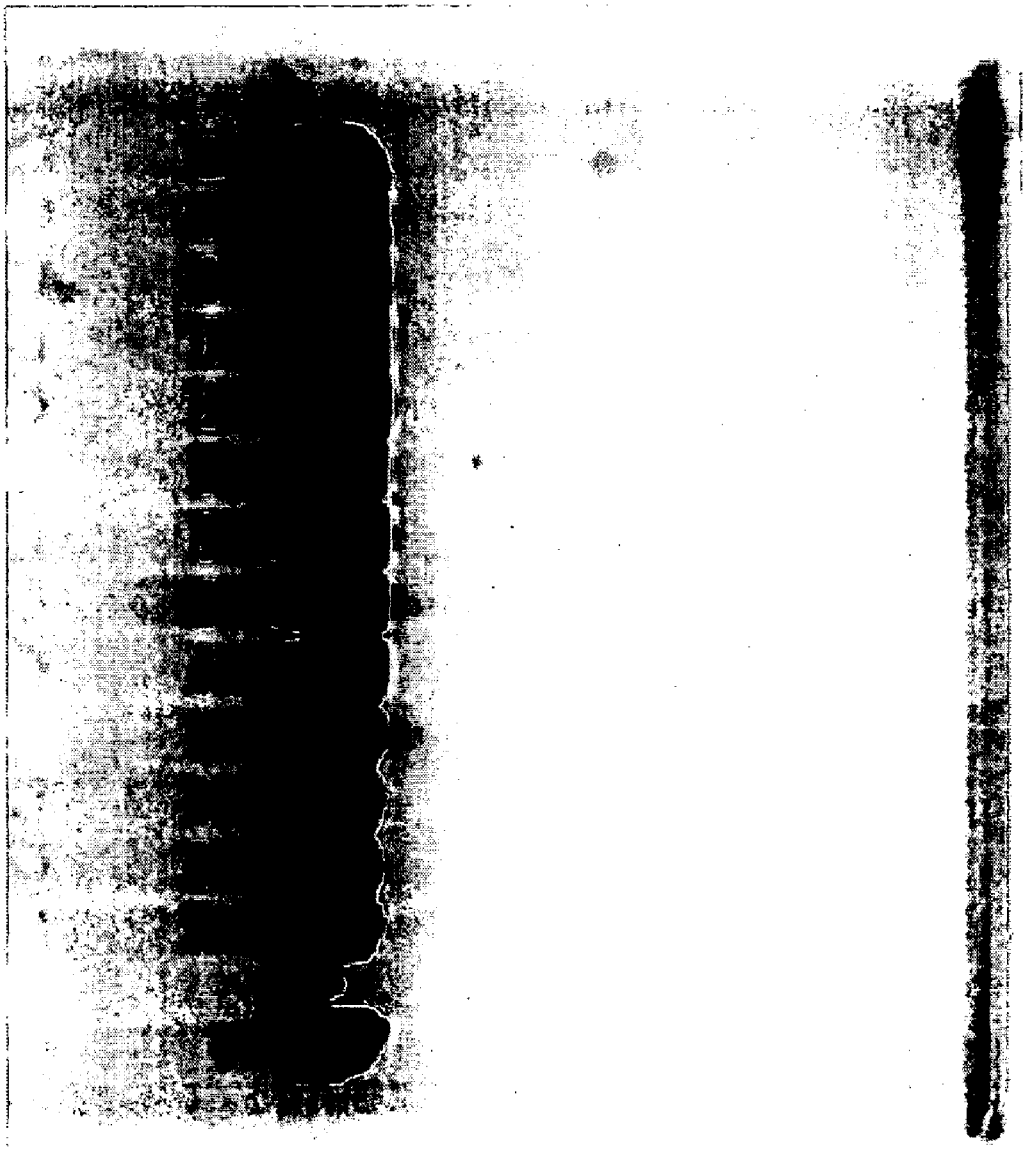
FIG. 56 shows an SDS-PAGE analysis (reduced) of samples stored at 40° C. for 6 weeks. Lane 1: PEG-hGH Standard; Lane 3: P6MT; Lane 4: S5MT; Lane 5: S5GT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 57:
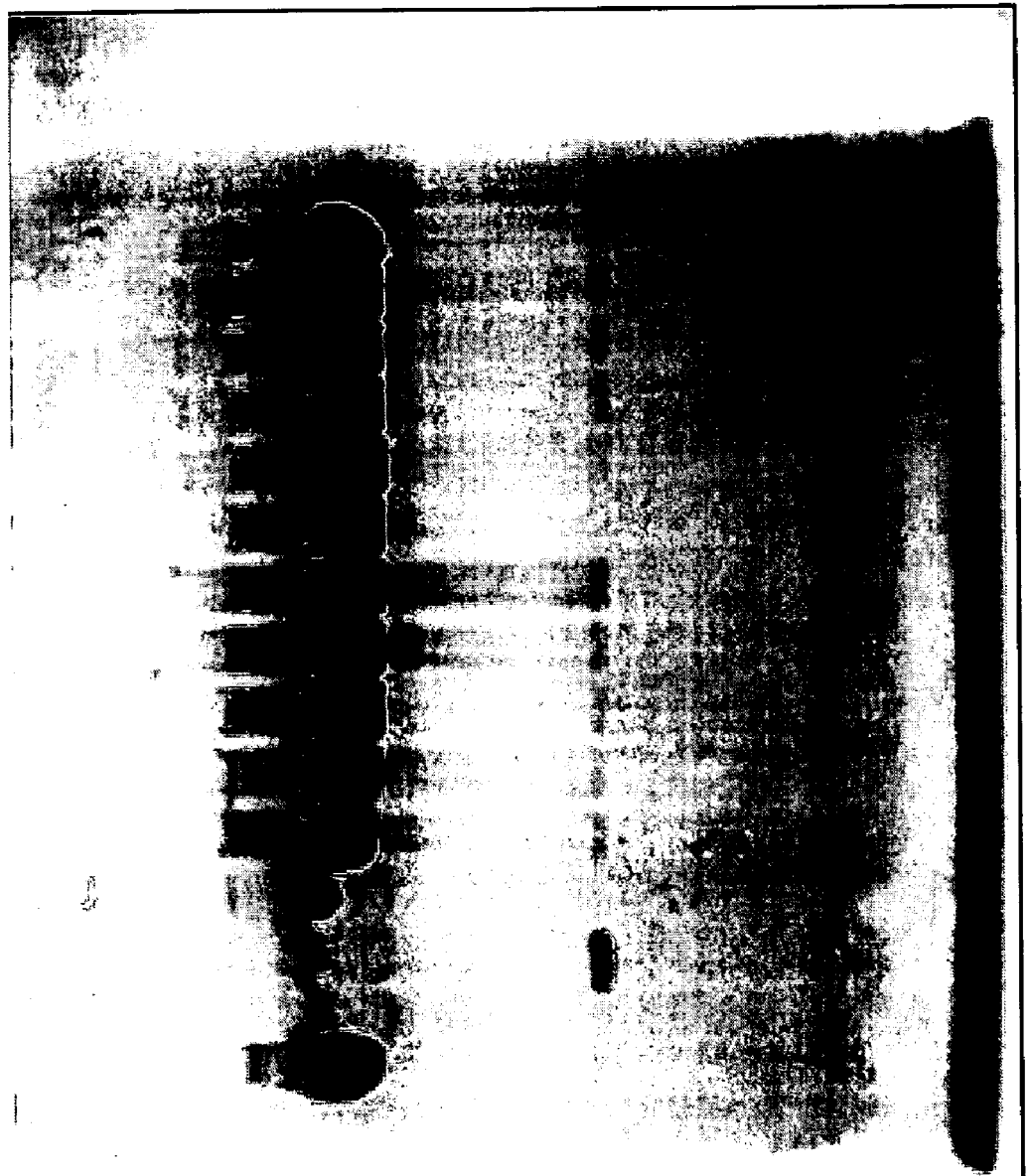
FIG. 57 shows an SDS-PAGE analysis (non-reduced) of samples stored at 40° C. for 2 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.
Figure 58:
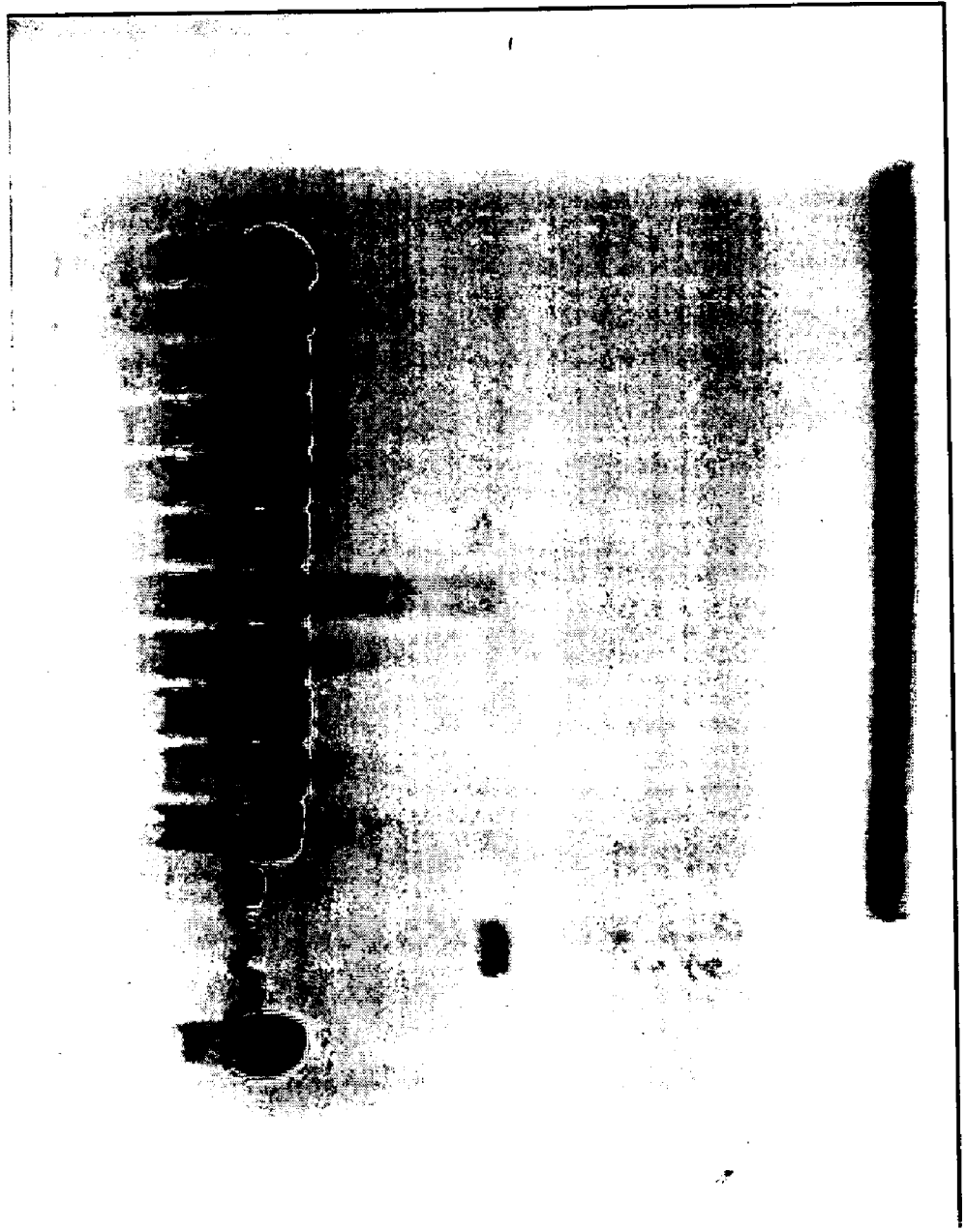
FIG. 58 shows an SDS-PAGE analysis (reduced) of samples stored at 40° C. for 2 months. Lane 1: PEG-hGH Standard; Lane 3: hGH (1 μg); Lane 5: P6MT; Lane 6: H6MT; Lane 7: P6GT; Lane 8: P6MS; Lane 9: P6MTMet; Lane 10: P6MT; Lane 11: P7GT; Lane 12: P6MGT; Lane 13: P6MGT-P; Lane 14: P6MT-P; Lane 15: P6GT-P.

SDS gels for this study are shown as FIGS. 22-58. Faint 21.5 kDa bands were visible in lanes 3 and 4 of FIG. 22.

Figure 20:
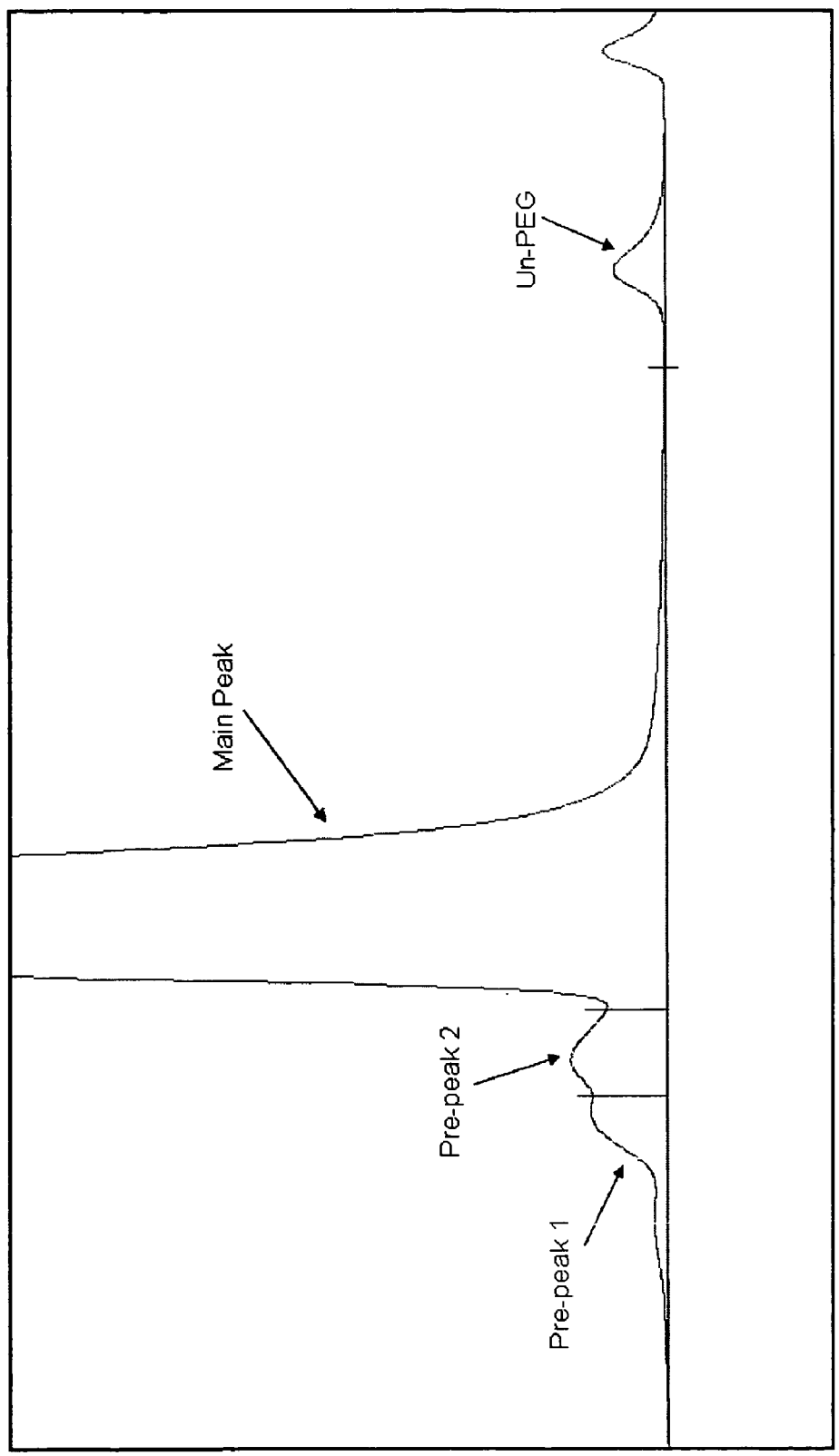
FIG. 20 shows an example of SEC-HPLC integration.

SEC-HPLC: FIG. 20 is an example SEC-HPLC integration. Tables 33-50 show the results from this study. The clip peak eluted between the main PEGylated hGH peak and the Un-PEG peak.

TABLE 33

SEC-HPLC (SUMMARY OF PEAK AREAS); T = 0

| Formulation ID | % Pre-peak | % Main Peak | Total Area |
|---|---|---|---|
| P6MT | 1.38 | 98.62 | 4.70E+04 |
| S4MT | 2.13 | 97.87 | 4.20E+04 |
| S5MT | 1.63 | 98.37 | 4.41E+04 |
| S5GT | 1.67 | 98.33 | 4.58E+04 |
| H6MT | 1.65 | 98.35 | 4.51E+04 |
| P6GT | 1.81 | 98.19 | 4.66E+04 |
| P6MA | 2.09 | 97.91 | 4.64E+04 |
| P6MS | 1.91 | 98.09 | 4.54E+04 |
| P6MTMet | 1.52 | 98.48 | 4.57E+04 |
| P7MT | 1.45 | 98.55 | 4.14E+04 |
| P7GT | 1.39 | 98.61 | 4.60E+04 |
| P6MGT | 1.57 | 98.43 | 4.55E+04 |
| P6MGT-P | 1.59 | 98.41 | 4.57E+04 |
| P6MT-P | 1.88 | 98.12 | 4.44E+04 |
| P6GT-P | 1.69 | 98.31 | 4.52E+04 |

TABLE 34

SEC-HPLC (SUMMARY OF PEAK AREAS); T = 1 week, 4° C.

| Formulation ID | % Pre-peak | % Main Peak | % Un-PEG | Total Area |
|---|---|---|---|---|
| P6MT | 1.81 | 98.08 | 0.11 | 4.42E+04 |
| S4MT | 2.72 | 96.50 | 0.78 | 4.26E+04 |
| S5MT | 2.49 | 97.20 | 0.32 | 4.20E+04 |
| S5GT | 2.17 | 97.55 | 0.27 | 4.58E+04 |
| H6MT | 2.23 | 97.64 | 0.13 | 4.71E+04 |
| P6GT | 2.52 | 97.48 | n/a | 4.99E+04 |
| P6MA | 2.39 | 97.44 | 0.17 | 4.67E+04 |
| P6MS | 2.11 | 97.71 | 0.18 | 4.83E+04 |
| P6MTMet | 2.00 | 97.83 | 0.17 | 4.68E+04 |
| P7MT | 1.91 | 97.90 | 0.19 | 4.29E+04 |
| P7GT | 1.71 | 98.12 | 0.17 | 4.75E+04 |
| P6MGT | 1.64 | 98.15 | 0.21 | 4.30E+04 |
| P6MGT-P | 2.24 | 97.62 | 0.14 | 4.51E+04 |
| P6MT-P | 2.30 | 97.58 | 0.12 | 4.54E+04 |
| P6GT-P | 2.04 | 97.77 | 0.18 | 4.47E+04 |

TABLE 35

SEC-HPLC (SUMMARY OF PEAK AREAS); T = 2 week, 4° C.

| Formulation ID | % Pre-peak | % Main Peak | % Un-PEG | Total Area |
|---|---|---|---|---|
| P6MT | 1.61 | 98.29 | 0.10 | 4.69E+04 |
| S4MT | 2.42 | 97.16 | 0.42 | 4.30E+04 |
| S5MT | 1.66 | 98.26 | 0.07 | 4.34E+04 |
| S5GT | 2.05 | 97.88 | 0.08 | 4.67E+04 |
| H6MT | 2.22 | 97.69 | 0.09 | 4.72E+04 |
| P6GT | 1.58 | 98.36 | 0.06 | 5.11E+04 |
| P6MA | 1.52 | 98.38 | 0.10 | 4.95E+04 |
| P6MS | 1.47 | 98.49 | 0.04 | 5.02E+04 |
| P6MTMet | 1.61 | 98.34 | 0.04 | 4.98E+04 |
| P7MT | 1.53 | 98.41 | 0.06 | 4.46E+04 |
| P7GT | 1.54 | 98.41 | 0.06 | 4.86E+04 |
| P6MGT | 1.48 | 98.44 | 0.08 | 4.59E+04 |
| P6MGT-P | 1.68 | 98.23 | 0.09 | 4.70E+04 |
| P6MT-P | 1.73 | 98.17 | 0.10 | 4.62E+04 |
| P6GT-P | 1.58 | 98.39 | 0.04 | 4.68E+04 |

TABLE 36

SEC-HPLC (SUMMARY OF PEAK AREAS); T = 4 week, 4° C.

| Formulation ID | % Pre-peak 1 | % Pre-peak 2 | % Main Peak | % Un-PEG | Total Area |
|---|---|---|---|---|---|
| P6MT | 1.13 | 1.30 | 97.44 | 0.14 | 4.54E+04 |
| S4MT | 1.18 | 2.31 | 95.81 | 0.69 | 4.09E+04 |
| S5MT | 1.62 | 1.43 | 96.70 | 0.25 | 4.33E+04 |
| S5GT | 1.26 | 1.64 | 96.81 | 0.29 | 4.38E+04 |
| H6MT | 1.37 | 1.26 | 97.24 | 0.12 | 4.77E+04 |
| P6GT | 1.49 | 1.60 | 96.80 | 0.11 | 4.76E+04 |
| P6MA | 1.08 | 1.44 | 97.31 | 0.17 | 4.89E+04 |
| P6MS | 1.56 | 1.35 | 96.96 | 0.13 | 4.72E+04 |
| P6MTMet | 1.11 | 1.29 | 97.44 | 0.17 | 4.88E+04 |
| P7MT | 1.07 | 1.30 | 97.46 | 0.17 | 4.32E+04 |
| P7GT | 0.83 | 1.46 | 97.48 | 0.23 | 4.68E+04 |
| P6MGT | 1.27 | 1.32 | 97.20 | 0.21 | 4.09E+04 |
| P6MGT-P | 1.69 | 1.24 | 96.88 | 0.19 | 4.38E+04 |
| P6MT-P | 1.80 | 1.38 | 96.66 | 0.15 | 4.59E+04 |
| P6GT-P | 1.90 | 1.61 | 96.33 | 0.16 | 4.33E+04 |

TABLE 37

SEC-HPLC (SUMMARY OF PEAK AREAS); T = 6 week, 4° C.

| Formulation ID | % Pre-peak 1 | % Pre-peak 2 | % Main Peak | % Un-PEG | Total Area |
|---|---|---|---|---|---|
| P6MT | 1.28 | 1.42 | 97.20 | 0.10 | 4.42E+04 |
| S5MT | 2.26 | 1.57 | 95.98 | 0.19 | 4.28E+04 |
| S5GT | 1.25 | 1.81 | 96.74 | 0.19 | 4.44E+04 |
| H6MT | 1.23 | 1.28 | 97.38 | 0.10 | 4.53E+04 |
| P6GT | 1.94 | 1.82 | 96.12 | 0.12 | 4.32E+04 |
| P6MS | 1.26 | 1.39 | 97.25 | 0.09 | 4.74E+04 |
| P6MTMet | 1.19 | 1.23 | 97.52 | 0.06 | 4.78E+04 |
| P7MT | 0.98 | 1.38 | 97.55 | 0.09 | 4.17E+04 |
| P7GT | 0.83 | 1.56 | 97.46 | 0.15 | 4.96E+04 |
| P6MGT | 0.97 | 1.31 | 97.60 | 0.12 | 4.30E+04 |
| P6MGT-P | 1.37 | 1.25 | 97.28 | 0.11 | 4.39E+04 |
| P6MT-P | 1.97 | 1.44 | 96.50 | 0.08 | 4.55E+04 |
| P6GT-P | 1.54 | 1.81 | 96.54 | 0.12 | 4.51E+04 |

TABLE 38

SEC-HPLC (SUMMARY OF PEAK AREAS); T = 2 month, 4° C.

| Formulation ID | % Pre-peak 1 | % Pre-peak 2 | % Main Peak | % Un-PEG | Total Area |
|---|---|---|---|---|---|
| P6MT | 1.02 | 1.30 | 97.58 | 0.11 | 5.04E+04 |
| H6MT | 1.14 | 1.17 | 97.62 | 0.06 | 4.88E+04 |
| P6GT | 1.26 | 1.60 | 97.01 | 0.12 | 5.23E+04 |
| P6MS | 1.34 | 1.29 | 97.31 | 0.06 | 4.99E+04 |
| P6MTMet | 1.26 | 1.30 | 97.33 | 0.11 | 5.00E+04 |
| P7MT | 0.74 | 1.30 | 97.89 | 0.07 | 4.38E+04 |
| P7GT | 0.77 | 1.52 | 97.51 | 0.21 | 4.80E+04 |
| P6MGT | 1.34 | 1.28 | 97.26 | 0.12 | 4.62E+04 |
| P6MGT-P | 1.54 | 1.14 | 97.21 | 0.10 | 4.66E+04 |
| P6MT-P | 1.97 | 1.34 | 96.60 | 0.09 | 4.65E+04 |
| P6GT-P | 1.33 | 1.52 | 97.08 | 0.07 | 4.79E+04 |

TABLE 39

SEC-HPLC (SUMMARY OF PEAK AREAS); T = 3 month, 4° C.

| Formulation | % Pre-peak 1 | % Pre-peak 2 | % Main Peak | % Un-PEG | Total Area |
|---|---|---|---|---|---|
| P6MT | 0.72 | 1.14 | 98.14 | 0.00 | 4.86E+04 |
| H6MT | 0.77 | 0.99 | 98.24 | 0.00 | 5.07E+04 |
| P6GT | 0.62 | 1.35 | 97.96 | 0.07 | 5.58E+04 |
| P6MS | 0.77 | 1.04 | 98.20 | 0.00 | 5.19E+04 |
| P6MTMet | 0.66 | 0.96 | 98.39 | 0.00 | 5.13E+04 |
| P7MT | 0.55 | 1.06 | 98.39 | 0.00 | 4.15E+04 |
| P7GT | 0.53 | 1.42 | 97.76 | 0.29 | 5.08E+04 |
| P6MGT | 0.73 | 1.05 | 98.22 | 0.00 | 4.41E+04 |
| P6MGT-P | 0.72 | 1.07 | 98.21 | 0.00 | 4.51E+04 |
| P6MT-P | 1.41 | 1.22 | 97.37 | 0.00 | 4.66E+04 |
| P6GT-P | 1.09 | 1.54 | 97.37 | 0.00 | 4.59E+04 |

TABLE 40

SEC-HPLC (SUMMARY OF PEAK AREAS); T = 1 week, 25° C.

| Formulation ID | % Pre-peak | % Main Peak | % Un-PEG | Total Area |
|---|---|---|---|---|
| P6MT | 2.17 | 97.70 | 0.14 | 4.64E+04 |
| S4MT | 3.79 | 95.39 | 0.82 | 4.15E+04 |
| S5MT | 2.42 | 97.31 | 0.27 | 4.46E+04 |
| S5GT | 2.35 | 97.40 | 0.25 | 4.59E+04 |
| H6MT | 2.10 | 97.75 | 0.15 | 4.63E+04 |
| P6GT | 2.31 | 97.54 | 0.15 | 5.01E+04 |
| P6MA | 1.95 | 97.92 | 0.13 | 4.97E+04 |
| P6MS | 2.06 | 97.82 | 0.12 | 4.72E+04 |
| P6MTMet | 2.14 | 97.71 | 0.15 | 4.85E+04 |
| P7MT | 1.79 | 98.01 | 0.19 | 4.37E+04 |
| P7GT | 2.15 | 97.56 | 0.30 | 4.62E+04 |
| P6MGT | 2.09 | 97.75 | 0.16 | 4.17E+04 |
| P6MGT-P | 2.19 | 97.70 | 0.11 | 4.33E+04 |
| P6MT-P | 2.51 | 97.41 | 0.08 | 4.23E+04 |
| P6GT-P | 2.60 | 97.21 | 0.19 | 4.20E+04 |

TABLE 41

SEC-HPLC (SUMMARY OF PEAK AREAS); T = 2 week, 25° C.

| Formulation ID | % Pre-peak | % Main Peak | % Un-PEG | Total Area |
|---|---|---|---|---|
| P6MT | 1.87 | 98.01 | 0.12 | 4.71E+04 |
| S4MT | 2.89 | 96.47 | 0.65 | 4.21E+04 |
| S5MT | 1.94 | 97.82 | 0.24 | 4.73E+04 |
| S5GT | 2.34 | 97.43 | 0.22 | 4.70E+04 |
| H6MT | 2.20 | 97.66 | 0.13 | 4.35E+04 |
| P6GT | 2.36 | 97.52 | 0.12 | 5.31E+04 |
| P6MA | 1.90 | 98.00 | 0.10 | 5.21E+04 |
| P6MS | 1.76 | 98.12 | 0.11 | 5.07E+04 |
| P6MTMet | 1.62 | 98.30 | 0.09 | 5.17E+04 |

TABLE 41-continued

SEC-HPLC (SUMMARY OF PEAK AREAS); T = 2 week, 25° C.

| Formulation ID | % Pre-peak | % Main Peak | % Un-PEG | Total Area |
|---|---|---|---|---|
| P7MT | 2.48 | 97.37 | 0.15 | 4.28E+04 |
| P7GT | 2.08 | 97.78 | 0.14 | 4.94E+04 |
| P6MGT | 2.22 | 97.66 | 0.12 | 4.38E+04 |
| P6MGT-P | 1.81 | 98.06 | 0.13 | 4.76E+04 |
| P6MT-P | 2.04 | 97.85 | 0.11 | 4.56E+04 |
| P6GT-P | 2.30 | 97.60 | 0.10 | 4.75E+04 |

TABLE 42

SEC-HPLC (SUMMARY OF PEAK AREAS); T = 4 week, 25° C.

| Formulation | % Pre-peak 1 | % Pre-peak 2 | % Main Peak | % Un-PEG | Total Area |
|---|---|---|---|---|---|
| P6MT | 1.50 | 2.31 | 95.91 | 0.27 | 4.37E+04 |
| S4MT | 1.25 | 3.17 | 94.82 | 0.76 | 4.15E+04 |
| S5MT | 2.47 | 3.80 | 93.42 | 0.32 | 4.70E+04 |
| S5GT | 1.29 | 2.77 | 95.57 | 0.36 | 4.64E+04 |
| H6MT | 2.09 | 1.42 | 96.25 | 0.23 | 4.57E+04 |
| P6GT | 1.10 | 2.29 | 96.39 | 0.21 | 4.79E+04 |
| P6MA | 1.19 | 2.48 | 96.17 | 0.17 | 4.72E+04 |
| P6MS | 1.60 | 2.40 | 95.82 | 0.19 | 4.81E+04 |
| P6MTMet | 1.00 | 1.65 | 97.26 | 0.09 | 4.87E+04 |
| P7MT | 0.92 | 1.63 | 97.28 | 0.17 | 4.19E+04 |
| P7GT | 1.02 | 2.46 | 96.18 | 0.34 | 4.50E+04 |
| P6MGT | 1.22 | 2.16 | 96.28 | 0.34 | 4.08E+04 |
| P6MGT-P | 1.80 | 1.81 | 96.19 | 0.20 | 4.21E+04 |
| P6MT-P | 1.67 | 1.96 | 96.18 | 0.18 | 4.59E+04 |
| P6GT-P | 1.45 | 2.35 | 95.96 | 0.24 | 4.66E+04 |

TABLE 43

SEC-HPLC (SUMMARY OF PEAK AREAS); T = 6 week, 25° C.

| Formulation ID | % Pre-peak 1 | % Pre-peak 2 | % Main Peak | % Un-PEG | Total Area |
|---|---|---|---|---|---|
| P6MT | 0.95 | 1.91 | 96.96 | 0.17 | 4.68E+04 |
| S5MT | 1.32 | 2.56 | 95.87 | 0.25 | 4.31E+04 |
| S5GT | 1.54 | 2.96 | 95.47 | 0.03 | 4.64E+04 |
| H6MT | 1.74 | 1.52 | 96.61 | 0.12 | 4.76E+04 |
| P6GT | 1.12 | 2.24 | 96.53 | 0.11 | 4.80E+04 |
| P6MS | 1.41 | 2.13 | 96.38 | 0.08 | 4.89E+04 |
| P6MTMet | 1.08 | 1.91 | 96.85 | 0.16 | 4.80E+04 |
| P7MT | 0.88 | 1.82 | 97.19 | 0.12 | 4.37E+04 |
| P7GT | 0.83 | 2.15 | 96.91 | 0.10 | 4.68E+04 |
| P6MGT | 1.25 | 2.77 | 95.76 | 0.21 | 4.37E+04 |
| P6MGT-P | 1.44 | 2.30 | 96.13 | 0.12 | 4.37E+04 |
| P6MT-P | 2.00 | 2.08 | 95.83 | 0.08 | 4.44E+04 |
| P6GT-P | 1.62 | 2.64 | 95.63 | 0.11 | 4.52E+04 |

TABLE 44

SEC-HPLC (SUMMARY OF PEAK AREAS); T = 2 month, 25° C.

| Formulation ID | % Pre-peak 1 | % Pre-peak 2 | % Main Peak | % Un-PEG | Total Area |
|---|---|---|---|---|---|
| P6MT | 1.38 | 2.16 | 96.28 | 0.18 | 4.85E+04 |
| H6MT | 1.56 | 1.50 | 96.69 | 0.25 | 5.07E+04 |
| P6GT | 1.30 | 2.61 | 95.92 | 0.17 | 5.22E+04 |
| P6MS | 1.36 | 2.04 | 96.51 | 0.09 | 5.04E+04 |
| P6MTMet | 1.16 | 1.76 | 96.98 | 0.10 | 5.05E+04 |
| P7MT | 0.79 | 1.81 | 97.27 | 0.13 | 4.29E+04 |
| P7GT | 0.63 | 2.58 | 96.40 | 0.39 | 4.99E+04 |
| P6MGT | 1.05 | 2.55 | 96.21 | 0.19 | 4.57E+04 |
| P6MGT-P | 1.39 | 2.22 | 96.22 | 0.16 | 4.56E+04 |
| P6MT-P | 1.69 | 1.96 | 96.24 | 0.12 | 4.69E+04 |
| P6GT-P | 1.42 | 2.57 | 95.87 | 0.14 | 4.69E+04 |

TABLE 45

SEC-HPLC (SUMMARY OF PEAK AREAS); T = 3 month, 25° C.

| Formulation | % Pre-peak 1 | % Pre-peak 2 | % Main Peak | % Un-PEG | Total Area |
|---|---|---|---|---|---|
| P6MT | 0.75 | 1.88 | 97.38 | 0.00 | 4.89E+04 |
| H6MT | 0.86 | 1.15 | 97.99 | 0.00 | 5.40E+04 |
| P6GT | 0.92 | 2.16 | 96.92 | 0.00 | 5.14E+04 |
| P6MS | 1.09 | 2.09 | 96.71 | 0.11 | 4.72E+04 |
| P6MTMet | 0.92 | 1.80 | 97.28 | 0.00 | 4.99E+04 |
| P7MT | 0.60 | 1.53 | 97.87 | 0.00 | 4.47E+04 |
| P7GT | 0.62 | 2.03 | 97.17 | 0.17 | 4.86E+04 |
| P6MGT | 0.86 | 2.27 | 96.66 | 0.20 | 4.49E+04 |
| P6MGT-P | 0.93 | 2.04 | 96.85 | 0.18 | 4.48E+04 |
| P6MT-P | 1.03 | 1.76 | 97.21 | 0.00 | 4.72E+04 |
| P6GT-P | 1.05 | 2.17 | 96.63 | 0.15 | 4.68E+04 |

TABLE 46

SEC-HPLC (SUMMARY OF PEAK AREAS); T = 1 week, 40° C.

| Formulation ID | % Pre-peak | % Main Peak | % Un-PEG | Total Area |
|---|---|---|---|---|
| P6MT | 2.32 | 97.51 | 0.17 | 4.61E+04 |
| S4MT | 7.69 | 91.40 | 0.91 | 4.01E+04 |
| S5MT | 3.01 | 96.68 | 0.30 | 4.69E+04 |
| S5GT | 3.18 | 96.52 | 0.30 | 4.36E+04 |
| H6MT | 2.44 | 97.34 | 0.22 | 4.80E+04 |
| P6GT | 2.67 | 97.17 | 0.16 | 5.01E+04 |
| P6MA | 5.24 | 94.52 | 0.24 | 4.77E+04 |
| P6MS | 3.69 | 96.13 | 0.18 | 4.84E+04 |
| P6MTMet | 2.33 | 97.44 | 0.23 | 4.55E+04 |
| P7MT | 2.60 | 97.24 | 0.16 | 4.31E+04 |
| P7GT | 2.59 | 97.18 | 0.23 | 4.61E+04 |
| P6MGT | 2.85 | 96.96 | 0.19 | 4.58E+04 |
| P6MGT-P | 3.20 | 96.69 | 0.12 | 4.24E+04 |
| P6MT-P | 3.42 | 96.44 | 0.13 | 3.95E+04 |
| P6GT-P | 3.30 | 96.57 | 0.13 | 4.27E+04 |

TABLE 47

SEC-HPLC (SUMMARY OF PEAK AREAS); T = 2 week, 40° C.

| Formulation ID | % Pre-peak | % Main Peak | % Un-PEG | Total Area |
|---|---|---|---|---|
| P6MT | 2.45 | 97.45 | 0.11 | 4.54E+04 |
| S4MT | 7.29 | 91.94 | 0.77 | 4.29E+04 |
| S5MT | 4.22 | 95.48 | 0.30 | 4.67E+04 |
| S5GT | 3.63 | 96.18 | 0.19 | 4.65E+04 |
| H6MT | 2.41 | 97.36 | 0.22 | 4.72E+04 |
| P6GT | 2.82 | 97.05 | 0.13 | 5.09E+04 |
| P6MA | 41.10 | 58.76 | 0.14 | 4.92E+04 |
| P6MS | 4.15 | 95.71 | 0.14 | 5.14E+04 |
| P6MTMet | 2.29 | 97.53 | 0.18 | 4.96E+04 |
| P7MT | 2.07 | 97.87 | 0.06 | 4.43E+04 |
| P7GT | 2.15 | 97.74 | 0.12 | 5.06E+04 |
| P6MGT | 3.29 | 96.53 | 0.19 | 4.40E+04 |
| P6MGT-P | 2.92 | 97.00 | 0.07 | 4.80E+04 |
| P6MT-P | 2.65 | 97.23 | 0.12 | 4.68E+04 |
| P6GT-P | 2.50 | 97.40 | 0.10 | 4.92E+04 |

TABLE 48

SEC-HPLC (SUMMARY OF PEAK AREAS); T = 4 week, 40° C.

| Formulation ID | % Pre-peak 1 | % Pre-peak 2 | % Main Peak | % Un-PEG | Total Area |
|---|---|---|---|---|---|
| P6MT | 1.22 | 3.47 | 94.87 | 0.44 | 4.55E+04 |
| S4MT | 0.00 | 12.63 | 86.23 | 1.14 | 4.06E+04 |
| S5MT | 1.43 | 4.82 | 93.21 | 0.54 | 4.53E+04 |
| S5GT | 1.29 | 4.54 | 93.79 | 0.38 | 4.48E+04 |
| H6MT | 1.55 | 2.05 | 95.93 | 0.47 | 4.45E+04 |
| P6GT | 1.21 | 4.14 | 94.37 | 0.28 | 4.90E+04 |
| P6MA | 0.00 | 63.87 | 35.95 | 0.18 | 4.75E+04 |
| P6MS | 0.00 | 8.35 | 91.27 | 0.37 | 4.71E+04 |
| P6MTMet | 1.32 | 3.60 | 94.35 | 0.73 | 4.59E+04 |
| P7MT | 0.80 | 2.18 | 96.89 | 0.12 | 4.21E+04 |
| P7GT | 0.75 | 2.81 | 96.13 | 0.31 | 4.60E+04 |
| P6MGT | 1.42 | 4.38 | 93.85 | 0.36 | 3.89E+04 |
| P6MGT-P | 1.36 | 3.46 | 94.93 | 0.25 | 4.23E+04 |
| P6MT-P | 1.69 | 3.52 | 94.47 | 0.32 | 4.04E+04 |
| P6GT-P | 1.45 | 3.60 | 94.70 | 0.25 | 4.50E+04 |

TABLE 49

SEC-HPLC (SUMMARY OF PEAK AREAS); T = 6 week, 40° C.

| Formulation ID | % Pre-peak 1 | % Pre-peak 2 | % Main Peak | % Clip | % Un-PEG | Total Area |
|---|---|---|---|---|---|---|
| P6MT | 1.13 | 3.12 | 95.54 | 0.00 | 0.21 | 4.52E+04 |
| S5MT | 1.68 | 6.59 | 91.30 | 0.00 | 0.42 | 4.34E+04 |
| S5GT | 1.05 | 4.82 | 93.78 | 0.00 | 0.34 | 4.48E+04 |
| H6MT | 1.36 | 2.16 | 96.12 | 0.00 | 0.35 | 4.61E+04 |
| P6GT | 0.88 | 3.38 | 95.65 | 0.00 | 0.10 | 4.93E+04 |
| P6MS | 0.00 | 10.02 | 88.34 | 1.31 | 0.33 | 4.82E+04 |
| P6MTMet | 1.24 | 3.35 | 93.80 | 1.16 | 0.46 | 4.98E+04 |
| P7MT | 1.03 | 3.38 | 95.35 | 0.00 | 0.25 | 4.15E+04 |
| P7GT | 0.77 | 3.19 | 95.86 | 0.00 | 0.19 | 4.73E+04 |
| P6MGT | 1.12 | 4.92 | 93.58 | 0.00 | 0.39 | 4.08E+04 |
| P6MGT-P | 1.35 | 4.23 | 94.16 | 0.00 | 0.25 | 4.46E+04 |
| P6MT-P | 1.80 | 3.70 | 94.29 | 0.00 | 0.21 | 4.51E+04 |
| P6GT-P | 1.41 | 3.81 | 94.59 | 0.00 | 0.19 | 4.56E+04 |

TABLE 50

SEC-HPLC (SUMMARY OF PEAK AREAS); T = 2 month, 40° C.

| Formulation | % Pre-peak 1 | % Pre-peak 2 | % Main Peak | % Un-PEG | Total Area |
|---|---|---|---|---|---|
| P6MT | 1.15 | 3.04 | 95.58 | 0.23 | 4.81E+04 |
| H6MT | 1.34 | 2.07 | 96.32 | 0.27 | 5.15E+04 |
| P6GT | 1.15 | 3.46 | 95.22 | 0.17 | 5.24E+04 |
| P6MS | 0.00 | 10.51 | 89.14 | 0.36 | 5.08E+04 |
| P6MTMet | 1.24 | 4.73 | 93.27 | 0.76 | 4.89E+04 |
| P7MT | 0.71 | 2.74 | 96.30 | 0.25 | 4.33E+04 |
| P7GT | 0.66 | 3.71 | 95.25 | 0.37 | 4.78E+04 |
| P6MGT | 0.93 | 4.25 | 94.53 | 0.28 | 4.60E+04 |
| P6MGT-P | 1.23 | 4.03 | 94.48 | 0.25 | 4.58E+04 |
| P6MT-P | 1.51 | 3.67 | 94.57 | 0.25 | 4.71E+04 |
| P6GT-P | 1.20 | 4.06 | 94.55 | 0.19 | 4.72E+04 |

Figure 21:
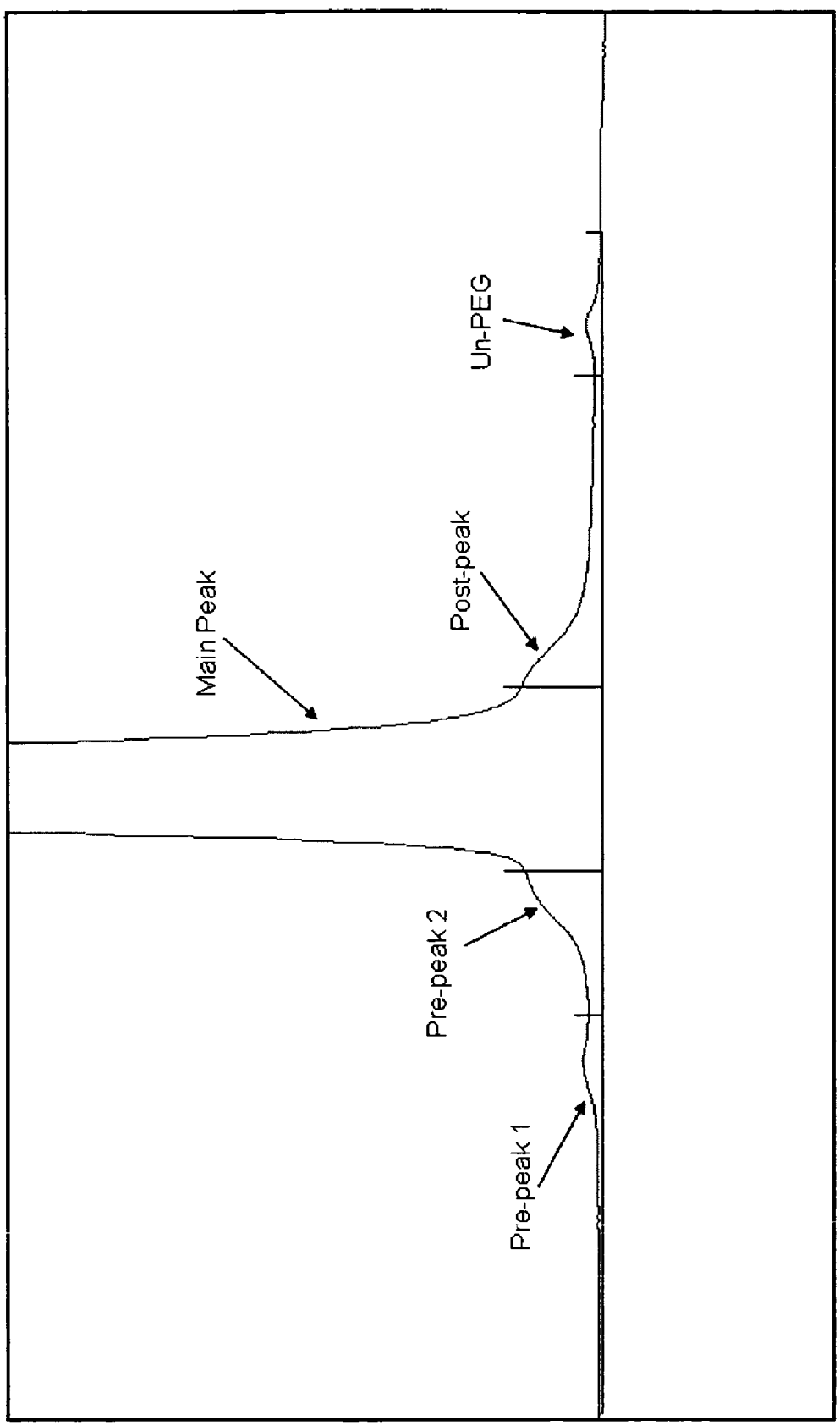
FIG. 21 shows an example of RP-HPLC integration.

RP-HPLC: FIG. 21 is an example RP-HPLC integration. Tables 51-68 show RP-HPLC results from this study.

TABLE 51

RP-HPLC (SUMMARY OF PEAK AREAS); T = 0

| Formulation ID | % Pre-peak | % Post-peak | % Main Peak | % Un-PEG | Total Area |
|---|---|---|---|---|---|
| P6MT | 0.78 | 1.09 | 98.02 | 0.11 | 5.78E+03 |
| S4MT | 0.83 | 2.42 | 96.53 | 0.22 | 5.36E+03 |
| S5MT | 0.69 | 1.08 | 98.34 | −0.11 | 5.92E+03 |
| S5GT | 0.83 | 1.57 | 97.52 | 0.08 | 6.26E+03 |
| H6MT | 0.93 | 0.95 | 98.06 | 0.06 | 6.57E+03 |
| P6GT | 0.73 | 0.98 | 98.21 | 0.07 | 6.75E+03 |
| P6MA | 1.00 | 0.70 | 98.38 | −0.08 | 6.32E+03 |
| P6MS | 0.92 | 0.77 | 98.30 | 0.01 | 6.74E+03 |
| P6MTMet | 0.93 | 0.81 | 98.27 | −0.01 | 6.49E+03 |
| P7MT | 1.12 | 0.77 | 98.11 | 0.01 | 6.64E+03 |
| P7GT | 0.95 | 0.81 | 98.20 | 0.04 | 6.12E+03 |
| P6MGT | 1.11 | 1.04 | 97.77 | 0.09 | 5.56E+03 |
| P6MGT-P | 0.98 | 0.88 | 98.29 | −0.15 | 5.48E+03 |
| P6MT-P | 1.18 | 0.83 | 98.07 | −0.08 | 5.63E+03 |
| P6GT-P | 0.89 | 1.05 | 98.10 | −0.04 | 4.72E+03 |

TABLE 52

RP-HPLC (SUMMARY OF PEAK AREAS); T = 1 week; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.30 | 1.15 | 1.47 | 96.90 | 0.19 | 7.38E+03 |
| S4MT | 0.31 | 1.26 | 2.55 | 95.41 | 0.46 | 6.76E+03 |
| S5MT | 0.54 | 1.37 | 1.72 | 96.18 | 0.19 | 6.47E+03 |
| S5GT | 0.26 | 1.32 | 1.73 | 96.45 | 0.24 | 6.40E+03 |
| H6MT | 0.28 | 1.23 | 1.05 | 97.38 | 0.06 | 6.51E+03 |
| P6GT | 0.29 | 1.32 | 1.50 | 96.64 | 0.25 | 7.22E+03 |
| P6MA | 0.37 | 1.36 | 1.02 | 97.19 | 0.06 | 7.22E+03 |
| P6MS | 0.22 | 1.03 | 1.09 | 97.57 | 0.09 | 7.12E+03 |
| P6MTMet | 0.25 | 1.14 | 1.16 | 97.28 | 0.17 | 7.07E+03 |
| P7MT | 0.26 | 1.11 | 1.13 | 97.34 | 0.17 | 7.05E+03 |
| P7GT | 0.28 | 2.31 | 1.28 | 95.98 | 0.14 | 6.71E+03 |
| P6MGT | 0.43 | 1.46 | 1.44 | 96.32 | 0.35 | 7.08E+03 |
| P6MGT-P | 0.39 | 1.19 | 1.43 | 96.89 | 0.10 | 6.21E+03 |
| P6MT-P | 0.38 | 1.27 | 1.08 | 97.02 | 0.25 | 7.70E+03 |
| P6GT-P | 0.47 | 1.39 | 1.30 | 96.47 | 0.37 | 7.64E+03 |

TABLE 53

RP-HPLC (SUMMARY OF PEAK AREAS); T = 2 week; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.27 | 0.85 | 0.78 | 98.05 | 0.04 | 7.17E+03 |
| S4MT | 0.29 | 1.09 | 2.48 | 95.59 | 0.55 | 5.75E+03 |
| S5MT | 0.14 | 1.16 | 1.45 | 97.25 | −0.01 | 5.57E+03 |
| S5GT | 0.21 | 1.29 | 1.46 | 96.99 | 0.04 | 6.41E+03 |
| H6MT | 0.34 | 1.14 | 0.99 | 97.50 | 0.03 | 6.34E+03 |
| P6GT | 0.27 | 1.26 | 1.33 | 97.02 | 0.12 | 6.78E+03 |
| P6MA | 0.33 | 1.17 | 0.87 | 97.70 | −0.07 | 7.96E+03 |
| P6MS | 0.42 | 1.31 | 0.84 | 97.43 | −0.01 | 7.16E+03 |
| P6MTMet | 0.77 | 1.37 | 0.90 | 96.99 | −0.03 | 7.32E+03 |
| P7MT | 0.27 | 1.32 | 0.66 | 97.83 | −0.08 | 6.08E+03 |
| P7GT | 0.45 | 1.40 | 1.23 | 96.85 | 0.06 | 6.67E+03 |
| P6MGT | 0.41 | 1.35 | 0.92 | 97.32 | 0.00 | 6.20E+03 |
| P6MGT-P | 0.38 | 1.42 | 0.88 | 97.35 | −0.03 | 6.34E+03 |
| P6MT-P | 0.48 | 1.29 | 0.90 | 97.36 | −0.03 | 6.83E+03 |
| P6GT-P | 0.40 | 1.64 | 1.23 | 96.68 | 0.06 | 6.18E+03 |

TABLE 54

RP-HPLC (SUMMARY OF PEAK AREAS); T = 4 week; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.19 | 0.95 | 1.03 | 97.71 | 0.12 | 6.82E+03 |
| S4MT | 0.23 | 1.06 | 2.57 | 95.56 | 0.58 | 5.80E+03 |
| S5MT | 0.21 | 1.15 | 1.56 | 96.97 | 0.11 | 7.10E+03 |
| S5GT | 0.18 | 1.41 | 2.08 | 96.09 | 0.24 | 5.23E+03 |
| H6MT | 0.11 | 1.07 | 0.88 | 97.82 | 0.13 | 7.73E+03 |
| P6GT | 0.14 | 1.17 | 1.14 | 97.41 | 0.14 | 7.40E+03 |
| P6MA | 0.20 | 1.01 | 0.98 | 97.72 | 0.10 | 7.18E+03 |
| P6MS | 0.14 | 0.90 | 1.06 | 97.78 | 0.13 | 7.38E+03 |
| P6MTMet | 0.17 | 0.79 | 0.99 | 97.97 | 0.09 | 7.86E+03 |
| P7MT | 0.05 | 1.00 | 1.12 | 97.83 | 0.00 | 6.25E+03 |
| P7GT | 0.15 | 0.87 | 1.38 | 97.44 | 0.17 | 7.06E+03 |
| P6MGT | −0.04 | 0.94 | 0.81 | 98.19 | 0.10 | 5.72E+03 |
| P6MGT-P | 0.17 | 1.07 | 1.11 | 97.60 | 0.05 | 6.30E+03 |
| P6MT-P | 0.08 | 1.07 | 0.96 | 97.90 | −0.02 | 6.66E+03 |
| P6GT-P | 0.08 | 1.17 | 1.39 | 97.25 | 0.12 | 6.33E+03 |

TABLE 55

RP-HPLC (SUMMARY OF PEAK AREAS); T = 6 week; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.09 | 1.19 | 1.68 | 96.95 | 0.09 | 6.40E+03 |
| S5MT | 0.08 | 1.27 | 2.12 | 96.28 | 0.26 | 6.09E+03 |
| S5GT | 0.18 | 1.47 | 2.38 | 95.74 | 0.22 | 6.67E+03 |
| H6MT | 0.14 | 1.08 | 1.55 | 97.15 | 0.07 | 6.73E+03 |
| P6GT | 0.26 | 1.34 | 1.83 | 96.32 | 0.25 | 6.76E+03 |
| P6MS | 0.26 | 1.10 | 1.36 | 97.25 | 0.03 | 7.26E+03 |
| P6MTMet | 0.14 | 1.15 | 1.40 | 97.29 | 0.02 | 7.34E+03 |
| P7MT | 0.28 | 1.29 | 1.60 | 96.73 | 0.11 | 6.21E+03 |
| P7GT | 0.36 | 1.21 | 1.81 | 96.33 | 0.29 | 6.67E+03 |
| P6MGT | 0.46 | 1.44 | 1.83 | 96.26 | 0.00 | 5.56E+03 |
| P6MGT-P | 0.30 | 1.19 | 1.43 | 97.05 | 0.03 | 6.41E+03 |
| P6MT-P | 0.13 | 1.10 | 1.22 | 97.58 | −0.03 | 6.41E+03 |
| P6GT-P | 0.16 | 1.04 | 1.37 | 97.32 | 0.11 | 6.28E+03 |

TABLE 56

RP-HPLC (SUMMARY OF PEAK AREAS); T = 2 month; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.10 | 0.79 | 1.39 | 97.54 | 0.18 | 6.73E+03 |
| H6MT | 0.31 | 0.80 | 1.34 | 97.37 | 0.17 | 6.50E+03 |
| P6GT | 0.37 | 0.97 | 1.48 | 96.94 | 0.24 | 7.49E+03 |
| P6MS | 0.45 | 0.69 | 1.28 | 97.43 | 0.15 | 6.90E+03 |
| P6MTMet | 0.20 | 0.74 | 1.23 | 97.67 | 0.17 | 7.07E+03 |
| P7MT | 0.32 | 0.76 | 1.26 | 97.61 | 0.06 | 5.84E+03 |
| P7GT | 0.38 | 0.77 | 1.68 | 96.79 | 0.38 | 7.10E+03 |
| P6MGT | 0.51 | 0.85 | 1.32 | 97.02 | 0.30 | 5.87E+03 |
| P6MGT-P | 0.17 | 0.96 | 1.41 | 97.19 | 0.27 | 6.46E+03 |
| P6MT-P | 0.13 | 0.90 | 1.52 | 97.37 | 0.09 | 6.20E+03 |
| P6GT-P | 0.18 | 0.91 | 1.59 | 97.09 | 0.23 | 6.56E+03 |

TABLE 57

RP-HPLC (SUMMARY OF PEAK AREAS); T = 3 month; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.30 | 1.06 | 1.44 | 96.79 | 0.41 | 7.70E+03 |
| H6MT | 0.38 | 1.08 | 1.47 | 96.79 | 0.27 | 7.70E+03 |
| P6GT | 0.39 | 1.24 | 1.57 | 96.43 | 0.37 | 9.07E+03 |
| P6MS | 0.45 | 1.29 | 1.29 | 96.90 | 0.07 | 8.43E+03 |
| P6MTMet | 0.23 | 1.11 | 1.30 | 97.22 | 0.14 | 8.48E+03 |
| P7MT | 0.29 | 1.13 | 1.51 | 96.96 | 0.11 | 7.25E+03 |
| P7GT | 0.45 | 1.26 | 2.04 | 95.83 | 0.42 | 8.53E+03 |
| P6MGT | 0.61 | 1.45 | 1.93 | 95.55 | 0.45 | 7.68E+03 |
| P6MGT-P | 0.19 | 1.24 | 1.58 | 96.74 | 0.26 | 7.71E+03 |
| P6MT-P | 0.25 | 1.04 | 1.50 | 97.08 | 0.14 | 7.80E+03 |
| P6GT-P | 0.33 | 1.22 | 1.79 | 96.32 | 0.35 | 7.83E+03 |

TABLE 58

RP-HPLC (SUMMARY OF PEAK AREAS); T = 1 week; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.46 | 1.41 | 1.51 | 96.48 | 0.14 | 7.80E+03 |
| S4MT | 0.60 | 1.45 | 3.15 | 94.13 | 0.66 | 6.90E+03 |
| S5MT | 0.52 | 1.49 | 1.98 | 95.77 | 0.24 | 6.64E+03 |
| S5GT | 0.48 | 1.68 | 1.93 | 95.70 | 0.21 | 6.45E+03 |
| H6MT | 0.50 | 1.39 | 1.33 | 96.59 | 0.19 | 8.69E+03 |
| P6GT | 0.50 | 1.82 | 1.76 | 95.63 | 0.30 | 7.78E+03 |
| P6MA | 0.61 | 1.43 | 1.11 | 96.76 | 0.09 | 8.95E+03 |
| P6MS | 0.60 | 1.44 | 1.32 | 96.59 | 0.05 | 7.14E+03 |
| P6MTMet | 0.37 | 1.34 | 1.41 | 96.81 | 0.06 | 6.83E+03 |
| P7MT | 0.53 | 1.38 | 1.28 | 96.77 | 0.03 | 6.52E+03 |
| P7GT | 0.63 | 1.60 | 1.78 | 95.69 | 0.30 | 7.06E+03 |
| P6MGT | 0.63 | 1.84 | 1.46 | 95.90 | 0.16 | 6.14E+03 |
| P6MGT-P | 0.77 | 1.74 | 1.60 | 95.71 | 0.19 | 6.68E+03 |
| P6MT-P | 0.70 | 1.55 | 1.35 | 96.34 | 0.07 | 7.01E+03 |
| P6GT-P | 0.64 | 1.92 | 1.73 | 95.42 | 0.29 | 6.68E+03 |

TABLE 59

RP-HPLC (SUMMARY OF PEAK AREAS); T = 2 week; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.41 | 1.39 | 1.35 | 96.77 | 0.08 | 6.97E+03 |
| S4MT | 0.35 | 1.35 | 3.06 | 94.75 | 0.48 | 5.69E+03 |
| S5MT | 0.44 | 1.38 | 2.08 | 96.02 | 0.08 | 6.96E+03 |
| S5GT | 1.48 | 3.74 | 4.43 | 90.02 | 0.32 | 3.34E+03 |
| H6MT | 0.58 | 1.38 | 1.32 | 96.54 | 0.17 | 7.68E+03 |
| P6GT | 0.52 | 1.82 | 1.84 | 95.57 | 0.26 | 7.72E+03 |
| P6MA | 0.44 | 1.31 | 0.85 | 97.44 | −0.05 | 7.58E+03 |
| P6MS | 0.46 | 1.39 | 1.02 | 97.13 | 0.00 | 7.65E+03 |
| P6MTMet | 0.43 | 1.44 | 1.39 | 96.59 | 0.15 | 7.00E+03 |
| P7MT | 0.47 | 1.33 | 1.13 | 97.14 | −0.07 | 6.10E+03 |
| P7GT | 0.64 | 1.80 | 2.24 | 94.87 | 0.44 | 7.21E+03 |
| P6MGT | 0.58 | 2.03 | 1.42 | 95.83 | 0.14 | 6.94E+03 |
| P6MGT-P | 0.53 | 1.94 | 1.23 | 96.22 | 0.07 | 6.55E+03 |
| P6MT-P | 0.50 | 1.39 | 1.27 | 96.78 | 0.05 | 6.98E+03 |
| P6GT-P | 0.54 | 1.82 | 1.38 | 96.25 | 0.01 | 6.60E+03 |

TABLE 60

RP-HPLC (SUMMARY OF PEAK AREAS); T = 4 week; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.18 | 1.08 | 2.33 | 96.16 | 0.26 | 6.68E+03 |
| S4MT | 0.39 | 1.27 | 3.61 | 94.06 | 0.67 | 5.94E+03 |
| S5MT | 0.19 | 1.09 | 2.98 | 95.49 | 0.25 | 6.68E+03 |
| S5GT | 0.20 | 1.55 | 3.20 | 94.70 | 0.35 | 6.31E+03 |
| H6MT | 0.28 | 0.91 | 1.59 | 96.95 | 0.28 | 6.37E+03 |
| P6GT | 0.30 | 1.88 | 2.40 | 95.10 | 0.32 | 7.03E+03 |
| P6MA | 0.16 | 1.37 | 1.79 | 96.57 | 0.11 | 6.95E+03 |
| P6MS | 0.22 | 1.22 | 1.52 | 96.95 | 0.09 | 7.06E+03 |
| P6MTMet | 0.19 | 1.09 | 1.25 | 97.40 | 0.07 | 7.21E+03 |
| P7MT | 0.22 | 1.06 | 1.31 | 97.35 | 0.06 | 6.68E+03 |
| P7GT | 0.44 | 1.42 | 2.07 | 95.37 | 0.70 | 6.47E+03 |
| P6MGT | 0.49 | 1.75 | 1.49 | 95.99 | 0.28 | 5.50E+03 |
| P6MGT-P | 0.42 | 2.04 | 1.31 | 96.14 | 0.08 | 6.06E+03 |
| P6MT-P | 0.38 | 0.90 | 1.33 | 97.28 | 0.12 | 6.70E+03 |
| P6GT-P | 0.35 | 1.75 | 1.76 | 95.90 | 0.24 | 7.52E+03 |

TABLE 61

RP-HPLC (SUMMARY OF PEAK AREAS); T = 6 week; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.26 | 0.99 | 1.47 | 97.05 | 0.23 | 6.36E+03 |
| S5MT | 0.40 | 1.05 | 2.47 | 95.91 | 0.17 | 6.09E+03 |
| S5GT | 0.42 | 1.85 | 2.96 | 94.46 | 0.31 | 6.52E+03 |
| H6MT | 0.48 | 0.86 | 1.65 | 96.87 | 0.14 | 5.97E+03 |
| P6GT | 0.25 | 1.57 | 1.65 | 96.38 | 0.15 | 7.14E+03 |
| P6MS | 0.35 | 1.02 | 1.08 | 97.58 | −0.03 | 7.07E+03 |
| P6MTMet | 0.20 | 1.05 | 1.73 | 96.81 | 0.21 | 6.93E+03 |
| P7MT | −0.01 | 0.91 | 1.27 | 97.90 | −0.07 | 6.09E+03 |
| P7GT | 0.10 | 1.08 | 1.28 | 97.58 | −0.05 | 6.66E+03 |
| P6MGT | 0.32 | 2.28 | 2.25 | 94.95 | 0.20 | 6.49E+03 |
| P6MGT-P | 0.26 | 2.03 | 1.79 | 95.77 | 0.15 | 6.82E+03 |
| P6MT-P | 0.08 | 0.95 | 1.33 | 97.67 | −0.03 | 5.91E+03 |
| P6GT-P | 0.43 | 2.52 | 1.79 | 95.17 | 0.09 | 6.78E+03 |

TABLE 62

RP-HPLC (SUMMARY OF PEAK AREAS); T = 2 month; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.44 | 1.13 | 2.42 | 95.52 | 0.49 | 7.00E+03 |
| H6MT | 0.54 | 0.84 | 2.35 | 95.38 | 0.90 | 7.53E+03 |
| P6GT | 0.52 | 1.73 | 2.39 | 94.84 | 0.52 | 6.99E+03 |
| P6MS | 0.27 | 1.14 | 1.46 | 96.91 | 0.21 | 7.02E+03 |
| P6MTMet | 0.18 | 1.25 | 1.81 | 96.43 | 0.34 | 6.96E+03 |
| P7MT | 0.38 | 1.06 | 1.93 | 96.39 | 0.24 | 6.10E+03 |
| P7GT | 0.64 | 1.76 | 3.07 | 93.62 | 0.91 | 7.35E+03 |
| P6MGT | 0.52 | 2.41 | 2.62 | 93.97 | 0.49 | 6.79E+03 |
| P6MGT-P | 0.46 | 2.26 | 2.54 | 94.33 | 0.41 | 6.56E+03 |
| P6MT-P | 0.37 | 1.28 | 1.98 | 96.12 | 0.25 | 7.89E+03 |
| P6GT-P | 0.51 | 2.04 | 2.69 | 94.21 | 0.54 | 6.63E+03 |

TABLE 63

RP-HPLC (SUMMARY OF PEAK AREAS); T = 3 month; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.41 | 1.31 | 2.57 | 95.23 | 0.48 | 8.23E+03 |
| H6MT | 0.43 | 1.18 | 1.86 | 96.24 | 0.29 | 8.73E+03 |
| P6GT | 0.42 | 1.82 | 2.27 | 95.02 | 0.47 | 8.61E+03 |
| P6MS | 0.47 | 1.23 | 1.98 | 96.09 | 0.24 | 8.22E+03 |
| P6MTMet | 0.28 | 1.19 | 2.84 | 95.06 | 0.63 | 8.13E+03 |
| P7MT | 0.36 | 1.03 | 1.74 | 96.70 | 0.16 | 7.47E+03 |
| P7GT | 0.39 | 1.70 | 1.77 | 95.77 | 0.38 | 8.46E+03 |
| P6MGT | 0.34 | 2.14 | 2.72 | 94.16 | 0.64 | 7.47E+03 |
| P6MGT-P | 0.35 | 2.28 | 2.53 | 94.26 | 0.58 | 7.58E+03 |
| P6MT-P | 0.27 | 1.28 | 1.89 | 96.38 | 0.18 | 7.62E+03 |
| P6GT-P | 0.36 | 1.70 | 2.56 | 94.98 | 0.40 | 7.95E+03 |

TABLE 64

RP-HPLC (SUMMARY OF PEAK AREAS); T = 1 week; 40° C.

| Formulation ID | % Pre-peak 1 | % Pre-peak 2 | % Post-peak | % Main Peak | % Un-PEG | Total Area |
|---|---|---|---|---|---|---|
| P6MT | 0.60 | 1.43 | 2.12 | 95.68 | 0.18 | 7.13E+03 |
| S4MT | 0.71 | 1.92 | 6.01 | 90.69 | 0.66 | 6.11E+03 |
| S5MT | 0.60 | 1.60 | 3.25 | 94.35 | 0.19 | 7.72E+03 |
| S5GT | 0.76 | 2.20 | 3.13 | 93.73 | 0.19 | 6.77E+03 |
| H6MT | 0.74 | 1.39 | 1.98 | 95.58 | 0.30 | 7.61E+03 |
| P6GT | 0.81 | 2.13 | 2.27 | 94.44 | 0.35 | 7.50E+03 |
| P6MA | 0.68 | 1.60 | 1.48 | 96.04 | 0.20 | 8.34E+03 |
| P6MS | 0.84 | 1.59 | 2.22 | 95.02 | 0.32 | 8.12E+03 |
| P6MTMet | 0.74 | 1.50 | 2.16 | 95.27 | 0.34 | 8.28E+03 |
| P7MT | 0.63 | 1.42 | 1.91 | 95.88 | 0.16 | 6.56E+03 |
| P7GT | 0.54 | 1.98 | 2.34 | 94.80 | 0.35 | 7.81E+03 |
| P6MGT | 0.70 | 2.41 | 2.19 | 94.30 | 0.41 | 7.73E+03 |
| P6MGT-P | 0.44 | 2.12 | 1.80 | 95.52 | 0.13 | 7.65E+03 |
| P6MT-P | 0.58 | 1.37 | 2.18 | 95.65 | 0.21 | 6.83E+03 |
| P6GT-P | 0.40 | 2.00 | 2.21 | 95.17 | 0.23 | 7.48E+03 |

TABLE 65

RP-HPLC (SUMMARY OF PEAK AREAS); T = 2 week; 40° C.

| Formulation ID | % Pre-peak 1 | % Pre-peak 2 | % Post-peak | % Main Peak | % Un-PEG | Total Area |
|---|---|---|---|---|---|---|
| P6MT | 0.59 | 1.58 | 2.44 | 95.12 | 0.27 | 7.33E+03 |
| S4MT | 0.46 | 2.13 | 8.25 | 88.50 | 0.66 | 5.73E+03 |
| S5MT | 0.46 | 1.54 | 4.45 | 93.42 | 0.12 | 6.88E+03 |
| S5GT | 0.44 | 2.30 | 3.92 | 93.07 | 0.28 | 6.73E+03 |
| H6MT | 0.70 | 1.28 | 2.54 | 94.85 | 0.63 | 7.06E+03 |
| P6GT | 0.56 | 2.02 | 2.43 | 94.80 | 0.20 | 6.86E+03 |

TABLE 65-continued

RP-HPLC (SUMMARY OF PEAK AREAS); T = 2 week; 40° C.

| Formulation ID | % Pre-peak 1 | % Pre-peak 2 | % Post-peak | % Main Peak | % Un-PEG | Total Area |
|---|---|---|---|---|---|---|
| P6MA | 0.55 | 1.58 | 6.98 | 90.67 | 0.22 | 7.78E+03 |
| P6MS | 0.47 | 1.39 | 2.27 | 95.63 | 0.24 | 7.56E+03 |
| P6MTMet | 0.29 | 1.39 | 2.71 | 95.34 | 0.27 | 6.20E+03 |
| P7MT | 0.34 | 1.12 | 1.83 | 96.65 | 0.07 | 6.91E+03 |
| P7GT | 0.36 | 1.55 | 1.80 | 96.20 | 0.09 | 7.28E+03 |
| P6MGT | 0.30 | 2.01 | 2.39 | 95.08 | 0.22 | 6.56E+03 |
| P6MGT-P | 0.35 | 2.11 | 2.49 | 94.91 | 0.13 | 6.70E+03 |
| P6MT-P | 0.38 | 1.23 | 2.37 | 95.90 | 0.12 | 7.00E+03 |
| P6GT-P | 0.49 | 1.96 | 2.58 | 94.83 | 0.14 | 7.03E+03 |

TABLE 66

RP-HPLC (SUMMARY OF PEAK AREAS); T = 4 week; 40° C.

| Formulation ID | % Pre-peak 1 | % Pre-peak 2 | % Post-peak | % Main Peak | % Un-PEG | Total Area |
|---|---|---|---|---|---|---|
| P6MT | 0.47 | 1.47 | 4.21 | 93.29 | 0.56 | 6.70E+03 |
| S4MT | 0.53 | 2.24 | 14.40 | 81.74 | 1.09 | 6.61E+03 |
| S5MT | 0.67 | 1.69 | 7.09 | 90.13 | 0.43 | 6.72E+03 |
| S5GT | 0.52 | 2.51 | 5.89 | 90.79 | 0.29 | 6.35E+03 |
| H6MT | 0.79 | 1.38 | 3.09 | 94.01 | 0.73 | 6.38E+03 |
| P6GT | 0.61 | 2.48 | 3.77 | 92.71 | 0.42 | 7.72E+03 |
| P6MA | 1.09 | 1.59 | 23.19 | 73.63 | 0.50 | 7.25E+03 |
| P6MS | 0.81 | 1.13 | 3.86 | 93.78 | 0.43 | 7.48E+03 |
| P6MTMet | 0.46 | 1.33 | 4.70 | 92.35 | 1.17 | 6.66E+03 |
| P7MT | 0.38 | 1.31 | 2.12 | 96.12 | 0.08 | 6.18E+03 |
| P7GT | 0.29 | 1.89 | 2.78 | 94.68 | 0.36 | 7.33E+03 |
| P6MGT | 0.32 | 1.97 | 4.59 | 92.73 | 0.38 | 6.82E+03 |
| P6MGT-P | 0.31 | 1.90 | 3.37 | 94.24 | 0.19 | 6.39E+03 |
| P6MT-P | 0.41 | 1.43 | 3.83 | 94.04 | 0.28 | 5.63E+03 |
| P6GT-P | 0.35 | 2.11 | 3.79 | 93.46 | 0.29 | 6.38E+03 |

TABLE 67

RP-HPLC (SUMMARY OF PEAK AREAS); T = 6 week; 40° C.

| Formulation ID | % Pre-peak 1 | % Pre-peak 2 | % Post-peak | % Main Peak | % Un-PEG | Total Area |
|---|---|---|---|---|---|---|
| P6MT | 0.48 | 1.58 | 3.29 | 94.59 | 0.07 | 6.70E+03 |
| S5MT | 0.27 | 2.23 | 9.81 | 87.58 | 0.11 | 6.66E+03 |
| S5GT | 0.15 | 2.99 | 6.37 | 90.33 | 0.16 | 6.71E+03 |
| H6MT | 0.33 | 1.36 | 2.71 | 95.19 | 0.41 | 6.64E+03 |
| P6GT | 0.11 | 2.43 | 3.30 | 94.12 | 0.05 | 7.39E+03 |
| P6MS | 0.90 | 2.67 | 6.46 | 89.44 | 0.53 | 6.93E+03 |
| P6MTMet | 0.00 | 1.59 | 2.87 | 94.76 | 0.78 | 7.26E+03 |
| P7MT | 0.32 | 1.26 | 3.09 | 95.11 | 0.21 | 5.32E+03 |
| P7GT | 0.29 | 2.12 | 2.38 | 94.97 | 0.23 | 6.63E+03 |
| P6MGT | 0.31 | 2.56 | 5.93 | 91.06 | 0.14 | 6.51E+03 |
| P6MGT-P | 0.22 | 2.62 | 4.53 | 92.48 | 0.16 | 6.75E+03 |
| P6MT-P | 0.23 | 1.83 | 3.76 | 94.03 | 0.15 | 6.93E+03 |
| P6GT-P | 0.17 | 2.65 | 3.06 | 93.99 | 0.12 | 7.11E+03 |

TABLE 68

RP-HPLC (SUMMARY OF PEAK AREAS); T = 2 month; 40° C.

| Formulation ID | % Pre-peak 1 | % Pre-peak 2 | % Post-peak | % Main Peak | % Un-PEG | Total Area |
|---|---|---|---|---|---|---|
| P6MT | 0.57 | 1.69 | 4.69 | 92.50 | 0.55 | 7.07E+03 |
| H6MT | 0.55 | 1.46 | 3.78 | 93.40 | 0.81 | 7.15E+03 |
| P6GT | 0.29 | 2.41 | 3.89 | 93.14 | 0.27 | 7.77E+03 |
| P6MS | 1.16 | 2.25 | 7.34 | 88.30 | 0.96 | 6.88E+03 |
| P6MTMet | 0.51 | 2.17 | 8.43 | 86.14 | 2.75 | 7.32E+03 |
| P7MT | 0.53 | 1.39 | 3.69 | 93.98 | 0.41 | 6.55E+03 |
| P7GT | 0.58 | 2.32 | 4.06 | 92.38 | 0.66 | 7.03E+03 |
| P6MGT | 0.56 | 2.39 | 6.49 | 90.06 | 0.50 | 7.32E+03 |
| P6MGT-P | 0.49 | 2.30 | 5.63 | 91.06 | 0.51 | 6.77E+03 |
| P6MT-P | 0.64 | 1.87 | 5.61 | 91.27 | 0.61 | 7.28E+03 |
| P6GT-P | 0.38 | 2.64 | 4.54 | 91.99 | 0.43 | 7.06E+03 |

CEX/IEX analysis from this study is shown in Tables 69-71.

TABLE 69

IEX-HPLC (SUMMARY OF PEAK AREAS); T = 0

| Formulation ID | % Pre-peak | % Main Peak | Post-peak | Total Area |
|---|---|---|---|---|
| P6MT | 6.27 | 91.01 | 2.72 | 1343 |
| S4MT | 2.95 | 93.19 | 3.86 | 991 |
| S5MT | 2.11 | 94.21 | 3.67 | 997 |
| S5GT | 2.19 | 94.46 | 3.35 | 1074 |
| H6MT | 1.92 | 95.63 | 2.46 | 1007 |
| P6GT | 4.55 | 93.11 | 2.34 | 1140 |
| P6MA | 4.80 | 94.17 | 1.03 | 1172 |
| P6MS | 3.67 | 95.03 | 1.31 | 1158 |
| P6MTMet | 4.47 | 94.04 | 1.49 | 987 |
| P7MT | 0.61 | 98.84 | 0.55 | 876 |
| P7GT | 0.94 | 96.39 | 2.67 | 993 |
| P6MGT | 1.62 | 95.31 | 3.07 | 959 |
| P6MGT-P | 1.68 | 96.16 | 2.15 | 920 |
| P6MT-P | 1.56 | 96.32 | 2.12 | 926 |
| P6GT-P | 1.89 | 94.83 | 3.28 | 1005 |

TABLE 70

IEX-HPLC (SUMMARY OF PEAK AREAS); T = 1 week; 40° C.

| Formulation ID | % Pre-peak | % Main Peak | Post-peak | Total Area |
|---|---|---|---|---|
| P6MT | 2.22 | 93.02 | 4.76 | 1.96E+03 |
| S4MT | 3.88 | 90.09 | 6.03 | 1.41E+03 |
| S5MT | 2.79 | 91.88 | 5.34 | 1.88E+03 |
| S5GT | 2.80 | 92.21 | 4.99 | 1.82E+03 |
| H6MT | 3.53 | 92.54 | 3.93 | 1.35E+03 |
| P6GT | 2.87 | 92.89 | 4.24 | 2.12E+03 |
| P6MA | 0.00 | 95.97 | 4.03 | 7.14E+02 |
| P6MS | 4.34 | 91.68 | 3.98 | 2.01E+03 |
| P6MTMet | 2.24 | 93.82 | 3.94 | 1.95E+03 |
| P7MT | 6.21 | 91.27 | 2.52 | 1.86E+03 |
| P7GT | 4.38 | 86.25 | 9.37 | 2.01E+03 |
| P6MGT | 1.25 | 96.69 | 2.06 | 1.60E+03 |
| P6MGT-P | 1.57 | 95.53 | 2.89 | 1.82E+03 |
| P6MT-P | 2.55 | 94.83 | 2.62 | 1.70E+03 |
| P6GT-P | 2.68 | 93.80 | 3.53 | 1.80E+03 |

TABLE 71

IEX-HPLC (SUMMARY OF PEAK AREAS); T = 2 week; 40° C.

| Formulation ID | % Pre-peak 1 | % Pre-peak 2 | % Main Peak | Post-peak | Total Area |
|---|---|---|---|---|---|
| P6MT | 0.00 | 5.28 | 89.24 | 5.48 | 1920.32 |
| S4MT | 3.16 | 8.27 | 79.70 | 8.87 | 1510.4 |
| S5MT | 1.46 | 3.52 | 88.48 | 6.54 | 1706.32 |
| S5GT | 1.65 | 3.63 | 88.79 | 5.93 | 1767.78 |
| H6MT | 0.00 | 4.04 | 90.95 | 5.02 | 1977.59 |

TABLE 71-continued

IEX-HPLC (SUMMARY OF PEAK AREAS); T = 2 week; 40° C.

| Formulation ID | % Pre-peak 1 | % Pre-peak 2 | % Main Peak | Post-peak | Total Area |
|---|---|---|---|---|---|
| P6GT | 0.00 | 3.13 | 91.63 | 5.24 | 2029.88 |
| P6MA | 0.00 | 5.18 | 85.28 | 9.54 | 2016.34 |
| P6MS | 0.00 | 3.60 | 90.91 | 5.49 | 1954 |
| P6MTMet | 0.00 | 5.21 | 92.41 | 2.38 | 1942.53 |
| P7MT | 0.00 | 3.10 | 93.61 | 3.29 | 1668.32 |
| P7GT | 0.00 | 3.48 | 91.71 | 4.80 | 1987.09 |
| P6MGT | 0.00 | 3.05 | 92.98 | 3.98 | 1703.47 |
| P6MGT-P | 0.00 | 2.89 | 92.00 | 5.12 | 1812.89 |
| P6MT-P | 0.00 | 4.49 | 90.40 | 5.12 | 1818.52 |
| P6GT-P | 0.00 | 3.76 | 91.13 | 5.10 | 1893.99 |

Lower pH formulations were studied for 4 weeks (pH 4) and 6 weeks (pH 5). For the time-frame studied, the following trends were found. SEC-HPLC and RP-HPLC analysis showed that lower pH formulations (pH 4 and 5) generated increased levels of unPEGylated material after storage of lyophilized material at 4° C. than higher pH formulations (pH 6 and 7). In addition, higher aggregate levels were observed at lower pH formulations at 25 and 40° C. than with the pH 6 and 7 formulations. Also, pH 6 and 7. formulations exhibited a greater % of main peak area than the lower pH formulations as analyzed by cIEX-HPLC.

Throughout the 3 month study timeframe with storage of lyophilized hGH at 25 and 40° C., formulations with Histidine showed the least amount of high molecular weight aggregates by SDS-PAGE. Formulations containing mannitol in combination with glycine were found to be stabilized hGH against agitation induced aggregation, showing that the combination is a good bulking agent. However, histidine in combination with mannitol also demonstrated stabilization of hGH against agitation induced aggregation. Trehalose was an effective stabilizer.

Example 15

Injection Feasibility Study

Injection feasibility studies were performed using a formulation of PEGylated hGH at four different concentrations. PEG-hGH in 20 mM sodium citrate, 2% glycine, 0.5% mannitol, pH 6 was buffer exchanged into 10 mM NaH$_2$PO$_4$, 4% mannitol, 2% trehalose, 0.01% polysorbate 20 (PS20), pH 6.0 (Formulation ID=P6MT) via centrifugal concentration. The PEG-hGH in P6MT buffer was concentrated to 8, 10, 12, and 14 mg/mL. 1 mL fill was placed into vials, and the samples were lyophilized. Lyophilized vials were reconstituted with 1 mL of water. Injection feasibility was tested by pushing 1 mL of each concentration through 27 gauge needle with 4 lbs of force. Instant reconstitution was found for all concentrations of PEGylated hGH tested. 8 mg/mL PEGylated hGH injected in 3.5 s (seconds); 10 mg/mL injected in 3.6 s; 12 mg/mL injected in 3.9 s; and 14 mg/mL injected in 4.5 s.

Additional injection feasibility studies were performed with 30 gauge needles. PEG-hGH, in 10 mM NaH$_2$PO$_4$, 4% mannitol, 2% trehalose, 0.01% polysorbate 20, pH 6.0 (Formulation ID=P6MT buffer), at 8, 10, 12, and 14 mg/mL was tested for injection feasibility with a 30 gauge needle. The samples were pushed through a 30 gauge needle under 8 lbs. of force and timed for duration. When 1 mL of each concentration was pushed through a 30 gauge needle under 8 lbs. of force, the 8 mg/mL, 10 mg/mL, 12 mg/mL and 14 mg/mL concentrations injected in 7.4 s (seconds), 9.9 s, 9.9 s, and 10.7 s, respectively.

Injection of 1 cc within 10 seconds under 8 lbs. of force is generally accepted as the standard for injection since the average person can apply up to 8 lbs. of force on a syringe.

Example 16

One Week Reconstitution Study

Figure 59:
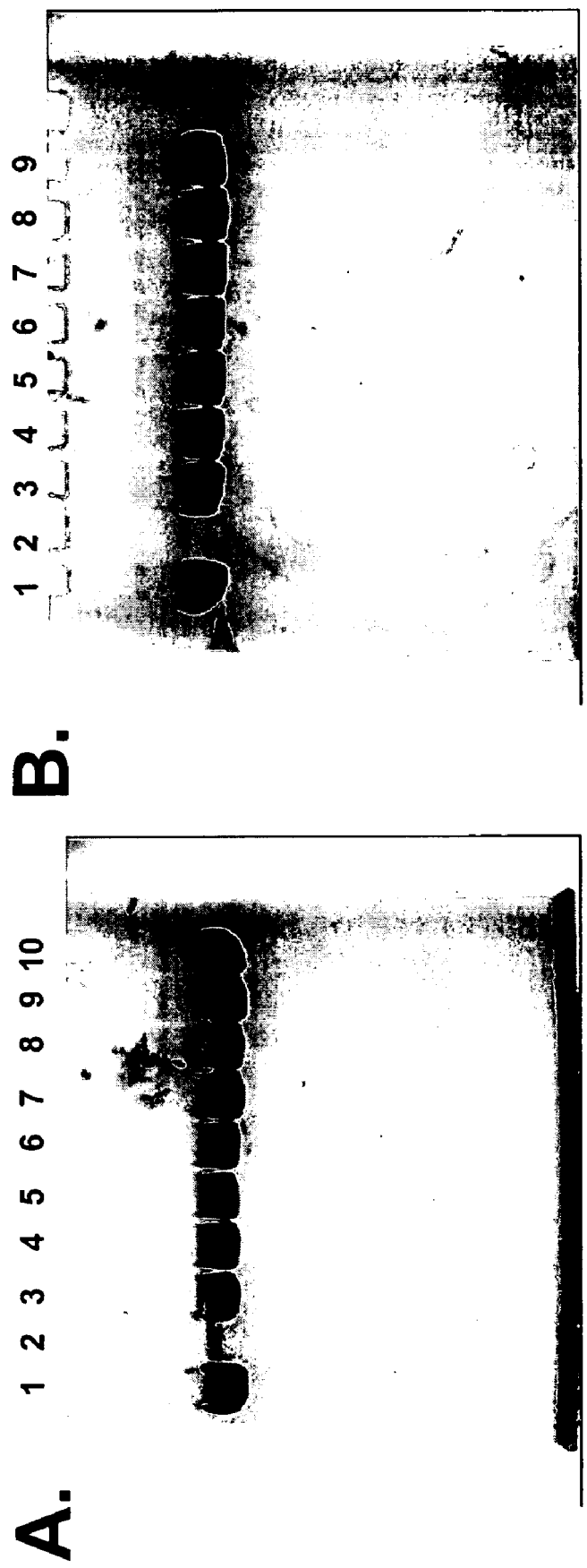
FIG. 59 shows an SDS-PAGE analysis (non-reduced) of reconstituted samples stored for 1 week at 4° C. For FIG. 59, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 59, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 60:
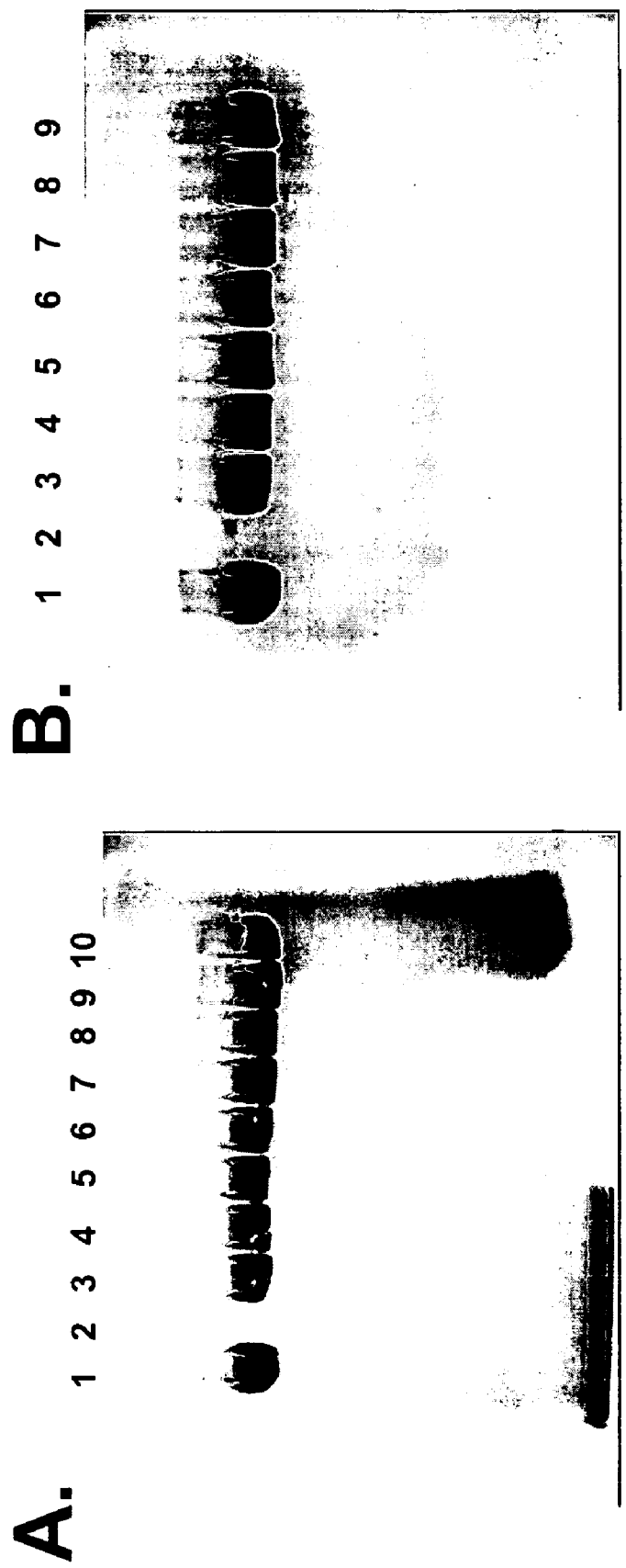
FIG. 60 shows an SDS-PAGE analysis (reduced) of reconstituted samples stored for 1 week at 4° C. For FIG. 60, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 60, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 62:
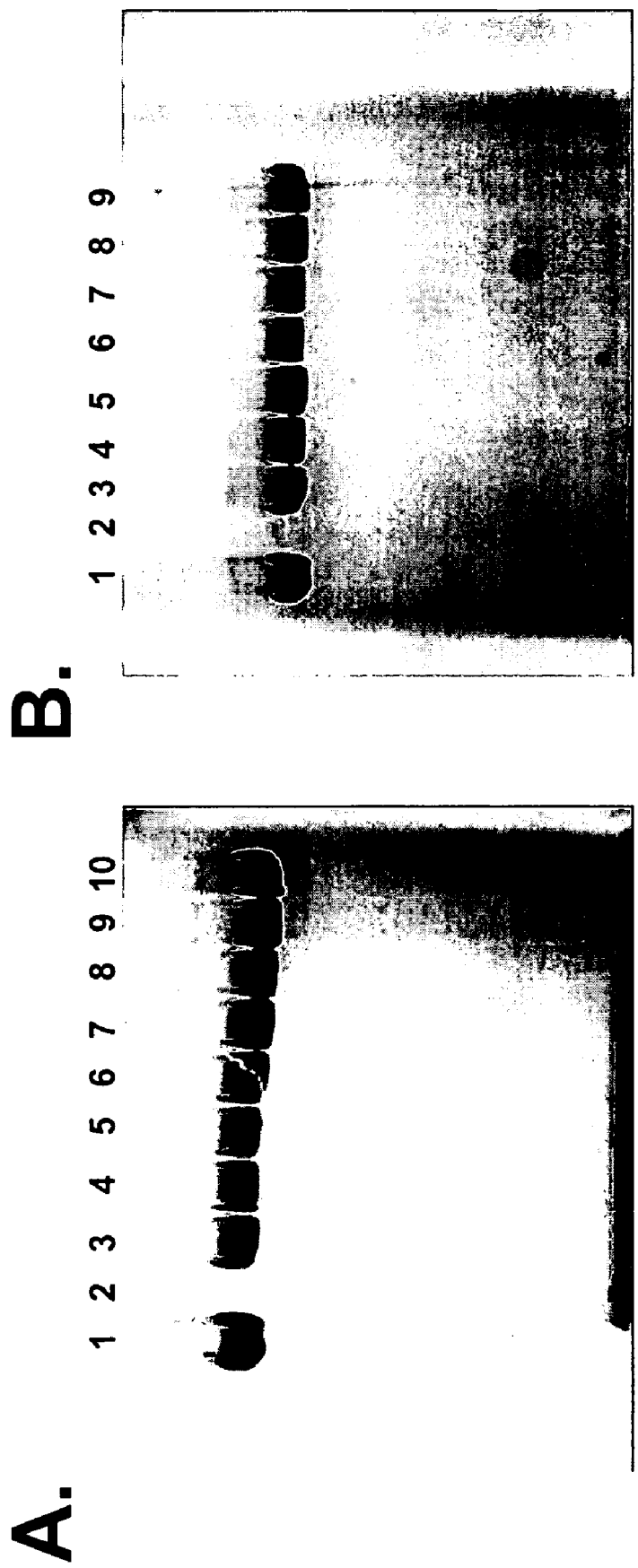
FIG. 62 shows an SDS-PAGE analysis (reduced) of control samples in a formulation study (agitation/UV controls). For FIG. 62, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 62, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 63:
FIG. 63 shows an SDS-PAGE analysis (non-reduced) of samples agitated for 4 hours at ambient room temperature. For FIG. 63, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 63, Panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 64:
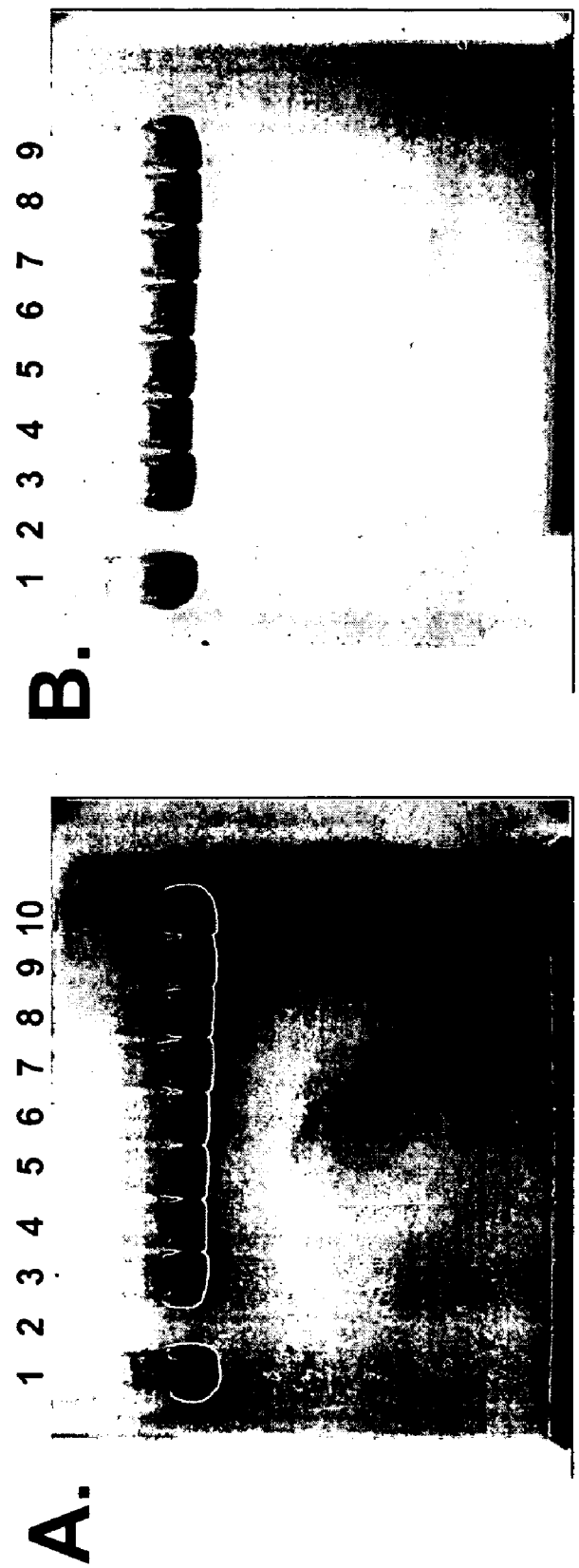
FIG. 64 shows an SDS-PAGE analysis (reduced) of samples agitated for 4 hours at ambient room temperature. For FIG. 64, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 64, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 65:
FIG. 65 shows an SDS-PAGE analysis (non-reduced) of samples exposed to UV light for 4 hours at ambient temperature. For FIG. 65, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 65, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 66:
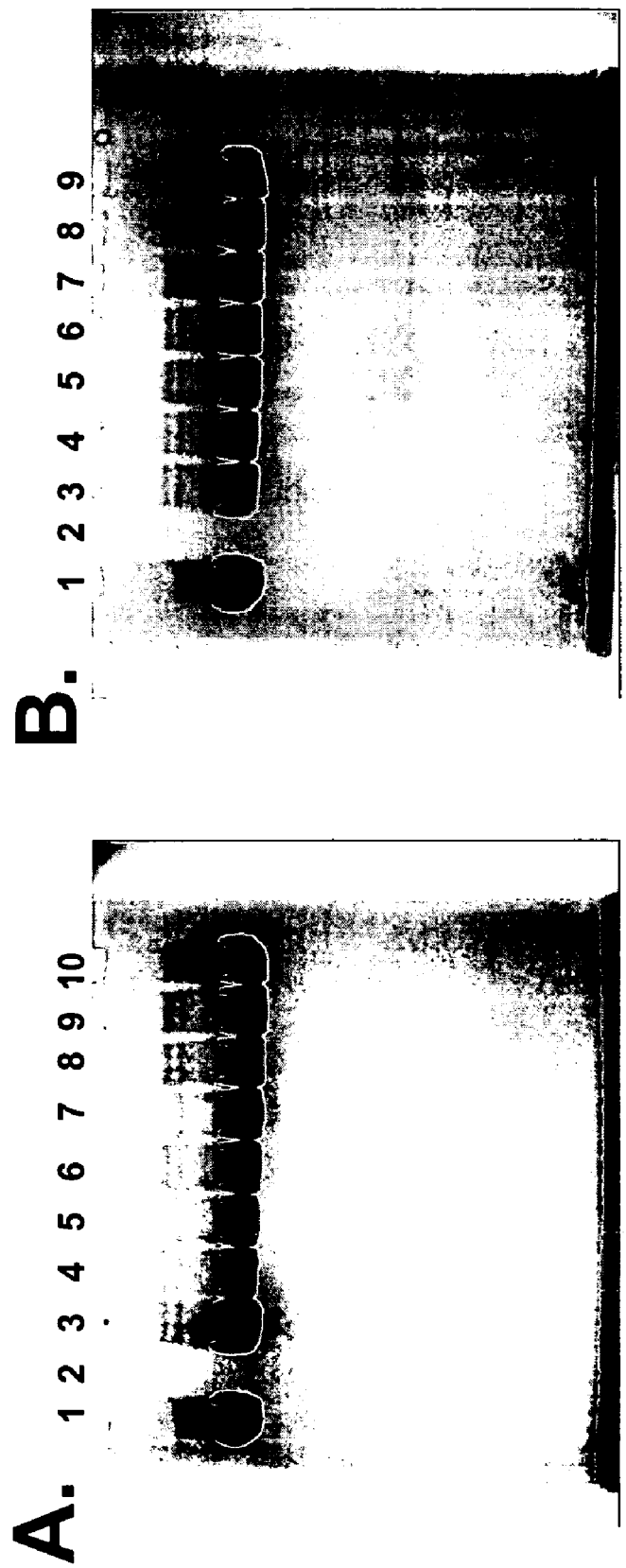
FIG. 66 shows an SDS-PAGE analysis (reduced) of samples exposed to UV light for 4 hours at ambient temperature. For FIG. 66, panel A, Lane 1: PEG-hGH Standard; Lane 3: P6MT; Lane 4: S4MT; Lane 5: S5MT; Lane 6: S5GT; Lane 7: H6MT; Lane 8: P6GT; Lane 9: P6MA; Lane 10: P6MS. For FIG. 66, panel B, Lane 1: PEG-hGH Standard; Lane 3: P6MTMet; Lane 4: P7MT; Lane 5: P7GT; Lane 6: P6MGT; Lane 7: P6MGT-P; Lane 8: P6MT-P; Lane 9: P6GT-P.
Figure 67:
FIG. 67 shows an SDS-PAGE analysis (non-reduced) of samples that were subject to freeze/thaw conditions (H7MT-P). Lane 1: PEG-hGH Standard; Lane 2: hGH (1 μg); Lane 3: H7MT-P 8 mg/mL t=0; Lane 4: H7MT-P 8 mg/mL F/T 1; Lane 5: H7MT-P 8 mg/mL F/T 2; Lane 6: H7MT-P 8 mg/mL F/T 3; Lane 7: H7MT-P 8 mg/mL F/T 4; Lane 8: H7MT-P 8 mg/mL F/T 5; Lane 10: H7MT-P 14 mg/mL t=0; Lane 11: H7MT-P 14 mg/mL F/T 1; Lane 12: H7MT-P 14 mg/mL F/T 2; Lane 13: H7MT-P 14 mg/mL F/T 3; Lane 14: H7MT-P 14 mg/mL F/T 4; Lane 15: H7MT-P 14 mg/mL F/T 5.
Figure 68:
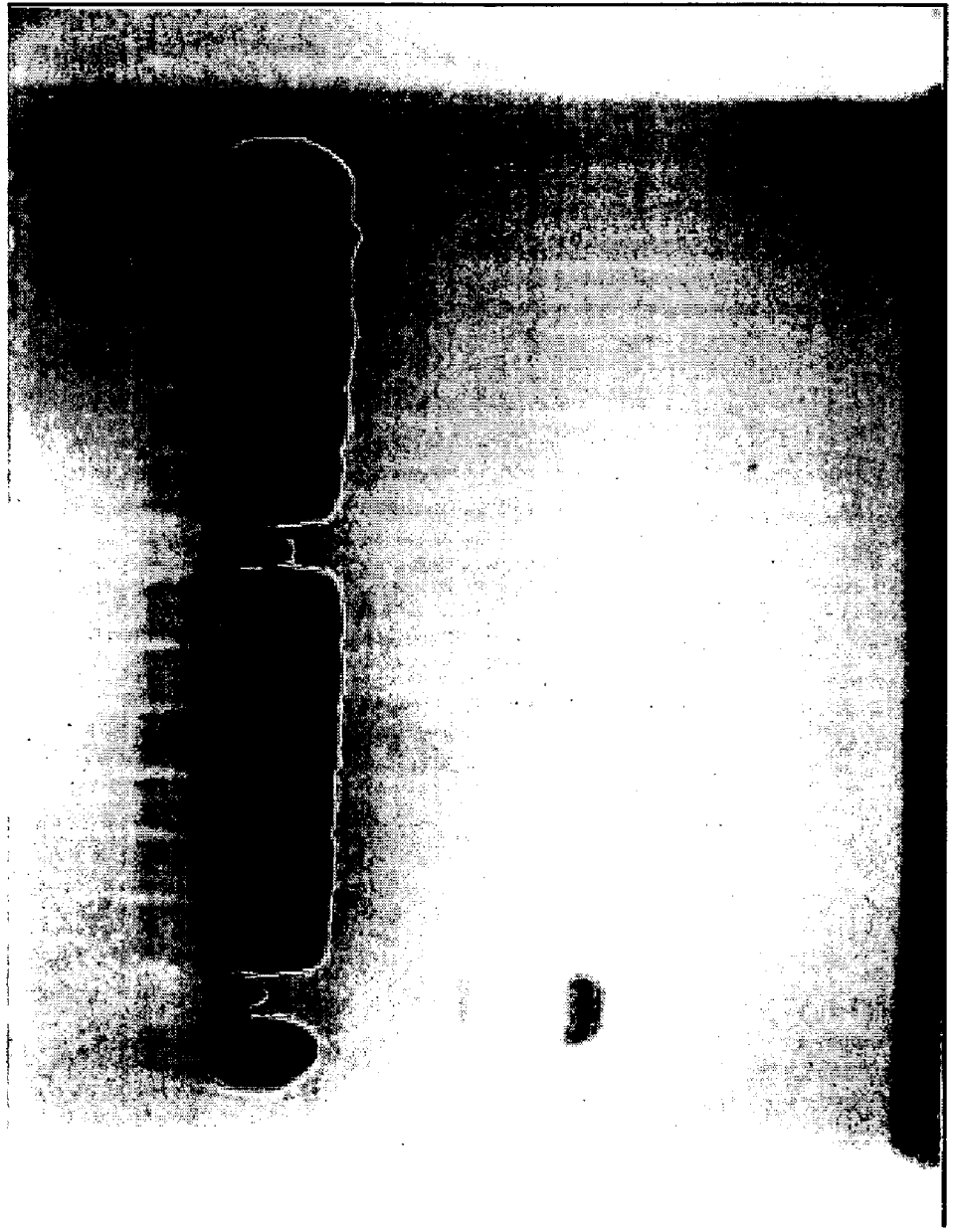
FIG. 68 shows an SDS-PAGE analysis (reduced) of samples that were subject to freeze/thaw conditions (H7MT-P). Lane 1: PEG-hGH Standard; Lane 2: hGH (1 μg); Lane 3: H7MT-P 8 mg/mL t=0; Lane 4: H7MT-P 8 mg/mL F/T 1; Lane 5: H7MT-P 8 mg/mL F/T 2; Lane 6: H7MT-P 8 mg/mL F/T 3; Lane 7: H7MT-P 8 mg/mL F/T 4; Lane 8: H7MT-P 8 mg/mL F/T 5; Lane 10: H7MT-P 14 mg/mL t=0; Lane 11: H7MT-P 14 mg/mL F/T 1; Lane 12: H7MT-P 14 mg/mL F/T 2; Lane 13: H7MT-P 14 mg/mL F/T 3; Lane 14: H7MT-P 14 mg/mL F/T 4; Lane 15: H7MT-P 14 mg/mL F/T 5.
Figure 69:
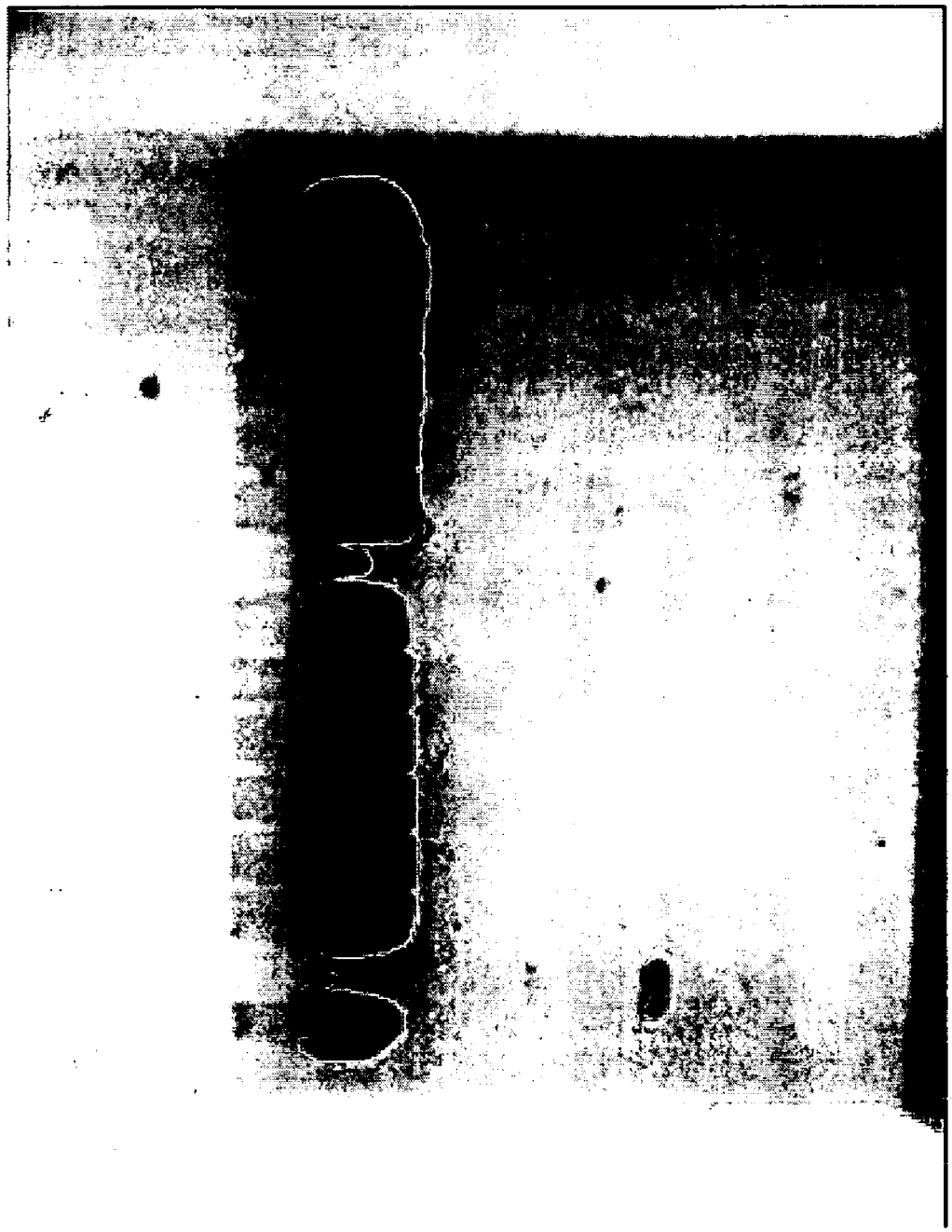
FIG. 69 shows an SDS-PAGE analysis (non-reduced) of samples that were subject to freeze/thaw conditions (H7MGT-P). Lane 1: PEG-hGH Standard; Lane 2: hGH (1 μg); Lane 3: H7MGT-P 8 mg/mL t=0; Lane 4: H7MGT-P 8 mg/mL F/T 1; Lane 5: H7MGT-P 8 mg/mL F/T 2; Lane 6: H7MGT-P 8 mg/mL F/T 3; Lane 7: H7MGT-P 8 mg/mL F/T 4; Lane 8: H7MGT-P 8 mg/mL F/T 5; Lane 10: H7MGT-P 14 mg/mL t=0; Lane 11: H7MGT-P 14 mg/mL F/T 1; Lane 12: H7MGT-P 14 mg/mL F/T 2; Lane 13: H7MGT-P 14 mg/mL F/T 3; Lane 14: H7MGT-P 14 mg/mL F/T 4; Lane 15: H7MGT-P 14 mg/mL F/T 5.

For this study, reconstituted samples were stored for one week at 4° C. The formulations matix used for this study was the same as Table 13. After storage for a week, the concentration and pH were measured. The samples were also analyzed by SEC-HPLC, RP-HPLC, and SDS-PAGE as shown in Tables 72-74 and FIGS. 59-60.

TABLE 72

CONCENTRATION, pH
1 week reconstitution 4° C.

| Formulation ID | Conc. (mg/mL) | pH |
|---|---|---|
| P6MT | 1.6 | 6.17 |
| S4MT | 1.5 | 4.05 |
| S5MT | 1.6 | 4.98 |
| S5GT | 1.7 | 5.06 |
| H6MT | 1.8 | 6.05 |
| P6GT | 1.9 | 6.10 |
| P6MA | 1.9 | 6.39 |
| P6MS | 1.8 | 6.24 |
| P6MTMet | 1.9 | 6.13 |
| P7MT | 1.6 | 6.93 |
| P7GT | 1.8 | 6.94 |
| P6MGT | 1.6 | 6.20 |
| P6MGT-P | 1.7 | 6.16 |
| P6MT-P | 1.7 | 6.14 |
| P6GT-P | 1.7 | 6.14 |

TABLE 73

SEC-HPLC (SUMMARY OF PEAK AREAS);
1 week reconstitution 4° C.

| Formulation ID | % Pre-peak 1 | % Pre-peak 2 | % Main Peak | % Un-PEG | Total Area |
|---|---|---|---|---|---|
| P6MT | 2.32 | 1.44 | 96.06 | 0.18 | 4.23E+04 |
| S4MT | 0.93 | 1.88 | 95.68 | 1.51 | 4.13E+04 |
| S5MT | 1.73 | 1.46 | 96.38 | 0.43 | 4.32E+04 |
| S5GT | 1.49 | 1.62 | 96.47 | 0.42 | 4.63E+04 |
| H6MT | 1.86 | 1.39 | 96.57 | 0.17 | 4.83E+04 |
| P6GT | 1.50 | 1.49 | 96.84 | 0.17 | 4.95E+04 |
| P6MA | 1.69 | 1.61 | 96.50 | 0.20 | 5.03E+04 |
| P6MS | 1.74 | 1.43 | 96.63 | 0.20 | 4.71E+04 |
| P6MTMet | 2.09 | 1.42 | 96.31 | 0.18 | 4.83E+04 |
| P7MT | 1.44 | 1.30 | 97.16 | 0.10 | 4.16E+04 |
| P7GT | 1.61 | 1.51 | 96.67 | 0.21 | 4.77E+04 |
| P6MGT | 1.47 | 1.24 | 97.02 | 0.27 | 4.43E+04 |
| P6MGT-P | 1.92 | 1.16 | 96.69 | 0.22 | 4.57E+04 |
| P6MT-P | 2.06 | 1.36 | 96.38 | 0.20 | 4.67E+04 |
| P6GT-P | 2.10 | 1.53 | 96.18 | 0.19 | 4.55E+04 |

TABLE 74

RP-HPLC (SUMMARY OF PEAK AREAS);
1 week reconstitution 4° C.

| Formulation ID | % Pre-peak 1 | % Pre-peak 2 | % Post-peak | % Main Peak | % Un-PEG | Total Area |
|---|---|---|---|---|---|---|
| P6MT | 0.52 | 1.13 | 1.76 | 96.43 | 0.16 | 6.16E+03 |
| S4MT | 0.33 | 1.11 | 3.27 | 94.38 | 0.90 | 5.96E+03 |

TABLE 74-continued

RP-HPLC (SUMMARY OF PEAK AREAS);
1 week reconstitution 4° C.

| Formulation ID | % Pre-peak 1 | % Pre-peak 2 | % Post-peak | % Main Peak | % Un-PEG | Total Area |
|---|---|---|---|---|---|---|
| S5MT | 0.27 | 1.21 | 1.89 | 96.49 | 0.13 | 7.11E+03 |
| S5GT | 0.21 | 1.34 | 1.91 | 96.40 | 0.14 | 6.49E+03 |
| H6MT | 0.31 | 1.16 | 1.24 | 97.17 | 0.11 | 8.40E+03 |
| P6GT | 0.18 | 1.19 | 1.37 | 97.04 | 0.22 | 8.09E+03 |
| P6MA | 0.27 | 1.15 | 1.40 | 97.09 | 0.09 | 6.15E+03 |
| P6MS | 0.29 | 1.16 | 1.45 | 96.95 | 0.15 | 6.51E+03 |
| P6MTMet | 0.16 | 1.02 | 1.27 | 97.45 | 0.10 | 7.45E+03 |
| P7MT | 0.38 | 1.17 | 1.11 | 97.31 | 0.03 | 6.47E+03 |
| P7GT | 0.29 | 1.26 | 1.12 | 97.11 | 0.21 | 8.23E+03 |
| P6MGT | 0.31 | 1.32 | 1.60 | 96.52 | 0.26 | 5.95E+03 |
| P6MGT-P | 0.25 | 1.23 | 1.15 | 97.26 | 0.10 | 6.84E+03 |
| P6MT-P | 0.24 | 1.05 | 1.31 | 97.26 | 0.14 | 7.22E+03 |
| P6GT-P | 0.27 | 1.27 | 1.29 | 96.92 | 0.26 | 6.73E+03 |

One week storage of reconstituted samples at 4° C. resulted in slight increase (~1%) of prepeak 1 of P6MT, P6MTMet, P7GT, and P6GT-P. Lower pH samples showed more dePEGylation than samples at pH 6 and 7.

Example 17

Agitation/UV Studies

Samples were subjected to stresses that may mimic long term storage conditions and the induction of degradation or aggregation products was observed. Degradation upon exposure to UV light may occur in the molecule, or specifically at the oxime or PEG. Two agitation studies were performed. In the 4 hour agitation study, reconstituted samples from Table 13 were vortexed vigorously at ambient room temperature for 4 hours prior to measuring concentration and pH, and analysis was performed by SEC-HPLC, RP-HPLC, and SDS-PAGE. A subset of these samples were analyzed one week later after storage at 4° C. by SEC-HPLC to investigate if aggregates might dissociate back to monomer. Control samples were reconstituted samples that were stored at ambient room temperature for 4 hours.

In the 2 hour agitation study, polysorbate-free samples, their polysorbate-containing counterparts, and P6MA were vortexed gently for 2 hours at ambient temperature to confirm the effect of Polysorbate on stability of PEGylated hGH after agitation. See Table 85.

For the UV Exposure study, controls were reconstituted samples stored at ambient room temperature for 4 hours. Lyophilized samples were exposed to UV light for 4 hours at ambient temperature and were reconstituted in water prior to analysis by SDS-PAGE, RP-HPLC, and SEC-HPLC.

See Tables 75-85. SDS-PAGE analysis of these samples is shown in FIGS. 61-66. SEC-HPLC data showed that all formulations containing Polysorbate 20 at 0.01% induced aggregation during agitation (30-80%). Bam, N B et al. describe the use of Tween 20 (Polysorbate 20) in the inhibition of insoluble aggregates during agitation of recombinant hGH (rhGH) (J Pharm Sci. 1998 December; 87(12):1554-9). Moreover, Maa, Y F et al. indicated that polysorbate 20 resulted in a reduction of insoluble protein aggregates in the production of a spray-dried rhGH powder (J Pharm Sci 1998 February;87(2):152-9). Agitation-induced aggregates were found to be irreversible non-covalent aggregates. Major light-induced degradation pathways were depegylation and formation of covalent prepeak 2.

TABLE 75

CONCENTRATION, pH
AGITATION/UV CONTROLS

| Formulation ID | Conc. (mg/mL) | pH |
|---|---|---|
| P6MT | 1.8 | 6.15 |
| S4MT | 1.7 | 4.03 |
| S5MT | 1.6 | 5.04 |
| S5GT | 1.8 | 5.09 |
| H6MT | 1.9 | 5.97 |
| P6GT | 2.0 | 6.04 |
| P6MA | 1.9 | 6.41 |
| P6MS | 1.8 | 6.23 |
| P6MTMet | 1.9 | 6.15 |
| P7MT | 1.6 | 6.90 |
| P7GT | 1.8 | 6.88 |
| P6MGT | 1.6 | 6.13 |
| P6MGT-P | 1.7 | 6.11 |
| P6MT-P | 1.6 | 6.13 |
| P6GT-P | 1.8 | 6.14 |

TABLE 76

CONCENTRATION, pH
4 HOUR AGITATION

| Formulation ID | Conc. (mg/mL) | pH |
|---|---|---|
| P6MT | 2.0 | 6.16 |
| S4MT | 1.7 | 3.97 |
| S5MT | 1.8 | 5.02 |
| S5GT | 1.9 | 5.11 |
| H6MT | 2.0 | 5.96 |
| P6GT | 2.1 | 6.13 |
| P6MA | 2.0 | 6.39 |
| P6MS | 1.9 | 6.20 |
| P6MTMet | 2.0 | 6.18 |
| P7MT | 1.6 | 6.89 |
| P7GT | 1.9 | 6.85 |
| P6MGT | 1.8 | 6.17 |
| P6MGT-P | 1.7 | 6.11 |
| P6MT-P | 1.8 | 6.10 |
| P6GT-P | 2.0 | 6.18 |

TABLE 77

CONCENTRATION, pH
UV EXPOSURE

| Formulation ID | Conc. (mg/mL) | pH |
|---|---|---|
| P6MT | 1.6 | 6.18 |
| S4MT | 1.5 | 4.06 |
| S5MT | 1.6 | 5.04 |
| S5GT | 1.6 | 5.09 |
| H6MT | 1.7 | 6.04 |
| P6GT | 1.8 | 6.10 |
| P6MA | 1.8 | 6.44 |
| P6MS | 1.7 | 6.20 |
| P6MTMet | 1.7 | 6.17 |
| P7MT | 1.5 | 6.96 |
| P7GT | 1.7 | 6.93 |
| P6MGT | 1.5 | 6.17 |
| P6MGT-P | 1.6 | 6.14 |
| P6MT-P | 1.6 | 6.15 |
| P6GT-P | 1.7 | 6.14 |

TABLE 78

SEC-HPLC (SUMMARY OF PEAK AREAS); AGITATION/UV CONTROLS

| Formulation ID | % Pre-peak 1 | % Pre-peak 2 | % Main Peak | % Un-PEG | Total Area |
|---|---|---|---|---|---|
| P6MT | 1.37 | 1.32 | 97.14 | 0.17 | 4.65E+04 |
| S4MT | 1.32 | 1.93 | 95.80 | 0.95 | 5.15E+04 |
| S5MT | 1.91 | 1.54 | 96.17 | 0.38 | 4.37E+04 |
| S5GT | 1.49 | 1.72 | 96.40 | 0.39 | 4.84E+04 |
| H6MT | 1.68 | 1.30 | 96.84 | 0.19 | 4.94E+04 |
| P6GT | 1.51 | 1.57 | 96.70 | 0.22 | 5.01E+04 |
| P6MA | 1.45 | 1.56 | 96.85 | 0.14 | 5.01E+04 |
| P6MS | 1.65 | 1.35 | 96.87 | 0.12 | 4.88E+04 |
| P6MTMet | 1.22 | 1.18 | 97.46 | 0.14 | 5.03E+04 |
| P7MT | 1.21 | 1.25 | 97.39 | 0.15 | 4.30E+04 |
| P7GT | 0.89 | 1.29 | 97.67 | 0.16 | 4.93E+04 |
| P6MGT | 1.46 | 1.35 | 97.04 | 0.15 | 4.35E+04 |
| P6MGT-P | 1.66 | 1.17 | 97.01 | 0.15 | 4.56E+04 |
| P6MT-P | 2.26 | 1.32 | 96.24 | 0.18 | 4.45E+04 |
| P6GT-P | 1.55 | 1.46 | 96.85 | 0.15 | 4.79E+04 |

TABLE 79

SEC-HPLC (SUMMARY OF PEAK AREAS); 4 HOUR AGITATION

| Formulation ID | % Pre-peak | % Main Peak | % Un-PEG | Total Area |
|---|---|---|---|---|
| P6MT | 83.90 | 15.99 | 0.10 | 5.14E+04 |
| S4MT | 63.92 | 35.73 | 0.35 | 4.49E+04 |
| S5MT | 76.56 | 23.33 | 0.11 | 4.74E+04 |
| S5GT | 86.15 | 13.72 | 0.13 | 4.93E+04 |
| H6MT | 84.89 | 15.04 | 0.08 | 5.35E+04 |
| P6GT | 73.79 | 26.08 | 0.13 | 5.45E+04 |
| P6MA | 28.65 | 71.22 | 0.13 | 5.31E+04 |
| P6MS | 47.49 | 52.37 | 0.14 | 5.13E+04 |
| P6MTMet | 82.26 | 17.64 | 0.10 | 4.09E+04 |
| P7MT | 53.28 | 46.55 | 0.17 | 4.27E+04 |
| P7GT | 50.31 | 49.50 | 0.19 | 5.05E+04 |
| P6MGT | 83.57 | 16.27 | 0.16 | 4.73E+04 |
| P6MGT-P | 3.49 | 96.41 | 0.10 | 4.51E+04 |
| P6MT-P | 5.46 | 94.38 | 0.16 | 4.64E+04 |
| P6GT-P | 62.52 | 37.33 | 0.15 | 4.98E+04 |

TABLE 80

SEC-HPLC (SUMMARY OF PEAK AREAS); 4 HOUR AGITATION (REPEAT)

| Formulation ID | % Pre-peak | % Main Peak | % Un-PEG | Total Area |
|---|---|---|---|---|
| P6MT | 84.40 | 15.54 | 0.06 | 4.21E+04 |
| P6GT | 73.20 | 26.74 | 0.06 | 4.53E+04 |
| P6MA | 26.51 | 73.38 | 0.10 | 4.48E+04 |
| P6MGT | 83.97 | 15.89 | 0.14 | 3.76E+04 |
| P6MGT-P | 2.57 | 97.31 | 0.12 | 3.75E+04 |
| P6MT-P | 4.24 | 95.62 | 0.14 | 3.76E+04 |
| P6GT-P | 61.25 | 38.66 | 0.08 | 3.97E+04 |

TABLE 81

SEC-HPLC (SUMMARY OF PEAK AREAS); UV EXPOSURE

| Formulation ID | % Pre-peak 1 | % Pre-peak 2 | % Main Peak | % Un-PEG | Total Area |
|---|---|---|---|---|---|
| P6MT | 1.56 | 1.86 | 95.57 | 1.02 | 4.45E+04 |
| S4MT | 1.20 | 2.59 | 94.27 | 1.94 | 4.20E+04 |
| S5MT | 1.69 | 1.95 | 95.43 | 0.93 | 4.42E+04 |
| S5GT | 1.37 | 2.11 | 95.59 | 0.93 | 4.62E+04 |
| H6MT | 1.60 | 1.88 | 95.65 | 0.87 | 4.64E+04 |
| P6GT | 1.41 | 1.99 | 95.83 | 0.76 | 5.03E+04 |
| P6MA | 1.30 | 2.51 | 95.26 | 0.94 | 5.04E+04 |
| P6MS | 1.68 | 2.01 | 95.48 | 0.83 | 4.68E+04 |
| P6MTMet | 1.23 | 1.81 | 96.04 | 0.92 | 4.79E+04 |
| P7MT | 1.21 | 2.00 | 95.61 | 1.18 | 4.05E+04 |
| P7GT | 1.15 | 2.32 | 94.83 | 1.70 | 4.69E+04 |
| P6MGT | 1.45 | 2.00 | 94.86 | 1.69 | 4.34E+04 |
| P6MGT-P | 1.97 | 2.52 | 94.01 | 1.50 | 4.28E+04 |
| P6MT-P | 2.13 | 2.50 | 94.13 | 1.24 | 4.58E+04 |
| P6GT-P | 1.44 | 2.42 | 94.70 | 1.43 | 4.67E+04 |

TABLE 82

RP-HPLC (SUMMARY OF PEAK AREAS); AGITATION/UV CONTROLS

| Formulation ID | % Pre-peak 1 | % Pre-peak 2 | % Post-peak | % Main Peak | % Un-PEG | Total Area |
|---|---|---|---|---|---|---|
| P6MT | 0.36 | 1.22 | 1.25 | 97.09 | 0.08 | 6.58E+03 |
| S4MT | 0.46 | 1.30 | 2.55 | 95.28 | 0.41 | 6.17E+03 |
| S5MT | 0.40 | 1.41 | 1.58 | 96.42 | 0.19 | 6.26E+03 |
| S5GT | 0.35 | 1.50 | 1.80 | 96.32 | 0.03 | 7.11E+03 |
| H6MT | 0.36 | 1.36 | 1.18 | 97.09 | 0.02 | 6.75E+03 |
| P6GT | 0.45 | 1.51 | 1.35 | 96.69 | −0.01 | 7.59E+03 |
| P6MA | 0.51 | 1.41 | 1.22 | 96.89 | −0.04 | 8.61E+03 |
| P6MS | 0.41 | 1.45 | 1.18 | 97.00 | −0.04 | 7.52E+03 |
| P6MTMet | 0.41 | 1.41 | 1.31 | 96.90 | −0.03 | 7.78E+03 |
| P7MT | 0.50 | 1.42 | 1.09 | 97.11 | −0.12 | 6.33E+03 |
| P7GT | 0.46 | 1.48 | 1.31 | 96.74 | 0.01 | 7.40E+03 |
| P6MGT | 0.45 | 1.54 | 1.23 | 96.84 | −0.06 | 6.74E+03 |
| P6MGT-P | 0.44 | 1.47 | 1.38 | 96.84 | −0.13 | 6.69E+03 |
| P6MT-P | 0.41 | 1.40 | 1.26 | 97.07 | −0.14 | 7.32E+03 |
| P6GT-P | 0.47 | 1.52 | 1.03 | 97.06 | −0.08 | 7.25E+03 |

TABLE 83

RP-HPLC (SUMMARY OF PEAK AREAS); 4 HOUR AGITATION

| Formulation ID | % Pre-peak 1 | % Pre-peak 2 | % Post-peak | % Main Peak | % Un-PEG | Total Area |
|---|---|---|---|---|---|---|
| P6MT | 0.41 | 1.48 | 1.45 | 96.70 | −0.03 | 7.55E+03 |
| S4MT | 0.58 | 1.50 | 2.86 | 94.70 | 0.36 | 6.42E+03 |
| S5MT | 0.46 | 1.47 | 1.87 | 96.21 | −0.01 | 6.97E+03 |
| S5GT | 0.56 | 1.63 | 1.98 | 95.73 | 0.09 | 7.34E+03 |
| H6MT | 0.43 | 1.44 | 1.29 | 96.88 | −0.04 | 7.93E+03 |
| P6GT | 0.54 | 1.63 | 1.51 | 96.26 | 0.05 | 7.81E+03 |
| P6MA | 0.49 | 1.39 | 1.19 | 96.96 | −0.03 | 8.22E+03 |
| P6MS | 0.36 | 1.42 | 0.92 | 97.37 | −0.07 | 7.67E+03 |
| P6MTMet | 0.51 | 1.41 | 1.44 | 96.65 | −0.01 | 7.91E+03 |
| P7MT | 0.63 | 1.32 | 1.32 | 96.85 | −0.11 | 6.69E+03 |
| P7GT | 0.49 | 1.51 | 1.48 | 96.48 | 0.03 | 7.81E+03 |
| P6MGT | 0.49 | 1.54 | 1.19 | 96.79 | −0.01 | 7.06E+03 |
| P6MGT-P | 0.38 | 1.41 | 1.15 | 97.12 | −0.06 | 7.53E+03 |
| P6MT-P | 0.37 | 1.39 | 1.31 | 96.90 | 0.03 | 7.25E+03 |
| P6GT-P | 0.32 | 1.23 | 1.08 | 97.39 | −0.02 | 7.31E+03 |

TABLE 84

RP-HPLC (SUMMARY OF PEAK AREAS); UV EXPOSURE

| Formulation ID | % Pre-peak 1 | % Pre-peak 2 | % Post-peak | % Main Peak | % Un-PEG | Total Area |
|---|---|---|---|---|---|---|
| P6MT | 0.39 | 1.33 | 3.00 | 93.94 | 1.34 | 7.07E+03 |
| S4MT | 0.70 | 1.30 | 3.60 | 93.42 | 0.98 | 6.34E+03 |
| S5MT | 0.34 | 1.19 | 2.49 | 95.63 | 0.35 | 6.93E+03 |
| S5GT | 0.30 | 1.35 | 2.28 | 95.46 | 0.61 | 7.14E+03 |
| H6MT | 0.37 | 1.14 | 2.22 | 95.08 | 1.19 | 7.92E+03 |
| P6GT | 0.30 | 1.28 | 2.36 | 94.89 | 1.17 | 8.43E+03 |
| P6MA | 0.32 | 1.30 | 1.56 | 95.68 | 1.14 | 7.54E+03 |
| P6MS | 0.32 | 1.19 | 1.40 | 96.14 | 0.96 | 7.78E+03 |
| P6MTMet | 0.29 | 1.14 | 2.51 | 94.92 | 1.13 | 7.62E+03 |
| P7MT | 0.30 | 1.31 | 2.71 | 94.08 | 1.60 | 6.61E+03 |
| P7GT | 0.52 | 1.44 | 4.40 | 91.07 | 2.57 | 7.41E+03 |
| P6MGT | 0.39 | 1.47 | 4.41 | 91.14 | 2.59 | 6.87E+03 |
| P6MGT-P | 0.31 | 1.49 | 3.22 | 93.04 | 1.95 | 6.88E+03 |
| P6MT-P | 0.25 | 1.36 | 2.77 | 94.02 | 1.60 | 6.98E+03 |
| P6GT-P | 0.36 | 1.56 | 3.73 | 92.20 | 2.15 | 6.94E+03 |

TABLE 85

SEC-HPLC (SUMMARY OF PEAK AREAS); 2 HOUR AGITATION

| Formulation ID | % Pre-peak | % Main Peak | % Un-PEG | Total Area |
|---|---|---|---|---|
| P6MT | 68.19 | 31.73 | 0.08 | 5.21E+04 |
| P6GT | 62.20 | 37.72 | 0.08 | 5.67E+04 |
| P6MA | 59.33 | 40.58 | 0.09 | 5.38E+04 |
| P6MGT | 70.27 | 29.65 | 0.07 | 4.86E+04 |
| P6MGT-P | 4.55 | 95.38 | 0.07 | 4.79E+04 |
| P6MT-P | 17.82 | 82.10 | 0.09 | 4.77E+04 |
| P6GT-P | 9.19 | 90.68 | 0.13 | 4.98E+04 |

Example 18

Agitation Study

Another agitation study was performed with the formulations matrix shown in Table 86. Agitation was performed on 2 mg/mL samples at 250 μL fill in glass vials. Samples were agitated for 4 hours at room temperature. Duplicate set of samples, incubated at room temperature undisturbed, was used as positive controls ("Controls"). The pH and concentration of the samples was measured, and SEC-HPLC analysis was performed on t=0, control, and agitated samples as shown in Tables 87-90.

TABLE 86

FORMULATIONS MATRIX

| Formulation ID | Buffer | pH | Bulking Agent | Stabilizer | Surfactant |
|---|---|---|---|---|---|
| P7MGT-P | 10 mM Phosphate | 7 | 2% Mannitol, 1.25% Glycine | 2% Trehalose | |

TABLE 86-continued

FORMULATIONS MATRIX

| Formulation ID | Buffer | pH | Bulking Agent | Stabilizer | Surfactant |
|---|---|---|---|---|---|
| P7MGT01P | 10 mM Phosphate | 7 | 2% Mannitol, 1.25% Glycine | 2% Trehalose | 0.01% PS20 |
| P7MGT005P | 10 mM Phosphate | 7 | 2% Mannitol, 1.25% Glycine | 2% Trehalose | 0.005% PS20 |
| P7MGT0025P | 10 mM Phosphate | 7 | 2% Mannitol, 1.25% Glycine | 2% Trehalose | 0.0025% PS20 |
| P7MGT001P | 10 mM Phosphate | 7 | 2% Mannitol, 1.25% Glycine | 2% Trehalose | 0.001% PS20 |
| H7MT-P | 10 mM Histidine | 7 | 4% Mannitol | 2% Trehalose | |
| H7MGT-P | 10 mM Histidine | 7 | 2% Mannitol, 1.25% Glycine | 2% Trehalose | |
| 7MHT-P | | 7 | 2% Mannitol, 1.25% Histidine | 2% Trehalose | |

TABLE 87

CONCENTRATION, pH

| Formulation ID | Conc. (mg/mL) | pH |
|---|---|---|
| P7MGT-P | 2.0 | 7.14 |
| P7MGT01P | 1.9 | 7.20 |
| P7MGT005P | 1.8 | 7.20 |
| P7MGT0025P | 2.0 | 7.19 |
| P7MGT001P | 2.0 | 7.22 |
| H7MT-P | 2.0 | 6.83 |
| H7MGT-P | 2.1 | 6.82 |
| 7MHT-P | 2.3 | 6.91 |

TABLE 88

SEC-HPLC (SUMMARY OF PEAK AREAS); AGITATION T = 0

| Formulation ID | % Pre-peak 1 | % Pre-peak 2 | % Main Peak | % Un-PEG | Total Area |
|---|---|---|---|---|---|
| P7MGT-P | 0.57 | 0.67 | 98.68 | 0.08 | 5.72E+04 |
| P7MGT01P | 0.45 | 0.58 | 98.91 | 0.06 | 5.75E+04 |
| P7MGT005P | 0.63 | 0.66 | 98.65 | 0.07 | 5.89E+04 |
| P7MGT0025P | 0.46 | 0.59 | 98.84 | 0.11 | 5.94E+04 |
| P7MGT001P | 0.49 | 0.59 | 98.84 | 0.07 | 6.13E+04 |
| H7MT-P | 0.66 | 0.72 | 98.56 | 0.06 | 5.78E+04 |
| H7MGT-P | 0.67 | 0.68 | 98.57 | 0.08 | 6.27E+04 |
| 7MHT-P | n/a | n/a | n/a | n/a | n/a |

TABLE 89

SEC-HPLC (SUMMARY OF PEAK AREAS); AGITATION CONTROLS

| Formulation ID | % Pre-peak 1 | % Pre-peak 2 | % Main Peak | % Un-PEG | Total Area |
|---|---|---|---|---|---|
| P7MGT-P | 0.57 | 0.66 | 98.71 | 0.06 | 6.28E+04 |
| P7MGT01P | 0.46 | 0.61 | 98.86 | 0.08 | 5.96E+04 |
| P7MGT005P | 0.46 | 0.61 | 98.83 | 0.10 | 5.51E+04 |
| P7MGT0025P | 0.42 | 0.59 | 98.90 | 0.08 | 6.06E+04 |
| P7MGT001P | 0.48 | 0.57 | 98.88 | 0.08 | 5.95E+04 |
| H7MT-P | 0.60 | 0.62 | 98.71 | 0.07 | 5.89E+04 |
| H7MGT-P | 0.67 | 0.61 | 98.61 | 0.11 | 6.08E+04 |
| 7MHT-P | 0.63 | 0.72 | 98.57 | 0.07 | 6.48E+04 |

TABLE 90

SEC-HPLC (SUMMARY OF PEAK AREAS); AFTER 4 HOUR AGITATION

| Formulation ID | % Pre-peak 1 | % Pre-peak 2 | % Main Peak | % Un-PEG | Total Area |
|---|---|---|---|---|---|
| P7MGT-P | 0.57 | 0.65 | 98.67 | 0.11 | 5.80E+04 |
| P7MGT01P | 0.00 | 19.03 | 80.87 | 0.10 | 6.07E+04 |
| P7MGT005P | 0.00 | 24.37 | 75.54 | 0.09 | 5.90E+04 |
| P7MGT0025P | 0.00 | 13.55 | 86.37 | 0.08 | 6.07E+04 |
| P7MGT001P | 0.00 | 7.54 | 92.36 | 0.10 | 6.13E+04 |
| H7MT-P | 0.80 | 0.69 | 98.39 | 0.11 | 5.52E+04 |
| H7MGT-P | 0.71 | 0.68 | 98.51 | 0.10 | 6.04E+04 |
| 7MHT-P | 0.59 | 0.70 | 98.61 | 0.09 | 6.55E+04 |

Trace amounts of polysorbate induced aggregation under agitation. When agitated, Histidine formulations performed comparably to glycine-containing formulations.

Example 19

Accelerated Aggregation Studies

Accelerated stress studies were performed to mimic long term storage conditions and identify potential degradation or aggregation products. Accelerated aggregation studies were performed using 2 formulations (Formulation ID H7MT-P and H7MGT-P) at approximately 8 and 14 mg/ml. The components of the formulations are described in Table 91. The "-P" designation indicates no polysorbate 20. Stresses studied were freeze-thaw conditions, agitation, UV exposure, and temperature. The methods described above were used to evaluate PEGylated hGH. Samples were evaluated by SDS-PAGE and SEC-HPLC methods described in Examples 9 and 11, respectively. Additional time points for analysis include 1 month, 2 month, etc. Additional techniques for analysis of samples include Dynamic Light Scattering (DLS) and Analytical Ultracentrifugation.

TABLE 91

FORMULATIONS MATRIX (ACCELERATED AGGREGATION STUDIES)

| Formulation ID | Buffer | pH | Bulking Agent | Stabilizer | Concentration |
|---|---|---|---|---|---|
| H7MT-P | 10 mM Histidine | 7 | 4% Mannitol | 2% Trehalose | 8 mg/mL |
| H7MT-P | 10 mM Histidine | 7 | 4% Mannitol | 2% Trehalose | 14 mg/mL |
| H7MGT-P | 10 mM Histidine | 7 | 2% Mannitol, 1.25% Glycine | 2% Trehalose | 8 mg/mL |
| H7MGT-P | 10 mM Histidine | 7 | 2% Mannitol, 1.25% Glycine | 2% Trehalose | 14 mg/mL |

63 mL of 5.7 mg/mL PEGylated hGH (in 20 mM sodium citrate, 2% glycine, 0.5% mannitol, pH 6) was concentrated to 14.2 mg/mL. Half of the concentrate was dialyzed against H7MT-P, and the other half against H7MGT-P. Since the dialysis caused the protein to be diluted, the sample in H7MT-P was concentrated to 13.6 mg/mL and the H7MGT-P was concentrated to 13.5 mg/mL. A portion of the the PEGylated hGH (approximately 4.5 mL) in H7MT-P at 13.6 mg/mL was diluted to 7.8 mg/mL with H7MT-P buffer. Similarly approximately 4.5 mL of PEGylated hGH in H7MGT-P at 13.5 mg/mL was diluted to 8.0 mg/mL with H7MGT-P buffer.

Freeze/Thaw Studies

The formulation was frozen at −70° C. for 15 minutes. It was then thawed at 25° C. The vial was then uncapped to remove a portion of the sample for SEC-HPLC and SDS-PAGE analysis, and the vial re-capped. This procedure was repeated five times. The results of the SEC-HPLC analysis are shown in Tables 92-95. SDS-PAGE analysis is shown in FIGS. 67-70.

TABLE 92

SEC-HPLC (SUMMARY OF PEAK AREAS);
FORMULATION ID: H7MT-P; Conc: 8 mg/mL

| Frequency F/T | % Pre-peak 1 | % Pre-peak 2 | % Main Peak | % Un-PEG | Total Area |
|---|---|---|---|---|---|
| 0 | 1.00 | 0.71 | 98.15 | 0.14 | 7.16E+04 |
| 1 | 0.70 | 0.65 | 98.57 | 0.08 | 7.50E+04 |
| 2 | 0.75 | 0.65 | 98.53 | 0.07 | 7.57E+04 |
| 3 | 0.78 | 0.66 | 98.43 | 0.12 | 7.69E+04 |
| 4 | 0.88 | 0.68 | 98.36 | 0.08 | 7.62E+04 |
| 5 | 1.04 | 0.77 | 98.10 | 0.08 | 7.89E+04 |

TABLE 93

SEC-HPLC (SUMMARY OF PEAK AREAS);
FORMULATION ID: H7MT-P; Conc: 14 mg/mL

| Frequency F/T | % Pre-peak 1 | % Pre-peak 2 | % Main Peak | % Un-PEG | Total Area |
|---|---|---|---|---|---|
| 0 | 0.66 | 0.62 | 98.63 | 0.09 | 6.81E+04 |
| 1 | 0.64 | 0.63 | 98.65 | 0.08 | 7.36E+04 |
| 2 | 0.65 | 0.63 | 98.64 | 0.08 | 7.35E+04 |
| 3 | 0.67 | 0.66 | 98.59 | 0.08 | 7.96E+04 |
| 4 | 0.76 | 0.66 | 98.47 | 0.10 | 8.08E+04 |
| 5 | 0.84 | 0.65 | 98.39 | 0.11 | 7.60E+04 |

TABLE 94

SEC-HPLC (SUMMARY OF PEAK AREAS);
FORMULATION ID: H7MGT-P; Conc: 8 mg/mL

| Frequency F/T | % Pre-peak 1 | % Pre-peak 2 | % Main Peak | % Un-PEG | Total Area |
|---|---|---|---|---|---|
| 0 | 0.73 | 0.64 | 98.51 | 0.12 | 7.41E+04 |
| 1 | 0.61 | 0.65 | 98.62 | 0.12 | 7.45E+04 |
| 2 | 0.77 | 0.62 | 98.47 | 0.14 | 7.42E+04 |
| 3 | 0.82 | 0.67 | 98.41 | 0.10 | 7.58E+04 |
| 4 | 0.69 | 0.67 | 98.55 | 0.08 | 7.58E+04 |
| 5 | 0.92 | 0.69 | 98.26 | 0.13 | 7.43E+04 |

TABLE 95

SEC-HPLC (SUMMARY OF PEAK AREAS);
FORMULATION ID: H7MGT-P; Conc: 14 mg/mL

| Frequency F/T | % Pre-peak 1 | % Pre-peak 2 | % Main Peak | % Un-PEG | Total Area |
|---|---|---|---|---|---|
| 0 | 0.81 | 0.66 | 98.43 | 0.09 | 7.26E+04 |
| 1 | 0.78 | 0.68 | 98.44 | 0.10 | 7.64E+04 |
| 2 | 0.75 | 0.65 | 98.47 | 0.13 | 7.44E+04 |
| 3 | 0.74 | 0.68 | 98.49 | 0.08 | 8.06E+04 |
| 4 | 0.89 | 0.65 | 98.37 | 0.09 | 7.42E+04 |
| 5 | 0.99 | 0.70 | 98.21 | 0.11 | 7.16E+04 |

The freeze/thawing of the samples caused a 0.2-0.3% increase in higher MW aggregates, with possible dissociation of higher MW aggregates after the first freeze-thaw cycle in 8 mg/mL samples.

Vortex/UV Exposure

For this study, the formulations matrix shown in Table 91 was used. For the control samples in the agitation (vortex) and UV exposure studies, formulations were held at room temperature for 6 hours. In the agitation study, liquid samples were vortexed at room temperature for 6 hours at high speed. In the UV exposure study, lyophilized samples were exposed to UV light at room temperature for 4 hours and reconstituted prior to analysis. Samples were removed for SEC-HPLC and SDS-PAGE analysis. Tables 96-98 show the SEC-HPLC data for the control samples, the vortexed samples, and the UV-exposed samples. SDS-PAGE analysis of these samples is shown as FIGS. 71 and 72.

TABLE 96

SEC-HPLC (SUMMARY OF PEAK AREAS); VORTEX/UV CONTROLS

| Formulation ID | % Pre-peak 1 | % Pre-peak 2 | % Main Peak | % Un-PEG | Total Area |
|---|---|---|---|---|---|
| H7MT-P; 8 mg/mL | 0.78 | 0.68 | 98.43 | 0.11 | 7.58E+04 |
| H7MT-P; 14 mg/mL | 0.66 | 0.66 | 98.57 | 0.11 | 7.63E+04 |
| H7MGT-P; 8 mg/mL | 0.69 | 0.69 | 98.49 | 0.13 | 7.52E+04 |
| H7MGT-P; 14 mg/mL | 0.77 | 0.68 | 98.43 | 0.12 | 7.58E+04 |

TABLE 97

SEC-HPLC (SUMMARY OF PEAK AREAS); VORTEXED SAMPLES (vortexed for 6 hours at room temperature)

| Formulation ID | % Pre-peak 1 | % Pre-peak 2 | % Main Peak | % Un-PEG | Total Area |
|---|---|---|---|---|---|
| H7MT-P; 8 mg/mL | 9.99 | n/a | 89.89 | 0.11 | 7.68E+04 |
| H7MT-P; 14 mg/mL | 14.75 | n/a | 85.13 | 0.12 | 7.11E+04 |
| H7MGT-P; 8 mg/mL | 16.85 | n/a | 83.04 | 0.10 | 7.78E+04 |
| H7MGT-P; 14 mg/mL | 4.22 | n/a | 95.69 | 0.09 | 7.40E+04 |

TABLE 98

SEC-HPLC (SUMMARY OF PEAK AREAS); UV-EXPOSED SAMPLES (exposed to UV light for 4 hours at room temperature)

| Formulation ID | % Pre-peak 1 | % Pre-peak 2 | % Main Peak | % Un-PEG | Total Area |
|---|---|---|---|---|---|
| H7MT-P; 8 mg/mL | 0.64 | 0.91 | 97.96 | 0.49 | 7.49E+04 |
| H7MT-P; 14 mg/mL | 0.67 | 0.84 | 98.17 | 0.32 | 7.14E+04 |
| H7MGT-P; 8 mg/mL | 0.53 | 0.82 | 98.14 | 0.50 | 7.55E+04 |
| H7MGT-P; 14 mg/mL | 0.71 | 0.83 | 98.13 | 0.33 | 7.38E+04 |

Histidine formulations without polysorbate 20 were confirmed to reduce the amount of aggregates formed with vigorous agitation.

DePEGylation was the main degradation event and was more pronounced in samples with the lower concentration of hGH. UV exposure resulted in an increase in % Pre-peak 2 (dimerization) compared to the control.

In another agitation study, lyophilized samples were stored at 4° C. or 40° C. for 1 week or 2 weeks. The samples were then reconstituted prior to analysis by SDS-PAGE and SEC-HPLC. Tables 99-102 show the SEC-HPLC results. FIGS. 73-74 show SDS-PAGE analysis for 1 week samples. FIGS. 75-76 show SDS-PAGE analysis for 2 week samples.

TABLE 99

SEC-HPLC (SUMMARY OF PEAK AREAS); T = 1 week, 4° C.

| Formulation ID | % Pre-peak 1 | % Pre-peak 2 | % Main Peak | % Un-PEG | Total Area |
|---|---|---|---|---|---|
| H7MT-P; 8 mg/mL | 0.63 | 0.65 | 98.59 | 0.13 | 7.45E+04 |
| H7MT-P; 14 mg/mL | 0.51 | 0.60 | 98.76 | 0.12 | 7.41E+04 |
| H7MGT-P; 8 mg/mL | 0.62 | 0.63 | 98.60 | 0.14 | 7.46E+04 |
| H7MGT-P; 14 mg/mL | 0.81 | 0.63 | 98.44 | 0.12 | 7.42E+04 |

TABLE 100

SEC-HPLC (SUMMARY OF PEAK AREAS); T = 2 week, 4° C.

| Formulation ID | % Pre-peak 1 | % Pre-peak 2 | % Main Peak | % Un-PEG | Total Area |
|---|---|---|---|---|---|
| H7MT-P; 8 mg/mL | 0.72 | 0.64 | 98.55 | 0.09 | 7.35E+04 |
| H7MT-P; 14 mg/mL | 0.58 | 0.66 | 98.69 | 0.07 | 7.12E+04 |
| H7MGT-P; 8 mg/mL | 0.42 | 0.51 | 98.98 | 0.09 | 7.18E+04 |
| H7MGT-P; 14 mg/mL | 0.50 | 0.66 | 98.75 | 0.08 | 7.15E+04 |

TABLE 101

SEC-HPLC (SUMMARY OF PEAK AREAS); T = 1 week, 40° C.

| Formulation ID | % Pre-peak 1 | % Pre-peak 2 | % Main Peak | % Un-PEG | Total Area |
|---|---|---|---|---|---|
| H7MT-P; 8 mg/mL | 0.51 | 0.87 | 96.83 | 1.79 | 7.65E+04 |
| H7MT-P; 14 mg/mL | 0.45 | 0.92 | 96.83 | 1.80 | 7.19E+04 |
| H7MGT-P; 8 mg/mL | 0.41 | 0.77 | 96.34 | 2.48 | 7.82E+04 |
| H7MGT-P; 14 mg/mL | 0.46 | 0.88 | 96.11 | 2.55 | 7.40E+04 |

TABLE 102

SEC-HPLC (SUMMARY OF PEAK AREAS); T = 2 week, 40° C.

| Formulation ID | % Pre-peak 1 | % Pre-peak 2 | % Main Peak | % Un-PEG | Total Area |
|---|---|---|---|---|---|
| H7MT-P; 8 mg/mL | 0.39 | 0.90 | 95.80 | 2.91 | 7.41E+04 |
| H7MT-P; 14 mg/mL | 0.39 | 1.02 | 95.37 | 3.22 | 6.97E+04 |
| H7MGT-P; 8 mg/mL | 0.32 | 0.77 | 94.50 | 4.41 | 7.36E+04 |
| H7MGT-P; 14 mg/mL | 0.39 | 0.97 | 94.15 | 4.49 | 6.89E+04 |

After 1 week, H7MT-P produced less higher molecular weight aggregate than H7MGT-P at 4° C. H7MT-P resulted in slightly more dimer formation, but less dePEGylated hGH than H7MGT-P at 40° C. After two weeks, an increased amount of dimerization was observed at 40° C. Significant de-PEGylation was observed at 40° C. H7MT-P formed less de-PEGylated hGH than H7MGT-P at 40° C. Additional time points include measurements at 4 weeks.

In addition, samples of PEGylated-hGH were exposed to thermal-unfolding conditions. The thermal-unfolding samples were incubated for 10 minutes at 85° C., which is above the melting temperature ($T_m$) of 82° C. Thermal-unfolding induced aggregation. Table 103 shows the SEC-HPLC analysis of the samples exposed to thermal-unfolding. SDS-PAGE analysis is shown in FIGS. 73-74.

TABLE 103

SEC-HPLC (SUMMARY OF PEAK AREAS); THERMAL-UNFOLDING

| Formulation ID | % Pre-peak 1 | % Pre-peak 2 | % Main Peak | % Un-PEG | Total Area |
|---|---|---|---|---|---|
| H7MT-P; 8 mg/mL | 89.23 | n/a | 10.77 | 0 | 8.14E+04 |
| H7MT-P; 14 mg/mL | 91.89 | n/a | 8.11 | 0 | 7.81E+04 |
| H7MGT-P; 8 mg/mL | 90.09 | n/a | 9.91 | 0 | 8.42E+04 |
| H7MGT-P; 14 mg/mL | 92.18 | n/a | 7.82 | 0 | 7.97E+04 |

Example 20

FT/IR (Fourier Transform Infrared Spectroscopy) Scans
Analysis of PEGylated hGH was performed with FT/IR. FT/IR scans were performed on a Jasco model FT/IR 660

Plus. Each sample was scanned 320 times at a resolution of 4 cm$^{-1}$ and analyzed with Jasco Spectra Manager v1.53.00. Air backgrounds and water blanks were taken before each day's sample runs. The elimination of signals derived from water was confirmed by the absence of absorbance at 1700 cm$^{-1}$. After the appropriate background and blank controls were subtracted from each sample spectrum, second derivative analysis of the remaining protein and excipient peaks was performed in the Amide I region (1600-1700 cm$^{-1}$). As a liquid control, PEG-hGH bulk at 6 mg/mL was used.

The Amide I signal of PEG-hGH was relatively weaker than other proteins even after lyophilization. However, most samples showed α-helix signal at 1651 cm$^{-1}$, so qualitative comparison among formulation candidates could be accomplished. Glycine shows a strong signal at Amide I region, so the signal could have been distorted during the course of subtracting glycine signal from original data.

Second-derivative FTIR spectra [signal intensity (y axis) vs. wave number in cm$^{-1}$ (x-axis)] of the P6MT, S4MT, S5MT, H6MT, P6GT, P6MS, P6MTmet, P7MT, and P6MT-P formulations compared to the liquid control showed: 1) Most mannitol formulations preserved good α-helix signal regardless of buffer or pH. 2) One formulation, P6GT containing glycine, showed significant shift in the band signal. 3) Other peaks were observed at 1620, 1630, 1725, and 1750. Second derivative FTIR spectra of the S5GT, P6MA, P7GT, P6MGT, P6MGT-P, and P6GT-P formulations had poor α-helix signal. Moreover, all glycine formulations showed significant deviation from the native signal of liquid sample. The arginine-containing formulation exhibited major structural changes during lyophilization.

After two months of storage of the lyophilized material at 4° C., FT/IR was performed. The Amide I signal of PEG-hGH was relatively weaker than other proteins even after lyophilization. However, most samples showed α-helix signal at 1651 cm$^{-1}$, so qualitative comparison among formulation candidates could be accomplished. Glycine showed a strong signal at Amide I region. At two months, all glycine formulations showed significant deviation from the native signal of liquid sample. Most mannitol formulations preserved good α-helix signal regardless of buffer or pH.

Example 21

Agitation (Surfactant Testing)

PEG-hGH in 20 mM sodium citrate, 2% glycine, 0.5% mannitol, pH 6 was diluted to 2 mg/mL with H7MT-P. 0.01% polysorbate 20 (PS) was added to one sample, 0.01% Pluronic F68 (F68) to another, and the third had no surfactant added. Agitation was performed with 500 μL fill in glass vials. Samples were agitated for 1 hour at room temperature. SEC-HPLC analysis of the samples is shown in Table 104; samples that were agitated are noted with "Vtx.".

TABLE 104

SEC-HPLC (SUMMARY OF PEAK AREAS); AGITATION WITH SURFACTANT

| Formulation ID | % Pre-peaks 1 + 2 | % Main Peak | % Un-PEG | Total Area |
|---|---|---|---|---|
| H7MT-P, t = 0 | 2.84 | 98.16 | 0 | 5.81E+04 |
| H7MT, 0.01% PS, t = 0 | 1.49 | 98.51 | 0 | 5.59E+04 |
| H7MT, 0.01% F68, t = 0 | 1.58 | 98.42 | 0 | 5.75E+04 |
| H7MT-P, 1 hr Vtx | 12.54 | 87.46 | 0 | 5.79E+04 |
| H7MT, 0.01% PS, 1 hr Vtx | 57.21 | 42.79 | 0 | 6.13E+04 |

TABLE 104-continued

SEC-HPLC (SUMMARY OF PEAK AREAS); AGITATION WITH SURFACTANT

| Formulation ID | % Pre-peaks 1 + 2 | % Main Peak | % Un-PEG | Total Area |
|---|---|---|---|---|
| H7MT, 0.01% F68, 1 hr Vtx | 4.43 | 95.57 | 0 | 5.58E+04 |

Relative to the other samples tested, Pluronic F68 was the most effective in preventing agitation induced aggregation as shown in Table 104.

Additional experiments may include, dialyzing the samples instead of diluting them to remove residual excipients and/or testing other surfactants, including but not limited to, polysorbate 80. A surfactant may be used alone or in combination with one or more other surfactants. Additional studies include testing the effect of the following surfactants on the stability of PEG-hGH in H7MT formulation against agitation-induced aggregation: 1) no surfactant (negative control); 2) polysorbate 20 at various amounts including, but not limited to, 0.01%; 3) Pluronic F68 (or Poloxamer 188) at various amounts including, but not limited to, 0.005%, 0.01%, 0.05%, and 0.1%; 4) polysorbate 80 at various amounts including, but not limited to, 0.01%; and 5) a combination of pluronic F68 and polysorbate 20 or pluronic F68 and other surfactants. Additional lyophilized formulations (H7MT) containing the best surfactant or combination of surfactants will be prepared and their stability at 40° C. will be compared to the H7MT formulation. The concentration of PEG-hGH will be 2 mg/ml, and time points for analysis will be at 0, 1, 2, 3, and 4 weeks, or longer. The techniques described herein will be used for analysis.

Example 22

Long Term Studies

Additional long term stability studies include evaluation of formulations after storage at various temperatures, including but not limited to, 4° C. and 29° C., for 0, 3, 6, 9, 12, 18, and 24 months. The stability of samples reconstituted after lyophilization may be investigated during storage at 2-8° C. for various lengths of time, such as 0, 1 day, 3 days, and 1 week.

Example 23

Lyophilized Formulation Study

Additional data was generated from the lyophilized formulation study discussed in Example 14. Data generated for the four month time point include: SDS-gels (samples stored at 4° C. and 25° C. for 4 months; FIGS. 77-80); concentration and pH post reconstitution (Tables 105-106); SEC-HPLC analysis of samples stored at 4° C. and 25° C. for 4 months (Tables 107-108); and RP-HPLC analysis of samples stored at 4° C. and 25° C. for 4 months (Tables 109-110). After four months, the formulation containing histidine continued to show the least amount of covalent aggregates via SDS-PAGE of the formulations tested. Over the last two months, H6MT and P7MT have showed minimal change at 25° C.

TABLE 105

CONCENTRATION, pH POST RECONSTITUTION; T = 4 months; 4° C.

| Formulation ID | Conc. (mg/mL) | pH |
|---|---|---|
| P6MT | 1.8 | 6.25 |
| H6MT | 2.5 | 6.09 |
| P6GT | 2.0 | 6.20 |
| P6MS | 1.8 | 6.29 |
| P6MTMet | 1.8 | 6.24 |
| P7MT | 1.6 | 7.04 |
| P7GT | 1.8 | 7.08 |
| P6MGT | 1.7 | 6.25 |
| P6MGT-P | 1.7 | 6.25 |
| P6MT-P | 1.7 | 6.20 |
| P6GT-P | 1.3 | 6.30 |

TABLE 106

CONCENTRATION, pH POST RECONSTITUTION; T = 4 months; 25° C.

| Formulation ID | Conc. (mg/mL) | pH |
|---|---|---|
| P6MT | 1.5 | 6.28 |
| H6MT | 1.9 | 6.06 |
| P6GT | 1.9 | 6.24 |
| P6MS | 1.9 | 6.28 |
| P6MTMet | 1.8 | 6.18 |
| P7MT | 1.6 | 7.10 |
| P7GT | 1.8 | 6.99 |
| P6MGT | 1.7 | 6.23 |
| P6MGT-P | 1.7 | 6.18 |
| P6MT-P | 1.6 | 6.23 |
| P6GT-P | 1.7 | 6.21 |

TABLE 107

SEC-HPLC (SUMMARY OF PEAK AREAS); T = 4 month; 4° C.

| Formulation ID | % Pre-peak 1 | % Pre-peak 2 | % Main Peak | % Un-PEG | Total Area |
|---|---|---|---|---|---|
| P6MT | 0.54 | 1.17 | 98.29 | 0.00 | 5.03E+04 |
| H6MT | 0.58 | 1.11 | 98.30 | 0.00 | 6.96E+04 |
| P6GT | 0.48 | 1.40 | 98.12 | 0.00 | 5.70E+04 |
| P6MS | 0.57 | 1.08 | 98.35 | 0.00 | 5.20E+04 |
| P6MTMet | 0.50 | 1.11 | 98.39 | 0.00 | 5.16E+04 |
| P7MT | 0.46 | 1.13 | 98.41 | 0.00 | 4.59E+04 |
| P7GT | 0.42 | 1.42 | 98.16 | 0.00 | 5.11E+04 |
| P6MGT | 0.49 | 1.07 | 98.44 | 0.00 | 4.67E+04 |
| P6MGT-P | 0.52 | 1.04 | 98.44 | 0.00 | 4.72E+04 |
| P6MT-P | 0.76 | 1.30 | 97.94 | 0.00 | 4.71E+04 |
| P6GT-P | 0.75 | 1.57 | 97.67 | 0.00 | 3.59E+04 |

TABLE 108

SEC-HPLC (SUMMARY OF PEAK AREAS); T = 4 month; 25° C.

| Formulation | % Pre-peak 1 | % Pre-peak 2 | % Main Peak | % Un-PEG | Total Area |
|---|---|---|---|---|---|
| P6MT | 0.59 | 1.88 | 97.53 | 0.00 | 4.20E+04 |
| H6MT | 0.76 | 1.44 | 97.80 | 0.00 | 5.27E+04 |
| P6GT | 0.49 | 2.34 | 97.17 | 0.00 | 5.33E+04 |
| P6MS | 0.71 | 2.80 | 96.49 | 0.00 | 5.57E+04 |
| P6MTMet | 0.58 | 2.97 | 96.45 | 0.00 | 5.10E+04 |
| P7MT | 0.39 | 1.63 | 97.98 | 0.00 | 4.54E+04 |
| P7GT | 0.36 | 2.10 | 97.54 | 0.00 | 5.12E+04 |
| P6MGT | 0.50 | 2.68 | 96.82 | 0.00 | 4.62E+04 |
| P6MGT-P | 0.57 | 2.58 | 96.85 | 0.00 | 4.74E+04 |
| P6MT-P | 0.96 | 2.13 | 96.92 | 0.00 | 4.58E+04 |
| P6GT-P | 0.71 | 2.34 | 96.95 | 0.00 | 4.98E+04 |

TABLE 109

RP-HPLC (SUMMARY OF PEAK AREAS); T = 4 month; 4° C.

| Formulation ID | % Pre-peak 1 | % Pre-peak 2 | % Post-peak | % Main Peak | % Un-PEG | Total Area |
|---|---|---|---|---|---|---|
| P6MT | 0.17 | 0.90 | 1.12 | 97.63 | 0.18 | 8.36E+03 |
| H6MT | 0.16 | 0.78 | 0.88 | 98.06 | 0.12 | 1.16E+04 |
| P6GT | 0.26 | 0.87 | 1.39 | 97.20 | 0.28 | 9.24E+03 |
| P6MS | 0.16 | 0.83 | 0.84 | 98.10 | 0.06 | 8.61E+03 |
| P6MTMet | 0.12 | 0.87 | 1.14 | 97.71 | 0.14 | 8.52E+03 |
| P7MT | 0.17 | 0.79 | 1.24 | 97.75 | 0.06 | 7.60E+03 |
| P7GT | 0.26 | 1.03 | 1.88 | 96.44 | 0.39 | 8.26E+03 |
| P6MGT | 0.17 | 1.03 | 1.40 | 97.01 | 0.38 | 7.78E+03 |
| P6MGT-P | 0.16 | 0.96 | 1.23 | 97.42 | 0.23 | 7.60E+03 |
| P6MT-P | 0.20 | 0.91 | 1.26 | 97.43 | 0.20 | 7.62E+03 |
| P6GT-P | 0.19 | 1.21 | 1.61 | 96.86 | 0.13 | 6.97E+03 |

TABLE 110

RP-HPLC (SUMMARY OF PEAK AREAS); T = 4 month; 25° C.

| Formulation ID | % Pre-peak 1 | % Pre-peak 2 | % Post-peak | % Main Peak | % Un-PEG | Total Area |
|---|---|---|---|---|---|---|
| P6MT | 0.25 | 1.10 | 2.46 | 95.74 | 0.44 | 6.74E+03 |
| H6MT | 0.59 | 0.99 | 3.05 | 94.51 | 0.86 | 8.56E+03 |
| P6GT | 0.25 | 1.53 | 2.36 | 95.38 | 0.48 | 8.55E+03 |
| P6MS | 0.28 | 1.06 | 1.84 | 96.60 | 0.22 | 8.82E+03 |
| P6MTMet | 0.27 | 1.39 | 5.63 | 90.48 | 2.22 | 8.21E+03 |
| P7MT | 0.20 | 0.90 | 1.47 | 97.22 | 0.20 | 7.17E+03 |
| P7GT | 0.22 | 1.37 | 1.72 | 96.33 | 0.36 | 8.01E+03 |
| P6MGT | 0.35 | 1.84 | 2.75 | 94.40 | 0.66 | 7.64E+03 |
| P6MGT-P | 0.28 | 2.05 | 2.76 | 94.46 | 0.44 | 7.78E+03 |
| P6MT-P | 0.32 | 1.06 | 2.33 | 95.81 | 0.48 | 7.47E+03 |
| P6GT-P | 0.29 | 1.46 | 2.58 | 95.16 | 0.51 | 7.81E+03 |

Example 24

Histidine Interaction Study with PEG-HGH

The objective of this study is to investigate the pH drop that has been observed in 10 mM histidine buffer, 4% mannitol, 2% trehalose, pH 7.0 when PEG-hGH is added at concentrations of at least 8 mg/mL. This study investigated whether the concentration dependent pH change in histidine formulations is due to the binding of histidine with PEG-hGH.

RP-HPLC and/or IEX-HPLC methods for determining free/bound histidine may be used in such studies.

Dialysis of 5 mg/mL and 25 mg/mL PEG-hGH

One or two concentrations of PEG-hGH were dialyzed against one of the following buffers: 10 mM $Na_2HPO_4$, pH 7.1; 10 mM histidine (pH 7.0), 10 mM histidine (free base), pH 7.7; 30 mM histidine (free base), pH 7.7. The pH of the protein was measured after dialysis. The amount of histidine was determined by running SEC-HPLC and measuring the histidine peak which elutes after protein peak. The 214 nm:280 nm was compared to determine if histidine bound to the PEG-hGH.

For 10 mM Histidine (free base), pH 7.7, the 4.5 mg/ml protein sample had a pH of 7.18, and the 14.0 mg/ml protein sample had a pH of 6.89. The 214 nm:280 nm ratios were the same (19.2) for both protein concentrations. For 30 mM Histidine (free base), pH 7.7, the 13.3 mg/ml protein sample had a pH of 7.19. The 214 nm:280 nm ratio was 1.9.2. For 10 mM His, pH 7.0, the 4.6 mg/ml protein sample had a pH of 6.94, and the 13.2 mg/ml protein sample had a pH of 6.76. The 214 nm:280 nm ratios were the same (19.1) for both protein concentrations. For 10 mM $Na_2HPO_4$, pH 7.1, the 4.6 mg/ml protein sample had a pH of 7.10, and the 13.2 mg/ml protein sample had a pH of 7.09. The 214 nm:280 nm ratios were 19.2 for the lower protein concentration, and 19.1 for the higher protein concentration.

pH Change During Concentration pH changes were measured of the protein during concentration. 10 mM histidine (free base) and 30 mM His (free base) were tested; the protein concentration started at 1 mg/ml. With 10 mM His (free base), pH 7.7, the following results were found: 1.0 mg/ml protein had pH 7.41; 11.7 mg/ml protein had pH 6.82; and 15.0 mg/ml protein had pH 6.71. With 30 mM His (free base), pH 7.7, the following results were found: 1.0 mg/ml protein had pH 7.58; 11.4 mg/ml protein had pH 7.22; and 17.1 mg/ml protein had pH 7.05.

Addition of Histidine

PEG-hGH was concentrated with 14 mg/ml and dialyzed against water. The histidine concentration was increased by adding small volumes of concentrated histidine to the protein. The pH was measured at each histidine increase. The following pH measurements were determined with the histidine concentration (mM): pH 5.57 at 0 mM Histidine, pH 5.68 at 0.25 mM Histidine, pH 5.74 at 0.5 mM Histidine, pH 5.86 at 1 mM Histidine, pH 6.13 at 2.5 mM Histidine, pH 6.36 at 5 mM Histidine, pH 6.63 at 10 mM Histidine, and pH 7.05 at 30 mM Histidine.

In these studies, it was found that histidine does not bind to the PEG-hGH. The buffering capacity of histidine was unable to overcome the buffering capacity of the protein. Monobasic phosphate is tested to determine if it can provide enough buffering capacity to maintain pH. Any buffer that has a buffering capacity between about pH 5.5 and about pH 8.0, including but not limited to, monobasic phosphate may be suitable. Formulations with histidine had lower amounts of covalent aggregates and aggregates from agitation.

Monobasic phosphate is tested in the following assay. PEG-hGH is concentrated to 14 mg/ml and dialyzed against water. The phosphate concentration is increased by adding small volumes of concentrated phosphate to the protein. The pH is measured at each phosphate increase, and a plot is generated with pH vs. phosphate concentration (mM)

Example 25

Additional data was generated from the accelerated aggregation study discussed in Example 19. Data generated for the four week time point include: SDS-gels (samples stored at 4° C. and 40° C. for 4 weeks; FIGS. 81-82); pH (Table 111); and SEC-HPLC analysis of samples stored at 4° C. and 40° C. for 4 weeks (Tables 112-113).

TABLE 111

Measured pH

| Formulation ID | Concentration | 4° C. pH | 40° C. pH |
|---|---|---|---|
| H7MT-P | 8 mg/mL | 6.32 | 6.29 |
| H7MT-P | 14 mg/mL | 6.17 | 6.17 |
| H7MGT-P | 8 mg/mL | 6.42 | 6.39 |
| H7MGT-P | 14 mg/mL | 6.28 | 6.25 |

TABLE 112

SEC-HPLC (SUMMARY OF PEAK AREAS); T = 4 week, 4° C.

| Formulation ID | % Pre-peak 1 | % Pre-peak 2 | % Main Peak | % Un-PEG | Total Area |
|---|---|---|---|---|---|
| H7MT-P 8 mg/mL | 0.57 | 0.72 | 98.56 | 0.15 | 8.15E+04 |
| H7MT-P 14 mg/mL | 0.47 | 0.69 | 98.68 | 0.16 | 7.92E+04 |
| H7MGT-P 8 mg/mL | 0.50 | 0.69 | 98.60 | 0.21 | 7.83E+04 |
| H7MGT-P 14 mg/mL | 0.64 | 0.71 | 98.44 | 0.21 | 7.78E+04 |

TABLE 113

SEC-HPLC (SUMMARY OF PEAK AREAS); T = 4 week, 40° C.

| Formulation ID | % Pre-peak 1 | % Pre-peak 2 | % Main Peak | % Un-PEG | Total Area |
|---|---|---|---|---|---|
| H7MT-P 8 mg/mL | 0.35 | 1.08 | 92.00 | 6.58 | 8.56E+04 |
| H7MT-P 14 mg/mL | 0.29 | 1.24 | 91.53 | 6.94 | 8.07E+04 |
| H7MGT-P 8 mg/mL | 0.35 | 0.92 | 89.66 | 9.06 | 8.05E+04 |
| H7MGT-P 14 mg/mL | 0.37 | 1.15 | 89.31 | 9.17 | 7.61E+04 |

After the four week time period, H7MT-P formed less de-PEGylated hGH than H7MGT-P at both 4° C. and 40° C., and a small amount of covalent aggregates at 40° C. Overall, at 40° C., the main degradation product was de-PEGylated hGH, and there was an increased amount of dimerization and more covalent aggregates than at 4° C.

Example 26

Agitation Study (Surfactants)

A follow-up study was performed to those described in Example 21. PEG-hGH was dialyzed with H7MT, and the dialyzed protein was diluted to 2 mg/ml with H7MT. Various amounts of the surfactant Pluronic F68 were added to the samples: no Pluronic F68, 0.01% Pluronic F68, 0.05% Pluronic F68, 0.1% Pluronic F68, 0.25% Pluronic F68, or 0.5% Pluronic F68. Two control samples contained H7MT buffer with 0.01% Pluronic Acid without protein. One sample was vortexed, whereas the other one was not (t=0). Agitation was performed with 500 uL fill in glass vials, and samples were agitated for 2 hours at room temperature. SEC-HPLC analysis was performed on the various samples, and the results are shown in Table 114.

TABLE 114

SEC-HPLC (SUMMARY OF PEAK AREAS); Agitation

| Formulation ID | % Pre-peak 1 + 2 | % Main Peak | Total Area |
|---|---|---|---|
| H7MT, no surfactant, t = 0 | 4.40 | 95.60 | 8.85E+04 |
| H7MT, no surfactant, 2 hr. vortex | 12.45 | 87.55 | 7.47E+04 |
| H7MT, 0.01% F68, 2 hr. vortex | 15.66 | 84.34 | 7.38E+04 |
| H7MT, 0.05% F68, 2 hr. vortex | 2.45 | 97.55 | 7.11E+04 |
| H7MT, 0.1% F68, 2 hr. vortex | 1.69 | 98.31 | 7.12E+04 |
| H7MT, 0.25% F68, 2 hr. vortex | 1.37 | 98.63 | 7.35E+04 |
| H7MT, 0.5% F68, 2 hr. vortex | 1.36 | 98.64 | 7.33E+04 |

In a study investigating aggregate reversibility, 0.1% Pluronic F68 was added to the vortexed control (no surfactant) sample to examine whether agitation-induced aggregates could be dissociated by Pluronic F68. The samples were analyzed by SEC-HPLC. The results of this study showed that Pluronic F68 can reduce agitation-induced aggregation, but does not dissociate it. H7MT with 0.1% Pluronic F68 had a smaller amount of aggregate than the formulations with lower amounts of Pluronic F68.

Example 27

Sedimentation Velocity Analysis

This analysis was performed to measure the aggregation of the following three samples: PEG-hGH polypeptide at 39.9 mg/ml, 24.3 mg/ml, and 1.0 mg/ml. These stocks were diluted to 0.6 mg/ml immediately prior to measurement with Dulbecco's phosphate buffered saline (Gibco part no. 144190-144). The high-resolution sedimentation coefficient distributions for these samples were generated with the vertical axis giving the concentration and the horizontal axis showing the separation on the basis of sedimentation coefficient. Each distribution was normalized to account for concentration differences among the samples. PEG-hGH at 39.9 mg/ml had its main peak at 1.27 S, and that peak represented 98.7% of the total absorbance. PEG-hGH at 24.3 mg/ml had its main peak at 1.29S, and that peak represented 97.5% of the total absorbance. Minor peaks that sediment faster than the main peak (monomer) were found.

Example 28

AUC/SEC Study

Samples with different concentrations of PEGylated hGH polypeptide (39.9 mg/ml, 24.3 mg/ml, and 1.1 mg/ml) and the formulations shown in Table 115 were found to show similar amounts of aggregation by SEC-HPLC, SDS-PAGE, and AUC. Table 116 shows SEC-HPLC results from 20 ug of material loaded onto the column. SDS-PAGE analysis (10 ug loaded in each lane) is shown as FIG. 83.

TABLE 115

| Buffer | pH | Bulking Agent | Stabilizer | Concentration |
|---|---|---|---|---|
| 30 mM Histidine | 7 | 4% Mannitol | 2% Trehalose | 39.9 mg/mL |
| 30 mM Histidine | 7 | 4% Mannitol | 2% Trehalose | 24.3 mg/mL |
| 10 mM Histidine | 7 | 4% Mannitol | 2% Trehalose | 1.1 mg/mL |

TABLE 116

| Concentration | % Pre-peak 1 | % Pre-peak 2 | % Main Peak | % Un-PEG | Total Area |
|---|---|---|---|---|---|
| 39.9 mg/mL | 0.56 | 1.46 | 97.98 | 0.00 | 5.98E+04 |
| 24.3 mg/mL | 0.48 | 1.46 | 98.06 | 0.00 | 7.55E+04 |
| 1.1 mg/mL | 0.67 | 1.55 | 97.79 | 0.00 | 7.58E+04 |

Example 29

Intermediate Stability Study

Table 117 details the intermediate stability study. Formulation ID H7.3MT is 30 mM Histidine, 4% Mannitol, 2% Trehalose, pH 7.3. Formulation ID H7.3MT+F is 30 mM Histidine, 4% Mannitol, 2% Trehalose, pH 7.3 with 0.1% Pluronic F68. Formulation ID HP7MT is 10 mM Histidine, 10 mM Phosphate, 4% Mannitol, 2% Trehalose, pH 7.0. Formulation ID HP7MT+F is 10 mM Histidine, 10 mM Phosphate, 4% Mannitol, 2% Trehalose, pH 7.0 with 0.1% Pluronic F68. Three different concentrations of PEGylated hIFN with para-acetylphenylalanine substituted at position 35 are used: 8 mg/ml, 12 mg/ml and 16 mg/ml. The study involves analyses at t=0, 1 week, 8 weeks, and 24 weeks, and temperatures of 4° C., 25° C., and 40° C. Methods involved in this study are as previously described: SDS-PAGE (reduced and non-reduced); SEC-HPLC, RP-HPLC, IEX, FTIR, moisture content, etc. Bioactivity is measured using a proliferation assay involving BrdU labeling. Briefly, this assay is performed with serum starved rat GHR (L43R) expressing BAF3 cell line, 2E2-2B12-F4. Cells are plated at specified densities of cells/well in a 96-well plate. The cells are activated with a multi-point dose range of PEGylated hGH polypeptide and are labeled at the same time with 50 uM BrdU (Sigma, St. Louis, Mo.). After 48 hours in culture, cells are fixed/permeabilized with 100 ul of BD cytofix/cytoperm solution (BD Biosciences) for 30 min at room temperature. To expose BrdU epitopes, fixed/permeablilized cells are treated with 30 ug/well of DNase. (Sigma) for 1 hour at 37° C. Immunofluorescent staining with APC-conjugated anti-BrdU antibody (BD Biosciences) enables sample analysis on the FACS Array. Variations to this method are known to those of ordinary skill in the art.

TABLE 117

| Buffer | Conc. | Time Point | Temp. | Analyses |
|---|---|---|---|---|
| H7.3MT (30 mM Histidine, 4% mannitol, 2% Trehalose, pH 7.3) | 8 mg/ml | zero | | SDS-PAGE (r + Nr), SEC, RP, cIEX, FTIR, moisture content, bioactivity |

TABLE 117-continued

| Buffer | Conc. | Time Point | Temp. | Analyses |
|---|---|---|---|---|
| H7.3MT | 8 mg/ml | 1 w | 40 C. | SDS-PAGE (r + Nr), SEC, RP, cIEX, bioactivity |
| H7.3MT | 8 mg/ml | 8 w | 4 C. | SDS-PAGE (r + Nr), SEC, RP, cIEX |
| H7.3MT | 8 mg/ml | 24 w | 4 C. | SDS-PAGE (r + Nr), SEC, RP, cIEX, FTIR, moisture content, bioactivity |
| H7.3MT | 12 mg/ml | zero | | SDS-PAGE (r + Nr), SEC, RP, cIEX, FTIR, moisture content, bioactivity |
| H7.3MT | 12 mg/ml | 1 w | 40 C. | SDS-PAGE (r + Nr), SEC, RP, cIEX, bioactivity |
| H7.3MT | 12 mg/ml | 8 w | 4 C. | SDS-PAGE (r + Nr), SEC, RP, cIEX |
| H7.3MT | 12 mg/ml | 8 w | 25 C. | SDS-PAGE (r + Nr), SEC, RP, cIEX |
| H7.3MT | 12 mg/ml | 24 w | 4 C. | SDS-PAGE (r + Nr), SEC, RP, cIEX, FTIR, moisture content, bioactivity |
| H7.3MT | 16 mg/ml | zero | | SDS-PAGE (r + Nr), SEC, RP, cIEX, FTIR, moisture content, bioactivity |
| H7.3MT | 16 mg/ml | 1 w | 40 C. | SDS-PAGE (r + Nr), SEC, RP, cIEX, bioactivity |
| H7.3MT | 16 mg/ml | 8 w | 4 C. | SDS-PAGE (r + Nr), SEC, RP, cIEX |
| H7.3MT | 16 mg/ml | 8 w | 25 C. | SDS-PAGE (r + Nr), SEC, RP, cIEX |
| H7.3MT | 16 mg/ml | 24 w | 4 C. | SDS-PAGE (r + Nr), SEC, RP, cIEX, FTIR, moisture content, bioactivity |
| H7.3MT + F | 8 mg/ml | zero | | SDS-PAGE (r + Nr), SEC, RP, cIEX, FTIR, moisture content, bioactivity |
| H7.3MT + F | 8 mg/ml | 1 w | 40 C. | SDS-PAGE (r + Nr), SEC, RP, cIEX, bioactivity |
| H7.3MT + F | 8 mg/ml | 8 w | 4 C. | SDS-PAGE (r + Nr), SEC, RP, cIEX |
| H7.3MT + F | 8 mg/ml | 24 w | 4 C. | SDS-PAGE (r + Nr), SEC, RP, cIEX, FTIR, moisture content, bioactivity |
| H7.3MT + F | 12 mg/ml | zero | | SDS-PAGE (r + Nr), SEC, RP, cIEX, FTIR, moisture content, bioactivity |
| H7.3MT + F | 12 mg/ml | 1 w | 40 C. | SDS-PAGE (r + Nr), SEC, RP, cIEX, bioactivity |
| H7.3MT + F | 12 mg/ml | 8 w | 4 C. | SDS-PAGE (r + Nr), SEC, RP, cIEX |
| H7.3MT + F | 12 mg/ml | 8 w | 25 C. | SDS-PAGE (r + Nr), SEC, RP, cIEX |
| H7.3MT + F | 12 mg/ml | 24 w | 4 C. | SDS-PAGE (r + Nr), SEC, RP, cIEX, FTIR, moisture content, bioactivity |
| H7.3MT + F | 16 mg/ml | zero | | SDS-PAGE (r + Nr), SEC, RP, cIEX, FTIR, moisture content, bioactivity |
| H7.3MT + F | 16 mg/ml | 1 w | 40 C. | SDS-PAGE (r + Nr), SEC, RP, cIEX, bioactivity |
| H7.3MT + F | 16 mg/ml | 8 w | 4 C. | SDS-PAGE (r + Nr), SEC, RP, cIEX |
| H7.3MT + F | 16 mg/ml | 8 w | 25 C. | SDS-PAGE (r + Nr), SEC, RP, cIEX |
| H7.3MT + F | 16 mg/ml | 24 w | 4 C. | SDS-PAGE (r + Nr), SEC, RP, cIEX, FTIR, moisture content, bioactivity |
| HP7MT (10 mM Histidine, 10 mM Phosphate, 4% mannitol, 2% Trehalose, pH 7.0) | 8 mg/ml | zero | | SDS-PAGE (r + Nr), SEC, RP, cIEX, FTIR, moisture content, bioactivity |
| HP7MT | 8 mg/ml | 1 w | 40 C. | SDS-PAGE (r + Nr), SEC, RP, cIEX, bioactivity |
| HP7MT | 8 mg/ml | 8 w | 4 C. | SDS-PAGE (r + Nr), SEC, RP, cIEX, |

TABLE 117-continued

| Buffer | Conc. | Time Point | Temp. | Analyses |
|---|---|---|---|---|
| HP7MT | 8 mg/ml | 24 w | 4 C. | SDS-PAGE (r + Nr), SEC, RP, cIEX, FTIR, moisture content, bioactivity |
| HP7MT | 12 mg/ml | zero | | SDS-PAGE (r + Nr), SEC, RP, cIEX, FTIR, moisture content, bioactivity |
| HP7MT | 12 mg/ml | 1 w | 40 C. | SDS-PAGE (r + Nr), SEC, RP, cIEX, bioactivity |
| HP7MT | 12 mg/ml | 8 w | 4 C. | SDS-PAGE (r + Nr), SEC, RP, cIEX |
| HP7MT | 12 mg/ml | 8 w | 25 C. | SDS-PAGE (r + Nr), SEC, RP, cIEX |
| HP7MT | 12 mg/ml | 24 w | 4 C. | SDS-PAGE (r + Nr), SEC, RP, cIEX, FTIR, moisture content, bioactivity |
| HP7MT | 16 mg/ml | zero | | SDS-PAGE (r + Nr), SEC, RP, cIEX, FTIR, moisture content, bioactivity |
| HP7MT | 16 mg/ml | 1 w | 40 C. | SDS-PAGE (r + Nr), SEC, RP, cIEX, bioactivity |
| HP7MT | 16 mg/ml | 8 w | 4 C. | SDS-PAGE (r + Nr), SEC, RP, cIEX |
| HP7MT | 16 mg/ml | 8 w | 25 C. | SDS-PAGE (r + Nr), SEC, RP, cIEX |
| HP7MT | 16 mg/ml | 24 w | 4 C. | SDS-PAGE (r + Nr), SEC, RP, cIEX, FTIR, moisture content, bioactivity |
| HP7MT + F | 8 mg/ml | zero | | SDS-PAGE (r + Nr), SEC, RP, cIEX, FTIR, moisture content, bioactivity |
| HP7MT + F | 8 mg/ml | 1 w | 40 C. | SDS-PAGE (r + Nr), SEC, RP, cIEX, bioactivity |
| HP7MT + F | 8 mg/ml | 8 w | 4 C. | SDS-PAGE (r + Nr), SEC, RP, cIEX |
| HP7MT + F | 8 mg/ml | 24 w | 4 C. | SDS-PAGE (r + Nr), SEC, RP, cIEX, FTIR, moisture content, bioactivity |
| HP7MT + F | 12 mg/ml | zero | | SDS-PAGE (r + Nr), SEC, RP, cIEX, FTIR, moisture content, bioactivity |
| HP7MT + F | 12 mg/ml | 1 w | 40 C. | SDS-PAGE (r + Nr), SEC, RP, cIEX, bioactivity |
| HP7MT + F | 12 mg/ml | 8 w | 4 C. | SDS-PAGE (r + Nr), SEC, RP, cIEX |
| HP7MT + F | 12 mg/ml | 8 w | 25 C. | SDS-PAGE (r + Nr), SEC, RP, cIEX |
| HP7MT + F | 12 mg/ml | 24 w | 4 C. | SDS-PAGE (r + Nr), SEC, RP, cIEX, FTIR, moisture content, bioactivity |
| HP7MT + F | 16 mg/ml | zero | | SDS-PAGE (r + Nr), SEC, RP, cIEX, FTIR, moisture content, bioactivity |
| HP7MT + F | 16 mg/ml | 1 w | 40 C. | SDS-PAGE (r + Nr), SEC, RP, cIEX, bioactivity |
| HP7MT + F | 16 mg/ml | 8 w | 4 C. | SDS-PAGE (r + Nr), SEC, RP, cIEX |
| HP7MT + F | 16 mg/ml | 8 w | 25 C. | SDS-PAGE (r + Nr), SEC, RP, cIEX |
| HP7MT + F | 16 mg/ml | 24 w | 4 C. | SDS-PAGE (r + Nr), SEC, RP, cIEX, FTIR, moisture content, bioactivity |

Reconstitution Study

Formulation ID H7.3MT is 30 mM Histidine, 4% Mannitol, 2% Trehalose, pH 7.3. Formulation ID H7.3MT+F is 30 mM Histidine, 4% Mannitol, 2% Trehalose, pH 7.3 with 0.1% Pluronic F68. Formulation ID HP7MT is 10 mM Histidine, 10 mM Phosphate, 4% Mannitol, 2% Trehalose, pH 7.0. Formulation ID HP7MT+F is 10 mM Histidine, 10 mM Phosphate, 4% Mannitol, 2% Trehalose, pH 7.0 with 0.1% Pluronic F68. After lyophilized samples are held at 4° C. for 8 weeks, samples are reconstituted and held at room temperature for t=0, 4, 8, and 24 hours and analyzed with methods described previously. See Table 118.

TABLE 118

| Buffer | Conc. | Time Point | Temp. | Holding after Reconstitution (at RT) | Analyses (2) |
|---|---|---|---|---|---|
| H7.3MT | 8 mg/ml | 8 w | 4 C. | 4, 8, 24 hours | SEC, RP, (SDS-PAGE (r + Nr), cIEX only for 24 hr) |
| H7.3MT | 12 mg/ml | 8 w | 4 C. | 4, 8, 24 hours | SEC, RP, (SDS-PAGE (r + Nr), cIEX only for 24 hr) |
| H7.3MT | 16 mg/ml | 8 w | 4 C. | 4, 8, 24 hours | SEC, RP, (SDS-PAGE (r + Nr), cIEX only for 24 hr) |
| H7.3MT + F | 8 mg/ml | 8 w | 4 C. | 4, 8, 24 hours | SEC, RP, (SDS-PAGE (r + Nr), cIEX only for 24 hr) |
| H7.3MT + F | 12 mg/ml | 8 w | 4 C. | 4, 8, 24 hours | SEC, RP, (SDS-PAGE (r + Nr), cIEX only for 24 hr) |
| H7.3MT + F | 16 mg/ml | 8 w | 4 C. | 4, 8, 24 hours | SEC, RP, (SDS-PAGE (r + Nr), cIEX only for 24 hr) |
| HP7MT | 8 mg/ml | 8 w | 4 C. | 4, 8, 24 hours | SEC, RP, (SDS-PAGE (r + Nr), cIEX only for 24 hr) |
| HP7MT | 12 mg/ml | 8 w | 4 C. | 4, 8, 24 hours | SEC, RP, (SDS-PAGE (r + Nr), cIEX only for 24 hr) |
| HP7MT | 16 mg/ml | 8 w | 4 C. | 4, 8, 24 hours | SEC, RP, (SDS-PAGE (r + Nr), cIEX only for 24 hr) |
| HP7MT + F | 8 mg/ml | 8 w | 4 C. | 4, 8, 24 hours | SEC, RP, (SDS-PAGE (r + Nr), cIEX only for 24 hr) |
| HP7MT + F | 12 mg/ml | 8 w | 4 C. | 4, 8, 24 hours | SEC, RP, (SDS-PAGE (r + Nr), cIEX only for 24 hr) |
| HP7MT + F | 16 mg/ml | 8 w | 4 C. | 4, 8, 24 hours | SEC, RP, (SDS-PAGE (r + Nr), cIEX only for 24 hr) |

Injection Feasibility Study

Injection feasibility is tested with 8, 12, 16, and 25 mg/ml of PEGylated hGH polypeptide (Formulation ID H7.3MT). Unconjugated PEG (Formulation ID H7.3MT) is also analyzed at approximately 16 mg/ml and 25 mg/ml, as well as a buffer control without polypeptide or PEG. An instron machine is used, and 4 lbs of force is used with 27 and 29 gauge needles.

Modifications to various conditions and/or parameters to the techniques described herein are known to those of ordinary skill in the art. Methods such as those described above or other methods known to those of ordinary skill in the art may be used in formulation studies. Potency studies on samples may be performed with assays known to those of ordinary skill in the art.

Suitable formulations include, but are not limited to, H7MT-P with Pluronic Acid; H7MGT-P with Pluronic Acid; H7MT-P; H7MGT-P; H6MT-P with Pluronic Acid; H6MGT-P with Pluronic Acid; H6MT-P; H6MGT-P; HP7MT; HP7MT with Pluronic Acid; H7.3MT; H7.3MT with Pluronic Acid. Suitable formulations may have a pH range of about 6 to about 7.3. Suitable formulations may have a pH range of about 5.5 to about 8. Suitable formulations may include histidine at about 5 to about 30 mM. Suitable formulations may optionally include mannitol at up to about 60 g/L. Suitable formulations may optionally include trehalose at up to about 50 g/L. Suitable formulations may optionally include glycine at up to about 60 g/L.

It is understood that the examples and embodiments described herein are for illustrative purposes only and that various modifications or changes in light thereof will be suggested to persons of ordinary skill in the art and are to be included within the spirit and purview of this application and scope of the appended claims. All publications, patents, and patent applications cited herein are hereby incorporated by reference herein in their entirety for all purposes.

TABLE 119

Sequences Cited.

| SEQ ID # | Sequence Name |
|---|---|
| 1 | Full-length amino acid sequence of hGH |
| 2 | The mature amino acid sequence of hGH (isoform 1) |
| 3 | The 20-kDa hGH variant in which residues 32-46 of hGH are deleted |

What is claimed is:

1. A pharmaceutical formulation of a human growth hormone (hGH) variant wherein said formulation comprises: a) a buffer; b) at least one carrier, excipient, or stabilizer, and; c) a pharmaceutically effective quantity of the hGH variant wherein the hGH variant comprises a non-naturally encoded amino acid at position 35 and wherein the non-naturally encoded amino acid is p-acetyl phenylalanine.

2. The formulation of claim 1 wherein the hGH is PEGylated.

3. The formulation of claim 1, wherein the pH of the buffer is between about pH 4.0 and about pH 8.5.

4. The formulation of claim 1, wherein the pH of the buffer is between about pH 6.0 and about pH 7.3.

5. The formulation of claim 1, wherein the pH of the buffer is between about pH 5.5 and about 8.0.

6. The formulation of claim 1, wherein the pharmaceutically effective quantity of hGH is between about 2mg/mL and about 50 mg/mL.

7. The formulation of claim 1, wherein the buffer is between about pH 5.0 and about pH 7.5.

8. The formulation of claim 1, wherein the buffer is histidine.

9. The formulation of claim 8, wherein the histidine is at a concentration of about 0.1 mM to about 200 mM.

10. The formulation of claim 9, wherein the histidine is at a concentration of about 1 mM to about 75 mM.

11. The formulation of claim 10, wherein the histidine is at a concentration of about 5 mM to about 30 mM.

12. The formulation of claim 1, wherein the formulation further comprises d) a surfactant.

13. The formulation of claim 12, wherein the surfactant is a non-ionic surfactant.

14. The formulation of claim 13, wherein the non-ionic surfactant is at about 0.0001% to about 10%.

15. The formulation of claim 13, wherein the non-ionic surfactant is at about 0.01% to about 10%.

16. The formulation of claim 13, wherein the non-ionic surfactant is at about 0.1% to about 5%.

17. The formulation of claim 13, wherein the non-ionic surfactant is at about 0.1% to about 1%.

18. The formulation of claim 13, wherein the non-ionic surfactant is at about 0.0001% to about 1%.

\* \* \* \* \*

SEQUENCE LISTING

<160> NUMBER OF SEQ ID NOS: 3

<210> SEQ ID NO 1
<211> LENGTH: 217
<212> TYPE: PRT
<213> ORGANISM: Homo sapiens

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

```
-continued

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 3
<211> LENGTH: 176
<212> TYPE: PRT
<213> ORGANISM: Homo sapiens

<400> SEQUENCE: 3

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
            35                  40                  45

Arg Glu Glu Thr Gln Gln Lys Ser Asn Leu Glu Leu Leu Arg Ile Ser
    50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
                100                 105                 110

Leu Glu Asp Gly Ser Pro Arg Thr Gly Gln Ile Phe Lys Gln Thr Tyr
            115                 120                 125

Ser Lys Phe Asp Thr Asn Ser His Asn Asp Asp Ala Leu Leu Lys Asn
    130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175
```